United States Patent
Aszodi et al.

(10) Patent No.: US 7,288,549 B2
(45) Date of Patent: *Oct. 30, 2007

(54) HETEROCYCLIC COMPOUNDS, METHOD FOR PREPARING SAME AND USE THEREOF AS MEDICINES, IN PARTICULAR AS ANTIBACTERIAL AGENTS

(75) Inventors: Joseph Aszodi, Tucson, AZ (US); Maxime Lampilas, St. Cloud (FR); Branislav Musicki, Paris (FR); David Alan Rowlands, Poissy (FR); Pascal Colette, Le Canet (FR)

(73) Assignee: Aventis Pharma S.A., Antony (FR)

( * ) Notice: Subject to any disclaimer, the term of this patent is extended or adjusted under 35 U.S.C. 154(b) by 230 days.

This patent is subject to a terminal disclaimer.

(21) Appl. No.: 10/480,019

(22) PCT Filed: Jun. 4, 2002

(86) PCT No.: PCT/FR02/01877

§ 371 (c)(1), (2), (4) Date: Apr. 14, 2004

(87) PCT Pub. No.: WO02/100860

PCT Pub. Date: Dec. 19, 2002

(65) Prior Publication Data

US 2005/0245505 A1 Nov. 3, 2005

(30) Foreign Application Priority Data

Jun. 8, 2001 (FR) .................................. 01 07520

(51) Int. Cl.
- A61P 31/04 (2006.01)
- A61K 31/44 (2006.01)
- C07D 471/08 (2006.01)

(52) U.S. Cl. .................. 514/292; 514/293; 546/82; 546/83; 546/84

(58) Field of Classification Search ................ 514/292, 514/293; 546/82, 83, 84
See application file for complete search history.

(56) References Cited

FOREIGN PATENT DOCUMENTS

| EP | 0 702 004 | * | 3/1996 |
| JP | 05-339263 | * | 12/1993 |
| WO | WO 90/15058 | * | 12/1990 |
| WO | WO 96/29327 | * | 9/1996 |
| WO | WO 97/23484 | * | 7/1997 |
| WO | WO 99/01434 | * | 1/1999 |
| WO | WO 99/16442 | * | 4/1999 |
| WO | WO 99/52875 | * | 10/1999 |
| WO | WO 00/37458 | * | 6/2000 |
| WO | WO 01/25228 | * | 4/2001 |
| WO | WO 01/79206 | * | 10/2001 |
| WO | WO 02/67937 | * | 9/2002 |

OTHER PUBLICATIONS

Shiotani et al., The Diazabenzobicyclo[3.3.1]nonane System. I. Synthesis of 3,4,5,6-tetrahydro-2H-1,5-methanobenzo[g][1,4]diazocine and Its Derivatives, Chem. Pharm. Bull., 1964, vol. 12, No. 6, pp. 647-651.*
Booker-Milburn et al., Azabenzocycloheptenones. Part 20. Synthesis and Utilisation of 4-amino-1,2,3,4-tetrahydro-1(1H)-benzazepines, Journal of the Chemical Society, Perkin Transactions 1: Organic and Bio-Organic Chemistry, 1997, vol. 21, pp. 3261-3273.*
Heier et al., An Asymmetric Synthesis of (R)-5,6-dihydro-5-(methylamino)-4H-imidazo-[4,5,1-ij]quinolin-2(1H)-one and its [2-14C]- and [6,7-3H2]-labeled Forms, Journal of Labelled Compounds & Radiopharmaceuticals (1996), vol. 38, No. 12, pp. 1087-1098.*
Romero et al., Oxidative Cyclization of Acyclic Ureas With Bis(trifluoroacetoxy)iodo Benzene to Generate N-Substituted 2-Benzimidazolinones, Tetrahedron Letters, Apr. 1, 1996, vol. 37, No. 14, pp. 2361-2364.*
Moon et al., Synthesis of Tritium-labeled (R)-5-(di[2,3-3H2]propylamino)-5,6-dihydro-4H-imidazo[4,5,1-ij]quinolin-2(1H)-one and (R)-5-([2,3-3H2]propylamino)-5,6-dihydro-4H-imidazo[4,5,1-ij]quinolin-2(1H)-one, Journal of Labelled Compounds and Radiopharmaceuticals, 1992, vol. 31, No. 11, pp. 933-943.*
Moon et al., Dopaminergic and Serotonergic Activities of Imidaoquinolinones and Related Compounds, Journal of Medicinal Chemistry, 1992, vol. 35, No. 6, pp. 1076-1092.*
Zhou et al., Studies Directed to the Total Synthesis of ET 743 and Analogues Thereof: An Expeditious Route to the ABFGH Subunit, Organic Letters, 2002, vol. 4, No. 1, pp. 43-46.*
Heier et al., Synthesis and Biological Activities of (R)-5,6-dihydro-N,N-dimethyl-4H-imidazol[4,5,1-ij]quinolin-5-amine and Its Metabolites, Journal of Medicinal Chemistry, 1997, vol. 40, No. 5, pp. 639-646.*
Moon et al., Medicinal Chemistry of Imidazoquinolinone Dopamine Receptor Agonists, Drug Design and Discovery, 1993, vol. 9, No. 3-4, pp. 313-322.*
Tirk et al., Hydroxyminoisoquinolin-3(2H)-ones, VI Synthesis and Biological Activity of Some Aminoisoquinoline Derivatives, Acta Chimica Hungarica, 1987, vol. 124, No. 2, pp. 195-207.*
Elliott et al., Syntheses and Stereochemistry of 4-Hydroxytetrahydroisoquinolines in teh 1-Benzyl and 1-Phenethyl Series. Efficient Routes to Isopavines and Homoisopavines, Tetrahedron Letters, 1980, Vol. 21, No. 48, pp. 4633-4636.*

* cited by examiner

Primary Examiner—Brenda Coleman
(74) Attorney, Agent, or Firm—Charles A. Muserlian

(57) ABSTRACT

The invention relates to new heterocyclic compounds of general formula (I), and their salts with a base or an acid:

(I)

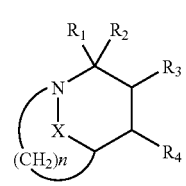

The invention also relates to a process for the preparation of these compounds, as well as their use as medicaments, in particular as anti-bacterial agents.

10 Claims, No Drawings

HETEROCYCLIC COMPOUNDS, METHOD FOR PREPARING SAME AND USE THEREOF AS MEDICINES, IN PARTICULAR AS ANTIBACTERIAL AGENTS

This application is a 371 of PCT/FR02/01877 filed Jun. 4, 2002.

The invention relates to new heterocyclic compounds, their preparation and their use as medicaments, in particular as anti-bacterial agents.

In the journal J. Org. Chem., Vol. 37, No. 5, 1972, pages 697 to 699 is described in particular the preparation of a bicyclic derivative of molecular formula $C_{10}H_{18}N_2O$.

In the journal J. Org. Chem., Vol. 45, No. 26, 1980, pages 5325-5326 is described in particular the preparation of bicyclic derivatives of molecular formulae $C_6H_9NO_2$ and $C_7H_{11}NO_2$.

In the review Chemical Reviews, 1983, vol. 83, No. 5, pages 549 to 555 is described in particular the preparation of bicyclic derivatives of molecular formulae $C_{10}H_{18}N_2O$ and $C_7H_{12}N_2O$.

In the journal Angew. Chem. Int. Ed. 2000, 39, No. 3, pages 625 to 628 is described in particular the preparation of a compound of molecular formula $C_{12}H_{12}N_2O$.

No particular use in the therapeutic field of these compounds has been described in these documents.

A subject of the invention is the compounds corresponding to the following formula (I):

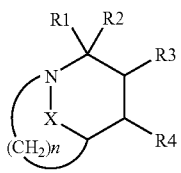

in which:

a) either R1 represents a hydrogen atom, a COOH, CN, COOR, $(CH_2)n'R_5$, $CONR_6R_7$ or

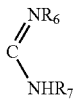

radical,

R is chosen from the group constituted by an alkyl radical containing 1 to 6 carbon atoms, optionally substituted by a pyridyl radical, a —$CH_2$-alkenyl radical containing in total 3 to 9 carbon atoms, a (poly)alkoxyalkyl group containing 1 to 4 oxygen atoms and 3 to 10 carbon atoms, an aryl radical containing 6 to 10 carbon atoms or an aralkyl radical containing 7 to 11 carbon atoms, the ring of the aryl or aralkyl radical being optionally substituted by an OH, $NH_2$, $NO_2$, alkyl radical containing 1 to 6 carbon atoms, an alkoxy radical containing 1 to 6 carbon atoms or by one or more halogen atoms, $R_5$ is chosen from the group constituted by a COOH, CN, OH, $NH_2$, CO—$NR_6R_7$, COOR, OR, OCOH, OCOR, OCOOR, OCONHR, $OCONH_2$, $OSO_2R$, NHR, NHCOR, NHCOH, $NHSO_2R$, NH—COOR, NH—CO—NHR, NH—CO—$NH_2$ or $N_3$ radical, R being defined as above, $R_6$ and $R_7$, identical or different, are chosen from the group constituted by a hydrogen atom, an alkyl radical containing 1 to 6 carbon atoms, an aryl radical containing 6 to 10 carbon atoms and an aralkyl radical containing 7 to 11 carbon atoms and an alkyl radical containing 1 to 6 carbon atoms substituted by a pyridyl radical, n' is equal to 1 or 2, $R_3$ and $R_4$ together form a phenyl or a heterocycle of aromatic character with 5 or 6 vertices containing 1 to 4 heteroatoms chosen from nitrogen, oxygen and sulphur, and optionally substituted by one or more R' groups, R' being chosen from the group constituted by a hydrogen atom and the alkyl radicals containing 1 to 6 carbon atoms, optionally substituted by one or more hydroxy, oxo, halogen or cyano radicals or by a nitro radical, alkenyl containing 2 to 6 carbon atoms, halogen, amino, OH, protected OH, —OR, —NHCOH, —NHCOR, NHCOOR, COOH, —COOR, —$C(C_6H_5)_3$ and —$CH_2$—$CH_2$—S(O)m-R radicals, R being as defined previously and m being equal to 0, 1 or 2, b) or $R_4$ represents a hydrogen atom or a $(CH_2)_{n'1}R_5$ group, n'1 being equal to 0, 1 or 2 and $R_5$ being as defined above, and $R_1$ and $R_3$ together form a phenyl or an optionally substituted heterocycle, as defined above, in both case a) and b)

$R_2$ is chosen from the group constituted by a hydrogen atom, a halogen atom and the R, $S(O)_mR$, OR, NHCOR, NHCOOR and $NHSO_2R$ radicals, m and R being as defined previously, X represents a divalent group —C(O)—B— linked to the nitrogen atom by the carbon atom, B represents a divalent group —O—$(CH_2)_{n''}$— linked with the carbonyl by the oxygen atom, an —$NR_8$—$(CH_2)_{n''}$— or —$NR_8$—O— group linked with the carbonyl by the nitrogen atom, n" is equal to 0 or 1 and $R_8$ is chosen from the group constituted by a hydrogen atom, an OH, R, OR, Y, OY, $Y_1$, $OY_1$, $Y_2$, $OY_2$, $Y_3$, O—$CH_2$—$CH_2$—S(O)m-R, SiRaRbRc and OSiRaRbRc radical, Ra, Rb and Rc representing individually a linear or branched alkyl radical containing 1 to 6 carbon atoms or an aryl radical containing 6 to 10 carbon atoms, and R and m being as defined previously.

Y is chosen from the group constituted by the COR, COOR, $CONH_2$, CONHR, CONHOH, $CONHSO_2R$, $CH_2COOH$, $CH_2COOR$, $CH_2CONHOH$, $CH_2CONHCN$, $CH_2$tetrazole, protected $CH_2$tetrazole, $CH_2SO_3H$, $CH_2SO_2R$, $CH_2PO(OR)_2$, $CH_2PO(OR)(OH)$, $CH_2PO(R)(OH)$ and $CH_2PO(OH)_2$ radicals, $Y_1$ is chosen from the group constituted by the $SO_2R$, $SO_2NHCOH$, $SO_2NHCOR$, $SO_2NHCOOR$, $SO_2NHCONHR$, $SO_2NHCONH_2$ and $SO_3H$ radicals, $Y_2$ is chosen from the group constituted by the $PO(OH)_2$, $PO(OR)_2$, PO(OH)(OR) and PO(OH)(R) radicals, $Y_3$ is chosen from the group constituted by the following radicals: tetrazole, tetrazole substituted by the R radical, squarate, NH or NR tetrazole, NH or NR tetrazole substituted by the R radical, $NHSO_2R$ and $NRSO_2R$, R being defined as above, n is equal to 1 or 2.

A sub-class of compounds of formula I as defined previously is preferred where $R_8$ in —$NR_8$—$(CH_2)_{n''}$ can only be methyl when in addition n=1, $R_4$ is hydrogen and $R_1$ and $R_3$ together form a phenyl.

A subject of the invention is also the salts of these compounds which can be obtained with bases or mineral or organic acids.

It is clear that the compounds according to the invention are distinguished structurally from the compounds of the prior art mentioned above.

The asymmetrical carbon atoms contained in the compounds of formula (I) can, independently of one another, have the R, S or RS configuration and therefore a subject of the invention is also the compounds of formula (I) in the form of pure enantiomers or pure diastereoisomers or in the form of a mixture of enantiomers in particular of racemates, or mixtures of diastereoisomers.

It follows from what has gone before that the substituents $R_1$, $R_2$, or $R_4$ taken individually on the one hand and X on the other can be in cis and/or trans position with respect to the ring on which they are fixed and that therefore a subject of the invention is the compounds of formula (I) in the form of cis isomers or trans isomers or mixtures.

By alkyl radical containing 1 to 6 carbon atoms, is meant the methyl, ethyl, propyl, isopropyl, as well as butyl, pentyl or hexyl linear or branched radical.

By —$CH_2$-alkenyl radical containing 3 to 9 atoms of carbon, is meant for example the allyl radical, or a butenyl, pentenyl or hexenyl radical.

By aryl radical containing 6 to 10 carbon atoms, is meant a phenyl or naphthyl radical.

By aralkyl radical containing 7 to 11 carbon atoms, is meant a benzyl, phenethyl or methylnaphthyl radical.

By alkoxy radical containing 1 to 6 carbon atoms, is meant in particular the methoxy, ethoxy, propoxy, isopropoxy, butoxy, isobutoxy, sec-butoxy or tert-butoxy radical.

By halogen radical or by halogen atom, is meant fluorine, chlorine, bromine or iodine.

By squarate radical, is meant the radical of formula:

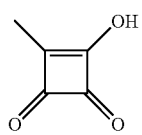

By heterocycle of aromatic character, is meant in particular those chosen from the following list, the two bonds symbolizing the junction with the nitrogenous ring ($R_3R_4$ or $R_1R_3$):

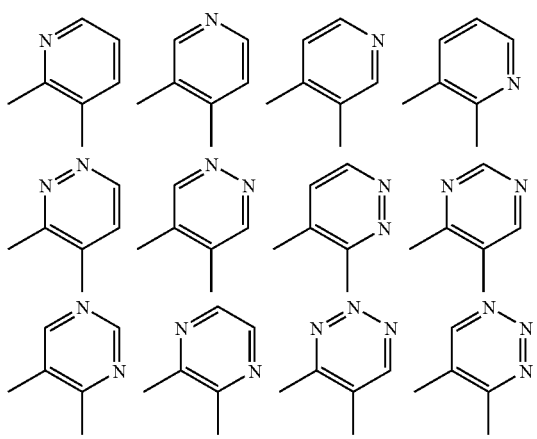

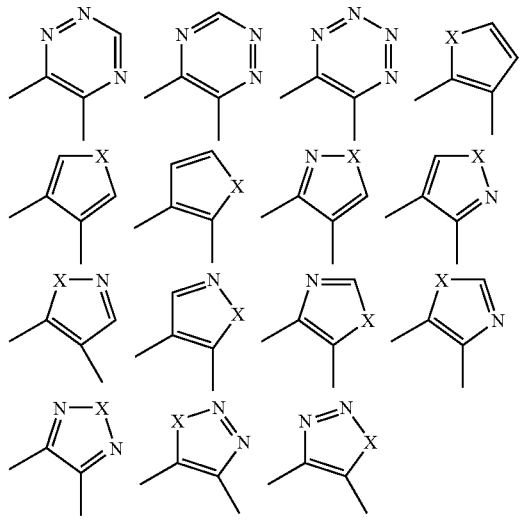

with X=NR', S, O

Among the salts of acids of the products of formula (I), there can be mentioned amongst others, those formed with mineral acids, such as hydrochloric, hydrobromic, hydroiodic, sulphuric or phosphoric acids or with organic acids such as formic, acetic, trifluoroacetic, propionic, benzoic, maleic, fumaric, succinic, tartaric, citric, oxalic, glyoxylic, aspartic acids, alkanesulphonic acids, such as methane and ethane sulphonic acids, arylsulphonic acids such as benzene and paratoluenesulphonic acids.

Among the salts of bases of the products of formula (I), there can be mentioned amongst others, those formed with mineral bases such as, for example, sodium, potassium, lithium, calcium, magnesium or ammonium hydroxide or with organic bases such as, for example, methylamine, propylamine, trimethylamine, diethylamine, triethylamine, N,N-dimethylethanolamine, tris(hydroxymethyl)amino methane, ethanolamine, pyridine, picoline, dicyclohexylamine, morpholine, benzylamine, procaine, lysine, arginine, histidine, N-methylglucamine, or also the salts of phosphonium, such as alkyl-phosphonium, aryl-phosphoniums, alkyl-aryl-phosphonium, alkenyl-aryl-phosphonium or the salts of quaternary ammoniums such as the salt of tetra-n-butylammonium.

Among the compounds of formula (I), a particular subject of the invention is those in which n is equal to 1 as well as those in which $R_2$ is a hydrogen atom.

The compounds of formula (I) in which $R_3$ and $R_4$ together form a phenyl or a heterocycle, optionally substituted, as defined previously, are preferred. Among the latter, there can be mentioned in particular the compounds of formula (I) in which $R_3$ and $R_4$ together form a phenyl or a heterocycle chosen from the group constituted by thienyl, imidazolyl, furyl, pyrazolyl and triazolyl, optionally substituted.

Among the compounds of formula (I), a particular subject of the invention is those in which R1 is chosen from the group constituted by the hydrogen atom and the $COOCH_3$, $COOC_2H_5$, $CONH_2$, $CONHCH_3$, $CONHCH_2$-phenyl and $CONHCH_2$-pyridyl groups.

Among the compounds of formula (I), a particular subject of the invention is also those in which X represents a divalent group —CO—B— in which B represents an —NR$_8$—(CH$_2$)$_{n''}$— group as defined above, in which n" is equal to O.

Among the latter there can be mentioned in particular, those in which R8 is a Y$_1$ or OY$_1$ group, in which Y$_1$ is chosen from the SO$_2$R, SO$_2$NHCOR, SO$_2$NHCOOR, SO$_2$NHCONHR and SO$_3$H groups and R is as defined above; or those in which the R$_8$ group is chosen from the group constituted by the hydrogen atom and the hydroxy, CO-phenyl, O-allyl, OPO$_3$H, OPO$_3$-benzyl, OCH$_2$COOH and O-benzyl groups.

Among the compounds of formula (I), a quite particular subject of the invention is the compounds the names of which follow:

the sodium salt of trans-3-oxo-4-(sulphooxy)-2,3,4,5-tetrahydro-2,5-methano-1H-2,4-benzodiazepine-1-carboxamide;

the sodium salt of 3-methyl-5-(sulphooxy)-5,6,7,8-tetrahydro-4,7-methano-4H-[1,2,3]-triazolo[4,5-e][1,3]diazepine-6(3H)-one;

the sodium salt of trans-1-methyl-6-oxo-5-(sulphooxy)-4,5,6,8-tetrahydro-4,7-methano-1H-pyrazolo[3,4-e][1,3]diazepine-8(7H)-carboxamide;

the sodium salt of trans-N-methyl-3-oxo-4-(sulphooxy)-2,3,4,5-tetrahydro-2,5-methano-1H-2,4-benzodiazepine-1-carboxamide;

the sodium salt of 5-(sulphooxy)-5,6,7,8-tetrahydro-4,7-methano-4H-furo[2,3-e][1,3]diazepine-6-one;

the pyridinium salt of 1-propyl-5-(sulphooxy)-4,5,7,8-tetrahydro-4,7-methano-imidazo[4,5-e][1,3]diazepine-6(1H)-one;

the sodium salt of trans methyl-6-oxo-5-(sulphooxy)-5,6,7,8-tetrahydro-4,7-methano-4H-furo[2,3-e][1,3]diazepine-8-carboxylate;

the sodium salt of 1-methyl-5-(sulphooxy)-5,6,7,8-tetrahydro-4,7-methano-4H-pyrazolo[3,4-e][1,3]diazepine-6(1H)-one;

the sodium salt of trans-3-oxo-N-(4-pyridinylmethyl)-4-(sulphooxy)-2,3,4,5-tetrahydro-2,5-methano-1H-2,4-benzodiazepine-1-carboxamide;

the sodium salt of trans-6-oxo-5-(sulphooxy)-5,6,7,8-tetrahydro-4,7-methano-4H-thieno[2,3-e][1,3]diazepine-8-carboxamide;

the sodium salt of trans-6-oxo-5-(sulphooxy)-5,6,7,8-tetrahydro-4,7-methano-4H-furo[2,3-e][1,3]diazepine-8-carboxamide.

the sodium salt of trans-1,2,3,5-tetrahydro-8-hydroxy-3-oxo-2-(sulphooxy)-1,4-methano-4H-2,4-benzodiazepine-5-carboxamide the sodium salt of trans-7-(acetylamino)-1,2,3,5-tetrahydro-8-hydroxy-3-oxo-2-(sulphooxy)-1,4-methano-4H-2,4-benzodiazepine-5-carboxamide the sodium salt of trans-1,5-dihydro-5-(hydroxymethyl)-2-(sulphooxy)-1,4-methano-4H-2,4-benzodiazepin-3(2H)-one the sodium salt of trans-4,5,6,8-tetrahydro-N-methyl-6-oxo-5-(sulphooxy)-4,7-methano-7H-thieno[2,3-e][1,3]diazepine-8-carboxamide the sodium salt of 7,8-dihydro-7-(sulphooxy)-5,8-methano-5H-thieno[2,3-e][1,3]diazepin-6(4H)-one the triethylammonium salt of trans-2-bromo-4,5,6,8-tetrahydro-6-oxo-5-(sulphooxy)-4,7-methano-7H-thieno[2,3-e][1,3]diazepine-8-carboxamide Another subject of the invention is a process allowing the preparation of the compounds of formula (I).

This process is characterized in that it comprises:
a) a stage during which a compound of formula (II) is reacted with a carbonylation agent, if appropriate in the presence of a base:

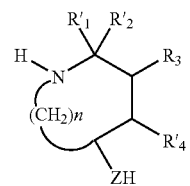

(II)

in which:
a) either R'$_1$ represents a hydrogen atom, a CN, protected COOH, COOR", (CH$_2$)$_n$R'$_5$, CONR$_6$R$_7$,

radical,

R" is chosen from the group constituted by an alkyl radical containing 1 to 6 carbon atoms, optionally substituted by a pyridyl radical, a —CH$_2$-alkenyl radical containing in total 3 to 9 carbon atoms, an aryl radical containing 6 to 10 carbon atoms or an aralkyl radical containing 7 to 11 carbon atoms, the ring of the aryl or aralkyl radical being optionally substituted by an NO$_2$, protected OH, protected NH$_2$ radical, an alkyl radical containing 1 to 6 carbon atoms, an alkoxy radical containing 1 to 6 carbon atoms or by one or more halogen atoms, R'$_5$ is chosen from the group constituted by the following radicals: a protected OH, CN, protected NH$_2$, CO—NR$_6$R$_7$, protected COOH, COOR", OR", OCOH, OCOR", OCOOR", OCONH$_2$, OCONHR", protected NHR", NHCOR", NHSO$_2$R", NH—COOR", NH—CO—NHR" or NH—CONH$_2$, R" being as defined above, n', R$_6$, R$_7$ and R$_3$ are as defined above and R'$_4$ represents an R$_4$ radical as defined above;

b) or R'$_4$ represents a hydrogen atom or a (CH$_2$)$_{n'1}$R'$_5$ group, n'1 being equal to 0, 1 or 2 and R'$_5$ being as defined above, and R'$_1$ and R$_3$ together form a phenyl or an optionally substituted heterocycle, as defined above for R$_3$ and R$_4$, in both case a) and b)

R'$_2$ is chosen from the group constituted by a hydrogen atom, a halogen atom and the R", S(O)$_m$R", OR", NHCOH, NHCOR", NHCOOR" and NHSO$_2$R" radicals, R" being as defined previously, ZH represents an HO—(CH$_2$)$_{n''}$, HNR'$_8$—(CH$_2$)$_{n''}$— or HNR$_8$—O— group, n" is as defined above and R'$_8$ represents a hydrogen atom, an R", protected OH, OR", Y', OY', Y'$_1$, OY'$_1$, Y'$_2$, OY'$_2$, Y'$_3$, O—CH$_2$—CH$_2$—S(O)$_m$—R", SiRaRbRc and OSiRaRbRc radical, Ra, Rb and Rc representing individually a linear or branched alkyl radical containing 1 to 6 carbon atoms or an aryl radical containing 6 to 10 carbon atoms and R" and m being as defined previously; preferably with the compounds where R'$_8$ in —NR'$_8$—(CH$_2$)$_{n''}$ can only be methyl when in addition n=1, R'$_4$ is hydrogen and R'$_1$ and R$_3$ together form a phenyl, Y' is chosen from the group constituted by the COH, COR", COOR", CONH$_2$, CONHR", CONHSO$_2$R", CH$_2$COOR", protected CH$_2$tetrazole, CH$_2$SO$_2$R", CH$_2$PO(OR")$_2$, protected CONHOH, protected CH$_2$COOH, protected CH$_2$CONHOH, protected CH$_2$SO$_3$, protected CH$_2$PO(OR)(OH), protected CH$_2$PO(R)(OH) and protected CH$_2$PO(OH)$_2$ radicals, Y'$_1$ is chosen from the group constituted by the SO$_2$R", SO$_2$NHCOH, SO$_2$NHCOR", SO$_2$NHCOOR", SO$_2$NHCONH$_2$, SO$_2$NHCONHR" and protected SO$_3$H radicals, Y'$_2$ is chosen from the group constituted by the PO(OR")$_2$, protected PO(OH)$_2$, protected PO(OH)(OR) and protected PO(OH)(R) radicals, Y'$_3$ is chosen from the group constituted by the protected tetrazole, tetrazole substituted by the R" radical, protected squarate, protected NH tetrazole, protected NR" tetrazole, protected NH, NR" tetrazole substituted by the R" radical, NHSO$_2$R" and NSO$_2$R" radicals, R" being defined as above.

n is as defined above;

in order to obtain an intermediate compound of formula:

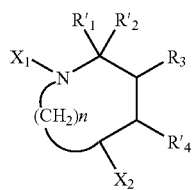

(III)

in which:

R'$_1$, R'$_2$, R$_3$, R'$_4$ and n have the same meanings as above and either X$_1$ is a hydrogen atom and X2 represents a -Z-CO—X$_3$ group, X$_3$ representing the remainder of the carbonylation agent, or X$_2$ is a -ZH group and X1 represents a CO—X$_3$ group, X$_3$ being defined as above;

b) a stage during which the intermediate obtained previously is cyclized, in the presence of a base;

and in that:

c) if appropriate, stage a) is preceeded by and/or stage b) is followed by one or more of the following reactions, in an appropriate order:
protection of the reactive functions,
deprotection of the reactive functions,
esterification
saponification,
sulphation,
phosphation
amidification,
acylation,
sulphonylation;
alkylation;
formation of a urea group;
introduction of a tetrazole group;
reduction of carboxylic acids;
dehydration of amide to nitrile;
salification;
ion exchange;
resolution or separation of diastereoisomers;
oxidation of sulphide to sulphoxide and/or sulphone;
nitration;
reduction of a nitro to amino;
halogenation;
thioalkylation;
carbamoylation;
formation of an azido group;
reduction of an azido to amine;
coupling reactions of aromatic halides with stannylated reagents;
hydrogenation to double bonds;
dihydroxylation of double bonds;
cleavage of diols by oxidation;
cyanidation.

As carbonylation agent, a reagent can be used such as phosgene, diphosgene, triphosgene, an aryl chloroformate such as phenyl or p-nitrophenyl chloroformate, an aralkyl chloroformate such as benzyl chloroformate, an alkyl or alkenyl chloroformate such as methyl or allyl chloroformate, an alkyl dicarbonate such as tert-butyl dicarbonate, carbonyl-diimidazole and their mixtures.

The reaction preferably takes place in the presence of a base or a mixture of bases which neutralize the acid formed. It can in particular be an amine such as triethylamine, diisopropylethylamine, pyridine, dimethylaminopyridine. However, the operation can also be carried out by using the starting product of formula II as base. It is then used in excess.

If appropriate, the product of formula II is used in the form of an acid salt, for example a hydrochloride or a trifluoroacetate.

As base in stage b), amines can also be used, or also hydrides, alcoholates, amides or carbonates of alkali or alkaline-earth metals.

The amines can be chosen for example from the list above.

As hydride sodium or potassium hydride can in particular be used.

As alkali metal alcoholate, potassium t-butylate is preferably used.

As alkali metal amide lithium bis(trimethylsilyl)amide can in particular be used.

As carbonate, sodium or potassium carbonate or bicarbonate can in particular be used.

If appropriate, the intermediate of formula III can be obtained in the form of an acid salt generated during the carbonylation reaction and in particular a hydrochloride. It is then used in the cyclization reaction in this form.

If appropriate, the cyclization can be carried out without isolation of the intermediate of formula III.

The reactions mentioned in stage c) are generally standard reactions, well known to a person skilled in the art.

The reactive functions which are suitable, if appropriate, to protect are the carboxylic acid, amine, amide, hydroxy and hydroxylamine functions.

Protection of the acid function is in particular carried out in the form of alkyl esters, allylic esters of benzyl, benzhydryl or p-nitrobenzyl.

Deprotection is carried out by saponification, acid hydrolysis, hydrogenolysis, or also cleavage using soluble complexes of Palladium O.

Examples of these protections and deprotections are provided hereafter in the experimental part.

Protection of the amines, heterocyclic nitrogens and amides is in particular carried out depending on the case in the form of benzylated or tritylated derivatives, in the form of carbamates, in particular of allyl, benzyl, phenyl or tertbutyl, or also in the form of silylated derivatives such as tertbutyl dimethyl, trimethyl, triphenyl or also diphenyl tertbutyl-silyl derivatives, or phenylsulphonylalkyl or cyanoalkyl derivatives.

Deprotection is carried out, according to the nature of the protective group, by sodium or lithium in liquid ammonia, by hydrogenolysis or using soluble complexes of Palladium O, by the action of an acid, or by the action of tetrabutylammonium fluoride or strong bases such as sodium hydride or potassium t.butylate.

Examples are provided hereafter in the experimental part.

Protection of the hydroxylamines is carried out in particular in the form of benzyl or allyl ethers.

Cleavage of the ethers is carried out by hydrogenolysis or using soluble complexes of Palladium O.

An illustration is provided hereafter in the experimental part.

Protection of the alcohols and phenols is carried out in a standard fashion, in the form of ethers, esters or carbonates. The ethers can be alkyl or alkoxyalkyl ethers, preferably methyl or methoxyethoxymethyl ethers, aryl or preferably aralkyl ethers, for example benzyl, or silylated ethers, for example the silylated derivatives mentioned above. The esters can be any cleavable ester known to a person skilled in the art and preferably the acetate, propionate or benzoate or p-nitrobenzoate. The carbonates can be for example methyl, tertbutyl, allyl, benzyl or p-nitrobenzyl carbonates.

Deprotection is carried out by means known to a person skilled in the art, in particular saponification, hydrogenolysis, the cleavage by soluble complexes of Palladium O, hydrolysis in an acid medium or also, for the silylated derivatives, treatment by tetrabutylammonium fluoride.

Examples are provided in the experimental part.

The sulphation reaction is carried out by the action of $SO_3$-amine complexes such as $SO_3$-pyridine or $SO_3$-dimethylformamide, operating in pyridine, the salt formed, for example the pyridine salt, can then be exchanged for example by a salt of another amine, of a quaternary ammonium or of an alkali metal. Examples are provided in the experimental part.

The phosphation reaction is carried out for example by the action of a chlorophosphate such as dimethyl, dibenzyl or diphenyl chlorophosphate.

The amidification reaction is carried out starting with carboxylic acid using an activation agent such as an alkyl chloroformate, EDCI or BOP by the action of ammonium hydroxide or an appropriate amine or their acid salts. Examples are provided hereafter in the experimental part.

The acylation and sulphonylation reactions are carried out on hydroxyureas, alcohols, amines or heterocyclic nitrogens, by the action depending on the case of a halide, an appropriate carboxylic acid anhydride or sulphonic acid, where appropriate in the presence of a base. Several examples are provided hereafter in the experimental part.

The alkylation reaction is carried out by the action on the hydroxylated derivatives, the ester or ketone enolates, amines or heterocyclic nitrogens, depending on the case, of an alkyl sulphate or of an alkyl or substituted alkyl halide, substituted in particular by a free or esterified carboxy radical. Illustrations are provided hereafter in the experimental part.

Reduction of the acids to alcohols can be carried out by the action of a borane or via a mixed anhydride intermediate, by the action of an alkaline borohydride. The mixed anhydride is prepared for example using an alkyl chloroformate. The reduction of the aldehyde to alcohol is preferably carried out by the action of sodium borohydride. Illustrations are provided in the experimental part.

Dehydration of the amide to nitrile can be carried out under the conditions of carbonylation and cyclization reactions.

Oxidation of the sulphides to sulphoxide and/or sulphone can be carried out by the action of a peracid such as metachloroperbenzoic or perphthalic acid or any other reagent known to a person skilled in the art.

Salification by acids is, if appropriate, carried out by adding an acid in soluble phase to the compound. Salification by bases can relate to the compounds comprising an acid function and in particular the compounds comprising a carboxy function, those comprising a sulphooxy function or derived from phosphoric acid or those comprising a heterocycle of acid character.

In the case of a carboxy function, the operation is carried out by adding an appropriate base such as those mentioned previously. In the case of a sulphooxy function or derivative of phosphoric acid, the pyridinium salt is obtained directly during the action of the SO3-pyridine complex and the other salts are obtained from this pyridinium salt. In one or the other case, the operation can also be carried out by ion exchange on resin. Examples of salification by acids or by bases and including a heterocycle of acid character, are provided hereafter in the experimental part.

Nitration can be carried out using nitric acid or one of the metallic salts, in an acid medium.

Reduction of a nitro group can be carried out using sodium dithionite or also using zinc in acetic acid.

By halogenation is meant the introduction of a halogenated substituent from a hydroxy or direct halogenation of an aromatic ring. Depending on the case, the reaction can for example be implemented by the action of iodine in the presence of triphenylphosphine, by the action of bromine in acetic acid or also iodine in the presence of $C_6H_5I$ $(OCOCF_3)_2$, or also by the reaction of an electrophilic halogenated derivative such as N-fluorosulphonylimide in the presence of a strong base. Such reagents are known to a person skilled in the art and examples are shown below in the experimental part.

The thioalkylation reaction can be carried out by implementing a reagent such as methyl methylthiosulphonate in the presence of a strong base, therefore by a reaction of electrophilic type.

The carbamoylation reaction can be carried out by implementing a chloroformate then an amine or, if appropriate, ammonia.

The introduction of an azido group can be carried out for example by the action of a sodium nitride on an intermediate of mesylate type.

The reduction of an azide group can be carried out by the action of trialkyl out triarylphosphine.

The aromatic halogen coupling reaction with tin derivatives is carried out using Stille's method which consists in initially forming an alkenylated derivative of an aromatic halide then reducing the alkenyl to alkyl, for example using hydrogen in the presence of a catalyst such as palladium on carbon. An illustration is given in the experimental part.

Dihydroxylation of the double carbon-carbon bond is carried out in particular by the action of osmium tetroxide.

Cleavage of the diols is preferably carried out using sodium periodate.

The introduction of a cyano is carried out by nucleophilic substitution using an alkaline cyanide.

Illustrations of these reactions are given below in the experimental part.

Separation of the enantiomers and diastereoisomers can be carried out according to techniques known to a person skilled in the art, in particular chromatography.

Apart from via the processes described previously, the compounds of formula (I) can of course be obtained by methods which use at the start a compound of formula (II) in which $R'_1$, $R'_2$, $R_3$, $R_4$ and HZ have the values which lead directly (without conversion) to those of the compounds that one wishes to prepare. If appropriate, those values which would contain reactive functions as mentioned above are then protected, deprotection occurring at the end of cyclization stage b or at any other opportune moment during the synthesis. The protections and deprotections are then carried out as described above.

Such methods are provided hereafter in the experimental part.

A subject of the invention is also a process according to what has gone before, characterized in that the compound of formula (II) in which ZH represents an HO—$(CH_2)_{n''}$— or $HNR'_8$—$(CH_2)_{n''}$— group in which n" is equal to O, or a $HNR'_8$—O— group, is obtained by a process according to which a compound of formula (IV):

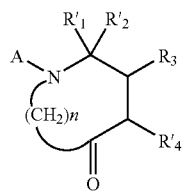

(IV)

in which $R'_1$, $R'_2$, $R_3$, $R'_4$ and n are as defined previously, and A represents a hydrogen atom or a protective group of nitrogen, is treated with a reducing agent, in order to obtain a compound of formula (V):

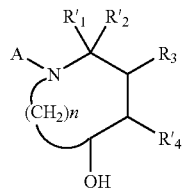

(V)

in which A, $R'_1$, $R'_2$, $R_3$, $R'_4$ and n retain their previous meaning, in which, if appropriate, the OH group is replaced by a parting group, in order to obtain a compound of formula (VI):

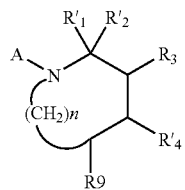

(VI)

in which A, $R'_1$, $R_3$, $R'_4$ and n retain their previous meaning and R9 represents a parting group, which is treated with a compound of formula $Z_1H_2$ in which $Z_1$ represents a divalent —$NR'_8$— or —$ONR'_8$— group, $R'_8$ retaining the previous meaning, then, if appropriate, with a deprotection agent of the appropriate nitrogen atom.

A subject of the invention is also a process according to what has gone before, characterized in that the compound of formula (II) in which ZH represents a $NHR'_8$—$(CH_2)_{n''}$— group in which n" is equal to 0 is obtained by a process according to which a compound of formula (IV) as defined previously, is treated with a compound of formula $H_2NR'_8$, in order to obtain a compound of formula (VII):

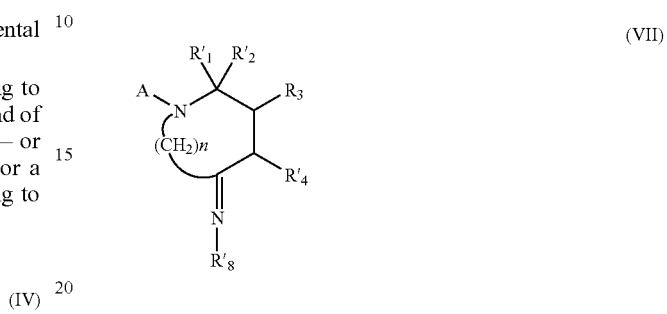

(VII)

in which A, $R'_1$, $R'_2$, $R_3$, $R'_4$, n and $R'_8$ are as defined previously, which is reacted with a reducing agent in order to obtain a compound of formula (VIII):

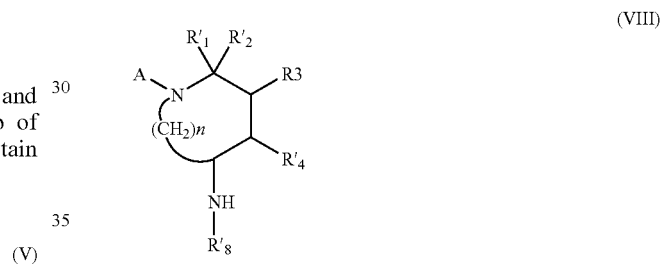

(VIII)

in which A, $R'_1$, $R'_2$, $R_3$, $R'_4$, n" and $R'_8$ are as defined previously, which is treated, if appropriate, with a deprotection agent of the appropriate nitrogen atom.

The compounds of formula (II) in which ZH represents an HO—$(CH_2)_{n''}$ group in which n" is equal to 1 can be obtained according to the methods described for example by S. Shiotani et al. Chem. Pharm. Bull. 15(1)88-93 (1967) (compound "IV" p. 89) or also by N. Itoh. Chem. Pharm. Bull 16 (3)455-470 (1968) (compound "XVIII" p. 461) using an appropriate starting compound. The compounds of formula (II) in which ZH represents an $NHR'_8$—$(CH_2)_{n''}$ group in which n" is equal to 1 can be obtained starting with the above compounds by a process which is identical to that described above for the preparation of the compounds in which n"=0.

The protective group of the nitrogen is in particular one of those which are mentioned above.

The reducing agent is in particular an alkaline borohydride.

The parting group is in particular a sulphonate, for example a mesylate or a tosylate, obtained by the action of the corresponding sulphonyl chloride in the presence of a base, or a halogen, more particularly a chlorine, a bromine or an iodine, obtained for example by the action of thionyl chloride or $P(C_6H_5)_3CBr_4$ or $PBr_3$ or, in the case of an iodine atom, by the action of an alkaline iodide on a sulphonate.

The deprotection agent is in particular one of those mentioned above.

The reducing agent which is reacted on the compound of formula (VII) is in particular a sodium cyano or acetoxyborohydride.

The products of general formula (I) have a very good antibiotic activity on gram (+) bacteria such as staphylococcia. Their effectiveness on gram (−) bacteria in particular on enterobacteria is particularly notable.

These properties make said products as well as their salts with pharmaceutically acceptable acids and bases suitable for use as medicaments in the treatment of germ-sensitive infections and, in particular, in that of staphylococcia, such as staphylococcal septicemias, malignant facial or cutaneous staphylococcia, pyodermitis, septic or suppurating wounds, anthrax, phlegmons, erysipelas, primitive or post-influenzal acute staphylococcias, bronchopneumonia, pulmonary suppurations.

These products can also be used as medicaments in the treatment of colibacillosis and associated infections, in *proteus, klebsiella* and *salmonella* infections and in other illnesses caused by gram (−) bacteria.

Therefore a subject of the present invention is, as medicaments and in particular antibiotic medicaments, the products of formula (I) as defined above as well as their salts with pharmaceutically acceptable acids and bases.

A more particular subject of the invention is, as medicaments, the products of formula (I) as described above in which n is equal to 1 as well as those in which $R_2$ is a hydrogen atom.

A quite particular subject of the invention is, as medicaments, the products of formula (I) in which $R_3$ and $R_4$ together form a phenyl or a heterocycle, optionally substituted, as defined previously and in particular a phenyl or a heterocycle chosen from the group constituted by thienyl, imidazolyl, furyl, pyrazolyl and triazolyl, optionally substituted.

Among the latter, there can be mentioned in particular those in which $R_1$ is chosen from the group constituted by the hydrogen atom and the $COOCH_3$, $COOC_2H_5$, $CONH_2$, $CONHCH_3$, $CONHCH_2$-phenyl and $CONHCH_2$-pyridyl groups.

Among the compounds of formula (I), a particular subject of the invention is also, as medicaments, the product of formula (I) in which X represents a divalent group —CO—B in which B represents an —$NR_8$—$(CH_2)_{n''}$— group as defined above, in which n" is equal to O.

Among the latter there can be mentioned in particular, those in which R8 is a $Y_1$ or $OY_1$ group, in which $Y_1$ is chosen from the $SO_2R$, $SO_2NHCOR$, $SO_2NHCOOR$, $SO_2NHCONHR$ and $SO_3H$ groups and R as defined above; or those in which the $R_8$ group is chosen from the group constituted by the hydrogen atom and the hydroxy, CO-phenyl, O-allyl, $OPO_3H$, $OPO_3$-benzyl, $OCH_2COOH$ and O-benzyl groups.

Among the compounds of formula (I), a quite particular subject of the invention is, as medicaments, the compounds the names of which follow:

the sodium salt of trans-3-oxo-4-(sulphooxy)-2,3,4,5-tetrahydro-2,5-methano-1H-2,4-benzodiazepine-1-carboxamide;

the sodium salt of 3-methyl-5-(sulphooxy)-5,6,7,8-tetrahydro-4,7-methano-4H-[1,2,3]-triazolo[4,5-e][1,3]diazepine-6(3H)-one;

the sodium salt of trans-1-methyl-6-oxo-5-(sulphooxy)-4,5,6,8-tetrahydro-4,7-methano-1H-pyrazolo[3,4-e][1,3]diazepine-8(7H)-carboxamide;

the sodium salt of trans-N-methyl-3-oxo-4-(sulphooxy)-2,3,4,5-tetrahydro-2,5-methano-1H-2,4-benzodiazepine-1-carboxamide;

the sodium salt of 5-(sulphooxy)-5,6,7,8-tetrahydro-4,7-methano-4H-furo[2,3-e][1,3]diazepine-6-one;

the pyridinium salt of 1-propyl-5-(sulphooxy)-4,5,7,8-tetrahydro-4,7-methano-imidazo[4,5-e][1,3]diazepine-6(1H)-one;

the sodium salt of trans methyl 6-oxo-5-(sulphooxy)-5,6,7,8-tetrahydro-4,7-methano-4H-furo[2,3-e][1,3]diazepine-8-carboxylate;

the sodium salt of 1-methyl-5-(sulphooxy)-5,6,7,8-tetrahydro-4,7-methano-4H-pyrazolo[3,4-e][1,3]diazepine-6(1H)-one;

the sodium salt of trans-3-oxo-N-(4-pyridinylmethyl)-4-(sulphooxy)-2,3,4,5-tetrahydro-2,5-methano-1H-2,4-benzodiazepine-1-carboxamide;

the sodium salt of trans-6-oxo-5-(sulphooxy)-5,6,7,8-tetrahydro-4,7-methano-4H-thieno[2,3-e][1,3]diazepine-8-carboxamide;

the sodium salt of trans-6-oxo-5-(sulphooxy)-5,6,7,8-tetrahydro-4,7-methano-4H-furo[2,3-e][1,3]diazepine-8-carboxamide.

the sodium salt of trans-1,2,3,5-tetrahydro-8-hydroxy-3-oxo-2-(sulphooxy)-1,4-methano-4H-2,4-benzodiazepine-5-carboxamide the sodium salt of trans-7-(acetylamino)-1,2,3,5-tetrahydro-8-hydroxy-3-oxo-2-(sulphooxy)-1,4-methano-4H-2,4-benzodiazepine-5-carboxamide the sodium salt of trans-1,5-dihydro-5-(hydroxymethyl)-2-(sulphooxy)-1,4-methano-4H-2,4-benzodiazepin-3(2H)-one the sodium salt of trans-4,5,6,8-tetrahydro-N-methyl-6-oxo-5-(sulphooxy)-4,7-methano-7H-thieno[2,3-e][1,3]diazepine-8-carboxamide the sodium salt of 7,8-dihydro-7-(sulphooxy)-5,8-methano-5H-thieno[2,3-e][1,3]diazepin-6(4H)-one the triethylammonium salt of trans-2-bromo-4,5,6,8-tetrahydro-6-oxo-5-(sulphooxy)-4,7-methano-7H-thieno[2,3-e][1,3]diazepine-8-carboxamide A subject of the invention is also the pharmaceutical compositions containing as active ingredient, at least one of the compounds according to the invention as defined above.

These compositions can be administered by buccal, rectal, parenteral, in particular intramuscular route or by local route as a topical application on the skin and the mucous membranes.

The compositions according to the invention can be solids or liquids and be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient(s) can be incorporated with the excipients usually used in these pharmaceutical compositions, such as talc, gum arabic, lactose, starch, magnesium stearate, cocoa butter, aqueous or non aqueous vehicles, fatty substances of animal or vegetable origin, paraffin derivatives, glycols, various wetting, dispersing or emulsifying agents, preservatives.

These compositions can in particular be presented in the form of a powder intended to be dissolved extemporaneously in an appropriate vehicle, for example apyrogenic sterile water.

The dose administered is variable according to the condition treated, the patient in question, the administration route and the product considered. It can be, for example, comprised between 0.250 g and 10 g per day by oral route in adults with the product described in Example 1 or also comprised between 0.25 g and 10 g per day by intramuscular or intravenous route.

The products of formula (I) can also be used as disinfectants for surgical instruments.

Finally, a subject of the invention is, as new industrial products and in particular as intermediate products necessary for the preparation of the products of formula (I), the products of formulae (III) as defined previously as well as their salts with acids and in particular their hydrochlorides and trifluoroacetates, except for the compound in which n=1, $R'_4$ represents a hydrogen atom, $R'_1$ and $R_3$ together form a phenyl, $X_1$ represents CO—$X_3$ with $X_3$=O-tBu and $X_2$ represents $HNR'_8$—$(CH_2)_{n''}$— with $R'_8$=$CH_3$ and n''=0.

The sub-class of products of formulae (III) as defined previously is preferred in which, when $R'_4$ represents a hydrogen atom and n=1, $R'_1$ and $R_3$ together form an optionally substituted heterocycle as defined for $R_3$ and $R_4$ as well as their salts with acids and in particular their hydrochlorides and trifluoroacetates the products of formula (II) as defined previously as well as their salts with acids and in particular their hydrochlorides and trifluoroacetates, as well as the products of formulae (IV), (V), (VI), (VII) and (VIII) as defined previously, as well as their salts with an acid and in particular their hydrochlorides and trifluoroacetates.

The products of formula (IV) can be prepared for example according to methods provided hereafter in the experimental part.

The following examples illustrate the invention, without however limiting the scope.

EXAMPLES

In the preceding description as well as in the examples which follow the following abbreviations have been used:
DEAD: diethyl azo-dicarboxylate
TEA: triethylamine
DMAP: 4-dimethylamino-pyridine
EDCI: 1-(3-dimethylamino-propyl)-3-ethylcarbo-diimide hydrochloride
THF: tetrahydrofuran
AcOEt: ethyl acetate
DMF: N,N-dimethylformamide
AIBN: 2.2'-azo-bis-isobutyronitrile
M: molecular molar mass
MS: mass spectrometry
EI: electron impact
SIMS: secondary ion mass spectrometry
FAB: fast atom bombardment
BOP: benzotriazol-1-yloxytripyrolidino-phosphonium hexafluorophosphate
HOBt: 1-hydroxybenzotriazole hydrate
DBU: diazabicycloundecene
(BOC)$_2$O: t-butyl dicarbonate
NaBH$_3$CN: sodium cyanoborohydride
DMSO: dimethylsulphoxide
DIEA: diisopropylethyldiamine
ClMEM: 2-methoxyethoxymethyl chloride
TMSCN: trimethylsilyl cyanide
BOC-ON: 2-(terbutoxycarbonyloxyimino)-2-phenylacetonitrile Example 1

3-benzoyl-1,3,4,5-tetrahydro-1,4-methano-2H-1,3-benzodiazepin-2-one

Stage A 50 mg (0.19 mmole) of N-(1,2,3,4-tetrahydro-3-quinolinyl)-benzamide (described in Chem. Pharm. Bull., 12(6), 647-651, (1964)) is dissolved in 2 ml of dichloromethane and 25 µl of TEA is added, followed by cooling down to 0° C. under nitrogen, then 22 µl of diphosgene is added.

Then dilution is carried out in dichloromethane, followed by washing with 10% tartaric acid, the organic phase is recovered and the solvent is evaporated off under reduced pressure.

The residue is purified by chromatography on silica, eluting with dichloromethane then with a dichloromethane/AcOEt mixture 98/2.

In this way 46 mg of the product of molecular formula $C_{17}H_{16}N_2O_2Cl$ (M=315.5 g) is recovered. The corresponding yield is 76%.

Stage B 119 mg (0.38 mmole) of the compound obtained in Stage A is dissolved under an argon atmosphere in 5 ml of anhydrous THF and the reaction medium is cooled down under argon to −78° C.

Then, 380 µl of a solution of lithium bis(trimethylsilyl) amide 1 M in the THF is added, the reaction medium is left to react at −78° C. for 15 minutes.

This is followed by diluting with AcOEt, washing with a 10% aqueous solution of tartaric acid, drying over sodium sulphate, then with a saturated solution of sodium chloride.

The organic phase is separated and the solvent is evaporated off under reduced pressure.

A crude product is obtained which is chromatographed on silica eluting with dichloromethane, then with a dichloromethane/AcOEt mixture 98/2.

In this way 94 mg of product is recovered which is purified again by chromatography on silica eluting with a dichloromethane/toluene mixture 50/50 then only with dichloromethane.

In this way 67 mg of the expected product is recovered, of product of molecular formula $C_{17}H_{14}N_2O_2$ (M=278.31 g).

The corresponding yield is 63%.

NMR Spectrum of the Proton

In CDCl$_3$, at 300 MHz, chemical shifts and multiplicity: 3.16 (dd), 3.21 (d), 3.49 (d) and 3.83 (ddd): CH—CH$_2$—N and CH—CH$_2$—C=; 4.94 (td): CH—N; 7.40 (d), 7.50 (tt) and 7.61 (d): CO—C$_6$H$_5$; 7.13 to 7.32 (m): C$_6$H$_4$ (aromatic).

MS (EI) m/z: [M]$^+$=278, 130, 105.

Example 2

4-benzoyl-1,2,4,5-tetrahydro-2,5-methano-3H-2,4-benzodiazepin-3-one

Stage A 288 mg (1 mmole) of N-(1,2,3,4-tetrahydro-4-isoquinolinyl)-benzamide hydrochloride (described in Yakugaku Zasshi, 87, 547, (1967)) is reacted with 280 µl of TEA and 60 µl of diphosgene in a similar manner to that indicated in Stage A of Example 1.

In this way 132 mg of 4-(benzoylamino)-3,4-dihydro-2 (1H)-isoquinolinecarbonyl chloride is recovered (M=314.5 g).

The corresponding yield is 42%.

Stage B 127 mg (0.4 mmole) of compound obtained in Stage A is reacted with 400 µl of a solution of lithium bis(trimethylsilyl) amide as indicated in Stage B of Example 1.

103 mg of a crude product is obtained which is chromatographed on silica eluting with dichloromethane.

In this way 41 mg of product is recovered of molecular formula $C_{17}H_{14}N_2O_2$ (M=278.31 g).

The corresponding yield is 37%.

NMR Spectrum of the Proton

In $CDCl_3$, at 300 MHz, chemical shifts and multiplicity: 3.34 (d) and 3.90 (dd): CO—C$\underline{H}_2$—CH; 4.49 (AB): CO—N—C$\underline{H}_2$—$C_6H_4$; 5.24 (d): CO—CH$_2$—C$\underline{H}$; 7.62 (m): aromatic 2H's in ortho position of CO; 7.03 (bd) and 7.22 to 7.56 (m): aromatic 7H's. MS (SIMS) m/z: $[M]^+$=279.

Example 3

Salt of methyl 1-propenyltriphenylphosphonium of trans-3-oxo-4-(sulphooxy)-2,3,4,5-tetrahydro-2,5-methano-1H-2,4-benzodiazepine-1-carboxylate Stage A 43.0 g of the hydrochloride of methyl alpha-aminobenzeneacetate $C_9H_{11}ClNO_2$ (M=165.19 g, described in J. Med. Chem., 26, 1267-1277, (1983)), 35.9 g of potassium carbonate and 430 ml of DMF are introduced into a flask,.

Then 65.6 ml of tertiobutyl bromoacetate is added and the reaction medium is heated for 5 hours 30 minutes at 50° C.

The insoluble part is filtered and the solvent evaporated off under reduced pressure.

In this way 101.4 g of an oil is obtained which is purified by chromatography on silica eluting with a dichloromethane/AcOEt mixture 95/5.

60.6 g of methyl alpha-[[[(1,1-dimethylethoxy)carbonyl]methyl]amino]-benzeneacetate is recovered of molecular formula $C_{15}H_{21}NO_4$ (M=279.34 g).

The corresponding yield is 83.4%.

Stage B 61.9 g (0.22 moles) of the product obtained in Stage A, 620 ml of anhydrous THF, 50 ml of diisopropylethylamine are introduced into a flask placed under an argon atmosphere.

After cooling down to 0-5° C., 20.6 ml of methyl chloroformate is added. The reaction medium is left in contact for 1 hour 30 minutes at 20° C.

This is followed by diluting with AcOEt, then washing with a 10% aqueous solution of tartaric acid and with demineralized water.

Then the organic phase is dried over magnesium sulphate, filtered and the solvent is evaporated off under reduced pressure.

In this way 72.8 g of methyl alpha-[[[(1,1-dimethylethoxy)carbonyl]methyl](methoxycarbonyl)amino]-benzeneacetate is obtained of molecular formula $C_{17}H_{23}NO_6$ (M=337.37 g).

The corresponding yield is 97%.

Stage C 72.8 g of the product obtained in Stage B is introduced into a flask, then cooled down to 0-5° C. and 730 ml of a trifluoroacetic acid/dichloromethane mixture 1/1 is added.

After leaving in contact at 20° C. for 1 hour, the solvents are evaporated off under reduced pressure.

In this way 60.7 g of methyl alpha-[(carboxymethyl) (methoxycarbonyl)amino]-benzeneacetate is obtained of molecular formula $C_{13}H_{15}NO_6$ (M=281.27 g) in the form of an oil. The yield is quantitative.

Stage D 60.7 g of the acid obtained in Stage C then 730 ml of $SOCl_2$ are introduced into a flask equipped with magnetic stirring, a condenser and a calcium chloride trap.

The reaction medium is heated to 70° C. and maintained for 4 hours, followed by evaporating to dryness under reduced pressure.

In this way 54.8 g of the hydrochloride of methyl 2,5-dioxo-alpha-phenyl-3-oxazolidineacetate is obtained of molecular formula $C_{12}H_{11}NO_5$ (M=249 g). The yield is quantitative.

Stage E 54.8 g of the acid chloride obtained in Stage D (0.22 moles) and 500 ml of dichloromethane are introduced into a flask placed under a nitrogen atmosphere.

Then 105 g of aluminium chloride is added.

The reaction medium is kept under agitation overnight at 20° C., followed by diluting with dichloromethane, adjusting to pH 8-9 by adding 2N soda while cooling, diluting with 1 l of water and 1 l of dichloromethane, decanting, extracting several times with dichloromethane, the organic phases are collected and dried over sodium sulphate.

Then the solvent is evaporated off under reduced pressure.

In this way 35.6 g of methyl 4-oxo-1,2,3,4-tetrahydro-1-isoquinolinecarboxylate is obtained of molecular formula $C_{11}H_{11}NO_3$ (M=205.22 g).

The corresponding yield is 88%.

Stage F 35.6 g of the product obtained in Stage E (0.173 moles) and 360 ml of THF are introduced into a flask.

After cooling down to 0° C., 41.5 g of $(BOC)_2O$ is added and the reaction medium is left to react for 2 hours 30 minutes at 20° C., followed by diluting with AcOEt, washing with a 10% aqueous solution of tartaric acid, then with demineralized water.

Then the organic phase is dried over magnesium sulphate.

The solvent is evaporated off under reduced pressure and then purified by chromatography on silica.

In this way 48.9 g of 2-(1,1-dimethylethyl) and 1-methyl 3,4-dihydro-4-oxo-1,2(1H)-isoquinolinedicarboxylate is obtained of molecular formula $C_{16}H_{19}NO_5$ (M=305.33 g)

The corresponding yield is 92%.

Stage G 20.5 g of the product obtained in Stage F (67.1 mmoles) and 40 ml of methanol are introduced into a flask placed under a nitrogen atmosphere and cooled down with an ice bath.

Then 2.67 g of $NaBH_4$ is added.

The reaction medium is agitated whilst being left to return to 20° C. over 30 minutes, followed by diluting with 200 ml of dichloromethane, washing with a 10% aqueous solution of tartaric acid, then with demineralized water and drying the organic phase over sodium sulphate.

The solvent is evaporated off under reduced pressure.

In this way 19.8 g of cis 2-(1,1-dimethylethyl) and 1-methyl 3,4-dihydro-4-hydroxy-1,2(1H)-isoquinolinedicarboxylate is obtained of formula $C_{16}H_{21}NO_5$ (M=307.25 g).

The corresponding yield is 96%.

Stage H 19.8 g of the product obtained in Stage G (64.4 mmoles) and 300 ml of dichloromethane are introduced into a flask place under an argon atmosphere.

The reaction medium is cooled down to 05° C., then 10.8 ml of TEA and 5.3 ml of methane sulphonyl chloride are added successively, followed by allowing the temperature to return to 20° C. and keeping under agitation for 1 hour 20 minutes at 20° C., diluting with dichloromethane, washing with a 10% aqueous solution of tartaric acid and with demineralized water. The organic phase is dried over sodium sulphate.

Then the solvent is evaporated off under reduced pressure.

In this way 23.7 g of cis 2-(1,1-dimethylethyl) and 1-methyl 3,4-dihydro-4-[(methylsulphonyl)oxy]-1,2(1H)-isoquinolinedicarboxylate is obtained of molecular formula $C_{17}H_{23}NO_7S$ (M=385.44 g).

The corresponding yield is 95%.

Stage I 24.5 ml of O-allylhydroxylamine is added to the mesylate freshly prepared in Stage H, then they are left in contact at 0-5° C. for 72 hours, followed by diluting with dichloromethane and washing with a 10% aqueous solution of tartaric acid then with demineralized water, drying the organic phase over sodium sulphate and evaporating the solvent under reduced pressure.

The dry extract obtained is purified by chromatography on silica eluting with a dichloromethane/AcOEt mixture 98/2.

12.3 g of trans 2-(1,1-dimethylethyl) and 1-methyl 3,4-dihydro-4-[(2-propenyloxy)amino]-1,2(1H)-isoquinoline dicarboxylate is recovered of molecular formula $C_{19}H_{26}N_2O_5$ (M=362.43 g).

The corresponding yield is 55.3%.

Stage J 12.3 g (33.9 mmoles) of the product obtained in Stage I is dissolved in 12 ml of AcOEt and the reaction medium is cooled down to 0° C.

74 ml of solution of hydrogen chloride in AcOEt at 4.6 moles/l is added. The reaction medium is left in contact for 1 hour at 20° C.

The solvent is evaporated off under reduced pressure then the product is crystallized from ethyl ether.

In this way 11.2 g of the hydrochloride of methyl trans-4-[(2-propenyloxy)amino]-1,2,3,4-tetrahydro-1-isoquinoline carboxylate is obtained of molecular formula $C_{14}H_{20}Cl_2N_2O_3$ (M=335.23 g).

The corresponding yield is 98%.

Stage K 11.2 g (33.4 mmoles) of the product obtained in Stage J is placed in suspension in 500 ml of dichloromethane.

67 ml of 1N soda is added, followed by decanting, washing with demineralized water and drying the organic phase over sodium sulphate.

Then the solvent is evaporated off under reduced pressure.

In this way 7.86 g of methyl trans-4-[(2-propenyloxy) amino]-1,2,3,4-tetrahydro-1-isoquinolinecarboxylate is obtained of molecular formula $C_{14}H_{18}N_2O_3$ (M=262.31 g).

The corresponding yield is 90%.

Stage L 7.86 g (29.9 mmole) of the diamine obtained in Stage K, 300 ml of acetonitrile and 8.3 ml of TEA are introduced into a flask placed under an argon atmosphere and cooled down with an ice bath.

The reaction medium is agitated for 2 minutes and then 1.8 ml (14.6 mmole) of diphosgene is introduced.

The solution is agitated at 20° C. for 1 hour, followed by diluting with AcOEt, washing with a 10% solution of tartaric acid then with water, drying the organic phase over magnesium sulphate and evaporating the solvent under reduced pressure.

The crude product is dissolved in 500 ml of dichloromethane with 0.45 ml of DBU. After 10 minutes of contact, the reaction mixture is washed with a 10% solution of tartaric acid then with water. After evaporation of the solvent under reduced pressure, 8.6 g of crude product is obtained which is purified by chromatography in order to produce 6.45 g of trans methyl 3-oxo-4-(2-propenyloxy)-2,3,4,5-tetrahydro-2,5-methano-1H-2,4-benzodiazepine-1-carboxylate of molecular formula $C_{15}H_{16}N_2O_4$ (M=288.30 g).

The corresponding yield is 75%.

Stage M 140 mg (0.486 mmole) of the product obtained in Stage L, 1.4 ml of dichloromethane is introduced into a flask placed under an argon atmosphere, then 56 µl of acetic acid and 280 mg of $Pd[P(C_6H_5)_3]_4$ are added.

After 15 minutes of contact, 232 mg of $SO_3$-pyridine complex in solution in 1.4 ml of pyridine is added.

The reaction medium is left under agitation at 20° C. for 1 hour 30 minutes, then evaporation is carried out without heating under reduced pressure.

50 ml of dichloromethane is added, followed by washing with water, drying the organic phase over sodium sulphate and evaporating to dryness under reduced pressure.

The dry extract obtained is purified by chromatography on silica eluting progressively with a dichloromethane/acetone mixture containing 0.1% by volume of TEA: 100/0 then 80/20 and 50/50.

In this way 132 mg of the 1-propenyltriphenylphosphonium salt of trans methyl 3-oxo-4-(sulphooxy)-2,3,4,5-tetrahydro-2,5-methano-1H-2,4-benzodiazepine-1-carboxylate of molecular formula $C_{33}H_{31}N_2O_7PS$ (M=630.66 g) is obtained.

The corresponding yield is 43.1%. IR ($CHCl_3$): 1753, 1638, 1611, 1603, 1587 $cm^{-1}$. MS (Negative electrospray) m/z: [M anion]$^-$=327 MS (Positive electrospray) m/z: [M cation]$^+$=303

Example 4

Sodium salt of trans methyl 3-oxo-4-(sulphooxy)-2,3,4,5-tetrahydro-2,5-methano-1H-2,4-benzodiazepine-1-carboxylate 132 mg (0.209 mmole) of the phosphonium salt obtained in Stage M of Example 3, is dissolved in 0.5 ml of water containing 10% THF.

The solution obtained is passed through a DOWEX 50WX8 resin column in the $Na^+$ form, eluting with water containing 10% THF.

The product collected is lyophilized in order to obtain 58 mg of the expected sodium salt, of molecular formula $C_{12}H_{11}N_2O_7SNa$ (M=350.28 g).

The corresponding yield is 79.1%.

Example 5

Sodium salt of 1-methyl-5-(sulphooxy)-5,6,7,8-tetrahydro-4,7-methano-4H-pyrazolo[3,4-e][1,3]diazepin-6(1H)-one Stage A 12.8 g (60 mmoles) of 1,1-dimethylethyl 3,5-dioxo-1-piperidinecarboxylate of molecular formula $C_{10}H_{15}NO_4$ (prepared by a similar process to that described in Heterocycles, 22, 2769-2773, (1984), replacing the methyl chloroformate with $(BOC)_2O$) in 128 ml of toluene) is put into suspension.

12.65 ml of 95% N,N-dimethylformamide dimethylacetal is added at ambient temperature.

Agitation is carried out for 30 minutes at 80° C. then for 3 hours at 50° C.

The solvent is evaporated off under reduced pressure.

In this way 18.03 g of 1,1-dimethylethyl 4-[(dimethylamino)methylene]-3,5-dioxo-1-piperidinecarboxylate is obtained of molecular formula $C_{13}H_{20}N_2O_4$.

Stage B 18.03 g of the resin obtained in Stage A is dissolved in 146 ml of absolute ethanol, then 3.55 ml of methylhydrazine is added.

Agitation is carried out for 3 hours 30 minutes at ambient temperature.

The solvent is evaporated off under reduced pressure and purifification is carried out by chromatography on silica eluting with a dichloromethane/AcOEt mixture 1/1.

In this way 12.47 g of 1,1-dimethylethyl 4,7-dihydro-1-methyl-4-oxo-1H-pyrazolo[3,4-c]pyridine-6(5H)-carboxylate is recovered of molecular formula $C_{12}H_{17}N_3O_3$ (M=251.29 g).

The corresponding yield is 83%.

Stage C 2.99 g (11.9 mmoles) of the product prepared in Stage B in 30 ml of ethanol, 1.32 g (12.1 mmoles) of O-allylhydroxylamine and 2.9 ml of pyridine are introduced into a flask under a nitrogen atmosphere.

The reaction medium is left under agitation for 1 hour, then diluted in 250 ml of dichloromethane, followed by washing with a 10% solution of tartaric acid, drying the organic phase over magnesium sulphate and evaporating the solvent under reduced pressure.

3.46 g of 1,1-dimethylethyl 4,7-dihydro-1-methyl-4-[(2-propenyloxy)imino]-1H-pyrazolo[3,4-c]pyridine-6(5H)-carboxylate is obtained, of molecular formula $C_{15}H_{22}N_4O_3$ (M=306.37 g).

The corresponding yield is 95%.

Stage D 3.02 g (9.86 mmole) of the product obtained in Stage C in 30 ml of ethanol, a few grains of methyl orange and in several goes 3.52 g (62.2 mmoles) of sodium cyanide are introduced into a flask under a nitrogen atmosphere and cooled down to 0° C. With each addition of sodium cyanide, a 2N aqueous solution of hydrochloric acid is also added in order to maintain the pH at 4-5.

The medium is left to react for 5 hours then an aqueous solution of sodium hydrogen carbonate is added and agitation is carried out for 15 minutes, followed by extracting with dichloromethane and washing with water.

The organic phase is dried over magnesium sulphate.

The solvent is evaporated off under reduced pressure.

The product obtained is purified by chromatography on silica eluting successively with a dichloromethane/AcOEt mixture 9/1, then 8/2.

In this way 1.49 g of 1,1-dimethylethyl 4,7-dihydro-1-methyl-4-[(2-propenyloxy)amino]-1H-pyrazolo[3,4-c]pyridine-6(5H)-carboxylate is obtained (M=308.38 g).

The corresponding yield is 46%.

Stage E 1.4 g (4.5 mmoles) of the product obtained in Stage B and 12 ml of a solution of hydrogen chloride in solution at 140 g/l (0.046 mole) in AcOEt are introduced into a flask.

The medium is left to react for 30 minutes at 0° C., then left to return to ambient temperature.

The solvent is evaporated off under reduced pressure in order to obtain 1.5 g of 1-methyl-N-(2-propenyloxy)-4,5,6,7-tetrahydro-1H-pyrazolo[3,4-c]pyridin-4-amine hydrochloride.

The corresponding yield is quantitative.

Stage F 980 mg (3.08 mmole) of the product obtained in Stage E and 20 ml of dichloromethane are introduced into a flask, 1.62 ml (9.25 mmole) of soda is added.

The reaction medium is left under agitation for a few minutes, then the aqueous phase is evaporated under reduced pressure and the residue is dissolved in 40 ml of a dichloromethane/ethanol mixture 9/1.

After filtering and rinsing with dichloromethane, the solvent is evaporated off under reduced pressure and 741 mg of product is obtained.

The corresponding yield is 98%.

Stage G 100 mg (0.43 mmole) of the product obtained in Stage F in 40 ml of acetonitrile and 300 µl (2.08 mmole) of TEA and 30 µl (0.24 mmole) of diphosgene are introduced into a flask placed under a nitrogen atmosphere and cooled down to 0° C.

The reaction medium is left to return to ambient temperature and reacted for 30 minutes, followed by diluting with AcOEt, washing with water and drying the organic phase over magnesium sulphate.

The solvent is evaporated off under reduced pressure.

The residue is purified by chromatography on silica eluting with a dichloromethane/AcOEt mixture 1/1 containing 0.1% by volume of TEA.

In this way 63.7 mg of 1-methyl-5-(propenyloxy)-5,6,7,8-tetrahydro-4,7-methano-4H-pyrazolo[3,4-e][1,3]diazepin-6-one is recovered.

The corresponding yield is 66%.

Stage H 86 mg (0.367 mmole) of the product obtained in Stage G in 2 ml of dichloromethane, 42 µl of acetic acid and 225 mg of $Pd[P(Ph)_3]_4$ are introduced into a flask placed under a nitrogen atmosphere and at ambient temperature.

After reaction for 15 minutes, 1 ml of pyridine, then 275 mg (1.723 mmole) of $SO_3$-pyridine complex are added.

The reaction medium is left to react for 4 hours, then diluted with dichloromethane.

The solvent is evaporated off under reduced pressure, followed by taking up in dichloromethane, washing with water and drying the organic phase over magnesium sulphate.

The solvent is evaporated off under reduced pressure. Then the residue is purified by chromatography on silica eluting with a dichloromethane/acetone 3/7 mixture containing 0.1% TEA.

In this way 99 mg of 1-propenyltriphenylphosphonium salt of 1-methyl-5-(sulphooxy)-5,6,7,8-tetrahydro-4,7-methano-4H-pyrazolo[3,4-e][1,3]diazepin-6(1H)-one is obtained.

The corresponding yield is 46%.

Stage I

The product obtained in Stage H is dissolved in 1 ml of water containing 10% THF.

The solution obtained is passed through a DOWEX 50WX8 resin column in Na$^+$ form, eluting with water containing 10% THF.

The product collected is lyophilized in order to obtain 42 mg of the expected sodium salt, of molecular formula $C_8H_9N_4O_5SNa$ (M=296.24 g).

The corresponding yield is 84%.

NMR Spectrum of the Proton

In D$_2$O, at 300 MHz, chemical shifts and multiplicity: 3.33 (d) and 3.78 (dd): N—C$\underline{H_2}$—CH; 3.69 (s): NCH$_3$; 4.52 (s): N—CH$_2$—C$=$; 4.93 (d): N—CH—C$=$; 7.58 (s): N$=$CH.

Example 6 methyl trans-3-oxo-4-(phenylmethoxy)-2,3,4,5-tetrahydro-2,5-methano-1H-2,4-benzodiazepine-1-carboxylate Stage A 50.0 g (0.163 moles) of the ketone obtained in Stage F of Example 3, of molecular formula C$_{16}$H$_{19}$NO$_5$, and 500 ml of ethanol are introduced into a flask.

Then 28.7 g of O-benzylhydroxylamine then 40 ml of pyridine are added.

Agitation is carried out for 1 hour at 20° C.

Then the solvent is evaporated off under reduced pressure followed by diluting with dichloromethane, washing with a 10% aqueous solution of tartaric acid then with demineralized water, drying the organic phase over sodium sulphate and evaporating the solvent under reduced pressure.

The crude product obtained is then chromatographed on silica eluting with a dichloromethane/AcOEt 95/5 mixture in order to produce 65.4 g of 2-(1,1-dimethylethyl) and 1-methyl 3,4-dihydro-4-[(phenylmethoxy)imino]-1,2(1H)-isoquinolinedicarboxylate of molecular formula C$_{23}$H$_{26}$N$_2$O$_5$ (M=410.47 g).

The corresponding yield is 97.3%.

Stage B 65.4 g (0.160 mole) of the product obtained in Stage A is introduced into 670 ml of methanol.

After cooling down to 0-5° C., 108 g of NaBH$_3$CN and 103 ml of boron trifluoride etherate in ethyl ether are added.

Agitation is carried out for 30 minutes while maintaining at 0-5° C., then the reaction medium is left for the temperature to return to 20° C. and agitation is carried out at this temperature for 30 minutes.

Then the reaction medium is poured into water saturated with sodium hydrogen carbonate. Agitation is carried out for 45 minutes, followed by decanting, washing the organic phase with demineralized water and drying over sodium sulphate.

Then the solvent is evaporated off under reduced pressure in order to obtain 67.9 g of crude product which is purified by chromatography on silica eluting with dichloromethane containing 2% acetone.

In this way 8.62 g of product of molecular formula C$_{23}$H$_{28}$N$_2$O$_5$ (M=412.49 g) and 54.5 g of a mixture of starting product and the expected product are recovered. This last fraction is again treated under the same conditions as previously with 50 g of sodium cyanoborohydride. In this way a total of 52.0 g of 2-(1,1-dimethylethyl) and 1-methyl 3,4-dihydro-4-[(phenylmethoxy)amino]-1,2(1H)-isoquinolinedicarboxylate of is obtained.

The corresponding yield is 77.4%.

Stage C 300 ml of AcOEt saturated with gaseous HCl is introduced slowly into a solution containing 52 g of the amine obtained in Stage B and 150 ml of AcOEt, which is cooled down to 0° C.

The reaction medium is left to return to ambient temperature and agitation is carried out for 1 hour. The solvents are evaporated off under reduced pressure, followed by diluting with water, neutralizing with 40 ml of ammonium hydroxide and extracting with dichloromethane after having saturated the aqueous phase with sodium chloride. In this way 38.97 g of a yellow oil is recovered which is purified by chromatography on silica, eluting with a dichloromethane/AcOEt mixture 95/5.

34.48 g of methyl 3,4-dihydro-4-[(phenylmethoxy)amino]-1,2(1H)-isoquinolinecarboxylate is obtained of molecular formula C$_{18}$H$_{20}$N$_2$O$_3$ (M=312.37 g).

The corresponding yield is 87.5%.

Stage D

A solution containing 34.48 g of the product obtained in Stage C, 1.3 liter of acetonitrile, 32 ml of TEA is cooled down to 0° C., then 6.6 ml (0.055 mole) of diphosgene is introduced over 10 minutes.

The reaction medium is left to return to ambient temperature and agitation is carried out for 1 hour, followed by diluting the reaction mixture with 1 l of ethyl acetate then washing the organic phase three times with 500 ml of water.

The solvents are evaporated off under reduced pressure, then the residue is taken up in 200 ml of dichloromethane and 17 ml of DBU.

Agitation is carried out for 45 minutes and the organic phase is washed 3 times with water, followed by evaporating under reduced pressure.

In this way a beige foam is obtained which is purified by chromatography. The pure fraction is taken up in ether. The mother liquors obtained are repurified by chromatography.

21.975 g of white crystals of the expected product is obtained of molecular formula C$_{19}$H$_{18}$N$_2$O$_4$ (M=338.37 g).

The corresponding yield is 68%.

NMR Spectrum of the Proton

In CDCl$_3$, at 300 MHz, chemical shifts and multiplicity: 3.51 (dd) and 3.64 (d): N—C$\underline{H_2}$—CH; 3.79 (d): N—CH$_2$—C$\underline{H}$; 3.82 (s): C$\underline{H_3}$—O—C(O)—CH; 5.15 (s): CH$_3$—O—C(O)—C$\underline{H}$; 4.87 and 4.99 (AB): O—C$\underline{H_2}$—C$_6$H$_5$; 6.98 (bd), 7.21 (td) and from 7.30 to 7.50 (m): aromatic 9H's.

Example 7

Sodium salt of trans-3-oxo-N-(phenylmethyl)-4-(sulphooxy)-2,3,4,5-tetrahydro-2,5-methano-1H-2,4-benzodiazepine-1-carboxamide Stage A 2.7 g (9.36 mmoles) of the methyl ester obtained in Stage L of Example 3 and 54 ml of a dioxane/water mixture 50/50 are introduced into a flask equipped with a magnetic stirrer.

Then 9.4 ml of 1N soda is added and agitation is carried out for one hour at 20° C., followed by diluting with AcOEt, acidifying with a saturated aqueous solution of NaH$_2$PO$_4$, decanting and reextracting with AcOEt. The organic phases are collected, washed with water and dried over magnesium sulphate.

The solvent is evaporated off under reduced pressure.

In this way 2.11 g of trans-3-oxo-4-(2-propenyloxy)-2,3,4,5-tetrahydro-2,5-methano-1H-2,4-benzodiazepine-1-carboxylic acid is obtained of molecular formula C$_{14}$H$_{14}$N$_2$O$_4$ (M=274.28 g).

The corresponding yield is 82.2%.

Stage B 152 mg (0.554 mmoles) of the acid obtained in Stage A and 5 ml of dichloromethane are mixed together in a flask placed under an argon atmosphere.

The reaction medium is cooled down to −20° C. and 71 µl of 2,6-lutidine and 78 µl of isobutyl chloroformate are added.

After contact for 5 minutes, 67 µl of benzylamine is added and the reaction medium is left to react for 30 minutes at −20° C., then left for the temperature to return to 20° C.

Agitation is continued for 1 hour 30 minutes, followed by diluting with dichloromethane, washing with a 10% aqueous solution of tartaric acid, then with a phosphate buffer at pH 7, finally with a saturated solution of sodium chloride.

After drying the organic phase over magnesium sulphate, the solvent is evaporated off under reduced pressure.

In this way 215 mg of crude product is obtained which is purified on silica eluting with a dichloromethane/AcOEt mixture 98/2 containing 0.1% TEA, then with a dichloromethane/AcOEt 95/5 mixture also containing 0.1% TEA.

146 mg of trans-3-oxo-N-(phenylmethyl)-4-(2-propenyloxy)-2,3,4,5-tetrahydro-2,5-methano-1H-2,4-benzodiazepine-1-carboxamide is recovered of molecular formula $C_{21}H_{21}N_3O_3$ (M=363.42 g).

The corresponding yield is 72%.

Stage C 146 mg (0.4 mmoles) of the product obtained in Stage B in 1.5 ml of dichloromethane is dissolved in a flask placed under an argon atmosphere.

46 µl of acetic acid and 232 mg of $Pd[P(C_6H_5)_3]_4$ are added at 20° C. Agitation is carried out for 15 minutes at 20° C.

Then 200 mg of $SO_3$-pyridine complex in solution in 1.4 ml of pyridine is added. The reaction medium is left under agitation at 20° C. for 5 hours.

The solvent is evaporated off under reduced pressure, followed by taking up in 50 ml of dichloromethane, washing with water and drying the organic phase over magnesium sulphate.

The solvent is evaporated off under reduced pressure.

In this way 400 mg of the crude product is obtained which is purified by chromatography on a silica column eluting progressively with a dichloromethane/acetone mixture containing 0.1% TEA: 100/0 then 80/20 and 50/50.

The 1-propenyltriphenylphosphonium salt of trans-3-oxo-N-(phenylmethyl)-4-(sulphooxy)-2,3,4,5-tetrahydro-2,5-methano-1H-2,4-benzodiazepine-1-carboxamide is recovered which is dissolved in 1 ml of water containing 10% THF.

The solution obtained is passed through a DOWEX 50WX8 resin column in $Na^+$ form, eluting with water containing 10% THF.

The product collected is lyophilized in order to obtain 89 mg of the sodium salt of trans-3-oxo-N-(phenylmethyl)-4-(sulphooxy)-2,3,4,5-tetrahydro-2,5-methano-1H-2,4-benzodiazepine-1-carboxamide, of molecular formula $C_{18}H_{16}N_3O_6SNa$ (M=425.40 g).

The overall yield of Stage C is 52%.

NMR Spectrum of the Proton

In $CDCl_3$, at 300 MHz, chemical shifts and multiplicity: 3.52 (bd) and 3.79 (bd): OC—N—$CH_2$; 4.50 (AB): N—C$H_2$—$C_6H_5$; 5.21 (s): N—CH—CO—N; 4.94: $CH_2$—C$H$N; 7.30 to 7.75: aromatic H. IR ($CHCl_3$): 1754, 1670, 1515, 1496 $cm^{-1}$. MS (Negative electrospray) m/z: $[M]^-$=402.

Example 8

Sodium salt of trans-3-oxo-N-(4-pyridinylmethyl)-4-(sulphooxy)-2,3,4,5-tetrahydro-2,5-methano-1H-2,4-benzodiazepine-1-carboxamide Stage A The operation is carried out as indicated in Stage B of Example 7 with 142.5 mg (0.52 mmoles) of the product of molecular formula $C_{14}H_{14}N_2O_4$ (M=274.28 g) obtained in Stage A of Example 7, 67 µl of 2,6-lutidine, 72 µl of isobutyl chloroformate and 58 µl of aminomethylpyridine.

In this way 75 mg of trans-3-oxo-4-(2-propenyloxy)-N-[(4-pyridinyl)methyl]-2,3,4,5-tetrahydro-2,5-methano-1H-2,4-benzodiazepine-1-carboxamide is obtained of molecular formula $C_{20}H_{20}N_4O_3$ (M=364.41 g).

The corresponding yield is 40%.

Stage B 75 mg (0.205 mmoles) of the product obtained in Stage A is dissolved in 1 ml of dichloromethane in a flask placed under an argon atmosphere.

23 µl of acetic acid and 120 mg of $Pd[P(C_6H_5)_3]_4$ are added at 20° C. Agitation is carried out for 1 hour at 20° C.

The intermediate hydroxyurea precipitates. The precipitate is filtered, then redissolved in 4 ml of pyridine and 100 mg of the $SO_3$-pyridine complex is added. The reaction medium is left under agitation at 20° C. for 4 hours, then concentrated under vacuum.

In this way 250 mg of crude pyridinium salt is obtained which is dissolved in 12 ml of an aqueous solution of $KH_2PO_4$.

The reaction medium is agitated for 15 minutes at 20° C., followed by washing three times with 5 ml of AcOEt, treating with 60 mg of $n-Bu_4N^+HSO_4^-$, adjusting the pH to 5 with a saturated solution of sodium hydrogen carbonate and extracting 8 times with 5 ml of AcOEt. The extracted phases are combined, dried and the solvent is evaporated off under vacuum.

After drying over magnesium sulphate the solvent is evaporated off under vacuum.

Purification is carried out on silica with a dichloromethane/acetone mixture 10/90 containing 2% TEA as eluent.

In this way 16.8 mg of 1-propenyltriphenylphosphonium salt of trans-3-oxo-N-[(4-pyridinyl)methyl]-4-(sulphooxy)-2,3,4,5-tetrahydro-2,5-methano-1H-2,4-benzodiazepine-1-carboxamide is obtained of molecular formula $C_{33}H_{51}N_5O_6S$ (M=645.867 g).

The salt obtained is exchanged on 4.5 g of DOWEX 50WX8 resin in $Na^+$ form, in order to produce, after lyophilization, 7.5 mg of the sodium salt of trans-3-oxo-N-(4-pyridinylmethyl)-4-(sulphooxy)-2,3,4,5-tetrahydro-2,5-methano-1H-2,4-benzodiazepine-1-carboxamide of molecular formula $C_{17}H_{15}N_4NaO_6S$ (M=426.39 g).

The corresponding yield is 8.5%.

MS (Negative electrospray) m/z: $[M]^-$=403.

Example 9

Sodium salt of trans-3-oxo-4-(sulphooxy)-2,3,4,5-tetrahydro-2,5-methano-1H-2,4-benzodiazepine-1-carboxamide Starting from 110 mg (0.40 mmoles) of the product of molecular formula $C_{14}H_{14}N_2O_4$ (M=274.28 g) obtained in Stage A of Example 7, the operation is carried out in a similar fashion to that indicated in Stages B and C of Example 7, except that in Stage B, instead of using benzylamine, 335 µl of concentrated ammonium hydroxide is used.

The 1-propenyltriphenylphosphonium salt of trans-3-oxo-4-(sulphooxy)-2,3,4,5-tetrahydro-2,5-methano-1H-2,4-benzodiazepine-1-carboxamide is obtained, which is lyophilized.

In this way, after lyophilization, 46 mg of the expected sodium salt is obtained of molecular formula $C_{11}H_{10}N_3O_6SNa$ (M=335.27 g).

The corresponding yield is 70.1%.

NMR Spectrum of the Proton

In $D_2O$, at 300 MHz, chemical shifts and multiplicity: 3.56 (bd) and 3.81 (bd): OC—N—$CH_2$; 4.83: $CH_2$—C$\underline{H}$N; 5.19 (s): N—CH—CO—N; 7.30 to 7.52: aromatic H's. IR ($CHCl_3$): 1749, 1680, 1585 $cm^{-1}$. MS (Negative electrospray) m/z: $[M]^-$=312.

Example 10

Trans-4-hydroxy-3-oxo-2,3,4,5-tetrahydro-2,5-methano-1H-2,4-benzodiazepine-1-carboxamide Stage A The operation is carried out as in Stage A of Example 7 with 676 mg (2 mmoles) of methyl trans-3-oxo-4-(phenylmethoxy)-2,3,4,5-tetrahydro-2,5-methano-1H-2,4-benzodiazepine-1-carboxylate of molecular formula $C_{19}H_{18}N_2O_4$ (M=338.37) obtained in Stage D of Example 6.

In this way 620 mg of trans-3-oxo-4-(phenylmethoxy)-2,3,4,5-tetrahydro-2,5-methano-1H-2,4-benzodiazepine-1-carboxylic acid is obtained of formula $C_{18}H_{16}N_2O_4$ (M=324.34 g).

The corresponding yield is 95%.

Stage B 620 mg of crude product obtained in Stage A in 10 ml of DMF is introduced into a flask equipped with magnetic stirring and under a nitrogen atmosphere.

1.27 g of BOP, then 0.387 g of HOBt, 0.204 g of $NH_4Cl$ and 1.33 ml of N,N diisopropylethylamine are added.

After reaction, dilution is carried out with AcOEt, followed by washing with 10 ml of HCl 0.1 N, then with 10 ml of a saturated solution of sodium hydrogencarbonate.

The organic phases are collected, dried over sodium sulphate, filtered and the solvent is eliminated by evaporation under reduced pressure.

In this way 800 mg of a solid is obtained which is crystallized from an ethyl ether and acetone mixture, then dried under reduced pressure.

In this way, 249.6 mg of trans-3-oxo-4-(phenylmethoxy)-2,3,4,5-tetrahydro-2,5-methano-1H-2,4-benzodiazepine-1-carboxamide is recovered in the form of a colourless solid with melting point 104-106° C., of molecular formula $C_{18}H_{17}N_3O_3$ (M=323.35 g).

The corresponding yield is 40%.

Stage C 763 mg (2.36 mmoles) of the product obtained in Stage B, 35 ml of ethanol, 35 ml of THF and 80 mg of catalyst Pd/C at 10% by weight are introduced into a flask equipped with a magnetic stirrer.

Agitation is carried out overnight under a hydrogen atmosphere at a pressure of 1.9 bar.

Then the catalyst is filtered, followed by washing with ethanol and the solvent is evaporated off under reduced pressure.

The product crystallizes from ether.

In this way 550 mg of the expected product is obtained of molecular formula $C_{11}H_{11}N_3O_3$ (M=233.23 g).

The corresponding yield is quantitative.

NMR Spectrum of the Proton

In DMSO d6, at 300 MHz, chemical shifts and multiplicity: 3.43 (dd) and 3.75 (d): N—C$\underline{H_2}$—OH; 4.26 (d): N—$CH_2$—O$\underline{H}$; 4.77 (s) C$\underline{H}$—CO—$NH_2$; 7.49 and 7.92: CH—CO—N$\underline{H_2}$; from 7.16 to 7.38 (m): aromatic 4H's; 9.73 (bs): N—OH. IR ($CHCl_3$): 1749, 1680, 1585 $cm^{-1}$. MS (Positive electrospray) m/z: $[2M+Na]^+$=489; $[M+H]^+$=234, 189.

Example 11

Disodium salt of trans-3-oxo-4-(sulphooxy)-2,3,4,5-tetrahydro-2,5-methano-1H-2,4-benzodiazepine-1-carboxylic acid Stage A 155 mg of trans-3-oxo-4-(phenylmethoxy)-2,3,4,5-tetrahydro-2,5-methano-1H-2,4-benzodiazepine-1-carboxylic acid, of molecular formula $C_{18}H_{16}N_2O_4$ (0.5 mmole) obtained at the end of Stage A of Example 10 in solution in 2 ml of ethanol is introduced into a flask, 55 mg of Pd/C at 10% by weight is introduced and the reaction medium is placed under a hydrogen atmosphere at normal pressure.

The reaction medium is left to react for 3 hours 30 minutes.

Then the catalyst is filtered and the solvent is evaporated off under reduced pressure.

In this way 98 mg of trans-4-hydroxy-3-oxo-2,3,4,5-tetrahydro-2,5-methano-1H-2,4-benzodiazepine-1-carboxylic acid is obtained of molecular formula $C_{11}H_{10}N_2O_3$ (M=218 g).

The corresponding yield is 89%.

Stage B 96 mg (0.44 mmole) of the product obtained in Stage A, 209 mg of the $SO_3$-pyridine complex and 2 ml of pyridine are introduced into a flask placed under an inert atmosphere.

The reaction medium is left to react overnight, then filtered and the solvent is evaporated off under reduced pressure.

In this way 370 mg of trans-3-oxo-4-(sulphooxy)-2,3,4,5-tetrahydro-2,5-methano-1H-2,4-benzodiazepine-1-carboxylic acid is obtained, which is converted to the sodium salt by passing through DOWEX 50WX8 resin in $Na^+$ form.

It is then purified on Diaion HP20 resin eluting with water in order to produce 79 mg of the expected disodium salt, of molecular formula $C_{11}H_8Na_2N_2O_7S$ (M=358.24 g).

The corresponding yield is 50%.

NMR Spectrum of the Proton

In DMSO d6, at 300 MHz, chemical shifts and multiplicity: 3.30 and 4.07 (d): N—C$\underline{H_2}$—CH—N; 4.46 (bs): C$\underline{H}$—$CO_2$; 4.51 (d): N—$CH_2$—C$\underline{H}$—N; 7.01 (bd), 7.09 (bt), 7.22 (td) and 7.52 (bd),: aromatic H's. MS (Negative electrospray) m/z: $[M]^-$=313, 269.

Example 12

Disodium salt of methyl trans-3-oxo-4-(phosphonooxy)-2,3,4,5-tetrahydro-2,5-methano-1H-2,4-benzodiazepine-1-carboxate Stage A The operation is carried out as indicated in Stage A of Example 11, with 1 g of product obtained in Stage D of Example 6 of molecular formula $C_{19}H_{18}N_2O_4$ (M=338.37) using a mixture of ethanol, THF and 150 mg of Pd/C catalyst at 10% by weight.

In this way 0.75 g of methyl trans-4-hydroxy-3-oxo-2,3,4,5-tetrahydro-2,5-methano-1H-2,4-benzodiazepine-1-carboxylate is recovered of molecular formula $C_{12}H_{12}N_2O_4$ (M=248.24 g).

The corresponding yield is quantitative.

Stage B 350 mg of the product obtained in Stage A is dissolved in 12 ml of acetonitrile in a flask placed under an inert atmosphere.

The reaction medium is cooled down to 0° C. and 1.3 ml of N,N diisopropylethyamine then 34 mg of DMAP, 153 ml of carbon tetrachloride and 1.5 ml of dibenzylphosphite are added.

The reaction medium is left to return to ambient temperature, then poured into a heptane/AcOEt mixture 33/66 and the organic phase is washed with a 1M aqueous solution of $NaH_2PO_4$ and dried over magnesium sulphate.

In this way 0.8 g of crude product is obtained which is purified on silica eluting firstly with an AcOEt/dichloromethane mixture 7/93, then with a heptane/AcOEt mixture 1/1.

In this way 0.140 mg of methyl trans-4-[[di(phenylmethoxy)phosphinyl]oxy]-3-oxo-2,3,4,5-tetrahydro-2,5-methano-1H-2,4-benzodiazepine-1-carboxylate is recovered of molecular formula $C_{26}H_{25}N_2O_7P$. (M=508.47 g).

The corresponding yield is 20%.

Stage C 140 mg of the product obtained in Stage B is dissolved in 3 ml of ethanol.

46 mg of sodium hydrogen carbonate is added, 15 mg of catalyst Pd/C at 10% by weight is introduced and the reaction medium is placed under a hydrogen atmosphere, left to react for 2 hours, then filtered, the catalyst is washed with 5 ml of ethanol, then with 2 ml of water.

After evaporating to dryness by entraining with toluene, the residue is impasted in ether, filtered and the solvent is evaporated off under reduced pressure.

In this way 63 mg of the expected disodium salt is obtained of molecular formula $C_{12}H_{11}N_2O_7PNa_2$ (M=372 g).

The corresponding yield is 58%.

IR ($CHCl_3$): 1746, 1622 to 1695 $cm^{-1}$.

MS (Negative electrospray) m/z: $[M^{2-}+H]^-=327.1$.

Example 13

Methyl trans-4-[[hydroxy(phenylmethoxy)phosphinyl]oxy]-3-oxo-2,3,4,5-tetrahydro-2,5-methano-1H-2,4-benzodiazepine-1-carboxylate 150 mg of methyl trans-4-[[di(phenylmethoxy)phosphinyl]oxy]-3-oxo-2,3,4,5-tetrahydro-2,5-methano-1H-2,4-benzodiazepine-1-carboxylate obtained in Stage B of Example 12 is dissolved in 3 ml of acetonitrile.

77 mg of lithium bromide is added. The suspension is heated for 2 hours under reflux.

Then the acetonitrile is evaporated off under reduced pressure, and the residue is dissolved in AcOEt. The solution is washed with a 1M aqueous solution of $NaH_2PO_4$, the organic phase is dried over magnesium sulphate followed by evaporating to dryness under reduced pressure and taking up in an ether/pentane mixture. Then, the suspension is filtered.

In this way 55 mg of beige crystals of the expected product is obtained of molecular formula $C_{19}H_{19}N_2O_7P$ (M=418.34 g).

The corresponding yield is 42%.

MS (Negative electrospray) m/z: $[M]^-=417, 187, 79$.

Example 14

Sodium salt of trans-N-methyl-3-oxo-4-(sulphooxy)-2,3,4,5-tetrahydro-2,5-methano-1H-2,4-benzodiazepine-1-carboxamide Stage A 109 mg (0.4 mmole) of the product of molecular formula $C_{14}H_{14}N_2O_4$ obtained in Stage A of Example 7 and 2 ml of THF are introduced into a flask placed under a nitrogen atmosphere.

The solution is cooled down to −8° C. and 0.83 ml of TEA in solution in 1 ml of dichloromethane is added.

0.3 ml of a solution of methylamine 2 M in THF, then a solution of 62 mg of HOBt in 2 ml of THF and 114.70 mg of EDCI are added.

The reaction medium is maintained under agitation at 0° C. for 2 hours, followed by pouring into water, extracting with AcOEt, washing with water and drying over magnesium sulphate. After evaporating the solvent under reduced pressure, approximately 300 mg of an oil is obtained which is purified by chromatography on silica eluting with AcOEt.

91 mg of trans-N-methyl-3-oxo-4-(2-propenyloxy)-2,3,4,5-tetrahydro-2,5-methano-1H-2,4-benzodiazepine-1-carboxamide is recovered of molecular formula $C_{15}H_{17}N_3O_3$ (M=287.321 g).

The corresponding yield is 79%.

Stage B

The operation is carried out as indicated in Stage C of Example 7 with 83 mg (0.288 mmole) of the product obtained in Stage A, 2.5 ml of dichloromethane, 33 μl of acetic acid, 166 mg of $Pd[P(C_6H_5)_3]_4$ and 137 mg of $SO_3$-pyridine complex.

In this way 100 mg of 1-propenyltriphenylphosphonium salt of trans-N-methyl-3-oxo-4-(sulphooxy)-2,3,4,5-tetrahydro-2,5-methano-1H-2,4-benzodiazepine-1-carboxamide is first obtained of molecular formula $C_{33}H_{32}N_3O_6PS$ (M=629.68 g, the corresponding yield is 55%), then, after passing through a DOWEX 50WX8 column in $Na^+$ form then lyophilization, 40 mg of the expected sodium salt of molecular formula $C_{12}H_{12}N_3NaO_6S$ (M=349.30 g) is obtained and which is in the form of an amorphous yellow solid. The corresponding yield for the exchange operation is 72%.

NMR Spectrum of the Proton

In DMSO d6, at 300 MHz, chemical shifts and multiplicity in ppm: 2.67 (d): $CH_3$—NH—C═O; 8.46 (bq): $CH_3$—NH—C═O; 3.43 (dd) and 3.79 (d): N—$CH_2$—CH; 4.64 (d): N—$CH_2$—CH; 4.80 (s): CH—CO—$NHCH_3$; 7.12 (bd), 7.23 (m) and 7.33 (td): aromatic H's. MS (Negative electrospray) m/z: $[M]^-=326$ Example 15

Methyl trans-4-(2-hydroxy-2-oxoethoxy)-3-oxo-2,3,4,5-tetrahydro-2,5-methano-1H-2,4-benzodiazepine-1-carboxylate Stage A 92 mg (0.319 mmole) of the product obtained in Stage L of Example 3, 1.5 ml of THF are introduced into a flask placed under an argon atmosphere, then 36 μl of acetic acid and 184 mg of $Pd[P(C_6H_5)_3]_4$ are added at 20° C.

The reaction medium is left under agitation at 20° C. for 1 hour, then 1 ml of dichloromethane is added and agitation is continued at ambient temperature for 2 hours.

The solvent is evaporated off under reduced pressure.

Then the residue is dissolved in 1.5 ml of THF, then 132 mg of potassium carbonate, 2.5 ml of water and 152 µl of benzyl bromoacetate are added.

The reaction medium is left under agitation for 4 hours at 20° C., followed by diluting with AcOEt, washing with a 10% aqueous solution of tartaric acid %, then with a phosphate buffer at pH 7 and with a saturated aqueous solution of sodium chloride.

The organic phase is dried over magnesium sulphate and the solvent is evaporated off under reduced pressure.

In this way 490 mg of crude product is obtained which is purified on silica eluting with dichloromethane containing 0.1% TEA, then with a dichloromethane/AcOEt mixture 95/5 containing 0.1% TEA.

62 mg of methyl trans-3-oxo-4-[[(phenylmethoxy) carbonyl]methoxy]-2,3,4,5-tetrahydro-2,5-methano-1H-2,4-benzodiazepine-1-carboxylate is recovered of molecular formula $C_{21}H_{20}N_2O_6$ (M=396.402 g).

The corresponding yield is 49%.

Stage B 30 mg (7.56 mmoles) of the product of Stage A in 1.5 ml of AcOEt is introduced into a flask.

15 mg of Pd/C catalyst at 10% by weight is added. The reaction medium is placed under a hydrogen atmosphere at normal pressure and left to react at ambient temperature for 30 minutes.

After filtering, the catalyst is rinsed with AcOEt.

The solvent is evaporated off under reduced pressure in order to collect 25 mg of product which is washed with 0.5 ml of ethyl ether.

The ether is evaporated off under reduced pressure in order to obtain 20.3 mg of the expected product, of molecular formula $C_{14}H_{14}N_2O_6$ (M=306.277 g).

The corresponding yield is 87%.

NMR Spectrum of the Proton

In $CDCl_3$, at 300 MHz, chemical shifts and multiplicity: 3.58 (dd) and 3.88 (d): N—C$\underline{H}_2$—CH; 3.87 (s): O—CH$_3$; 4.56 (d): N—C$\underline{H}$—CH$_2$; 4.59 (AB): O—CH$_2$—CO; 5.22 (s): N—C$\underline{H}$—C=O; 7.27 and 7.42: aromatic H's. IR (CHCl$_3$): 1749, 1600 cm$^{-1}$. MS (Negative electrospray) m/z: [2M–H]$^-$=611; [M]$^-$=305, 231, 199, 171.

Example 16

Sodium salt of methyl trans-3-oxo-4-sulpho-2,3,4,5-tetrahydro-2,5-methano-1H-2,4-benzodiazepine-1-carboxylate Stage A 5.98 g (15.51 mmoles) of the product obtained in Stage H of Example 3 of molecular formula $C_{17}H_{23}NO_7S$ (M=385.44 g) and 40 ml of DMSO are introduced into a flask placed under an argon atmosphere.

1.1 g of sodium nitride is added at 20° C. and the reaction medium is left under agitation at 20° C. for 18 hours, followed by diluting the reaction medium with AcOEt and washing with a dilute solution of sodium hydrogencarbonate, then 3 times with water, then with a saturated solution of sodium chloride.

After drying the organic phase over magnesium sulphate, the solvent is evaporated off under reduced pressure.

In this way 6 g of crude product is obtained in the form of an oil, which is purified on silica, eluting with a dichloromethane/AcOEt mixture 99/1.

4.15 g of 2-(1,1-dimethylethyl) and 1-methyl trans-4-azido-3,4-dihydro-1,2(1H)-isoquinolinedicarboxylate is recovered of molecular formula $C_{16}H_{20}N_4O_4$ (M=332.362 g).

The corresponding yield is 80%.

Stage B 4.15 g (12.48 mmoles) of the azide obtained in Stage A in 110 ml of methanol is dissolved in a flask equipped with magnetic stirring.

470 mg of Pd/C catalyst at 10% by weight is added, the reaction medium is placed under a hydrogen atmosphere at normal pressure and left to react at ambient temperature for 30 minutes.

After filtering, the catalyst is rinsed with methanol.

The filtrate solvent is evaporated in order to collect 4 g of an oil which is taken up in dichloromethane, filtered again and the solvent is evaporated off under reduced pressure.

In this way 3.65 g of 2-(1,1-dimethylethyl) and 1-methyl trans-4-amino-3,4-dihydro-1,2(1H)-isoquinolinedicarboxylate is obtained of molecular formula $C_{16}H_{22}N_2O_4$ (M=306.364 g).

The corresponding yield is 95%.

Stage C 2.57 g (8.39 mmoles) of the amine obtained in Stage B is dissolved in 25 ml of dichloromethane in an equipped flask placed under an argon atmosphere.

Then 0.85 ml of pyridine, 1.5 ml of benzyl chloroformate are added successively, at 5° C., then the reaction medium is left to react at 20° C. for 2 hours, followed by diluting with dichloromethane, washing with a 10% aqueous solution of tartaric acid, then with dilute sodium hydrogen carbonate, then with water.

After drying the organic phase over magnesium sulphate, the solvent is evaporated off under reduced pressure.

In this way 4 g of an oil is obtained which is purified on silica eluting with a dichloromethane/AcOEt mixture 9/1.

2.98 g of 2-(1,1-dimethylethyl) and 1-methyl trans-3,4-dihydro-4-[[(phenylmethoxy)carbonyl]amino]-1,2(1H)-isoquinolinedicarboxylate is recovered of formula $C_{24}H_{28}N_2O_6$ (M=440.5 g).

The corresponding yield is 80%.

Stage D 2.96 g (6.71 mmoles) of the carbamate obtained in Stage C is dissolved in 4 ml of AcOEt in a flask cooled down with an ice bath.

The reaction medium is cooled down to 0-5° C. and 14.6 ml of a solution of hydrogen chloride in AcOEt at 4.6 mol/l is added at this temperature.

The temperature of the reaction medium is left to rise to 20° C. over one hour, then the solvent is evaporated off under reduced pressure. The hydrochloride crystallizes from ethyl ether.

In this way 2.55 g of the hydrochloride of methyl trans-4-[[(phenylmethoxy)carbonyl]amino]-1,2,3,4-tetrahydro-1-isoquinolinecarboxylate is obtained of molecular formula $C_{19}H_{21}N_2O_4Cl$ (M=376.843 g).

The corresponding yield is quantitative.

Stage E

The operation is carried out as indicated in Stage A of Example 1, with 2.62 g (6.68 mmoles) of the product obtained in Stage D, 1.08 ml of pyridine and 443 µl of diphosgene.

In this way 2.29 g of methyl trans-2-(chlorocarbonyl)-4-[[(phenylmethoxy)carbonyl]amino]-1,2,3,4-tetrahydro-1-isoquinolinecarboxylate is obtained of molecular formula $C_{20}H_{19}N_2O_5Cl$ (M=402.837 g).

The corresponding yield is 85%.

Stage F

The operation is carried out as indicated in Stage B of Example 1, with 1.79 g (4.438 mmoles) of the product obtained in Stage E and 5.8 ml of a 1 M solution of lithium bis(trimethylsilyl)amide in THF.

In this way 373 mg of product is obtained after purification.

The corresponding yield is 22.9%.

These 373 mg (1.02 mmole) are dissolved in 20 ml of dichloromethane. 30 μl of DBU is added and agitation is carried out at 20° C. for 30 minutes, followed by diluting with dichloromethane, washing with a 10% aqueous solution of tartaric acid, then with a phosphate buffer at pH 7 and with a saturated solution of sodium chloride.

The organic phase is dried over magnesium sulphate and the solvent is evaporated off under reduced pressure.

In this way 358 mg of trans 1-methyl and 4-phenylmethyl 3-oxo-2,3-dihydro-2,5-methano-1H-2,4-benzodiazepine-1.4 (5H)-dicarboxylate is obtained of molecular formula $C_{20}H_{11}N_2O_5$ (M=366.376 g).

The corresponding yield of this stage is 96%.

Stage G 357 mg (0.974 mmoles) of the carbamate obtained in Stage F is dissolved in 30 ml of AcOEt.

212 mg of Pd/C catalyst at 10% by weight is added. The reaction medium is left to react at ambient temperature for 1 hour 45 minutes, under a pressure of hydrogen of 1 atmosphere.

After filtering, the catalyst is rinsed with AcOEt.

The solvent is evaporated off under reduced pressure in order to collect 223 mg of methyl trans-3-oxo-2,3,4,5-tetrahydro-2,5-methano-1H-2,4-benzodiazepine-1-carboxylate of molecular formula $C_{12}H_{12}N_2O_3$ (M=232.241 g).

The corresponding yield is 98.6%.

Stage H 180 mg (0.775 mmoles) of the product obtained in Stage G is dissolved in 2 ml of DMF in a flask placed under an argon atmosphere.

7 ml of a 0.33 M solution of $SO_3$-pyridine complex in DMF is added at 20° C.

The reaction medium is left under agitation at 20° C. for 6 hours.

Then the solvent is evaporated off under reduced pressure in order to obtain 672 mg of a pyridinium salt of molecular formula $C_{17}H_{17}N_3O_6S$ (M=391.40 g).

These 672 mg (0.775 mmoles) are dissolved in 45 ml of a 0.5 M solution of $KH_2PO_4$ in water.

The aqueous phase is washed 3 times with 15 ml of AcOEt.

Then 237 mg of $HSO_4^-NBu_4^+$ is added to the aqueous phase, followed by extracting 10 times with 15 ml of AcOEt, drying the combined organic phases over magnesium sulphate and the solvent is evaporated off under reduced pressure.

In this way 259 mg of a product is obtained which is purified on silica eluting with dichloromethane, then with a dichloromethane/acetone mixture 6/4 containing 0.1% TEA.

170 mg of a product is recovered which is passed through a column of DOWEX 50WX8 resin in $Na^+$ form, eluting with water containing 10% THF.

The product collected is lyophilized.

91 mg of the sodium salt of methyl trans-3-oxo-4-sulpho-2,3,4,5-tetrahydro-2,5-methano-1H-2,4-benzodiazepine-1-carboxylate is obtained of molecular formula $C_{12}H_{11}N_2O_6SNa$ (M 334.29 g).

The corresponding yield is 35%.

NMR Spectrum of the Proton

In $D_2O$, at 300 MHz, chemical shifts and multiplicity: 3.60 (d) and 3.76 (dd): $NCH_2$—CH; 3.87 (S): $CO_2CH_3$; 5.00 (d): $NCH_2$—CH; 5.32 (s): NCH—C=O; 7.37 and 7.48: aromatic H's. IR (nujol): 1738, 1634 $cm^{-1}$. MS (Negative electrospray) m/z: $[M]^-$=311, 279, 171.

Example 17

Sodium salt of 1-propyl-5-(sulphooxy)-5,6,7,8-tetrahydro-4,7-methano-4H-pyrazolo[3,4-e][1,3]diazepin-6-one Stage A 50 g of $BOC-NH-NH_2$ is dissolved in 250 ml of anhydrous DMF into a flask placed under an inert atmosphere. The reaction medium is cooled down to –10° C., then 16.5 g of sodium hydride at 50% in oil is added by small fractions.

Then propylene bromide is added and the reaction medium is left under agitation overnight at ambient temperature. Then water and a 1M solution of sodium hydrogen phosphate, then 200 ml of an AcOEt/heptane mixture 2/1 are added slowly, followed by extracting, drying the organic phase over magnesium sulphate, filtering and evaporating the solvent under reduced pressure. The crude product obtained is purified on silica eluting with a dichloromethane/AcOEt mixture 95/5.

In this way 24 g of pure 1,1-dimethylethyl 2-(2-propenyl)-hydrazinecarboxylate is recovered.

The corresponding yield is 76%.

Stage B 24 g of the product obtained in Stage A is dissolved in 80 ml of AcOEt.

The reaction medium is cooled down to 0° C., then 332 ml of a 5.5 N solution of hydrochloric acid in AcOEt is added. The reaction medium is agitated for 1 hour 30 minutes at ambient temperature, followed by filtering and washing with ether.

In this way 15 g of (2-propenyl)-hydrazine is obtained of molecular formula $C_3H_8N_2,2HCl$ in the form of white crystals.

The corresponding yield is 84%.

Stage C 11 g of the product of molecular formula $C_{14}H_{21}N_3O_4$ obtained in Stage A of Example 5 is dissolved in 130 ml of ethanol.

6.51 g of the product obtained in Stage B and 11.33 g of potassium carbonate are added.

The suspension is agitated for 45 minutes, then the ethanol is evaporated off under reduced pressure. The residue is solubilized in AcOEt, then the organic phase is washed with water, then dried over magnesium sulphate, filtered and the solvent is evaporated off under reduced pressure.

In this way 10.8 g of 1,1-dimethylethyl 3,5-dioxo-4-[[2-(2-propenyl)hydrazino]methylene]-1-piperidinecarboxylate is obtained of molecular formula $C_{14}H_{21}N_3O_3$ (M=295.34 g).

The corresponding yield is 80%.

Stage D 10.8 g of the product obtained in Stage C is dissolved in 120 ml of toluene.

1 g of monohydrated p-toluene sulphonic acid is added and the reaction medium heated to reflux for one hour, followed by leaving to cool down, pouring into AcOEt, washing the organic phase with water and drying over magnesium sulphate. The solvent is evaporated off under reduced pressure.

In this way 8.5 g of crude product is obtained which is purified by chromatography on silica eluting with a heptane/AcOEt mixture 2/1.

In this way 7.5 g of 1,1-dimethylethyl 4,7-dihydro-4-oxo-1-(2-propenyl)-1H-pyrazolo[3,4-c]pyridine-6(5H)-carboxylate is recovered of molecular formula $C_{14}H_{19}N_3O_3$ (M=277.33 g).

The corresponding yield is 74%.

Stage E

The operation is carried out as indicated in Stage A of Example 6, with 7.5 g of the product obtained in Stage D in 150 ml of pyridine and 4.74 g of O-benzylhydroxylamine.

In this way 9.72 g of 1,1-dimethylethyl 4,7-dihydro-4-[(phenylmethoxy)imino]-1-(2-propenyl)-1H-pyrazolo[3,4-c]pyridine-6(5H)-carboxylate is obtained of molecular formula $C_{21}H_{26}N_4O_3$ (M=382.47 g).

The corresponding yield is 90%.

Stage F

The operation is carried out as indicated in Stage B of Example 6 with 9.2 g of the product obtained in Stage E in 750 ml of methanol, 24.2 g of $NaBH_3CN$ and 36.51 ml of boron trifluoride etherate.

In this way 5.3 g of 1,1-dimethylethyl 4,7-dihydro-4-[(phenylmethoxy)amino]-1-(2-propenyl)-1H-pyrazolo[3,4-c]pyridine-6(5H)-carboxylate is obtained of molecular formula $C_{21}H_{28}N_4O_3$ (M=384.48 g).

The corresponding yield is 60%.

Stage G

The operation is carried out as indicated in Stages J and K of Example 3 with 5.25 g of the product obtained in Stage F and a 5.5 N solution of hydrogen chloride.

In this way 3.95 g of N-(phenylmethoxy)-1-(2-propenyl)-4,5,6,7-tetrahydro-1H-pyrazolo[3,4-c]pyridin-4-amine is obtained of molecular formula $C_{16}H_{20}N_4O$ (M=284.36 g).

The corresponding yield is 90%.

Stage H

The operation is carried out as indicated in Stage L of Example 3 with 3.8 g of the product obtained in Stage G, 4.2 ml of TEA and 0.8 ml of diphosgene.

In this way 2.5 g of 5-(phenylmethoxy)-1-(2-propenyl)-4,5,7,8-tetrahydro-4,7-methano-pyrazolo[3,4-e][1,3]diazepin-6(1H)-one is obtained of molecular formula $C_{17}H_{18}N_4O_2$ (M=310.36 g).

The corresponding yield is 68%.

Stage I

The operation is carried out as in Stage A of Example 11 with 0.1 g of the product obtained in Stage H and 20 mg of Pd/C catalyst at 10% by weight.

In this way 75 mg of 5-hydroxy-1-propyl-4,5,7,8-tetrahydro-4,7-methano-pyrazolo[3,4-e][1,3]diazepin-6(1H)-one is obtained of molecular formula $C_{10}H_{14}N_4O_2$ (M=222.25 g).

The corresponding yield is quantitative.

Stage J 75 mg of the product obtained in Stage I is dissolved in 3 ml of pyridine in a flask placed under an inert atmosphere.

0.161 g of the $SO_3$-pyridine complex is added and the reaction medium left to react overnight at ambient temperature.

The solvent is evaporated off under reduced pressure and the residue is passed through a column of DOWEX 50WX8 resin in $Na^+$ form, eluting with water containing 10% THF.

After evaporating the solvent under reduced pressure, the product is solubilized in acetone and the sodium sulphate is eliminated by filtration. The solvent is then evaporated off under reduced pressure and the product crystallizes from ethyl ether.

In this way 80 mg of the expected sodium salt is obtained of molecular formula $C_{10}H_{13}N_4O_5SNa$ (M=301.30 g).

The corresponding yield is 80%.

NMR Spectrum of the Proton

In DMSO d6, at 300 MHz, chemical shifts and multiplicity: 0.80 (t): C$\underline{H}_3$—CH$_2$—CH$_2$—N; 1.69 (m): CH$_3$—C$\underline{H}_2$—CH$_2$—N; 3.86 (m): CH$_3$—CH$_2$—C$\underline{H}_2$—N; 3.12 (d) and 3.47 (dd): N—C$\underline{H}_2$—CH; 4.67 (bs): N—CH$_2$—C$\underline{H}$; 4.33 (bs): N—C$\underline{H}_2$—C=; 7.36 (s): N=C$\underline{H}$ IR (CHCl$_3$): 1752, 1644, 1540, 1505 cm$^{-1}$. MS (Negative electrospray) m/z: $[M]^-$=301

Example 18

Sodium salt of methyl trans-1-methyl-6-oxo-5-(sulphooxy)-5,6,7,8-tetrahydro-4,7-methano-4H-pyrazolo[3,4-e][1,3]diazepine-8-carboxylate Stage A 12.05 g of the ketone obtained in Stage B of Example 5 is dissolved in 157 ml of methanol in a flask placed under a nitrogen atmosphere, then cooled down with an ice bath and 1.82 g of sodium borohydride is introduced by small fractions, over 20 minutes.

The reaction medium is left to return to ambient temperature over two hours, then 1 liter of dichloromethane and 354 ml of a 10% aqueous solution of tartaric acid are added successively.

The reaction medium is agitated vigorously followed by decanting and reextracting with dichloromethane.

The organic phases are combined and dried over magnesium sulphate, followed by filtering and the filtrate solvent is evaporated off under reduced pressure.

The residue is taken up in approximately 500 ml of dichloromethane, then filtered and the solvent is again evaporated off under reduced pressure.

In this way 11.36 g of 1,1-dimethylethyl 4,7-dihydro-4-hydroxy-1-methyl-1H-pyrazolo[3,4-c]pyridine-6(5H)-carboxylate is obtained of molecular formula $C_{12}H_{19}N_3O_3$ (M=253.3 g).

The corresponding yield is 94%.

Stage B 3.03 g (12 mmoles) of the alcohol obtained in Stage A is dissolved in 52 ml of THF in a flask placed under a nitrogen atmosphere, then the reaction medium is cooled down to −78° C. and 18 ml of a 1.7 M solution of terbutyllithium in pentane is introduced.

The reaction medium is left to react for 15 minutes at −78° C., then carbon dioxide in excess is introduced over 10 minutes, then the medium is left to return to ambient temperature.

Then 95 ml of AcOEt is added, followed by acidifying to pH=4 with 31 ml of 1N HCl, saturating with sodium chloride and reextracting with AcOEt. The organic phase is dried over magnesium sulphate, filtered then the solvent is evaporated off under reduced pressure.

In this way 3.37 g of 6-(1,1-dimethylethyl)4,7-dihydro-4-hydroxy-1-methyl-1H-pyrazolo[3,4-c]pyridine-6(5H),7-dicarboxylate is obtained.

The corresponding yield is 95%.

Stage C

Then the crude acid obtained in Stage B is dissolved in 10 ml of dichloromethane, then an excess of diazomethane in solution in dichloromethane is added, the reaction medium is left to react for 20 minutes, then the solvent is evaporated off under reduced pressure.

In this way 3.34 g of 6-(1,1-dimethylethyl) and 7-methyl 4,7-dihydro-4-hydroxy-1-methyl-1H-pyrazolo[3,4-c]pyridine-6(5H),7-dicarboxylate is obtained of molecular formula $C_{14}H_{21}O_5N_3$ (M=311.34 g).

The corresponding yield is 90%.

Stage D 3.30 g of pyridinium chlorochromate, 6.6 g of 4 Å molecular sieve in powder form and 60 ml of dichloromethane are introduced into a flask.

Agitation is carried out for 40 minutes, then a solution comprising 3.34 g of the product obtained in Stage C and 40 ml of dichloromethane is added.

Agitation is carried out for 1 hour 20 minutes. Then the reaction mixture is filtered and the solvent is evaporated off under reduced pressure.

After taking up in AcOEt and refiltering, the solvent is evaporated off under reduced pressure. The residue is purified by chromatography on silica eluting with dichloromethane containing 15% AcOEt.

In this way 1.33 g of 6-(1,1-dimethylethyl) and 7-methyl 4,7-dihydro-1-methyl-4-oxo-1H-pyrazolo[3,4-c]pyridine-6(5H),7-dicarboxylate is recovered of molecular formula $C_{14}H_{19}N_3O_5$ (M=309.32 g).

The corresponding yield is 36%.

Stage E

The operation is carried out as indicated in Stage A of Example 6 with 2.63 g (8.5 mmoles) of the product obtained in Stage D, 26.3 ml of ethanol, 6.2 ml of pyridine and 2.85 g (25.5 mmoles) of hydroxylamine hydrochloride.

In this way 1.68 g of 6-(1,1-dimethylethyl) and 7-methyl 4,7-dihydro-1-methyl-4-[(2-propenyloxy)imino]-1H-pyrazolo[3,4-c]pyridine-6(5H),7-dicarboxylate is obtained of molecular formula $C_{17}H_{24}N_4O_5$ (M=364.4 g).

The corresponding yield is 54%.

Stage F 1.34 g (3.68 mmoles) of the product obtained in Stage E, 13.4 ml of acetic acid and 3 ml of dichloromethane are introduced into a flask equipped with magnetic stirring.

The temperature is lowered to 10° C., then 1.04 g of $NaBH_3CN$ is added and agitation is carried out at ambient temperature for 7 hours.

The reaction medium is then poured into a mixture of a saturated solution of sodium hydrogen carbonate in water and AcOEt.

Agitation is carried out for 40 minutes until there is no more release of gas, followed by decanting and extracting 4 times with AcOEt.

The organic phases are dried over sodium sulphate, then filtered and the solvent is evaporated off under reduced pressure.

In this way 1.4 g of a product is obtained which is purified on silica eluting with a dichloromethane/AcOEt mixture 50/50.

0.493 g of cis 6-(1,1-dimethylethyl) and 7-methyl 4,7-dihydro-1-methyl-4-[(2-propenyloxy)amino]-1H-pyrazolo[3,4-c]pyridine-6(5H),7-dicarboxylate is recovered of molecular formula $C_{17}H_{26}N_4O_5$ (M=366.48 g).

The corresponding yield is 36%.

Stage G

The operation is carried out as indicated in Stages J and K of Example 3, with 0.704 g (1.92 mmoles) of the product obtained in Stage F, 15 ml of a solution of hydrogen chloride at 143 g/l in AcOEt and replacing the soda with ammonium hydroxide.

In this way 0.519 g of cis methyl 1-methyl-4-[(2-propenyloxy)amino]-4,5,6,7-tetrahydro-1H-pyrazolo[3,4-c]pyridine-7-carboxylate is obtained of molecular formula $C_{12}H_{18}N_4O_3$ (M=266.3 g).

The corresponding yield is quantitative.

Stage H

The operation is carried out as indicated in Stage L of Example 3 with 0.519 g (1.92 mmoles) of the product obtained in Stage G, 1.33 ml of TEA and 131 µl of diphosgene.

0.557 g of methyl trans-1-methyl-6-oxo-5-(2-propenyloxy)-4,5,6,8-tetrahydro-4,7-methano-1H-pyrazolo[3,4-e][1,3]diazepine-8(7H)-carboxylate is obtained of molecular formula $C_{13}H_{16}N_4O_4$ (M=292.30 g).

The corresponding yield is quantitative.

Then 0.540 g (1.85 mmoles) of the product obtained is dissolved in 35.7 ml of dichloromethane.

55.3 µl of DBU is added and the reaction medium is left under agitation for one hour, followed by washing with a 10% aqueous solution of tartaric acid, then with demineralized water.

The organic phase is dried over magnesium sulphate, rinsed then the solvent is evaporated off under reduced pressure.

In this way 472.3 mg of product is obtained which is purified by chromatography on silica eluting with a dichloromethane/AcOEt mixture 80/20.

In this way 0.194 g of purified methyl trans-1-methyl-6-oxo-5-(2-propenyloxy)-4,5,6,8-tetrahydro-4,7-methano-1H-pyrazolo[3,4-e][1,3]diazepine-8(7H)-carboxylate is recovered of molecular formula $C_{13}H_{16}N_4O_4$ (M=292.30 g).

The corresponding yield is 48%.

Stage I

The operation is carried out as indicated in Stage C of Example 7 with 80 mg (0.274 mmoles) of the product obtained in Stage H, 50 µl of acetic acid, 158.3 mg of $Pd[P(C_6H_5)_3]_4$, 2.4 ml of pyridine and 126 mg of pyridine-$SO_3$ complex.

In this way 0.246 g of a crude product is obtained which is purified by chromatography on silica eluting with a dichloromethane/methanol mixture 94/6, then with a dichloromethane/acetone/TEA mixture 1/1/2%.

9.8 mg of the 1-propenyltriphenylphosphonium salt of methyl trans-1-methyl-6-oxo-5-(sulphooxy)-4,5,6,8-tetrahydro-4,7-methano-1H-pyrazolo[3,4-e][1,3]diazepine-8(7H)-carboxylate is recovered of molecular formula $C_{31}H_{31}N_4O_7PS$ (M=634.65 g).

The corresponding yield is 6%.

After passing through a column of DOWEX 50WX8 resin in Na$^+$ form and lyophilization, 3.5 mg of the expected sodium salt is recovered of molecular formula $C_{10}H_{11}N_4O_7SNa$ (M=331 g).

The corresponding yield for this exchange operation is 64%.

MS (Negative electrospray) m/z: [M]$^-$=331

Example 19

Sodium salt of trans-1-methyl-6-oxo-5-(sulphooxy)-4,5,6,8-tetrahydro-4,7-methano-1H-pyrazolo[3,4-e][1,3]diazepine-8(7H)-carboxamide Stage A The operation is carried out as indicated in Stage A of Example 7 with 189 mg (0.646 mmole) of the product obtained in Stage H of Example 18.

17.6 mg of trans-1-methyl-6-oxo-5-(2-propenyloxy)-4,5,6,8-tetrahydro-4,7-methano-1H-pyrazolo[3,4-e][1,3]diazepine-8(7H)-carboxylic acid is obtained of molecular formula $C_{12}H_{14}N_4O_4$ (M=278.27 g).

The corresponding yield is 84%.

Stage B

The operation is carried out as indicated in Stage B of Example 10 with 149.3 mg (0.536 mmoles) of the product obtained in Stage A, 355.6 mg of BOP, 111 mg of HOBT, 57.3 mg (1.07 mmole) of ammonium chloride and 0.373 ml of DIPEA.

In this way 81.1 mg of trans-1-methyl-6-oxo-5-(2-propenyloxy)-4,5,6,8-tetrahydro-4,7-methano-1H-pyrazolo[3,4-e][1,3]diazepine-8(7H)-carboxamide is recovered of molecular formula $C_{12}H_{15}N_5O_3$ (M=277.29 g).

The corresponding yield is 55%.

Stage C

The operation is carried out as indicated in Stage C of Example 7 with 80 mg (0.288 mmoles) of the product obtained in Stage B, 35.2 µl of acetic acid and 44 mg of $Pd[P(C_6H_5)_3]_4$.

In this way 17.4 mg of the 1-propenyltriphenylphosphonium salt trans-1-methyl-6-oxo-5-(sulphooxy)-4,5,6,8-tetrahydro-4,7-methano-1H-pyrazolo[3,4-e][1,3]diazepine-8(7H)-carboxamide is obtained of molecular formula $C_{30}H_{30}N_5O_6PS$ (M=619.64 g).

The corresponding yield is 10%.

After passing through a column of DOWEX 50WX8 resin in $Na^+$ form and lyophilization, 6.8 mg of the expected sodium salt is recovered of molecular formula $C_9H_{10}N_5O_6SNa$ (M=339.26 g).

The corresponding yield for this exchange stage is 78%.

NMR Spectrum of the Proton

In $D_2O$, at 300 MHz, chemical shifts and multiplicity: 3.32 (d) and 3.75 (dd): O=C—N$CH_2$—CH; 4.99 (d): O=C—N$CH_2$—C$H$; 5.50 (s): N—CH—C=O; 7.67 (s): N=CH; 3.81 (s): $CH_3$—N

Example 20

Sodium salt of phenylmethyl 6-oxo-7-(sulphooxy)-5,6,7,8-tetrahydro-5,8-methano-4H-thiazolo[4,5-e][1,3]diazepine-2-carbamate Stage A 21.3 g (100 mmole) of 3,5-dioxo-1-piperidinecarboxylate of 1,1-dimethylethyl of molecular formula $C_{10}H_{15}NO_4$ (M=213.24 g) used in Stage A of Example 5 and 532 ml of carbon tetrachloride are introduced into a flask placed under an inert atmosphere and cooled down with an ice bath.

21.35 g of N-bromosuccinimide (120 mmoles), and 1.6 g of AIBN are added whilst cooling.

The mixture is agitated for 1 hour 30 minutes at a temperature of 10-15° C.

Then, the solvent is evaporated off under reduced pressure.

40 ml of AcOEt then 300 ml of water are added, followed by extracting, washing the organic phase with water, drying over sodium sulphate and the solvent is evaporated off under reduced pressure.

In this way 30 g of 1,1-dimethylethyl 4-bromo-3,5-dioxo-1-piperidinecarboxylate is obtained of molecular formula $C_{10}H_{14}BrNO_4$ (M=292.13 g).

The corresponding yield is quantitative.

Stage B 30 g (100 mmole) of the product obtained in Stage A, 300 ml of ethanol and 15.2 g of thiourea (200 mmoles) are introduced.

The solution is heated under reflux for 5 hours. The mixture is cooled down to ambient temperature and the precipitate which forms is washed with ethanol, filtered and dried under reduced pressure.

In this way 15 g of 2-amino-5,6-dihydro-thiazolo[4,5-c]pyridin-7(4H)-one hydrobromide is obtained of molecular formula $C_6H_8BrN_3OS$ (M=250 g).

The corresponding yield is 60%.

Stage C 15 g of the product obtained in Stage B and 150 ml of DMF are introduced into a flask placed under an inert atmosphere and cooled down with an ice bath.

Then 19 ml of TEA and 16.2 g of $(BOC)_2O$ are added and agitation is carried out for 2 hours at ambient temperature.

Then the reaction mixture is poured into 600 ml of water, then the precipitate formed is separated, washed with water and dried under reduced pressure.

In this way 16.5 g of 1,1-dimethylethyl 2-amino-6,7-dihydro-7-oxo-thiazolo[4,5-c]pyridine-5(4H)-carboxylate is obtained of molecular formula $C_{11}H_{15}N_3O_3$ (M=269.32 g).

The corresponding yield is quantitative.

Stage D 6.9 g of the product obtained in Stage C and 140 ml of THF introduced into a flask placed under a nitrogen atmosphere.

The reaction medium is cooled down to −20° C., then 6.1 g (50 mmoles) of 4-dimethylaminopyridine and 7.11 ml (50 mmoles) of benzyl chloroformate in solution in 35 ml of THF are added.

The reaction medium is then left to return to ambient temperature over one hour, followed by pouring into 300 ml of water containing ice, extracting with AcOEt, washing 3 times with water, then the organic phases are reunited and dried over sodium sulphate. The solvent is evaporated off under reduced pressure.

In this way 11 g of 1,1-dimethylethyl 6,7-dihydro-7-oxo-2-[[(phenylmethoxy)carbonyl]amino]-thiazolo[4,5-c]pyridine-5(4H)-carboxylate is obtained of formula $C_{19}H_{21}N_3O_5S$ (M=403.46 g).

The corresponding yield is quantitative.

Stage E

The operation is carried out as indicated in Stage A of Example 6, with 11 g of the product obtained in Stage D, 18 ml of pyridine and 8.2 g of O-allylhydroxylamine hydrochloride.

In this way 7.9 g of 1,1-dimethylethyl 6,7-dihydro-2-[[(phenylmethoxy)carbonyl]amino]-7-[(2-propenyloxy)imino]-thiazolo[4,5-c]pyridine-5(4H)-carboxylate is obtained.

The corresponding yield is 69%.

Stage F

The operation is carried out as indicated in Stage B of Example 6 with 2.29 g of the product obtained in Stage E, 5.02 g of sodium cyanoborohydride and 7.3 ml of boron trifluoride etherate.

In this way 1.2 g of 1,1-dimethylethyl 6,7-dihydro-2-[[(phenylmethoxy)carbonyl]amino]-7-[(2-propenyloxy)amino]-thiazolo[4,5-c]pyridine-5(4H)-carboxylate is obtained of molecular formula $C_{22}H_{28}N_4O_5S$ (M=460.56 g).

The corresponding yield is 52%.

Stage G

The operation is carried out as indicated in Stages J and K of Example 3 with 1.2 g of the product obtained in Stage F and 12 ml of hydrogen chloride and replacing the soda with ammonium hydroxide.

In this way 800 mg of phenylmethyl[7-[(2-propenyloxy)amino]-4,5,6,7-tetrahydro-thiazolo[4,5-c]pyridin-2-yl]-carbamate is obtained of formula $C_{17}H_{20}N_4O_3S$ (M=360.44 g).

The corresponding yield is 85%.

Stage H 720 mg (2 mmole) of the product obtained in Stage G and 240 ml of acetonitrile are introduced into a flask placed under an inert atmosphere.

The solution is cooled down to 0° C. and 140 µl of diphosgene (1.16 mmoles) is added.

At the end of the addition, the reaction medium is left to return to ambient temperature and a solution of 840 µl of TEA in 8 ml of acetonitrile is added.

The solution is agitated overnight at ambient temperature.

The solvent is evaporated off under reduced pressure, followed by redissolving in AcOEt, washing with water, decanting, filtering and drying the organic phase over sodium sulphate.

The solvent is evaporated off under reduced pressure.

In this way 860 mg of a pale yellow foam is obtained which is purified by chromatography on silica, eluting with an acetone/dichloromethane mixture 1/9.

In this way a principal fraction of 370 mg of phenylmethyl [6-oxo-7-(2-propenyloxy)-5,6,7,8-tetrahydro-5,8-methano-4H-thiazolo[4,5-e] [1,3]diazepin-2-yl]-carbamate is recovered of molecular formula $C_{18}H_{18}N_4O_4S$ (M=386.43 g).

The corresponding yield is 48%.

Stage I

The operation is carried out as indicated in Stage C of Example 7, with 58 mg (0.15 mmole) of the product obtained in Stage H, 17 µl of acetic acid, 86 mg of Pd[P(C$_6$H$_5$)$_3$]$_4$ and 72 mg of SO$_3$-pyridine.

In this way 24 mg of the 1-propenyltriphenylphosphonium salt of phenylmethyl[6-oxo-7-(sulphooxy)-5,6,7,8-tetrahydro-5,8-methano-4H-thiazolo[4,5-e][1,3]diazepin-2-yl]-carbamate is obtained of molecular formula $C_{36}H_{33}N_4O_7PS_2$.

The corresponding yield is 22%.

After passing through a column of DOWEX 50WX8 resin in Na$^+$ form and lyophilization, 12.5 mg of the expected sodium salt is obtained of molecular formula $C_{15}H_{13}N_4O_7S_2$ (M=448.41 g).

The yield of this exchange stage is 86%.

NMR Spectrum of the Proton

In DMSO d6, at 300 MHz, chemical shifts and multiplicity: 3.32 (d) and 3.55 (d): N—C$\underline{H}_2$—CH—C; 4.85 (d): N—CH$_2$—C$\underline{H}$—C; 4.07 (d) and 4.28 (d): N—CH$_2$—C=; 5.24 (AB): OC—OC$\underline{H}_2$—C$_6$H$_5$; 7.40 (m) C$_6$H$_5$ Example 21

Sodium salt of 2-methyl-5-(sulphooxy)-5,6,7,8-tetrahydro-4,7-methano-4H-oxazolo[4,5-e][1,3]diazepin-6-one Stage A 5.44 g (23.9 mmoles) of p-carboxybenzene sulphonazide (M=227.20 g), 55 ml of acetonitrile and 3.33 ml of TEA are introduced into a flask cooled down with an ice bath and placed under an argon atmosphere.

The reaction medium is cooled down to 0-5° C. and 5.096 g of 1,1-dimethylethyl 3,5-dioxo-1-piperidinecarboxylate of molecular formula $C_{10}H_{15}NO_4$ (23.9 mmoles–M=213.24 g) used in Stage A of Example 5, 51 ml of acetonitrile and 3.33 ml of TEA are added whilst agitating.

The reaction medium is left in contact for 30 minutes at 0-5° C., then for 40 minutes at ambient temperature.

After filtering, the solid is rinsed with AcOEt, then the filtrate is diluted with 400 ml of AcOEt, followed by washing successively with a saturated aqueous solution of sodium hydrogen carbonate, then with a 10% aqueous solution of tartaric acid and with water saturated in sodium chloride.

The organic phase is decanted and dried over magnesium sulphate, then the solvent is evaporated off under reduced pressure.

In this way a brown oily product is obtained which is purified by chromatography on silica eluting with a dichloromethane/AcOEt mixture 90/10.

4.13 g of 1,1-dimethylethyl 4-azo-3,5-dioxo-1-piperidinecarboxylate is recovered of molecular formula $C_{10}H_{13}N_3O_4$ (M=239.23 g).

The corresponding yield is 72.3%.

Stage B 3.07 g (12.83 mmoles) of the diazoketone obtained in Stage A and 40 ml of acetonitrile, then 153 mg of rhodium tetraacetate are introduced into a flask placed under an argon atmosphere.

The reaction medium is heated at 60° C. for 9 hours.

The solvent is evaporated off under reduced pressure and the residue is purified by chromatography on silica eluting with a dichloromethane/AcOEt mixture 9/1.

742 mg of 1,1-dimethylethyl 6,7-dihydro-2-methyl-7-oxo-oxazolo[5,4-c]pyridine-5(4H)-carboxylate is recovered of molecular formula $C_{12}H_{16}N_2O_4$ (M=252.27 g).

The corresponding yield is 22.9%.

Stage C

The operation is carried out as indicated in Stage A of Example 6 with 740 mg (2.93 mmoles) of the product obtained in Stage B, 321 mg of O-allylhydroxylamine hydrochloride and 0.7 ml of pyridine.

In this way 760 mg of 1,1-dimethylethyl 6,7-dihydro-2-methyl-7-[(2-propenyloxy)imino]-oxazolo[5,4-c]pyridine-5(4H)-carboxylate is obtained of molecular formula $C_{15}H_{21}N_3O_4$ (M=307.35 g).

Stage D

The operation is carried out as indicated in Stage B of Example 6 with 600 mg (1.95 mmoles) of the product obtained in Stage C, 1.84 g of sodium cyanoborohydride and 2.96 ml of boron trifluoride etherate.

In this way 386 mg of 1,1-dimethylethyl 6,7-dihydro-2-methyl-7-[(2-propenyloxy)amino]-oxazolo[5,4-c]pyridine-5(4H)-carboxylate is obtained of molecular formula $C_{15}H_{23}N_3O_4$ (M=309.37 g).

The corresponding yield is 63.9%.

Stage E

The operation is carried out as indicated in Stages J and K of Example 3 with 410 mg (1.32 mmoles) of the product obtained in Stage D, 3.1 ml of solution of hydrogen chloride in AcOEt.

In this way 239 mg of 2-methyl-N-(2-propenyloxy)-4,5,6,7-tetrahydro-oxazolo[5,4-c]pyridin-7-amine is obtained of formula $C_{10}H_{15}N_3O_2$ (M=209.25 g).

The corresponding yield is 86.2%.

Stage F

The operation is carried out as indicated in Stage L of Example 3 with 204 mg (0.975 mmoles) of the product obtained in Stage E, 680 µl of TEA and 59 µl of diphosgene.

In this way 109 mg of 2-methyl-5-(2-propenyloxy)-4,5,7,8-tetrahydro-4,7-methano-6H-oxazolo[4,5-e][1,3]diazepin-6-one is obtained of molecular formula $C_{11}H_{13}N_3O_3$ (M=235.24 g).

The corresponding yield is 41.1%.

Stage G

The operation is carried out as indicated in Stage C of Example 7 with 39 mg (0.166 mmoles) of the product obtained in Stage F, 19 µl of acetic acid, 96 mg of Pd[P($C_6H_5$)$_3$]$_4$, 79 mg of $SO_3$-pyridine complex.

In this way 53 mg of the 1-propenyltriphenylphosphonium salt of 2-methyl-5-(sulphooxy)-4,5,7,8-tetrahydro-4,7-methano-6H-oxazolo[4,5-e][1,3]diazepin-6-one is obtained of molecular formula $C_8H_8N_3O_6S^+$, $^-PC_{21}H_2O$ (M=577.6 g).

The corresponding yield is 55.4%.

After passing the product through a column of DOWEX 50WX8 resin in $Na^+$ form, 56 mg of the expected sodium salt is recovered of molecular formula $C_8H_8N_3O_6SNa$ (M=297.22 g).

The corresponding yield for this exchange stage is 84.3%.

NMR Spectrum of the Proton

In DMSO d6, at 300 MHz, chemical shifts and multiplicity: 2.39 (s): $CH_3$—C=N; 3.24 (d) and 3.50 (dd): N—C$\underline{H}_2$—CH; 4.19 and 4.37 (AB): N—$CH_2$—C=; 4.63 (d): N—$CH_2$—C$\underline{H}$ IR (CHCl$_3$): 1761, 1648, 1569 MS (Negative electrospray) m/z: [2M–H]$^-$=549; [M]$^-$=274

Example 22

Pyridinium salt of 1-propyl-5-(sulphooxy)-4,5,7,8-tetrahydro-4,7-methano-imidazo[4,5-e][1,3]diazepin-6(1H)-one Stage A 15 g (0.089 mole) of ethyl 5-formyl-1H-imidazole-4-carboxylate of molecular formula $C_7H_8N_2O_3$ (M=168.15 g, prepared according to a method similar to that described in J. Chem. Soc. Perkin Trans. I, 495-505 (1980), replacing the butanol with ethanol) is introduced into DMF.

12.31 g of potassium carbonate, then 7.5 ml of allyl bromide is added dropwise.

The reaction medium is agitated for 1 hour 30 minutes, then poured into water, followed by extracting three times with a heptane/AcOEt mixture 2/8, the organic phase is washed with water, separated and dried over magnesium sulphate.

After filtering, the solvent is evaporated off under reduced pressure.

The residue is purified on silica eluting with a dichloromethane/acetone mixture 95/5.

In this way 10.1 g of a first isomer of ethyl 5-formyl-1-(2-propenyl)-1H-imidazole-4-carboxylate of molecular formula $C_{10}H_{12}N_2O_3$ (M=208.22 g) in the form of white crystals (10.1 g) is obtained and 4.5 g of a second isomer in the form of a yellow oil (4.5 g) is obtained.

Stage B 9.5 g (0.045 mole) of the white crystals obtained in Stage A is dissolved in 100 ml of ethanol.

The reaction medium is cooled down to 0° C., then 0.52 g of $NaBH_4$ is added, then the medium is left to react for one hour at 0° C.

Then, AcOEt is added followed by pouring into a saturated solution of sodium chloride, extracting, drying the organic phase over magnesium sulphate and the solvent is evaporated off under reduced pressure.

In this way 10.1 g of ethyl 5-(hydroxymethyl)-1-(2-propenyl)-1H-imidazole-4-carboxylate is obtained of molecular formula $C_{10}H_{14}N_2O_3$ (M=210.23 g).

The corresponding yield is quantitative.

Stage C 10.1 g (0.048 mole) of white crystals obtained in Stage B is dissolved in 100 ml of trichloromethane.

The reaction medium is cooled down to –10° C., 17.5 ml of $SOCl_2$ is added, then the medium is left to react for 30 minutes at –10° C. and then left to return to ambient temperature.

Then, 300 ml of toluene is added and the solvent is evaporated off under reduced pressure.

In this way 12.8 g of ethyl 5-(chloromethyl)-1-(2-propenyl)-1H-imidazole-4-carboxylate is obtained of molecular formula $C_{10}H_{13}N_2O_2Cl$, HCl.

The corresponding yield is quantitative.

Stage D 12.8 g (0.048 mole) of the white crystals obtained in Stage C is dissolved in acetonitrile.

29.83 g of potassium carbonate and 16.4 g of t-butyl glycinate are added at ambient temperature.

The reaction medium is left to react overnight at ambient temperature.

The insoluble part is filtered, then the solvent is evaporated off under reduced pressure.

The residue is solubilized in 200 ml of an AcOEt/heptane mixture 2/1, followed by washing with a 1M solution of $NaH_2PO_4$, separating the organic phase and drying over magnesium sulphate.

The solvent is evaporated off under reduced pressure.

In this way 14.1 g of ethyl 5-[[[[(1,1-dimethylethoxy)carbonyl]methyl]amino]methyl]-1-(2-propenyl)-1H-imidazole-4-carboxylate is obtained of molecular formula $C_{16}H_{25}N_3O_4$ (M=323.40 g).

The corresponding yield is of 91%.

Stage E 14.1 g (0.043 mole) of the yellow oil obtained in Stage D is introduced into 150 ml of THF in a flask placed under an argon atmosphere.

10.2 g of (BOC)$_2$O is added at ambient temperature and the reaction medium is left to react for one hour, then the solvent is evaporated off under reduced pressure.

The residue is solubilized in a heptane/AcOEt mixture 10/20, the organic phase is washed with a 1M aqueous solution of $NaH_2PO_4$ and the organic phase is dried over magnesium sulphate.

Then the crude product obtained is purified on silica eluting with a heptane/AcOEt mixture 2/1.

In this way 15.07 g of ethyl 5-[[[(1,1-dimethylethoxy) carbonyl][[(1,1-dimethylethoxy)carbonyl]methyl]amino] methyl]-1-(2-propenyl)-1H-imidazole-4-carboxylate is recovered of molecular formula $C_{21}H_{33}N_3O_6$ (M=423.51 g).

The corresponding yield is 82%.

Stage F 6.5 g (0.015 mole) of the colourless oil obtained in Stage E is dissolved in 400 ml of THF.

0.65 g of Pd/C catalyst at 10% by weight is added. The reaction medium is placed under a hydrogen atmosphere and left to react at ambient temperature for one hour 30 minutes.

The catalyst is filtered and evaporation under reduced pressure is carried out in order to collected 6.6 g of ethyl 5-[[[(1,1-dimethylethoxy)carbonyl][[(1,1-dimethylethoxy) carbonyl]methyl]amino]methyl]-1propyl-1H-imidazole-4-carboxylate of molecular formula $C_{21}H_{37}N_3O_6$ (M=427.55 g).

The corresponding yield is quantitative.

Stage G 6.6 g (0.0174 mole) of the gomme obtained in Stage F is introduced into 100 ml of THF in a flask placed under an argon atmosphere and cooled down with an ice bath.

Then 3.85 g of t-BuOK is added and the reaction medium is left to react for 1 hour at 0° C., followed by diluting with a heptane/AcOEt mixture 10/20, washing with a 1M solution of sodium hydrogen phosphate, separating the organic phase and drying over magnesium sulphate.

The solvent is evaporated off under reduced pressure.

In this way 5.62 g of 5,6-di(1,1-dimethylethyl)7-hydroxy-3-propyl-3H-imidazo[4,5-c]pyridine-5(4H),6-dicarboxylate of an oil is obtained of molecular formula $C_{19}H_{29}N_3O_5$ (M=379.46 g).

The corresponding yield is quantitative.

Stage H 5.62 g (0.0174 mole) of the oil obtained in Stage G is dissolved in 60 ml of trifluoroacetic acid at ambient temperature.

The reaction medium is left to react at ambient temperature for 45 minutes, then toluene is added and the solvent is evaporated off under reduced pressure.

Then the residue is solubilized in 120 ml of THF. 7.5 ml of TEA, then 4.55 g of (Boc)$_2$O are added.

The reaction medium is left to react for 1 hour at ambient temperature, followed by extracting with a heptane/AcOEt mixture 10/20, washing with a 1M solution of NaH$_2$PO$_4$, the organic phase is separated and dried over magnesium sulphate.

The solvent is evaporated off under reduced pressure.

In this way 5.2 g of 1,1-dimethylethyl 7-oxo-3-propyl-6, 7-dihydro-3H-imidazo[4,5-c]pyridine-5(4H)-carboxylate is obtained of molecular formula $C_{14}H_{21}N_3O_3$ (M=279.34 g).

The corresponding yield is quantitative.

Stage I

The operation is carried out as indicated in Stage A of Example 6 with 5.2 g (0.0146 mole) of the product obtained in Stage H and 2.56 g of O-benzylhydroxylamine hydrochloride.

In this way 4.1 g of 1,1-dimethylethyl 7-[(phenylmethoxy)imino]-3-propyl-6,7dihydro-3H-imidazo[4,5-c] pyridine-5(4H)-carboxylate is obtained of molecular formula $C_{21}H_{28}N_4O_3$ (M=384.48 g).

The corresponding yield is 73%.

Stage J 4.1 g (0.0106 mole) of the product obtained in Stage I is dissolved in 8 ml of acetic acid.

The reaction medium is cooled down to 0° C. and 1.98 g of sodium cyanoborohydride is added by portions of 0.33 g every 30 minutes, then the reaction medium is left to react at ambient temperature for 30 minutes.

Then the reaction medium is neutralized with a saturated solution of sodium bicarbonate, followed by extracting with an AcOEt/heptane mixture, drying the organic phase over magnesium sulphate and the solvent is evaporated off under reduced pressure.

The residue is purified by chromatography on silica eluting with a dichloromethane/acetone mixture 90/10.

In this way 3.5 g of 1,1-dimethylethyl 7-[(phenylmethoxy)amino]-3-propyl-6,7dihydro-3H-imidazo[4,5-c] pyridine-5(4H)-carboxylate is recovered of molecular formula $C_{21}H_{30}N_4O_3$ (M=386.5 g).

The corresponding yield is 81%.

Stage K 3.5 g (0.009 mole) of the product obtained in Stage J is introduced into 7 ml of AcOEt.

The reaction medium is cooled down to 0° C. and 17.5 ml of hydrogen chloride in 5.3 N solution in AcOEt is added.

The reaction medium is left to react under agitation for one hour and 30 minutes at ambient temperature.

The solvent is evaporated off under reduced pressure.

The crystallized product obtained is solubilized in 900 ml of acetonitrile, then after cooling down to 0° C., 5.22 ml of TEA is added.

Then 0.55 ml of diphosgene is added dropwise, followed by agitating for 45 minutes. 1.3 ml of TEA is added, agitation is carried out for 30 minutes followed by evaporating to dryness. Dichloromethane is added, followed by washing with a solution of sodium hydrogen phosphate, then drying the organic phase over magnesium sulphate.

Then, the solvent is evaporated off under reduced pressure.

The crude product obtained is purified by chromatography on silica eluting with a toluene/isopropanol mixture 80/20.

In this way 0.46 g of 5-(phenylmethoxy)-1-propyl-4,5,7, 8-tetrahydro-4,7-methano-imidazo[4,5-e][1,3]diazepin-6 (1H)-one is recovered of molecular formula $C_{17}H_{20}N_4O_2$ (M=312.37 g).

The corresponding yield is 16%.

Stage L

The operation is carried out as indicated in Stage A of Example 11 with 0.46 g of the product obtained in Stage K and 0.9 g of Pd/C catalyst at 10% by weight and using acetic acid in place of the ethanol.

In this way 0.32 g of 5-hydroxy-1-propyl-4,5,7,8-tetrahydro-4,7-methano-imidazo[4,5-e][1,3]diazepin-6(1H)-one is obtained of molecular formula $C_{10}H_{14}N_4O_2$ (M=222.25 g).

The corresponding yield is 98%.

Stage M

The operation is carried out as indicated in Stage J of Example 17 with 0.314 g (0.0014 mole) of the product obtained in Stage L, 10 ml of pyridine and 0.675 g of SO$_3$-pyridine complex.

0.215 g of the expected pyridine salt is obtained of molecular formula $C_{10}H_{14}N_4O_5S$ (M=302.31 g).

The corresponding yield is 50.8%.

NMR Spectrum of the Proton

In DMSO d6, at 300 MHz, chemical shifts and multiplicity: 0.84 (t): CH$_3$—CH$_2$—CH$_2$—N; 1.73(m): CH$_3$—CH$_2$—CH$_2$—N; 4.03(m): CH$_3$—CH$_2$—CH$_2$—N; 3.34 (d) and 3.63 (dd): N—CH$_2$—CH—N; 4.92 (d): N—CH$_2$—CH—N; 4.40 and 4.47 (AB): N—CH$_2$—C=; 8.99 (s): N=CH IR (Nujol): 1766, 1615, 1520 cm$^{-1}$ MS (Negative electrospray) m/z: [2M+H]$^-$=603; [M]$^-$=301

Example 23

Sodium salt of ethyl 6,8-dimethoxy-3-oxo-4-(sulphooxy)-2,3,4,5-tetrahydro-2,5-methano-1H-pyrido[3,4-e][1,3]diazepine-1-carboxylate Stage A 2.9 g (17.35 mmole) of 3,5-dimethoxy-4-pyridine carboxaldehyde of molecular formula $C_8H_9NO_3$ (M=167.166 g, described in J. Heterocycl. Chem., 11, 251, (1974)) is dissolved in 30 ml of dichloromethane and 2.3 ml of trimethylsilyl cyanide.

The reaction medium is brought to 0° C., then 0.120 ml of TEA is added.

Agitation is carried out for 15 minutes, then the solvent is evaporated off under reduced pressure.

The residue is redissolved in 30 ml of ethanol and 30 ml of concentrated hydrochloric acid, followed by taking to reflux for 1 hour.

The reaction medium is returned to ambient temperature, diluting with ice, AcOEt is added, then ammonium hydroxide is added, whilst cooling. The decanted organic phase is washed 3 times with water then dried over sodium sulphate and filtered. After evaporating the solvent under reduced pressure, 2.34 g of 2,6-dimethoxy-alpha-hydroxy-4-pyridineethyl acetate is obtained of molecular formula $C_{11}H_{15}NO_5$ (M=241.24 g).

The corresponding yield is 55.9%.

Stage B 5.34 g (17.35 mmole) of the product obtained in Stage A is introduced into 55 ml of dichloromethane in a flask placed under a nitrogen atmosphere.

4 ml of TEA, 0.270 g of DMAP are added.

After cooling down to 0° C. 1.85 ml of mesyl chloride is introduced. Agitation is carried out for 1 hour at 0° C.

Then the reaction medium is poured into a water and dichloromethane mixture, followed by extracting twice with dichloromethane, washing twice with water, the organic phases are combined and dried over sodium sulphate, then the solvent is evaporated off under reduced pressure.

In this way 7.34 g of 2,6-dimethoxy-alpha-[(methylsulphonyl)oxy]-4-pyridineethyl acetate is obtained of molecular formula $C_{12}H_{17}NO_7S$ (M=319.34 g).

Stage C 8.38 g (24.4 mmole) of the product obtained in Stage B and 40 ml of DMF are introduced into a flask placed under a nitrogen atmosphere. 3.6 ml of 2,6-lutidine and 6.5 ml of tertbutyl glycinate are added.

The reaction medium is taken to 80° C. for 6 hours, left to return to ambient temperature, then 1.3 ml of terbutyl glycinate is added and taken to 80° C. for 4 hours 30 minutes.

The reaction medium is left to return to ambient temperature and poured into an ice and sulphuric ether mixture, followed by extracting once with ether, washing the ethereal phase 4 times with water, drying the organic phase over sodium sulphate, then filtering and the solvent is evaporated off under reduced pressure.

Entraining with toluene is carried out.

The crude product is taken up in AcOEt, followed by washing with a 10% aqueous solution of tartaric acid then twice with water and then with a saturated aqueous solution of sodium hydrogen carbonate, drying the organic phase over sodium sulphate, filtering and the solvent is evaporated off under reduced pressure.

7.65 g of 2,6-dimethoxy-alpha-[[[(1,1-dimethylethoxy)carbonyl]methyl]amino]-4-pyridineethyl acetate is recovered of molecular formula $C_{17}H_{26}N_2O_6$ (M=354.41 g).

The corresponding yield is 97.6%.

Stage D 4.68 g (13.21 mmole) of the product obtained in Stage C, 2.2 ml of triethylamine and 60 ml of dichloromethane are introduced into a flask cooled down with an ice bath.

The reaction medium is cooled down to 0° C. and 2.4 ml of trifluoroacetic anhydride is added.

The reaction medium is left in contact for 2 hours 30 minutes, then poured into an ice/ammonium hydroxide/dichloromethane mixture, followed by washing with water, extracting with dichloromethane, drying the organic phases over sodium sulphate, filtering and the solvent is evaporated off under reduced pressure.

In this way 5.86 g of ethyl 2,6-dimethoxy-alpha-[[[(1,1-dimethylethoxy)carbonyl]methyl](trifluoroacetyl)amino]-4-pyridineacetate is obtained of molecular formula $C_{19}H_{25}F_3N_2O_7$ (M=450.42 g).

The corresponding yield is 98.5%.

Stage E 5.86 g (13 mmoles) of the product obtained in Stage D and 40 ml of dichloromethane are introduced into a flask placed under a nitrogen atmosphere.

The reaction medium is cooled down to 0° C. and 40 ml of trifluoroacetic acid is introduced rapidly, followed by leaving to rise to ambient temperature then leaving under agitation for 4 hours.

The solvent is evaporated off under reduced pressure.

The product is dissolved in AcOEt, washed successively with a dilute solution of ammonium hydroxide then with a saturated aqueous solution of $NaH_2PO_4$.

Then the organic phases are dried over sodium sulphate, filtered and the solvent is evaporated off under reduced pressure.

In this way 4.54 g of an oil is obtained which is purified by passing via a cyclohexylamine salt. After returning to the expected acid, 3.84 g of alpha-[(carboxymethyl)(trifluoroacetyl)amino]-2,6-dimethoxy-4-pyridineethyl acetate is obtained in the form of colourless crystals melting at 134-136° C., of molecular formula $C_{15}H_{17}F_3N_2O_7$ (M=394.31 g).

The corresponding yield is 74.9%.

Stage F 1.97 g (5 mmoles) of the product obtained in Stage E, 10 ml of dichloromethane and 77 μl of DMF are introduced into a flask placed under a nitrogen atmosphere.

The reaction medium is cooled down to 0° C. and a solution of 480 μl of oxalyl chloride in 2 ml of dichloromethane is introduced.

After the end of gas evolution, the reaction medium is left to return to ambient temperature. After the end of a second gas evolution, the solvent is evaporated off under reduced pressure.

In this way alpha-[(2-chloro-2-oxoethyl)(trifluoroacetyl)amino]-2,6-dimethoxy-4-pyridineethyl acetate is obtained.

Stage G

The acid chloride prepared in Stage F, put into solution in 30 ml of chlorobenzene beforehand is introduced into a flask placed nitrogen atmosphere.

The reaction medium is taken to 90° C., then 12 ml of a 1M solution of boron trichloride in dichloromethane is added rapidly.

The reaction medium is maintained under reflux for 5 minutes then poured into an ice/AcOEt mixture, followed by extracting twice with AcOEt and washing with salt water.

The organic phases are combined, dried over sodium sulphate, filtered then the solvent is evaporated off under reduced pressure.

1.96 g of crude product is obtained which is purified by chromatography on silica eluting with a dichloromethane/isopropanol mixture 95/5.

In this way 1.41 g of ethyl 5-hydroxy-7-methoxy-4-oxo-1,2,3,4-tetrahydro-2-(trifluoroacetyl)-2,6-naphthyridine-1-carboxylate is recovered, of molecular formula $C_{14}H_{13}F_3N_2O_6$ (M=362.26 g).

The corresponding yield is 78%.

Stage H

The operation is carried out as in Stage A of Example 6 with 1.81 (5 mmoles) of the product obtained in Stage G, 0.603 g (5.5 mmoles) of O-allylhydroxylamine hydrochloride and 1.2 ml of pyridine.

2.14 g of ethyl 5-hydroxy-7-methoxy-4-[(2-propenyloxy)imino]-1,2,3,4-tetrahydro-2-(trifluoroacetyl)-2,6-naphthhyridine-1-carboxylate is obtained of molecular formula $C_{17}H_{18}F_3N_3O_6$ (M=417.34 g).

The corresponding yield is quantitative.

Stage I 24 ml of methanol, then 500 mg of $NaBH_4$ are introduced into a flask cooled down with an ice bath.

2.14 g (5 mmoles) of the product prepared in Stage H put into solution in 26 ml of dichloromethane and 4 ml of methanol are introduced while maintaining the temperature at 0° C.

When gas evolution ceases, dilution with AcOEt is carried out, followed by washing with a saturated solution of $NaH_2PO_4$, extracting twice with AcOEt, then washing the organic phases with salt water and drying over sodium sulphate, filtering and the solvent is evaporated off under reduced pressure.

1.86 g of ethyl 5-hydroxy-7-methoxy-4-[(2-propenyloxy)imino]-1,2,3,4-tetrahydro-2,6-naphthhyridine-1-carboxylate is obtained of molecular formula $C_{15}H_{21}N_3O_5$ (M=325.35 g).

Stage J 1.86 g of the product obtained in Stage I is dissolved in 20 ml of THF.

The reaction medium is cooled down to −10° C., then 2.18 g of $(BOC)_2O$ and 1.5 ml of TEA are added.

Agitation is carried out for 1 hour 30 minutes while maintaining the temperature below 0° C., then 1.09 of diterbutylcarbonate and 0.75 ml of TEA are added.

The operation is repreated twice and the reaction medium is agitated for 2 hours at −10° C., followed by diluting with AcOEt, washing with a saturated solution of sodium chloride, separating, drying the organic phase over sodium sulphate, filtering and the solvent is evaporated off under reduced pressure.

In this way 6.52 g of an oil is obtained which is purified by chromatography on silica eluting with a dichloromethane/AcOEt mixture 9/1.

1.66 g of 1-ethyl and 2-(1,1-dimethylethyl)5-hydroxy-7-methoxy-4-[(2-propenyloxy)imino]-3,4-dihydro-2,6-naphthhyridine-1,2(1H)-dicarboxylate is recovered of molecular formula $C_{20}H_{27}N_3O_7$ (M=421.25 g).

The corresponding yield is 78.8%.

Stage K 1.66 g of the product obtained in Stage J is dissolved in 33 ml of methanol and an excess of diazomethane in solution in dichloromethane is added until the starting product disappears.

Silica is added to the reaction medium until gas evolution stops, followed by filtering and the solvent is evaporated off under reduced pressure. The crude product obtained is purified by chromatography on silica eluting with an AcOEt/hexane mixture 3/7.

1.18 g of 1-ethyl and 2-(1,1-dimethylethyl)5,7-dimethoxy-4-[(2-propenyloxy)imino]-3,4-dihydro-2,6-naphthhyridine-1,2(1H)-dicarboxylate is recovered of molecular formula $C_{21}H_{29}N_3O_7$ (M=435.48 g).

The corresponding yield is 69%.

Stage L 399 mg (0.92 mmoles) of the product obtained in Stage K is dissolved in 5 ml of methanol and 288 mg of $NaBH_3CN$ is added.

The pH is adjusted to approximately 2 using a solution of hydrogen chloride in methanol. The reaction medium is agitated for two hours at ambient temperature, diluting with dichloromethane, an aqueous solution of sodium hydrogen carbonate is added in order to adjust the pH to 9, followed by washing with salt water, extracting the aqueous phases with dichloromethane, separating, drying the organic phases over sodium sulphate, filtering and the solvent is evaporated off under reduced pressure.

In this way 388 mg of 1-ethyl and 2-(1,1-dimethylethyl) 5,7-dimethoxy-4-[(2-propenyloxy)amino]-3,4-dihydro-2,6-naphthhyridine-1,2(1H)-dicarboxylate is obtained of molecular formula $C_{21}H_{31}N_3O_7$ (M=437.50 g).

The corresponding yield is 96%.

Stage M 690 mg (1.58 mmoles) of the product obtained in Stage L is dissolved in 4 ml of dichloromethane.

The reaction medium is cooled down to 0° C., then 24 ml of hydrogen chloride in solution in AcOEt at 4 moles/l is added.

The reaction medium is left in contact for 3 hours.

The solvent is evaporated off under reduced pressure, followed by taking up in AcOEt, sodium hydrogen carbonate is added, then water. After separating, the organic phase is dried over sodium sulphate, filtered, then the solvent is evaporated off under reduced pressure.

In this way 0.49 g of ethyl 5,7-dimethoxy-4-[(2-propenyloxy)amino]-1,2,3,4-tetrahydro-2,6-naphthhyridine-1-carboxylate is obtained of molecular formula $C_{16}H_{23}N_3O_5$ (M=337.38 g).

The corresponding yield is 92%.

Stage N

The operation is carried out as indicated in Stage L of Example 3 with 102 mg (0.3 mmoles) of the product obtained in Stage M, 168 µml of TEA and 20 µl of diphosgene.

70 mg of ethyl 6,8-dimethoxy-3-oxo-4-(2-propenyloxy)-2,3,4,5-tetrahydro-2,5-methano-1H-pyrido[3,4-e][1,3]diazepine-1-carboxylate is obtained of molecular formula $C_{17}H_{21}N_3O_6$ (M=363.37 g).

The corresponding yield is 63.6%.

Stage O

The operation is carried out as indicated in Stage C of Example 7 with 94 mg (0.26 mmole) of the product obtained in Stage N, 44 µl of acetic acid, 149 mg of $Pd[P(C_6H_5)_3]_4$, 123 mg of $SO_3$-pyridine complex.

53 mg of the 1-propenyltriphenylphosphonium salt of ethyl 6,8-dimethoxy-3-oxo-4-(sulphooxy)-2,3,4,5-tetrahydro-2,5-methano-1H-pyrido[3,4-e][1,3]diazepine-1-carboxylate is obtained.

The corresponding yield is 29%.

After passing through a column of DOWEX 50WX8 resin in $Na^+$ form 26 mg of the expected sodium salt is obtained of molecular formula $C_{14}H_{16}N_3NaO_9S$ (M=425.35 g).

The corresponding yield for this exchange is 81%.

NMR Spectrum of the Proton

In $CDCl_3$, at 300 MHz, chemical shifts and multiplicity: 1.24 (t): C$\underline{H}_3$—CH$_2$—O—C═O; 4.21 (q): CH$_3$—C$\underline{H}_2$—O—C═O; 3.38 (d) and 3.50 (dd): N—C$\underline{H}_2$—CH—N; 4.93 (d): N—CH$_2$—C$\underline{H}$—N; 3.89 (s) and 3.86 (s): C(O)O—CH$_3$; 4.99 (s): N—CH—C═O; 6.33 (s): CH$_3$—O—C(N)═C$\underline{H}$.

Example 24 methyl trans-6-oxo-5-(2-propenyloxy)-5,6,7,8-tetrahydro-4,7-methano-4H-thieno[2,3-e][1,3]diazepine-8-carboxylate Stage A 48.14 g (0.281 mole) of methyl alpha-amino-2-thiopheneacetate of molecular formula $C_7H_{19}NO_2S$ (prepared from commercial alpha-aminothiophene acetic acid according to a similar technique to that described in J. Med. Chem., 26, 1267-1277 (1983)) is dissolved in 930 ml of acetonitrile.

38.8 g of potassium carbonate (0.281 mole) then 55.5 ml of $BrCH_2CO_2tBu$ (0.337 mole) are added.

The reaction medium is heated at 70° C. for 6 hours and 30 minutes, then left to return to 20° C. and the insolubles are eliminated by filtration, followed by partially concentrating under reduced pressure, taking up in 550 ml of AcOEt, washing with water, then with a saturated solution of sodium chloride. The organic phase is dried over sodium sulphate, filtered and the solvent is evaporated off under reduced pressure.

In this way 90 g of methyl alpha-[[[(1,1-dimethylethoxy)carbonyl]methyl]amino]-2-thiopheneacetate is obtained of molecular formula $C_{13}H_{19}NO_4S$ (M=285.36 g).

The corresponding yield is quantitative.

Stage B

The operation is carried out as indicated in Stage B of Example 3 with 90 g of the ester obtained in Stage A, 61.7 ml (0.354 mole) of diisopropylethylamine and 25.2 ml (0.326 mole) of methyl chloroformate.

70.9 g of methyl alpha-[[[(1,1-dimethylethoxy)carbonyl]methyl](methoxycarbonyl)amino]-2-thiopheneacetate is recovered of molecular formula $C_{15}H_{21}NO_6S$ (M=343.40 g).

The corresponding yield of Stages A and B is 73.4%.

Stage C

The operation is carried out as indicated in Stage C of Example 3 with 70 g (0.203 mole) of the butyl ester obtained in Stage B and a solution of 450 ml of trifluoroacetic acid in 450 ml of dichloromethane.

In this way 75 g of crude product is obtained.

This crude product is purified in the following manner.

The 75 g of crude product is introduced into 300 ml of ether, then 33 ml of cyclohexylamine (0.29 mole) is added dropwise at 20° C.

The salt having precipitated filtration is carried out followed by washing twice with 50 ml of ether.

The product obtained is redissolved in 200 ml of water, then 36 ml of 6N hydrochloric acid is added dropwise at 20° C., followed by decanting and extracting the aqueous phase twice with 300 ml of AcOEt.

The aqueous phases are combined and washed with water, then with a saturated solution of sodium chloride, followed by filtering and drying the organic phase over magnesium sulphate.

The solvent is evaporated off under reduced pressure.

In this way 59.95 g of methyl alpha-[(carboxymethyl)(methoxycarbonyl)amino]-2-thiopheneacetate is obtained of molecular formula $C_{11}H_{13}NO_6S$ (M=287.29 g).

The corresponding yield is quantitative.

Stage D

The operation is carried out as indicated in Stage D of Example 3 with 49.76 g (0.173 mole) of the acid obtained in Stage C and 57 ml of thionyl chloride.

In this way 44.50 g of methyl 2,5-dioxo-alpha-(2-thienyl)-3-oxazolidineacetate is obtained of molecular formula $C_{10}H_9NO_5S$ (M=255.25 g).

The corresponding yield is quantitative.

Stage E

The operation is carried out as indicated in Stage E of Example 3 with 44.5 g (0.173 mole) of the crude anhydride obtained in Stage D, 92.3 g of aluminium trichloride and replacing the treatment with soda by a treatment with tartaric acid and ammonium hydroxide.

In this way 32.5 g of methyl 4-oxo-4,5,6,7-tetrahydro-thieno[2,3-c]pyridine-7-carboxylate is obtained of molecular formula $C_9H_9NO_3S$ (M=211.24 g).

The corresponding yield is 88%.

Stage F

The operation is carried out as indicated in Stage F of Example 3 with 30 g (0.142 mole) of the product obtained in Stage E and 93 g of $(BOC)_2O$.

In this way 27.91 g of 6-(1,1-dimethylethyl) and 7-methyl 4,5-dihydro-4-oxo-thieno[2,3-c]pyridine-6(7H),7-dicarboxylate is obtained of molecular formula $C_{14}H_{17}NO_5S$ (M=311.36 g).

The corresponding yield is 63%.

Stage G

The operation is carried out as indicated in Stage A of Example 6 with 6 g (19.3 mmoles) of the product obtained in Stage F and 2.11 g (19.3 mmoles) of O-allyl-hydroxylamine hydrochloride.

In this way 7.26 g of 6-(1,1-dimethylethyl) and 7-methyl 4,5-dihydro-4-[(2-propenyloxy)imino]-thieno[2,3-c]pyridine-6(7H),7-dicarboxylate is obtained of molecular formula $C_{17}H_{22}N_2O_5S$ (M=366.44 g).

The corresponding yield is quantitative.

Stage H

The operation is carried out as indicated in Stage B of Example 6 with 7.25 g (0.0198 mole) of the oxime obtained in Stage G, 32.3 g of sodium cyanoborohydride and 53.7 ml of boron trifluoride in ether.

In this way 7.28 g of cis 6-(1,1-dimethylethyl) and 7-methyl 4,5-dihydro-4-[(2-propenyloxy)amino]-thieno[2,3-c]pyridine-6(7H),7-dicarboxylate is obtained of molecular formula $C_{17}H_{24}N_2O_5S$ (M=368.45 g).

The corresponding yield is quantitative.

Stage I

The operation is carried out as indicated in Stages J and K of Example 3 with 7.26 g (19.7 mmole) of the product obtained in Stage H and 65 ml of a 4.3 M solution of hydrogen chloride in AcOEt then 20 ml of 2N soda.

In this way 4.87 g of cis methyl 4-[(2-propenyloxy) amino]-4,5,6,7-tetrahydro-thieno[2,3-c]pyridine-7-carboxylate is obtained of molecular formula $C_{12}H_{16}N_2O_3S$ (M=268.33 g).

The corresponding yield is 92%.

Stage J

The operation is carried out as indicated in Stage L of Example 3 with 2.16 g (8.04 mmoles) of the product obtained in Stage I, 2.24 ml of TEA, 535 µl of diphosgene and 98 mg of DMAP.

1.227 g of methyl trans-6-oxo-5-(2-propenyloxy)-5,6,7, 8-tetrahydro-4,7-methano-4H-thieno[2,3-e][1,3]diazepine-8-carboxylate is obtained of molecular formula $C_{13}H_{14}N_2O_4S$ (M=294.33 g)

The corresponding yield is 51%.

NMR Spectrum of the Proton

In CDCl₃, at 300 MHz, chemical shifts and multiplicity: 2.53 (d), 3.65 (dd): N—C$\underline{H}_2$—CH; 3.85 (s): CH₃—O; 4.42 (m): N—CH₂—C$\underline{H}$; 4.43 (m): O—C$\underline{H}_2$—CH=CH₂; 5.31 (bd) and 5.36 (bd): O—CH₂—CH=C$\underline{H}_2$; 5.34 (s): CH—C (O)—O; 6.02 (m): O—CH₂—C$\underline{H}$=CH₂; 6.95 (d) and 7.25 (d): thiophene MS (EI) m/z: [M]⁺=294, 266, 238, 235, 199, 41

Example 25

Sodium salt of trans-6-oxo-5-(sulphooxy)-5,6,7,8-tetrahydro-4,7-methano-4H-thieno[2,3-e][1,3]diazepine-8-carboxamide Stage A The operation is carried out as indicated in Stage A of Example 7 with 1.55 g (5.26 mmoles) of the methyl ester obtained in Stage J of Example 24 and 5.3 ml of 1N soda.

In this way 1.357 g of trans-6-oxo-5-(2-propenyloxy)-5, 6,7,8-tetrahydro-4,7-methano-4H-thieno[2,3-e][1,3]diazepine-8-carboxylic acid is obtained of molecular formula $C_{12}H_{12}N_2O_4S$ (M=280.30 g).

The corresponding yield is 92%.

Stage B

The operation is carried out as indicated in Stage B of Example 10 with 327 mg (1.16 mmoles) of the acid obtained in Stage A, 774 mg of BOP, 236 mg of HOBt, 125 mg of ammonium chloride and 0.81 ml of N,N diisopropylethylamine.

305 mg of trans-6-oxo-5-(2-propenyloxy)-5,6,7,8-tetrahydro-4,7-methano-4H-thieno[2,3-e][1,3]diazepine-8-carboxamide is obtained of molecular formula $C_{12}H_{13}N_3O_3S$ (M=279.32 g).

The corresponding yield is 93.7%.

Stage C

The operation is carried out as indicated in Stage C of Example 7 with 481 mg (1.722 mmoles) of the amide obtained in Stage B, 196 µl of acetic acid, 1 g of Pd[P(C₆H₅)₃]₄ and 1 g of SO₃-pyridine complex.

In this way 464 mg of the 1-propenyltriphenylphosphonium salt of trans-6-oxo-5-(sulphooxy)-5,6,7,8-tetrahydro-4,7-methano-4H-thieno[2,3-e][1,3]diazepine-8-carboxamide is obtained of molecular formula $C_{30}H_{28}N_3O_6PS_2$ (M=621.67 g).

The corresponding yield is 43%.

This product is converted to a sodium salt by passing through a column of DOWEX 50WX8 resin in Na⁺ form.

In this way 164 mg of the sodium salt of trans-6-oxo-5-(sulphooxy)-5,6,7,8-tetrahydro-4,7-methano-4H-thieno[2, 3-e][1,3]diazepine-8-carboxamide is obtained of molecular formula $C_9H_8N_3O_6S_2Na$ (M=341.30 g).

The corresponding yield in this exchange stage is 85%.

NMR Spectrum of the Proton

In D₂O, at 300 MHz, chemical shifts and multiplicity: 3.46 (d), 3.80 (dd): N—C$\underline{H}_2$—CH; 4.96 (d): N—CH₂—C$\underline{H}$; 5.36 (s): C$\underline{H}$—CO—NH₂; 7.15 (d) and 7.51 (d): S—C$\underline{H}$=C $\underline{H}$— MS (SIMS) m/z: [M+Na]⁺=364

Example 26

Sodium salt of methyl trans-6-oxo-5-(sulphooxy)-5, 6,7,8-tetrahydro-4,7-methano-4H-thieno[2,3-e][1,3] diazepine-8-carboxylate The operation is carried out as indicated in Stage C of Example 7 with 255 mg (0.866 mmoles) of the methyl ester obtained in Stage J of Example 24, 100 µl of acetic acid, 505 mg of Pd[P(C₆H₅)₃]₄ and 484 mg of SO₃-pyridine complex.

In this way 395 mg of the 1-propenyltriphenylphosphonium salt of methyl trans-6-oxo-5-(sulphooxy)-5,6,7,8-tetrahydro-4,7-methano-4H-thieno[2,3-e][1,3]diazepine-8-carboxylate is obtained of molecular formula $C_{31}H_{29}N_2O_7PS_2$ (M=636.69 g).

The corresponding yield is 71%.

This product is converted to a sodium salt by passing through a column of DOWEX 50WX8 resin in Na⁺ form.

In this way 182 mg of the expected sodium salt is obtained of molecular formula $C_{10}H_9N_2O_7S_2Na$ (M=356.31 g).

The corresponding yield in this exchange stage is 74%.

NMR Spectrum of the Proton

In D₂O, at 300 MHz, chemical shifts and multiplicity: 3.60 (d), 3.79 (dd): N—C$\underline{H}_2$—CH; 3.89: COOCH₃; 4.96 (d): N—CH₂—C$\underline{H}$; 5.58 (bs): N—CH—C=O; 7.14 (bd) and 7.51 (bd): S—C$\underline{H}$=C$\underline{H}$— MS (Negative electrospray) m/z: [M]⁻=333

Example 27

Sodium salt of trans-6-oxo-N-(phenylmethyl)-5-(sulphooxy)-5,6,7,8-tetrahydro-4,7-methano-4H-thieno[2,3-e][1,3]diazepine-8-carboxamide Stage A The operation is carried out as indicated in Stage B of Example 7 with 102 mg (0.36 mmoles) of the product obtained in Stage A of Example 25, 46 µl of dimethylpyridine, 50 µl of isobutyl chloroformate and 44 µl (0.396 mole) of benzylamine.

In this way 100 mg of trans-6-oxo-N-(phenylmethyl)-5-(2-propenyloxy)-5,6,7,8-tetrahydro-4,7-methano-4H-thieno [2,3-e][1,3]diazepine-8-carboxamide is obtained of molecular formula $C_{19}H_{19}N_3O_3S$ (M=369.45 g).

The corresponding yield is 83%.

Stage B 150 mg (0.406 mmoles) of the product obtained in Stage B is introduced into 2 ml of dichloromethane in a flask placed under an argon atmosphere.

46 µl of acetic acid, then 237 mg of Pd[P(C₆H₅)₃]₄ are added.

The reaction medium is left to react for 10 minutes.

Then, the solvent is evaporated off under reduced pressure.

The residue is taken up in dichloromethane, followed by washing with water, separating, drying the organic phase over magnesium sulphate, filtering and the solvent is evaporated off under reduced pressure.

The residue is purified by chromatography on silica eluting with a dichloromethane/acetone mixture 95/5 containing 0.1% TEA, then with a dichloromethane/Acetone mixture 90/10 containing 0.1% TEA.

In this way 95 mg of methyl trans-5-hydroxy-6-oxo-5,6,7,8-tetrahydro-4,7-methano-4H-thieno[2,3-e][1,3]diazepine-8-carboxylate is obtained of molecular formula $C_{16}H_{15}N_3O_3S$ (M=329.38 g) containing 63% by weight of triphenylphosphine oxide.

This product is used as it is in following stage.

Stage C 51 mg (0.057 mmole) of the product obtained in Stage B is introduced into 1 ml of pyridine in a flask placed under an inert atmosphere.

71 mg (0.446 mmole) of $SO_3$-pyridine complex is added.

Agitation is carried out for 3 hours.

Then, the reaction mixture is filtered, rinsed with dichloromethane and the solvent is evaporated off under reduced pressure.

The residue is taken up in 9 ml of a solution of $KH_2PO_4$ in water (0.5 M).

Agitation is carried out for 15 minutes at ambient temperature followed by washing 3 times with AcOEt.

47 mg of tetrabutylammonium is added and extraction is carried out 8 times with AcOEt.

The organic phases are combined, dried over magnesium sulphate, filtered and the solvent is evaporated off under reduced pressure.

The residue is deposited on a column of DOWEX 50WX8 resin in.

$Na^+$ form and eluted with water containing 10% THF.

The product collected is lyophilized in order to obtain 8.5 mg of the expected sodium salt, of molecular formula $C_{16}H_{14}N_3O_6S_2Na$ (M=431.43 g).

The corresponding yield is 34%.

MS (Negative electrospray) m/z: $[M]^-$=408

Example 28

Sodium salt of 5-(sulphooxy)-5,6,7,8-tetrahydro-4,7-methano-4H-furo[2,3-e][1,3]diazepin-6-one Stage A 4.34 ml (30 mmoles) of chloroacetaldehyde at 45% in water, 2.52 g of sodium hydrogen carbonate and 20 ml of water are introduced into a flask cooled down with an ice bath.

Then a suspension of 5.33 g (25 mmoles) of 1,1-dimethylethyl 3,5-dioxo-1-piperidinecarboxylate of molecular formula $C_{10}H_{15}NO_4$ (used as starting product in Stage A of Example 5) in 100 ml of THF is added.

The reaction medium is left to return to ambient temperature and left overnight under agitation.

Then the reaction medium is poured into a mixture of ice and 30 ml of 1N hydrochloric acid, then extracted 6 times with AcOEt, the organic phases are washed with a saturated solution of sodium chloride, dried over sodium sulphate, filtered and the solvent is evaporated off under reduced pressure.

In this way 6.78 g of a yellow foam is obtained which is purified by chromatography on silica eluting with dichloromethane containing 3% methanol.

In this way 2.86 g of 1,1-dimethylethyl 2-hydroxy-2,3,4,7-tetrahydro-4-oxo-furo[2,3-c]pyridine-6(5H)-carboxylate is recovered of formula $C_{12}H_{17}NO_5$ (M=255.27 g) which is used as it is in the following stage.

Stage B

The 2.86 g obtained in Stage A (11 mmoles) is dissolved in 40 ml of toluene.

418 mg of monohydrated p-toluene sulphonic acid is added and the reaction medium is taken to reflux for 1 hour, then poured into a mixture of 1 N soda and ice and extracted 3 times with 50 ml of AcOEt and the organic phases washed with a saturated solution of sodium chloride.

The organic phases are combined and dried over sodium sulphate, filtered and the solvent is evaporated off under reduced pressure.

The yellow resin obtained is purified by chromatography on silica, eluting with an AcOEt/hexane mixture 2/8.

In this way 1.23 g of 1,1-dimethylethyl 4,7-dihydro-4-oxo-furo[2,3-c]pyridine-6(5H)-carboxylate is recovered of molecular formula $C_{12}H_{15}NO_4$ (M=237.26 g).

The corresponding yield in Stages A and B is 20%.

Stage C

The operation is carried out as indicated in Stage A of Example 6 with 6.12 g of the product obtained in Stage B (25.8 mmoles), 2.90 g (25.9 mmoles) of O-allylhydroxylamine hydrochloride and 2.12 ml of pyridine.

In this way 6.8 g of 1,1-dimethylethyl 4,7-dihydro-4-[(2-propenyloxy)imino]-furo[2,3-c]pyridine-6(5H)-carboxylate is obtained of molecular formula $C_{15}H_{20}N_2O_4$ (M=292.34 g).

The corresponding yield is 96%.

Stage D

The operation is carried out as indicated in Stage B of Example 6 with 6.50 g of the product obtained in Stage C (23 mmoles) and 22.11 g of sodium cyanoborohydride and 33.5 ml of boron trifluoride etherate.

In this way 5.9 g of 1,1-dimethylethyl 4,7-dihydro-4-[(2-propenyloxy)amino]-furo[2,3-c]pyridine-6(5H)-carboxylate is obtained of molecular formula $C_{15}H_{22}N_2O_4$ (M=294.35 g).

The corresponding yield is 87%.

Stage E

The operation is carried out as indicated in Stages J and K of Example 3 with 5.98 g of the product obtained in Stage D (19.6 mmoles) and 42.9 ml of 5M hydrogen chloride in AcOEt and replacing the soda by ammonium hydroxide.

In this way 3.54 g of N-(2-propenyloxy)-4,5,6,7-tetrahydro-furo[2,3-c]pyridin-4-amine is obtained of molecular formula $C_{10}H_{14}N_2O_2$ (M=194.24 g).

The corresponding yield is 93%.

Stage F

The operation is carried out as indicated in Stage L of Example 3 with 1.10 g of the product obtained in Stage E (6.19 mmoles), 1.58 ml of TEA and 0.34 ml of diphosgene.

In this way 709 mg of 5-(2-propenyloxy)-5,6,7,8-tetrahydro-4,7-methano-4H-furo[2,3-e][1,3]diazepin-6-one is obtained of molecular formula $C_{11}H_{22}N_2O_3$ (M=220.23 g).

The corresponding yield is 52%.

Stage G

The operation is carried out as indicated in Stage C of Example 7 with 418 mg of the product obtained in Stage F (1.9 mmoles), 0.217 ml of acetic acid, 1.10 g (0.95 mmole) of $Pd[P(C_6H_5)_3]_4$ and 1.2 g of $SO_3$-pyridine-complex.

In this way 251 mg of the 1-propenyltriphenylphosphonium salt of 5-(sulphooxy)-5,6,7,8-tetrahydro-4,7-methano-4H-furo[2,3-e][1,3]diazepin-6-one is obtained of molecular formula $C_{29}H_{27}N_2O_6PS$ (M=562.59 g).

The corresponding yield is 24%.

After passing a solution of the brown foam through a column of DOWEX 50WX8 resin in $Na^+$ form, 92 mg of the expected sodium salt is recovered of molecular formula $C_8H_7N_2O_6SNa$ (M=282.21 g).

The corresponding yield in this exchange stage is 73%.

NMR Spectrum of the Proton

In DMSO d6, at 300 MHz, chemical shifts and multiplicity: 3.20 (d) and 3.45 (dd): N—C$\underline{H}_2$—CH; 4.65 (d): N—CH$_2$—C$\underline{H}$; 4.15 and 4.35 (AB): N—C$\underline{H}_2$—C=; 6.52 (d) and 7.55 (d): O—C$\underline{H}$=C$\underline{H}$— MS (Negative electrospray) m/z: [M]$^-$=259, 96

Example 29

Methyl trans-6-oxo-5-(2-propenyloxy)-5,6,7,8-tetrahydro-4,7-methano-4H-furo[2,3-e][1,3]diazepine-8-carboxylate Stage A 24.9 g (0.177 mole) of α-oxo 2-furan-acetic acid is dissolved at ambient temperature in 500 ml of methanol in a flask placed under a nitrogen atmosphere.

Then, 3.5 ml of thionyl chloride is added dropwise, at ambient temperature over 5 minutes.

The reaction medium is taken to reflux for 2 hours, then the solvent is evaporated off under reduced pressure, sodium bicarbonate is added, followed by extracting with AcOEt, washing with salt water, drying, then the solvent is evaporated off under reduced pressure.

The residue is dissolved at ambient temperature under a nitrogen atmosphere in 280 ml of ether, then 100 of 6 M hydrochloric acid is added.

The reaction medium is agitated for 45 minutes at ambient temperature, followed by decanting, washing with sodium bicarbonate, with salt water, separating the organic phase, drying, filtering and the solvent is evaporated off under reduced pressure.

In this way 24.45 g of crystals of methyl alpha-oxo-2-furanacetate is obtained of molecular formula $C_7H_6O_4$ (M=154.12 g).

The corresponding yield is 89%.

Stage B 10.65 g (69.1 mmol) of the product obtained in Stage A, 9.6 g of hydroxylamine hydrochloride, 50 ml of ethanol and 50 ml of pyridine are introduced into a flask placed under a nitrogen atmosphere.

The reaction medium is taken to reflux for 55 minutes, then the solvent is evaporated off under reduced pressure.

The residue is dissolved in 200 ml of dichloromethane, washed with a 10% aqueous solution of tartaric acid, then with water, separated, dried and the organic phase is filtered and the solvent is evaporated off under reduced pressure.

In this way 11.43 g of methyl alpha-(hydroxyimino)-2-furanacetate is obtained of molecular formula $C_7H_7NO_4$ (M=161.14 g).

The corresponding yield is 98%.

Stage C 25.86 g (0.152 mole) of the product obtained in Stage B is dissolved in 100 ml of ethanol in a flask placed under a nitrogen atmosphere.

Then 100 ml of water and 100 ml of 99% formic acid is added.

Then, 37 g (0.566 mole) of zinc in 325 mesh powder form is added over 5 hours at 15-20° C. (ice-cold water bath).

The reaction medium is agitated for 5 hours 45 minutes, then filtered, washed with methanol and with AcOEt, the solvent is evaporated off under reduced pressure.

Then, alkalinization is carried out with a 10% solution of potassium carbonate, followed by extracting twice with 500 ml of an AcOEt/THF mixture 1/1, washing with salt water, separating the organic phase, drying, filtering and the solvent is evaporated off under reduced pressure.

In this way 21.13 g of methyl alpha-amino-2-furanacetate is obtained of molecular formula $C_7H_9NO_3$ (M=155.16 g).

The corresponding yield is 90%.

Stage D

The operation is carried out as indicated in Stage A of Example 3 with the 21.13 g (0.136 mole) of the product obtained in Stage C, 31 ml of TEA and 38 ml (0.24 mole) of t-butyl bromoacetate.

In this way 21.65 g of methyl alpha-[[[(1,1-dimethylethoxy)carbonyl]methyl]amino]-2-furanacetate is obtained of molecular formula $C_{13}H_{19}NO_5$ (M=269.30 g).

The corresponding yield is 59%.

Stage E

The operation is carried out as indicated in Stage B of Example 3 with 26.31 g (0.0977 mole) of the product obtained in Stage D, 22.19 ml of N-ethyldiisopropylamine and 9.31 ml (0.117 mole) of methyl chloroformate.

In this way 31.87 g of methyl alpha-[[[(1,1-dimethylethoxy)carbonyl]methyl](methoxycarbonyl)amino]-2-furanacetate is obtained of molecular formula $C_{15}H_{21}NO_7$ (M=327.34 g).

The corresponding yield is quantitative.

Stage F

The operation is carried out as indicated in Stage C of Example 3 with 31.87 g (0.0977 mole) of the ter-butyl ester obtained in Stage E and 127 ml of trifluoroacetic acid.

In this way 26.45 g of methyl alpha-[(carboxymethyl)(methoxycarbonyl)amino]-2-furanacetate is obtained of molecular formula $C_{11}H_{13}NO_7$ (M=271.23 g).

The corresponding yield is quantitative.

Stage G 10 g (0.037 mole) of the product obtained in Stage F is dissolved in 13 ml of thionyl chloride.

The reaction medium is taken to 70° C. for 5 hours.

Then, dichloromethane is added and the solvent is evaporated off under reduced pressure.

In this way 9.99 g of an oily residue is obtained.

26 g of aluminium trichloride and 1.2 liter of dichloromethane are introduced into a flask.

The oily residue obtained previously, in solution in 800 ml of dichloromethane is added dropwise over one hour.

The reaction medium is taken to reflux for 1 hour 30 minutes and left overnight at ambient temperature, then poured into 1.4 l of a molar solution of potassium and sodium double tartrate containing ice and ammonium hydroxide.

Extraction is then carried out 3 times with 700 ml of dichloromethane followed by washing with a saturated solution of sodium chloride.

The organic phase is separated, dried over magnesium sulphate, filtered and the solvent is evaporated off under reduced pressure.

In this way 3.681 g of methyl 4-oxo-4,5,6,7-tetrahydrofuro[2,3-c]pyridine-7-carboxylate is obtained of molecular formula $C_9H_9NO_4$ (M=195.17 g).

The corresponding yield is 51%.

Stage H

The operation is carried out as indicated in Stage F of Example 3 with 3.68 g (0.019 mole) of the product obtained in Stage G and 14.61 g of (BOC)$_2$O.

In this way 1.77 g of 6-(1,1-dimethylethyl) and 7-methyl 4,7-dihydro-4-oxo-furo[2,3-c]pyridine-6(5H),7-dicarboxylate is obtained of molecular formula $C_{14}H_{17}NO_6$ (M=295.29 g).

The corresponding yield is 31%.

Stage I

The operation is carried out as indicated in Stage A of Example 6 with 3.36 g (11.34 mmoles) of the product obtained in Stage H, 1.27 g of O-allylhydroxylamine hydrochloride (11.62 mmoles) and 2.75 ml of pyridine.

In this way 3.97 g of 6-(1,1-dimethylethyl) and 7-methyl 4,7-dihydro-4-[(2-propenyloxy)imino]-furo[2,3-c]pyridine-6(5H),7-dicarboxylate is obtained of molecular formula $C_{17}H_{22}N_2O_6$ (M=350.37 g).

The corresponding yield is 99%.

Stage J

The operation is carried out as indicated in Stage B of Example 6 with 3.70 g (0.0105 mole) of the product obtained in Stage I, 9.92 g of sodium cyanoborohydride and 16 ml of boron trifluoride etherate in ether.

In this way 3.83 g of product is obtained which contains a mixture of starting product and reduced product. This crude product is reacted again under the same conditions as previously.

In this way 3.92 g of a yellow oil is obtained which is purified by chromatography eluting with an ethanol/AcOEt mixture 8/2.

In this way 3.36 g of cis 6-(1,1-dimethylethyl) and 7-methyl 4,7-dihydro-4-[(2-propenyloxy)amino]-furo[2,3-c]pyridine-6(5H),7-dicarboxylate is recovered of molecular formula $C_{17}H_{24}N_2O_6$ (M=352.29 g).

The corresponding yield is 90%.

Stage K

The operation is carried out as indicated in Stages J and K of Example 3 with 3.36 g (0.0095 mole) of the product obtained in Stage J and 36 ml of a 4 M solution of hydrogen chloride in AcOEt then 2N soda.

In this way 1.81 g of cis methyl 4-[(2-propenyloxy)amino]-4,5,6,7-tetrahydro-furo[2,3-c]pyridine-7-carboxylate is obtained of molecular formula $C_{12}H_{16}N_2O_4$ (M=252.27 g).

The corresponding yield is 75%.

Stage L

The operation is carried out as indicated in Stage L of Example 3 with 0.842 g (3.33 mmoles) of the product obtained in Stage K, 1.2 ml of TEA and 0.2 ml of diphosgene.

The product obtained is then epimerized in the following fashion.

0.1 ml of DBU is added and agitation is carried out for 40 minutes.

Then 50 ml of AcOEt is added followed by washing with 20 ml of a 10% aqueous solution of tartaric acid, then with 20 ml of a solution of phosphate buffer at pH 7 and with 50 ml of a solution of sodium chloride.

The organic phase is dried over magnesium sulphate, filtered then the solvent is evaporated off under reduced pressure.

The residue is purified by chromatography on silica, eluting with a dichloromethane/AcOET mixture 97/3 containing 0.1% TEA.

In this way 0.431 g of a slightly yellow product is recovered of molecular formula $C_{13}H_{14}N_2O_5$ (M=278.27 g).

The corresponding yield is 46%.

NMR Spectrum of the Proton

In CDCl$_3$, at 300 MHz, chemical shifts and multiplicity: 3.48 (bd) and 3.54 (dd): N—C$\underline{H}_2$—CH—N; 4.39 (d): N—CH$_2$—C$\underline{H}$—N; 4.40 and 4.47: O—C$\underline{H}_2$—CH=CH$_2$; 6.01 (m): O—CH$_2$—C$\underline{H}$=CH$_2$; 5.31 (m) and 5.36 (m): O—CH$_2$—CH=C$\underline{H}_2$; 3.89 (s): C$\underline{H}_3$—O—C=O; 6.45 (d) and 7.34 (d): O—C$\underline{H}$=C$\underline{H}$— MS (Positive electrospray) m/z: [MH]$^+$=279

Example 30

Sodium salt of trans methyl 6-oxo-5-(sulphooxy)-5,6,7,8-tetrahydro-4,7-methano-4H-furo[2,3-e][1,3]diazepine-8-carboxylate The operation is carried out as indicated in Stage C of Example 7 with 0.120 g (0.43 mmole) of the product obtained in Stage L of Example 29, 0.05 ml of acetic acid, 0.25 g (0.21 mmole) of Pd[P(C$_6$H$_5$)$_3$]$_4$ and 0.20 g (1.29 mmole) of SO$_3$-pyridine complex.

In this way 0.133 g of the 1-propenyltriphenylphosphonium salt of methyl trans-6-oxo-5-(sulphooxy)-5,6,7,8-tetrahydro-4,7-methano-4H-furo[2,3-e][1,3]diazepine-8-carboxylate is obtained in the form of an oil.

The corresponding yield is 49%.

After passing the yellow oil through a column of DOWEX 50WX8 resin in Na$^+$ form 54 mg of the expected sodium salt is recovered of molecular formula $C_{10}H_9N_2O_8SNa$ (M=340.245 g).

The corresponding yield is 74%.

NMR Spectrum of the Proton

In D$_2$O, at 300 MHz, chemical shifts and multiplicity: 3.53(d) and 3.71(dd): N—C$\underline{H}_2$—CH; 3.88(s): OCH$_3$; 4.91 (d): N—CH$_2$—C$\underline{H}$; 5.42 (s): C$\underline{H}$—C(O); 6.66 (d) and 7.54 (d): O—C$\underline{H}$=C$\underline{H}$ MS (Negative electrospray) m/z: [M]$^-$=317

Example 31

Sodium salt of trans-6-oxo-5-(sulphooxy)-5,6,7,8-tetrahydro-4,7-methano-4H-furo[2,3-e][1,3]diazepine-8-carboxamide Stage A The operation is carried out as indicated in Stage A of Example 7 with 0.718 g (0.026 mole) of the product obtained in Stage N of Example 29 and 2.84 ml of 1N soda.

In this way 0.538 g of trans-6-oxo-5-(2-propenyloxy)-5,6,7,8-tetrahydro-4,7-methano-4H-furo[2,3-e][1,3]diazepine-8-carboxylic acid is obtained of molecular formula $C_{12}H_{12}N_2O_5$ (M=264.24 g).

Stage B

The operation is carried out as indicated in Stage B of Example 10 with 0.284 g (0.0011 mole) of the product obtained in Stage A, 0.71 g of BOP, 0.22 g of HOBt, 0.12 g (0.0022 mole) of ammonium hydrochlorate and 0.77 ml of N,N diisopropylethylamine.

In this way 0.173 g of crystals of trans-6-oxo-5-(2-propenyloxy)-5,6,7,8-tetrahydro-4,7-methano-4H-furo[2,3-e][1,3]diazepine-8-carboxamide is obtained of molecular formula $C_{12}H_{13}N_3O_4$ (M=263.26 g).

The corresponding yield is 75%.

Stage C

The operation is carried out as indicated in Stage C of Example 7 with 0.173 g (0.66 mmole) of the product obtained in Stage B, 0.075 ml of acetic acid, 0.38 g (0.33 mmoles) of Pd[P(C$_6$H$_5$)$_3$]$_4$ and 0.31 g (1.97 mmoles) of SO$_3$-pyridine complex in 6 ml of pyridine.

The reaction medium is agitated at 20° C. for 5 hours, then 0.104 g (0.66 mmole) of SO$_3$-pyridine complex is added.

In this way 0.177 g of the 1-propenyltriphenylphosphonium salt of trans-6-oxo-5-(sulphooxy)-5,6,7,8-tetrahydro-4,7-methano-4H-furo[2,3-e][1,3]diazepine-8-carboxamide is obtained of molecular formula $C_{30}H_{28}N_3O_7PS$ (M=605.61 g).

The corresponding yield is 44%.

After passing of the white foam through a column of DOWEX 50WX8 resin in Na$^+$ form 87 mg of the expected sodium salt is recovered of molecular formula $C_9H_8N_3O_7SNa$ (M=325.234 g).

The corresponding yield in this exchange stage is 91%.

NMR Spectrum of the Proton

In $D_2O$, at 300 MHz, chemical shifts and multiplicity: 3.41 (d) and 3.70 (dd): N—C$\underline{H}_2$—CH; 4.90 (d): N—CH$_2$—C$\underline{H}$; 5.26 (s): C$\underline{H}$—C(O)—NH$_2$; 6.69 (m) and 7.54 (d): O—C$\underline{H}$=C$\underline{H}$— MS (Negative electrospray) m/z: [M]$^-$=302

Example 32

6,8-dimethoxy-4-hydroxy-3-oxo-2,3,4,5-tetrahydro-2,5-methano-1H-pyrido[3,4-e][1,3]diazepine-1-carboxamide Stage A The operation is carried out as indicated in Stage A of Example 7 with 135 mg (0.37 mole) of the product obtained in Stage N of Example 23 and 0.4 ml of 1N soda.

In this way 103 mg of 6,8-dimethoxy-3-oxo-4-(2-propenyloxy)-2,3,4,5-tetrahydro-2,5-methano-1H-pyrido[3,4-e][1,3]diazepine-1-carboxylic acid is obtained of molecular formula $C_{15}H_{17}N_3O_6$ (M=335.32 g).

The corresponding yield is 83%.

Stage B

The operation is carried out as indicated in Stage B of Example 10 with 29 mg (0.1 mmole) of the product obtained in Stage A, 66 mg of BOP, 20 mg of HOBt, 11 mg (0.2 mmoles) of ammonium chloride and 70 µl of N,N-diisopropylethylamine.

In this way 15 mg of 6,8-dimethoxy-3-oxo-4-(2-propenyloxy)-2,3,4,5-tetrahydro-2,5-methano-1H-pyrido[3,4-e][1,3]diazepine-1-carboxamide is obtained of molecular formula $C_{15}H_{18}N_4O_5$ (M=334.33 g).

The corresponding yield is 45%.

Stage C

The operation is carried out as indicated in Stage B of Example 8 with 41 mg (0.12 mmole) of the product obtained in Stage B, 21 µl of acetic acid, 71 mg (0.06 mmole) of Pd[P(C$_6$H$_5$)$_3$]$_4$ and 58.5 mg of SO$_3$-pyridine complex and 41 mg of tetrabutylammonium hydrogen sulphate.

After passing through a column of DOWEX 50WX8 resin in Na$^+$ form and lyophilization, 5 mg of the expected sodium salt is recovered of molecular formula $C_{12}H_{13}N_4O_8SNa$ (M=396.31 g).

The corresponding yield in this exchange stage is 10.4%.

NMR Spectrum of the Proton

In DMSO d6, at 300 MHz, chemical shifts and multiplicity: 3.42 (dd) and 3.65 (d): N—C$\underline{H}_2$—CH; 4.90 (d): N—CH$_2$—C$\underline{H}$; 4.77 (s): N—C$\underline{H}$—C(O)—NH$_2$; 7.45 and 7.89: N—CH—C(O)—N$\underline{H}_2$; 6.24 (s): aromatic CH=; 3.84 (s) and 3.85 (s): OCH$_3$ MS (Negative electrospray) m/z: [2M+Na]$^-$=769; [M]$^-$=373

Example 33

Sodium salt of 5-(sulphooxy)-5,6,7,8-tetrahydro-4,7-methano-4H-furo[3,4-e][1,3]diazepin-6-one Stage A 850 mg (5 mmoles) of 4-methyl 3,4-furandicarboxylate of molecular formula $C_7H_6O_5$ (M=170.12 g) and 25 ml of anhydrous THF are introduced into a flask placed under an argon atmosphere.

The reaction medium is cooled down to 0° C. and 0.728 ml of N-methylmorpholine and 0.778 ml of isobutyl chloroformate are added using a syringe.

The reaction medium is cooled down to −70° C., then 9 ml of methanol is introduced and 700 mg (17.5 mmoles) of 95% sodium borohydride (NaBH$_4$) is added.

The reaction medium is left to react for 4 hours then 7.5 ml of glacial acetic acid is added, still at −70° C.

The reaction medium is left to return to ambient temperature, then poured into 100 ml of a saturated solution of sodium bicarbonate, extracted with dichloromethane, followed by washing with a solution of sodium chloride, drying over magnesium sulphate, filtering and the solvent is evaporated off under reduced pressure.

The residue is purified by chromatography on silica eluting with a dichloromethane/methanol mixture 97/3.

In this way 675 mg of methyl 4-(hydroxymethyl)-3-furancarboxylate is recovered of molecular formula $C_7H_8O_4$ (M=156.14 g).

The corresponding yield is 86%.

Stage B 0.77 g (4.9 mmoles) of the product obtained in Stage A and 16 ml of dichloromethane are introduced into a flask placed under a nitrogen atmosphere.

The temperature is lowered to −25° C., then 2.04 g (6.2 mmoles) of tetrabromomethane is introduced.

The reaction medium is cooled down to −40° C., then 1.6 g (6.2 mmoles) of triphenylphosphine is introduced.

The reaction medium is left to react for 15 minutes at −40° C., then left for the temperature to rise to 0° C.

After reaction for 30 minutes, the solvent is evaporated off under reduced pressure.

The residue is purified by chromatography on silica eluting with dichloromethane.

960 mg of methyl 4-(bromomethyl)-3-furancarboxylate is recovered of molecular formula $C_7H_7BrO_3$ (M=219.04 g).

The yield is quantitative.

Stage C 960 mg (4.4 mmoles) of the product obtained in Stage B, 18 ml of DMF, 1.82 g of potassium carbonate and 1.2 ml of t-butyl glycinate are introduced into a flask placed under a nitrogen atmosphere.

The reaction medium is left under agitation for 30 minutes, filtered in order to recover the precipitate which is washed with AcOEt. The filtrate is poured into a saturated solution of sodium hydrogen phosphate, followed by extracting 3 times with 50 ml of AcOEt, washing twice with 50 ml of water, drying, filtering and the solvent is evaporated off under reduced pressure.

The residue is purified by chromatography on silica eluting with a dichloromethane/AcOEt mixture 80/20.

In this way 570 mg of methyl 4-[[[[(1,1-dimethylethoxy) carbonyl]methyl]amino]methyl]-3-furancarboxylate is recovered of molecular formula $C_{13}H_{19}NO_5$ (M=269.30 g).

The corresponding yield is 48%.

Stage D

The operation is carried out as indicated in Stage E of Example 22 with 660 mg (2.45 mmoles) of the product obtained in Stage C and 0.588 g (2.7 mmoles) of $(BOC)_2O$.

In this way 1.01 g of methyl 4-[[[(1,1-dimethylethoxy) carbonyl][[(1,1-dimethylethoxy)carbonyl]methyl]amino] methyl]-3-furancarboxylate is obtained of molecular formula $CO_8H_{27}NO_7$ (M=369.42 g).

The corresponding yield is quantitative.

Stage E

The operation is carried out as indicated in Stage G of Example 22 with 185 mg (0.5 mmoles) of the product obtained in Stage D and 1 ml of a 1M solution of potassium t-butylate in THF.

In this way 150 mg of crystals of bis-(1,1-dimethylethyl) 4,7-dihydro-7-oxo-furo[3,4-c]pyridine-5(6H),6-dicarboxylate is obtained of molecular formula $C_{17}H_{23}NO_6$ (M=337.38 g).

The corresponding yield is 89%.

Stage F

The operation is carried out as indicated in Stage H of Example 22 with 540 mg (1.6 mmoles) of the product obtained in Stage E and 5.4 ml of trifluoroacetic acid.

Secondly, the intermediate product is reacted with 418 mg of $(BOC)_2O$ and 0.67 ml of TEA.

In this way 345 mg of 1,1-dimethylethyl 4,7-dihydro-7-oxo-furo[3,4-c]pyridine-5(6H)-carboxylate is obtained of molecular formula $C_{12}H_{15}NO_4$ (M=237.26 g).

The corresponding yield is 90%.

Stage G

The operation is carried out as indicated in Stage A of Example 6 with 345 mg (1.45 mmoles) of the product obtained in Stage G, and 174 mg of O-allylhydroxylamine hydrochloride.

In this way 320 mg of 1,1-dimethylethyl 4,7-dihydro-7-[(2-propenyloxy)imino]-furo[3,4-c]pyridine-5(6H)-carboxylate is obtained of molecular formula $C_{15}H_{20}N_2O_4$ (M=292.34 g).

The corresponding yield is 75%.

Stage H 118 mg (0.403 mmoles) of the product obtained in Stage H and 1 ml of glacial acetic acid are introduced into a flask placed under a nitrogen atmosphere.

The reaction medium is cooled down to 10° C. and approximately 183 mg of sodium cyanoborohydride is added.

The reaction medium is left to return to ambient temperature and left to react for 5 hours, followed by taking up in 20 ml of AcOEt, pouring into 50 ml of 1N soda, decanting, extracting several times with AcOEt, washing again with 1N soda, then with water then with a solution of sodium chloride.

After drying the aqueous phase over magnesium sulphate and filtering the solvent is evaporated off under reduced pressure.

The residue is purified by chromatography on silica eluting with a dichloromethane/AcOEt mixture 97/3.

In this way 80 mg of 1,1-dimethylethyl 4,7-dihydro-7-[(2-propenyloxy)amino]-furo[3,4-c]pyridine-5(6H)-carboxylate is recovered of molecular formula $C_{15}H_{22}N_2O_4$ (M=294.35 g).

The corresponding yield is 67%.

Stage I

The operation is carried out as indicated in Stages J and K of Example 3 with 180 mg (0.61 mmoles) of the product obtained in Stage I and 1.5 ml of a 5.5 M solution of hydrochloric acid in AcOEt and 1 ml of 2N soda.

In this way 100 mg of N-(2-propenyloxy)-4,5,6,7-tetrahydro-furo[3,4-c]pyridin-7-amine is obtained of molecular formula $C_{10}H_{14}N_2O_2$ (M=194.24 g).

The corresponding yield is 84%.

Stage J

The operation is carried out as indicated in Stage H of Example 20 with 1.037 g (5.38 mmoles) of the product obtained in Stage J, 0.333 ml of diphosgene, 2.222 ml of TEA and 656 mg of DMAP.

In this way 690 mg of 5-(2-propenyloxy)-5,6,7,8-tetrahydro-4,7-methano-4H-furo[3,4-e][1,3]diazepin-6-one is obtained of molecular formula $C_{11}H_{12}N_2O_3$ (M=220.23 g).

The corresponding yield is 58%.

Stage K

The operation is carried out as indicated in Stage C of Example 7 with 310 mg (1.4 mmoles) of the product obtained in Stage K, 0.790 g of $Pd[P(C_6H_5)_3]_4$ catalyst (0.7 mmole) and 0.650 g (4.2 mmoles) of $SO_3$-pyridine complex.

In this way 320 mg of the 1-propenyltriphenylphosphonium salt of 5-(sulphooxy)-5,6,7,8-tetrahydro-4,7-methano-4H-furo[3,4-e][1,3]diazepin-6-one is obtained of molecular formula $C_{29}H_{27}N_2O_6PS$ (M=562.59 g).

The corresponding yield is 41%.

After passing the resin through a column of DOWEX 50WX8 resin in $Na^+$ form 60 mg of the expected sodium salt is recovered, of molecular formula $C_8H_7N_2O_6SNa$ (M=282.21 g).

The corresponding yield in this exchange stage is 70%.

NMR Spectrum of the Proton

In $D_2O$, at 300 MHz, chemical shifts and multiplicity: 3.38 (d) and 3.82 (dd): N—C$\underline{H}_2$—CH; 5.02 (d): N—CH$_2$—C$\underline{H}$; 4.36 and 4.46 (AB): N—C$\underline{H}_2$—C=; 7.35 (bs) and 7.63 (bs): C=C$\underline{H}$—O—C$\underline{H}$=C MS (Negative electrospray) m/z: $[M]^-$=259

Example 34

5-(phenylmethoxy)-2-[2-(phenylthio)ethyl]-5,6,7,8-tetrahydro-4,7-methano-4H-[1,2,3]-triazolo[4,5-e][1,3]diazepin-6(2H)-one Stage A 19.88 g of 1H-1,2,3-triazole-4,5-dicarboxylic acid complexed with 1H-benzotriazole and obtained according to Chem. Heterocycl. Compd. (Engl. Transl.), 17, 510-515, (1981), is introduced into 600 ml of water, 148 ml of 1N soda is added, followed by extracting three times with 600 ml of ethyl acetate each time.

The aqueous phase is acidified by adding 163 ml of 1N aqueous hydrochloric acid (163 mmoles), followed by evaporating to dryness, taking up in 200 ml of toluene, which is then evaporated under vacuum. This operation is repeated twice.

In this way 19.86 g of crude product is obtained.

245 ml of methanol saturated in hydrochloric acid is added to this crude product and agitation is carried out for 20 hours at ambient temperature.

The reaction mixture is diluted with 490 ml of methanol, the suspension is agitated for 10 minutes, followed by filtering, washing three times with 20 ml of methanol.

The solvent is evaporated off under reduced pressure.

A product is obtained which is taken up in 650 ml of AcOEt, followed by washing three times with 100 ml of a saturated aqueous solution of sodium chloride, drying the organic phase over magnesium sulphate, filtering and the solvent is evaporated off under reduced pressure.

A residue is obtained which is recrystallized from toluene.

After drying under reduced pressure, 10.92 g of methyl 1H-1,2,3-triazole-4,5-dicarboxylate is obtained of molecular formula $C_6H_7N_3O_4$ (M=185.41 g).

The corresponding yield is 81.9%.

Stage B 16.9 ml of 2-hydroxyethylphenylsulphide (0.125 moles), 21.21 g (0.114 moles) of the product obtained in Stage B and 672 ml of anhydrous THF are introduced into an equipped flask placed under an argon atmosphere.

Then, 60.11 g (0.209 moles) of triphenylphosphine is added dropwise.

The reaction medium is cooled down to 3.5° C., then 19.6 ml of diethyl azodicarboxylate (125.91 mmoles) is added, then it is left to return to ambient temperature.

The solvent is evaporated off under reduced pressure, then the residue is taken up in 368 ml of dichloromethane, filtered, then the solvent is evaporated off under reduced pressure.

A crude product is obtained to which 200 ml of a dichloromethane/AcOEt mixture 97.5/2.5 is added, followed by filtering to eliminate the precipitate.

The filtrate is purified by chromatography on silica eluting with a dichloromethane/AcOEt mixture 97.5/2.5.

15.07 g of isomer A, dimethyl 1-[2-(phenylthio)ethyl]-1H-1,2,3-triazole-4,5-dicarboxylate and 10.64 g of isomer B of this product, dimethyl 2-[2-(phenylthio)ethyl]-2H-1,2,3-triazole-4,5-dicarboxylate are recovered as well as 5.66 g of a mixture of these two A and B isomers.

The mixture is chromatographed on silica eluting with a dichloromethane/AcOEt mixture 97.5/2.5, in order to also obtain 2.84 g of isomer A and 1.97 g of isomer B.

The total yield of isomer A is therefore 37% and the total yield of isomer B is 46%.

Stage C 17.04 g of the diester B obtained in Stage B in 0.341 ml of methanol, then 55.7 ml of 1N soda are introduced into an equipped flask placed under an argon atmosphere.

The reaction medium is agitated at ambient temperature for 15 ours, then 61.3 ml of 1N hydrochloric acid is added.

The methanol is evaporated off under reduced pressure, then 250 ml of water is added to the residue, followed by extracting with AcOEt, washing with water, then with a saturated aqueous solution of sodium chloride, drying over magnesium sulphate, filtering and the solvent is evaporated off under reduced pressure.

15.97 g of 4-methyl 2-[2-(phenylthio)ethyl]-2H-1,2,3-triazole-4,5-dicarboxylate is obtained of molecular formula $C_{13}H_{13}N_3O_4$ (M=307.33 g).

The corresponding yield is 98%.

Stage D

The operation is carried out as indicated in Stage A of Example 33 with 15.97 g (51.963 mmoles) of the monoester obtained in Stage C, 6.3 ml of N-methyl morpholine and 7.1 ml of isobutyl chloroformate.

In this way 10.39 g of methyl 5-(hydroxymethyl)-2-[2-(phenylthio)ethyl]-2H-1,2,3-triazole-4-carboxylate is obtained of molecular formula $C_{13}H_{15}N_3O_3S$ (M=293.34 g).

The corresponding yield is 68.1%.

Stage E

The operation is carried out as indicated in Stage B of Example 33 with 10.39 g (35.41 mmoles) of the product obtained in Stage D, 14.68 g (44.27 mmoles) of tetrabromomethane and 11.61 g of triphenylphosphine (44.27 mmoles).

In this way 10.04 g of methyl 5-(bromomethyl)-2-[2-(phenylthio)ethyl]-2H-1,2,3-triazole-4-carboxylate is obtained of molecular formula $C_{13}H_{14}N_3O_2SBr$ (M=356.25 g).

The corresponding yield is 79.6%.

Stage F

The operation is carried out as indicated in Stage C of Example 33 with 9.71 g (27.25 mmoles) of the product obtained in Stage E and 7.45 ml (54.51 mmoles) of t-butyl glycinate and replacing the DMF with acetonitrile.

In this way 7.47 g of methyl 5-[[[[(1,1-dimethylethoxy)carbonyl]methyl]amino]methyl]-2-[2-(phenylthio)ethyl]-2H-1,2,3-triazole-4-carboxylate is obtained of molecular formula $C_{19}H_{26}N_4O_4S$ (M=406.50 g).

The corresponding yield is 67.4%.

Stage G

The operation is carried out as indicated in Stage E of Example 22 with 7.57 g (18.62 mmoles) of the product obtained in Stage F and 5.28 g (24.20 mmoles) of $(BOC)_2O$.

In this way 10.66 g of methyl 5-[[[(1,1-dimethylethoxy)carbonyl][[(1,1-dimethylethoxy)carbonyl]methyl]amino]methyl]-2-[2-(phenylthio)ethyl]-2H-1,2,3-triazole-4-carboxylate is obtained of molecular formula $C_{24}H_{34}N_4O_6S$ (M=506.62 g).

The corresponding yield is quantitative.

Stage H

The operation is carried out as indicated in Stage G of Example 22 with 10.66 g (18.62 mmoles) of the product obtained in Stage G and 41 ml of a 1M solution of potassium t-butylate in THF.

In this way 5.35 g of bis(1,1-dimethylethyl)4,7-dihydro-7-oxo-2-[2-(phenylthio)ethyl]-2H-[1,2,3]-triazolo[4,5-c]pyridine-5(6H),6-dicarboxylate is obtained of molecular formula $C_{23}H_{30}N_4O_5S$ (M=474.58 g).

The corresponding yield is 60.5%.

Stage I 5.35 g of the product obtained in Stage H and 54 ml of trifluoroacetic acid are introduced into a flask placed under an argon atmosphere.

After contact for 45 minutes at ambient temperature, the solvent is evaporated off under reduced pressure.

The residue is dissolved in 116 ml of THF, 4.7 ml of TEA, then 2.95 of $(BOC)_2O$ are added.

The medium is left to react at ambient temperature for 1 hour 30 minutes followed by diluting with 700 ml of AcOEt, washing with a 1M aqueous solution of sodium hydrogen phosphate, then with a saturated aqueous solution of sodium chloride, drying the organic phase over magnesium sulphate, filtering and the solvent is evaporated off under reduced pressure.

In this way a crude product is obtained which is purified by chromatography on silica eluting with a dichloromethane/AcOEt mixture 97.5/2.5.

In this way 4.05 g of 1,1-dimethylethyl 4,7-dihydro-7-oxo-2-[2-(phenylthio)ethyl]-2H-[1,2,3]-triazolo[4,5-c]pyridine-5(6H)-carboxylate is obtained of molecular formula $C_{18}H_{22}N_4O_3S$ (M=374.46 g).

The corresponding yield is 95.9%.

Stage J

The operation is carried out as indicated in Stage A of Example 6 with 3.03 g (8.09 mmoles) of the product obtained in Stage I and 1.42 g (8.90 mmole) of O-benzyl-hydroxylamine hydrochloride.

In this way 3.82 g of 1,1-dimethylethyl 4,7-dihydro-7-[(phenylmethoxy)imino]-2-[2-(phenylthio)ethyl]-2H-[1,2,3]-triazolo[4,5-c]pyridine-5(6H)-carboxylate is obtained of molecular formula $C_{25}H_{29}N_5O_3S$ (M=479.60 g).

The corresponding yield is 98.4%.

Stage K

The operation is carried out as indicated in Stage B of Example 6 with 3.82 g (7.96 mmoles) of the product obtained in Stage J, 7.51 g of cyanoborohydride and 12.1 ml of boron trifluoride etherate.

In this way 3.29 g of 1,1-dimethylethyl 4,7-dihydro-7-[(phenylmethoxy)amino]-2-[2-(phenylthio)ethyl]-2H-[1,2,3]-triazolo[4,5-c]pyridine-5(6H)-carboxylate is obtained of molecular formula $C_{25}H_{31}N_5O_3S$ (M=481.62 g).

The corresponding yield is 85.7%.

Stage L

The operation is carried out as indicated in Stages J and K of Example 3 with 3.26 g (6.8 mmoles) of the product obtained in Stage K and 29.7 ml (216.71 mmoles) of 7.3 M hydrochloric acid in AcOEt, then 13.6 ml of soda 1N.

In this way 2.46 g of 4,5,6,7-dihydro-N-(phenylmethoxy)-2-[2-(phenylthio)ethyl]-2H-[1,2,3]-triazolo[4,5-c]pyridin-7-amine is obtained of molecular formula $C_{20}H_{23}N_5O_5$ (M=381.50 g).

The corresponding yield is 95%.

Stage M

The operation is carried out as indicated in Stage H of Example 30 with 2.44 g (6.41 mmoles) of the product obtained in Stage L, 425 µl (3.52 mmoles) of diphosgene, 2.68 ml (19.23 mmoles) of TEA and 783 mg of 4-DMAP.

In this way 1.66 g of 5-(phenylmethoxy)-2-[2-(phenylthio)ethyl]-5,6,7,8-tetrahydro-4,7-methano-4H-[1,2,3]-triazolo[4,5-e][1,3]diazepin-6(2H)-one is recovered of molecular formula $C_{21}H_{21}N_5O_2S$ (M=407.49 g).

The corresponding yield is 63.4%.

1.64 g of the oil obtained is dissolved in a flask placed under an argon atmosphere with 66 ml of dichloromethane.

Then, 2.38 g of 70% metachloroperbenzoic acid is added at ambient temperature, followed by agitating for 1 hour, diluting with 210 ml of AcOEt and pouring the reaction medium into a saturated aqueous solution of sodium bicarbonate, extracting with AcOEt, washing with an aqueous solution of $Na_2S_2O_3$, with a saturated aqueous solution of sodium bicarbonate and with a saturated aqueous solution of sodium chloride.

The organic phase is dried over magnesium sulphate, the solvent is evaporated off under reduced pressure.

The white foam obtained is purified by chromatography on silica eluting with a dichloromethane/methanol mixture 97.5/2.5 containing 0.1% TEA.

In this way 1.32 g of 5-(phenylmethoxy)-2-[2-(phenylsulphonyl)ethyl]-5,6,7,8-tetrahydro-4,7-methano-4H-[1,2,3]-triazolo[4,5-e][1,3]diazepin-6(2H)-one is recovered of molecular formula $C_{21}H_{21}O_4N_5S$ (M=439.496).

The corresponding yield is 74.4%.

NMR Spectrum of the Proton

In $CDCl_3$, at 300 MHz, chemical shifts and multiplicity: 2.90 (d) and 3.59 (dd): N—C$\underline{H_2}$—CH; 4.19 (d): N—CH$_2$—C$\underline{H}$; 3.78 (bt): S—C$\underline{H_2}$—CH$_2$—N; 4.12 and 4.43 (AB): N—C$\underline{H_2}$—C=; 4.73 (m): S—CH$_2$—C$\underline{H_2}$—N; 4.88 and 4.98 (AB): O—C$\underline{H_2}$—C$_6$H$_5$; 7.82 (bd), 7.65 (bt), 7.53 (bt): SO$_2$—C$_6$H$_5$; from 7.34 to 7.46 (m): O—CH$_2$—C$_6\underline{H_5}$ MS (Positive electrospray) m/z: [2M+H]$^+$=879; [M+H+CH$_3$CN]$^+$=481; [M+Na]$^+$=462; [M+H]$^+$=440, 332, 291, 142

Stage N

The operation is carried out as indicated in Stage A of Example 11 with 419 mg (0.953 mmole) of the product obtained in Stage M and 419 mg of Pd/C catalyst at 10% by weight.

303 mg of 5-hydroxy-2-[2-(phenylsulphonyl)ethyl]-5,6,7,8-tetrahydro-4,7-methano-4H-[1,2,3]-triazolo[4,5-e][1,3]diazepin-6(2H)-one is obtained of molecular formula $C_{24}H_{15}N_5O_4S$ (M=349.37 g).

The corresponding yield is 88.7%.

Stage O 303 mg (0.867 mmole) of the product obtained in Stage N is introduced into an equipped flask placed under an argon atmosphere.

After entraining 3 times with toluene, 3.45 ml of pyridine and 414.4 mg (2.60 mmoles) of SO$_3$-pyridine complex are added.

The white suspension obtained is agitated at ambient temperature for 18 hours, then 0.5 ml of water is added, followed by agitating for 5 minutes and evaporating under reduced pressure.

Then the residue is purified by chromatography on silica eluting with a dichloromethane/ethanol mixture 70/30 containing 0.5% TEA.

In this way 377 mg of the triethylammonium salt of 2-[2-(phenylsulphonyl)ethyl]-5-(sulphooxy)-5,6,7,8-tetrahydro-4,7-methano-4H-[1,2,3]-triazolo[4,5-e][1,3]diazepin-6(2H)-one is recovered of molecular formula $C_{20}H_{30}N_6O_7S_2$ (M=530.62 g).

The corresponding yield is 81.8%.

The 377 mg of the salt obtained is dissolved in 3 ml of water containing 10% THF.

The solution obtained is passed through a column of DOWEX 50WX8 resin in Na$^+$ form, eluting with water containing 10% THF.

The product collected is lyophilized in order to obtain 288 mg of the sodium salt of 2-[2-(phenylsulphonyl)ethyl]-5-(sulphooxy)-5,6,7,8-tetrahydro-4,7-methano-4H-[1,2,3]-triazolo[4,5-e][1,3]diazepin-6(2H)-one, of molecular formula $C_{14}H_{14}N_5O_7S_2Na$ (M=451.41 g).

The corresponding yield for this exchange operation is 73.6%.

NMR Spectrum of the Proton

In $D_2O$, at 300 MHz, chemical shifts and multiplicity: 3.22 (d) and 3.86 (dd): N—C$\underline{H_2}$—CH; 4.19(m) and 4.88(m): O—C$\underline{H_2}$—C$\underline{H_2}$—SO$_2$—C$_6$H$_5$; 4.29 (bs): N—C$\underline{H_2}$—C=; 4.96 (d): N—CH$_2$—C$\underline{H}$; 7.58 (m) and 7.72 (m): —SO$_2$—C$_6$$\underline{H_5}$ MS (Negative electrospray) m/z: [M+HCO$_2$H]$^-$=474; [M]$^-$=428

Example 35

Bis(triethylammonium) salt of 5-(sulphooxy)-5,6,7,8-tetrahydro-4,7-methano-4H-[1,2,3]-triazolo[4,5-e][1,3]diazepin-6(1H)-one 97.7 mg (0.216 mmole) of the product obtained in Stage C of Example 36 is dissolved in 2.5 ml of DMF in a flask placed under an argon atmosphere.

The reaction medium is cooled down to −10° C., then 12.4 mg of sodium hydride at 50% in oil is added, then agitation is carried out for 1 hour at −10° C.

Then, 50 μl of acetic acid (0.873 mmoles) is added followed by evaporating to dryness under reduced pressure.

The residue is purified by chromatography on silica, eluting with a dichloromethane/methanol mixture 70/30 containing 0.1% TEA.

In this way 33.6 mg of the expected product is recovered of molecular formula $C_{18}H_{37}N_7O_5$ (M=463.604 g).

The corresponding yield is 42.8%.

NMR Spectrum of the Proton

In $D_2O$, at 300 MHz, chemical shifts and multiplicity: 1.29 (bt): C$\underline{H}_3$—CH$_2$—N; 3.21 (bq): CH$_3$—C$\underline{H}_2$—N; 3.50 (d) and 3.94 (dd): N—C$\underline{H}_2$—CH; 4.60 (bs): N—C$\underline{H}_2$—C=; 5.19 (d): N—CH$_2$—C$\underline{H}$ IR (nujol): 1765, 1695, 1560, 1540 cm$^{-1}$. MS (Negative electrospray) m/z: $[M^{2-}+H]^-=260$

Example 36

Sodium salt of 2-methyl-5-(sulphooxy)-4,5,7,8-tetrahydro-4,7-methano-4H-[1,2,3]-triazolo[4,5-e][1,3]diazepin-6(2H)-one Stage A 1.23 g (2.81 mmole) of the product obtained in Stage N of Example 34 is dissolved in 41 ml of THF in an equipped flask placed under an argon atmosphere.

The solution is cooled down to −40° C., then 3.36 ml of a 1M solution of potassium tbutylate in THF is added.

The reaction medium is agitated at −40° C. for 25 minutes, then poured into a saturated aqueous solution of ammonium chloride, followed by extracting with AcOEt, washing with a 1M aqueous solution of sodium hydrogen phosphate, then with a saturated aqueous solution of sodium chloride.

The organic phase is dried over magnesium sulphate and the solvent is evaporated off under reduced pressure.

The residue is purified by chromatography on silica eluting with a dichloromethane/methanol mixture 95/5.

In this way 623 mg of 5-(phenylmethoxy)-5,6,7,8-tetrahydro-4,7-methano-4H-[1,2,3]-triazolo[4,5-e][1,3]diazepin-6(1H)-one is recovered of molecular formula $C_{13}H_{13}N_5O_2$ (M=271.28 g).

The corresponding yield is 81.8%.

Stage B 200 mg (0.737 mmole) of the product obtained in Stage A is dissolved in 6.7 ml of DMF in a flask placed under an argon atmosphere.

The reaction medium is cooled down to 0° C., then 140 μl of methyl iodide (2.21 mmole), 46 mg of sodium hydride at 50% in the oil are added.

The reaction medium is left under agitation for 1 hour, then poured into a saturated aqueous solution of ammonium chloride, followed by extracting with AcOEt, washing with a 1M aqueous solution of NaH$_2$PO$_4$, then with a saturated aqueous solution of sodium chloride.

The organic phase is dried over magnesium sulphate, followed by filtering, the solvent is evaporated off under reduced pressure.

The residue is purified by chromatography on silica eluting with a dichloromethane/methanol mixture 97.5/2.5.

In this way 82 mg of a first isomer, 2-methyl-5-(phenylmethoxy)-5,6,7,8-tetrahydro-4,7-methano-4H-[1,2,3]-triazolo[4,5-e][1,3]diazepin-6(2H)-one and 57 mg of a mixture of the other two isomers, 1-methyl-5-(phenylmethoxy)-5,6,7,8-tetrahydro-4,7-methano-4H-[1,2,3]-triazolo[4,5-e][1,3]diazepin-6 (1H)-one and 3-methyl-5-(phenylmethoxy)-5,6,7,8-tetrahydro-4,7-methano-4H-[1,2,3]-triazolo[4,5-e][1,3]diazepin-6(3H)-one are recovered.

The corresponding yield for the first isomer is 34%.

The corresponding yield for the mixture of isomers is 24%.

Stage C

The operation is carried out as indicated in Stage A of Example 11 with 73.1 mg (0.256 mmole) of the first isomer obtained in Stage B and 146 mg of Pd/C catalyst at 10% by weight.

In this way 47.5 mg of 5-hydroxy-2-methyl-5,6,7,8-tetrahydro-4,7-methano-4H-[1,2,3]-triazolo[4,5-e][1,3]diazepin-6(2H)-one is obtained of molecular formula $C_7H_9N_5O_2$ (M=195.18 g).

The corresponding yield is 95%.

Stage D

The operation is carried out as indicated in Stages O and P of Example 34 with 47.5 mg (0.2433 mmole) of the product obtained in Stage C, and 116.2 mg (0.730 mmole) of SO$_3$-pyridine complex.

In this way 66.3 mg of triethylammonium salt of 2-methyl-5-(sulphooxy)-5,6,7,8-tetrahydro-4,7-methano-4H-[1,2,3]-triazolo[4,5-e][1,3]diazepin-6(2H)-one is obtained of molecular formula $C_{13}H_{24}N_6O_5S$ (M=376.41 g).

The corresponding yield is 72.4%.

After passing through a column of DOWEX 50WX8 resin in Na$^+$ form, 48.7 mg of the expected sodium salt is obtained of molecular formula $C_7H_8N_5O_5SNa$ (M=297.22 g).

The corresponding yield is 93%.

NMR Spectrum of the Proton

In $D_2O$, at 400 MHz, chemical shifts and multiplicity: 3.51 (d) and 3.94 (dd): N—C$\underline{H}_2$—CH; 4.17 (s): N—CH$_3$; 4.55 (s) N—CH$_2$—C=N; 5.14 (d): N—CH$_2$—C$\underline{H}$ MS (Negative electrospray) m/z: $[M]^-=274$

Example 37

Sodium salt of 1-methyl-5-(sulphooxy)-5,6,7,8-tetrahydro-4,7-methano-4H-[1,2,3]-triazolo[4,5-e][1,3]diazepin-6(1H)-one The operation is carried out as indicated in Stages O and P of Example 34 with 55 mg (0.192 mmole) of the mixture of isomers obtained in Stage B of Example 36 and 110 mg of Pd/C catalyst at 10% by weight and 92 mg (0.578 mmole) of SO$_3$-pyridine complex.

In this way 16.6 mg of a first isomer, the triethylammonium salt of 1-methyl-5-(sulphooxy)-5,6,7,8-tetrahydro-4,7-methano-4H-[1,2,3]-triazolo[4,5-e][1,3]diazepin-6(1H)-one and 17.3 mg of a second isomer, the triethylammonium salt of 3-methyl-5-(sulphooxy)-5,6,7,8-tetrahydro-4,7-methano-4H-[1,2,3]-triazolo[4,5-e][1,3]diazepin-6(3H)-one are obtained.

The corresponding yield of the first isomer is 22.9%.

The corresponding yield of the second isomer is 23.8%.

17.3 mg of the second isomer is dissolved in 3 ml of water containing 10% THF.

The solution obtained is passed through a column of DOWEX 50WX8 resin in $Na^+$ form, eluting with water containing 10% THF.

The product collected is lyophilized in order to obtain 11.3 mg of the expected sodium salt, the sodium salt of 1-methyl-5-(sulphooxy)-5,6,7,8-tetrahydro-4,7-methano-4H-[1,2,3]-triazolo[4,5-e][1,3]diazepin-6(1H)-one, of molecular formula $C_7H_8N_5O_5SNa$ (M=297.22 g).

The corresponding yield is 82.7%.

NMR Spectrum of the Proton

In $D_2O$, at 400 MHz, chemical shifts and multiplicity: 3.41 (d) and 3.91 (dd): N—C$\underline{H}_2$—CH; 3.97 (s): N—CH$_3$; 4.61 (s): N—CH$_2$—C=; 5.15 (d): N—CH$_2$—C$\underline{H}$ MS (Negative electrospray) m/z: $[2M+Na]^-$=571; $[M]^-$=274

Example 38

Sodium salt of 3-methyl-5-(sulphooxy)-5,6,7,8-tetrahydro-4,7-methano-4H-[1,2,3]-triazolo[4,5-e][1,3]diazepin-6(3H)-one 16.6 mg of the first isomer obtained in Stage B of Example 37 is dissolved in 1 ml of water containing 10% THF.

The solution obtained is passed through a column of DOWEX 50WX8 resin in $Na^+$ form, eluting with water containing 10% THF.

The product collected is lyophilized in order to obtain 11.9 mg of the expected sodium salt, of molecular formula $C_7H_8N_5O_5SNa$ (M=297.22 g).

The corresponding yield is 90.8%.

NMR Spectrum of the Proton

In $D_2O$, at 400 MHz, chemical shifts and multiplicity: 3.48 (d) and 3.93 (dd): N—C$\underline{H}_2$—CH; 4.11 (s): N—CH$_3$; 4.56 [AB]: N—CH$_2$—C=; 5.34 (d): N—CH$_2$—C$\underline{H}$; MS (Negative electrospray) m/z: $[2M+Na]^-$=571; $[M]^-$=274

Example 39

Trans ethyl 1,2,3,5-tetrahydro-3-oxo-2-(phenylmethoxy)-8-(2-propenyloxy)-1,4-methano-4H-2,4-benzodiazepine-5-carboxylate Stage A Step 1

51.72 g of a 50% solution of ethyl glyoxalate in toluene is introduced hot into a solution of 48 g (0.253 mole) of D,L-Norphenylephrine hydrochloride in 94 ml of methanol heated to reflux.

After 30 minutes under reflux, the hydrochloride of the expected product precipitates. The suspension is left under reflux for a further 30 minutes before being cooled down by an ice bath in order to crystallize the expected hydrochloride.

After adding 50 ml of ether, the precipitate is filtered, washed with ether to produce 46 g of ethyl 1,2,3,4-tetrahydro-4,6-dihydroxy-1-isoquinolinecarboxylate.

Step 2

25 ml of TEA is added to a suspension cooled down to 0° C. of 44 g (0.160 mole) of the compound obtained in the previous step in 500 ml of THF. Then after the appearance of the suspension changes, 38.7 g (0.177 mole) of $(BOC)_2O$ is added.

Agitation is carried out for 2 hours at 20° C. before the reaction medium is poured into a 10% aqueous solution of sodium hydrogen sulphate.

After extraction with THF and with ethyl acetate, the organic phase is washed again with a first solution of sodium hydrogen sulphate then with a second 1 molar solution of sodium dihydrogen phosphate. The organic phase is dried over magnesium sulphate then filtered and the solvent is evaporated off under reduced pressure in order to obtain 60.2 g of 2-(1,1-dimethylethyl) and 1-ethyl 3,4-dihydro-4,6-dihydroxy-1,2(1H)-isoquinolinedicarboxylate of molecular formula $C_{17}H_{23}NO_6$ is obtained (M=337.38 g).

Stage B 60 g (1.177 mole) of the compound obtained in Stage A is introduced into 600 ml of acetone. Then 49.4 g of potassium carbonate is added followed by 29 ml of allyl bromide dropwise. The reaction medium is heated under reflux for 2 hours 30 minutes then the salts are filtered, and the acetone is evaporated off.

The residue is dissolved in a heptane/ACOEt mixture. The organic phase is then washed with a saturated solution of sodium bicarbonate, dried over magnesium sulphate, then the solvent is evaporated off under reduced pressure.

66 g of 2-(1,1-dimethylethyl) and 1-ethyl 3,4-dihydro-4-hydroxy-6-(2-propenyloxy)-1,2(1H)-isoquinolinedicarboxylate of molecular formula $C_{20}H_{27}NO_6$ is obtained (M=377.44 g).

The corresponding yield is 98%.

Stage C 57.5 g of pyridinium chlorochromate and 120 g of molecular sieve are introduced into 1 liter of dichloromethane. Then a solution of 65.5 g (0.178 mole) of the compound obtained in Stage B in 300 ml of dichloromethane is introduced at 0° C.

The solution is agitated for 1 hour 30 minutes while allowing it to return to ambient temperature then it is filtered on 1 kg of Florisil eluting with dichloromethane.

After evaporation of the solvent under reduced pressure 49.92 g of 2-(1,1-dimethylethyl) and 1-ethyl 3,4-dihydro-4-oxo-6-(2-propenyloxy)-1,2(1H)-isoquinolinedicarboxylate of molecular formula $C_{20}H_{25}NO_6$ is obtained (M=375.40 g).

The corresponding yield is 78%.

Stage D 49.9 g of the compound obtained in Stage C is introduced into 500 ml of pyridine then 23.3 g of $PhCH_2ONH_2$, HCl is added and the reaction medium is agitated for 1 hour.

The solvent is evaporated off under reduced pressure then the residue is dissolved in a solvent mixture of heptane/ACOEt-1/2

The organic phase is washed 3 times with a 10% solution of sodium hydrogen sulphate then dried over magnesium sulphate.

57 g of 2-(1,1-dimethylethyl) and 1-ethyl 3,4-dihydro-4-[(phenylmethoxy)-imino]-6-(2-propenyloxy)-1,2(1H)-isoquinolinedicarboxylate of molecular formula $C_{27}H_{32}N_2O_6$ is obtained in the form of an oil (M=480.57 g).

The corresponding yield is 89%.

Stage E

The process is carried out as indicated in H of Example 33 with 56 g of the product obtained in Stage D, 44 g sodium cyanoborohydride and 500 ml of glacial acetic acid.

22 g of 2-(1,1-dimethylethyl) and 1-ethyl 3,4-dihydro-4-[(phenylmethoxy)amino]-6-(2-propenyloxy)-1,2(1H)-isoquinolinedicarboxylate of molecular formula $C_{27}H_{34}N_2O_6$ is obtained (M=482.58 g).

The corresponding yield is 40%.

Stage F 22 of the product obtained in Stage E is dissolved in 22 ml of ethyl acetate at 0° C. then 95 ml of a 4.59M solution of hydrochloric acid in ACOEt is added.

Agitation is carried out for 1 hour at 20° C. then the crystals obtained are filtered.

The crystals obtained are then introduced into 180 ml of dichloromethane and 45 ml of 2N soda is added.

After agitation for 45 minutes at 20° C., decanting is carried out then the organic phase is dried over magnesium sulphate.

Then after evaporation of the solvent under reduced pressure 16.5 g of ethyl 1,2,3,4-tetrahydro-4-[(phenylmethoxy)amino]-6-(2-propenyloxy)-1-isoquinoline carboxylate of molecular formula $C_{22}H_{26}N_2O_4$ is obtained (M=382.46 g).

The corresponding yield is quantitative.

Stage G 16.4 g (0.043 mole) of the product obtained in Stage F is introduced into 3.5 liters of ethyl acetate then 14.2 ml of TEA is added at 0° C. and finally 4.2 g of diphosgene is added dropwise.

The reaction medium is agitated for 3 hours at 20° C. then the ethyl acetate is evaporated off and dichloromethane is added.

The organic phase is washed with a 10% solution of sodium sulphate then dried over magnesium sulphate and finally the solvent is evaporated off under reduced pressure.

The residue obtained is solubilized in 500 ml of dichloromethane then isomerized by agitation in the presence of 1 equivalent of DBU for 1 hour.

The crude product obtained is purified by chromatography on a silica column eluting with a mixture of heptane/ethyl acetate—1/1.

3.5 g of trans ethyl 1,2,3,5-tetrahydro-3-oxo-2-(phenylmethoxy)-8-(2-propenyloxy)-1,4-methano-4H-2,4-benzodiazepine-5-carboxylate of molecular formula $C_{23}H_{24}N_2O_5$ is obtained (M=408 g).

The corresponding yield is 20%.

NMR Spectrum of the Proton

In CDCl$_3$, at 300 MHz, chemical shift and multiplicity: 1.31(t): C$\underline{H}_3$—CH$_2$—O; 4.25(m): CH$_3$—C$\underline{H}_2$—O; 3.47(dd) and 3.63(d): N—C$\underline{H}_2$—CH; 3.68(d): N—CH$_2$—C$\underline{H}$; 4.50 (dt): O—C$\underline{H}_2$—CH; 4.93(AB): O—CH$_2$-Ph; 5.03 (s): N—CH—O; 5.30(qd) and 5.40(qd): C$\underline{H}_2$=CH; 6.03(m); CH$_2$=C$\underline{H}$; 6.53(d) and 6.84(dd): aromatic H$_2$'s and H$_6$'s in ortho position of C—O—; 7.27(m): H$_5$ in meta position of C—O— and 7.44(m): aromatic H of O—CH$_2$-Ph MS (positive electrospray) m/z: [MH]$^+$=409, [MNa]$^+$=431. IR (CHCl$_3$): 1755, 1746, 1649, 1617, 1611, 1573, 1495 cm$^{-1}$ Example 40

Sodium salt of trans ethyl 1,2,3,5-tetrahydro-3-oxo-8-propoxy-2-(sulphooxy)-1,4-methano-4H-2,4-benzodiazepine-5-carboxylate Stage A The process is carried out as indicated in Stage A of Example 11 with 0.15 g of the product obtained in Example 39, 35 mg of Pd/C at 10% by weight and 3 ml of ethanol.

0.12 g of ethyl 1,2,3,5-tetrahydro-2-hydroxy-3-oxo-8-propoxy-1,4-methano-4H-2,4-benzodiazepine-5-carboxylate of molecular formula $C_{16}H_2ON_2O_5$ is obtained (M=320.35 g).

The yield is quantitative.

Stage B

The process is carried out as indicated in Stage B of Example 11 with 0.12 g of the product obtained in the previous step A and 0.172 g of SO$_3$-pyridine complex and 1.5 ml of pyridine.

0.106 g of the sodium salt of trans ethyl 1,2,3,5-tetrahydro-3-oxo-8-propoxy-2-(sulphooxy)-1,4-methano-4H-2,4-benzodiazepine-5-carboxylate of molecular formula $C_{16}H_{19}N_2O_8S.Na$ is obtained (M=436.42 g).

The corresponding yield is 93%.

NMR Spectrum of the Proton

In DMSO-d$_6$, at 300 MHz, chemical shifts and multiplicity: 0.97(t): C$\underline{H}_3$—CH$_2$—CH$_2$—O—C=; 1.73(m): CH$_3$—C$\underline{H}_2$—CH$_2$—O—C=; 3.91(t): CH$_3$—CH$_2$—C$\underline{H}_2$—O—C=; 1.24(t): C$\underline{H}_3$—CH$_2$—O—C=; 4.20(q): CH$_3$—C$\underline{H}_2$—O—C=; 3.51(m): N—C$\underline{H}_2$—CH—N; 4.63 (d) N—CH$_2$—C$\underline{H}$(—N)(C=); 4.92(s): =C—C$\underline{H}$(N—)(—C=); 6.67(d) and 6.94(dd): aromatic H$_2$ and H6 in ortho position of C—O; 7.23(d): aromatic H$_5$ in meta position of C—O. MS (negative electrospray) m/z: (2M+Na)$^-$=821.3; M$^-$=399.1 IR (CHCl$_3$): 1745, 1611.1575, 1499 cm$^{-1}$ Example 41

Sodium salt of trans-1,2,3,5-tetrahydro-8-[(2-methoxyethoxy)methoxy]-3-oxo-2-(sulphooxy)-1,4-methano-4H-2,4-benzodiazepine-5-carboxamide Stage A 3.5 g of the product obtained in Example 39 is dissolved in 35 ml of toluene. 0.191 g of Pd(PPh$_3$)$_4$ followed by 0.52 g of acetic acid and finally dropwise 2.89 g of Bu$_3$SnH are introduced under argon at OC.

The reaction medium is agitated for 45 minutes at 0° C. then the solvent is evaporated off under reduced pressure and the residue is purified by chromatography on silica with a heptane/AcOEt mixture 1/1.

2.92 g of ethyl 1,2,3,5-tetrahydro-3-oxo-8-hydroxy-2-(phenylmethoxy)-1,4-methano-4H-2,4-benzodiazepine-5-carboxylate of molecular formula $C_{20}H_{20}N_2O_5$ (M=368 g) is obtained in the form of white crystals. The corresponding yield is 96%.

Stage B 3.68 g of the product obtained in Stage A is dissolved in 40 ml of dichloromethane then 2.72 g of ClMEM and dropwise 2.84 g of DIEA are added.

The reaction medium is agitated for 1 hour at 0° C. then into water and then the organic phase is washed with a 1 molar solution of sodium dihydrogen phosphate.

The extracted organic phase is then evaporated under reduced pressure then the residue is purified on silica eluting with a dichloromethane solution with 5% acetone.

2.8 g of ethyl 1,2,3,5-tetrahydro-8-[(2-methoxyethoxy) methoxy]-3-oxo-2-(phenylmethoxy)-1,4-methano-4H-2,4-benzodiazepine-5-carboxylate of molecular formula $C_{24}H_{28}N_2O_7$ is obtained (M=456.50 g).

The corresponding yield is 63%.

Stage C 2.8 g (0.0061 mole) of the product obtained in Stage B is dissolved in 30 ml of dioxane and 30 ml of water then 6.13 ml of N soda is added dropwise without exceeding 15° C.

The solution is agitated for 45 minutes then 15 ml of water is added and the basic organic phase is extracted with 100 ml of ethyl acetate.

The aqueous phase is acidified to pH=4, then the organic phase is extracted with 5×100 ml of AcOEt.

The solvent is evaporated off under reduced pressure and 2.18 g of 1,2,3,5-tetrahydro-8-[(2-methoxyethoxy)methoxy]-3-oxo-2-(phenylmethoxy)-1,4-methano-4H-2,4-benzodiazepine-5-carboxylic acid of formula $C_{22}H_{24}N_2O_0$ is obtained (M=428.45 g).

The corresponding yield is 86%.

Stage D

The process is carried out as in Stage B of Example 10 with 1.83 g (4.27 mmoles) of the product obtained in the previous Stage C, 2.71 g of BOP, 0.865 g of HOBt, 0.456 g of $NH_4Cl$, 2.97 ml of DIEA and 30 ml of DMF.

1.22 g of 1,2,3,5-tetrahydro-8-[(2-methoxyethoxy)methoxy]-3-oxo-2-(phenylmethoxy)-1,4-methano-4H-2,4-benzodiazepine-5-carboxamide of formula $C_{22}H_{25}N_3O_6$ is obtained (M=427.46 g).

The corresponding yield is 67%.

Stage E

The process is carried out as in Stage A of Example 11 with 0.15 g of the product obtained in the previous Stage D with 20 mg of Pd/C to 10% by weight and 2 ml of acetic acid.

0.12 g of 1,2,3,5-tetrahydro-2-hydroxy-8-[(2-methoxyethoxy)methoxy]-3-oxo-1,4-methano-4H-2,4-benzodiazepine-5-carboxamide of molecular formula $C_{15}H_{19}N_3O_6$ (M=337.34 g) is obtained in the form of white crystals.

The yield is quantitative.

Stage F

The process is carried out as in Stage B of Example 11 with 0.12 g of the product obtained in the previous Stage E, 0.170 g of $SO_3$-pyridine complex and 1.5 ml of pyridine.

0.12 g of the sodium salt of trans-1,2,3,5-tetrahydro-8-[(2-methoxyethoxy)methoxy]-3-oxo-2-(sulphooxy)-1,4-methano-4H-2,4-benzodiazepine-5-carboxamide of molecular formula $C_{15}H_{18}N_3O_9S.Na$ is obtained in the form of a beige powder.

The corresponding yield is 78. %.

NMR Spectrum of the Proton.

In DMSO $d_6$, at 300 MHz, chemical shifts and multiplicity: 3.23(s): C$\underline{H}_3$—O—$(CH_2)_2$—O—$CH_2$—O—; 3.46(m) and 3.72(m): $CH_3$—O—(C$\underline{H}_2)_2$—O—$CH_2$—O—; 5.23(se): $CH_3$—O—$(CH_2)_2$—O—C$\underline{H}_2$—O—; 3.42(dd) and 3.74(m): N—C$\underline{H}_2$—CH—N; 4.59(d) N—$CH_2$—C$\underline{H}$—N; 6.76(d) and 7.01(dd), aromatic $H_2$ and H6 in ortho position of C—O; 7.17(d): aromatic $H_5$ in meta position of C—O; 7.41 and 7.88 N$\underline{H}_2$—C(=O)CH; 4.74(s): $NH_2$—C(=O)C$\underline{H}$. MS (negative electrospray) m/z: $M^-$=416.1.

Example 42

Triethylammonium salt of trans-1,2,3,5-tetrahydro-8-hydroxy-3-oxo-2-(sulphoxy)-1,4-methano-4H-2,4-benzodiazepine-5-carboxamide 90 mg of the product obtained in Example 41 is dissolved in 2 ml of a dichloromethane/trifluoroacetic acid mixture 1/1 containing 0.4 ml of anisole.

Agitation is carried out for 30 minutes at 20° C. then toluene is introduced and the solvent is evaporated off under reduced pressure.

The residue, taken up in ether in order to eliminate the anisole, crystallizes in the form of green crystals, followed by purifying on a 0.5 mm silica plate eluting with a dichloromethane/methanol mixture 70/30 and 0.1% triethylamine.

20 mg of the triethylammonium salt of trans-1,2,3,5-tetrahydro-8-hydroxy-3-oxo-2-(sulphoxy)-1,4-methano-4H-2,4-benzodiazepine-5-carboxamide of molecular formula $C_{11}H_{10}N_3O_7S.C_6H_{16}N$ is obtained (M=328 g).

The corresponding yield is 30%

NMR Spectrum of the Proton.

In DMSO $d_6$, at 300 MHz, chemical shifts and multiplicity: 3.38(m) and 3.75(d): N—C$\underline{H}_2$—CH—N; 4.50(d) N—$CH_2$—C$\underline{H}$—N; 4.67(s): C$\underline{H}$—C(=O)—$NH_2$; 7.36(bs) and 7.83(bs): CH—C(=O)—N$\underline{H}_2$ 6.55(d) and 6.71(dd): aromatic $H_2$ and H6 in ortho position of C—O; 7.03 (d): aromatic $H_5$ in meta position of C—O; 9.52 (s) Ph-OH MS (negative electrospray) m/z: $(2M^-+Na)^-$=678.9, $M^-$=328.1.

Example 43

Sodium salt of trans-7-(acetylamino)-1,2,3,5-tetrahydro-8-hydroxy-3-oxo-2-(sulphooxy)-1,4-methano-4H-2,4-benzodiazepine-5-carboxamide Stage A 3.69 g of the product obtained in Stage A of Example 41 is dissolved in 40 ml of ethanol and 40 ml of dichloromethane.

This solution is added to a solution containing 0.84 g of $NaNO_3$ in 12 ml of water and 7.9 ml of concentrated hydrochloric acid.

After adding 200 µl of $Ac_2O$, agitation is carried out for 5 hours at 20° C.

The reaction medium is diluted with methylene chloride and a 1M solution of $NaH_2PO_4$ then after decanting, the organic phase is dried over magnesium sulphate. The solvent is evaporated off under reduced pressure then the expected isomer crystallizes from an ether/dichloromethane mixture 1/1.

1.24 g of ethyl 1,2,3,5-tetrahydro-8-hydroxy-7-nitro-3-oxo-2-(phenylmethoxy)-1,4-methano-4H-2,4-benzodiazepine-5-carboxylate of molecular formula $C_{20}H_{19}N_3O_7$ is obtained (M=413 g).

The corresponding yield is 30%.

Stage B

The process is carried out as in Stage B of Example 41 with 0.71 g of the product obtained in the previous Stage A, 0.218 ml of ClMEM, 0.313 ml of DIEA and 12 ml of dichloromethane.

0.88 g of ethyl 1,2,3,5-tetrahydro-8-[(2-methoxyethoxy)methoxy]-7-nitro-3-oxo-2-(phenylmethoxy)-1,4-methano-4H-2,4-benzodiazepine-5-carboxylate of molecular formula $C_{24}H_{27}N_3O_9$ is obtained (M=501 g).

The corresponding yield is quantitative.

Stage C

The process is carried out as in Stage A of Example 7 with 0.88 g of the product obtained in the previous Stage B, 1.8 ml of 1N soda, 25 ml of a dioxane/water mixture 15 ml/10 ml.

0.688 g of 1,2,3,5-tetrahydro-8-[(2-methoxyethoxy)methoxy]-7-nitro-3-oxo-2-(phenylmethoxy)-1,4-methano-4H-2,4-benzodiazepine-5-carboxylic acid of molecular formula $C_{22}H_{23}N_3O_9$ is obtained (M=473 g).

Stage D

The process is carried out as in Stage C of Example 10 with 0.68 g of the product obtained in the previous Stage C, 0.911 g of BOP, 0.28 g of HOBT and 0.153 of $NH_4Cl$ and 0.995 ml of DIEA.

0.290 g of 1,2,3,5-tetrahydro-8-[(2-methoxyethoxy)methoxy]-7-nitro-3-oxo-2-(phenylmethoxy)-1,4-methano-4H-2,4-benzodiazepine-5-carboxyamide, of molecular formula $C_{22}H_{24}N_4O_8$, is obtained (M=472 g) is obtained in the form of yellow crystals.

Stage E 0.265 g (0.56 mmole) of the product obtained in the previous Stage D is dissolved in 6.5 ml of an ethanol/water mixture 4:1. The reaction medium is heated to 60° C. then 0.66 g of sodium dithionite is added, followed by heating at 60° C. for 45 minutes. Then the solution is poured into $H_2O$ followed by extracting several times with ethyl acetate saturating the aqueous phase with NaCl.

Drying is carried out over magnesium sulphate, and the solvent is evaporated off under reduced pressure. 0.125 g of 7-amino-1,2,3,5-tetrahydro-8-[(2-methoxyethoxy)methoxy]-3-oxo-2-(phenylmethoxy)-1,4-methano-4H-2,4-benzodiazepine-5-carboxamide, of molecular formula $C_{23}H_{28}N_3O_6$ is obtained (M=442 g), is obtained in the form of white crystals.

Stage F 80 mg of the product obtained in the previous Stage E is dissolved in pyridine then 8 mg of DMAP and at 0° C. an equivalent of acetic anhydride are added followed by agitation for 30 minutes. Then the pyridine is evaporated under reduced pressure and the residue is solubilized in an ethyl acetate/THF mixture. The solution is washed with a 1M solution of $NH_2PO_4$ then the latter is dried over $MgSO_4$ before being evaporated under reduced pressure. The crude product is impasted in ether.

88 mg of 7-(acetylamino)-1,2,3,5-tetrahydro-8-[(2-methoxyethoxy)methoxy]-3-oxo-2-(phenylmethoxy)-1,4-methano-4H-2,4-benzodiazepine-5-carboxamide, of molecular formula $C_{24}H_{28}N_4O_7$ (M=484 g) is obtained in the form of white crystals.

The corresponding yield is quantitative.

Stage G

The process is carried out as in Stage A of Example 11 with 88 mg of the product obtained in the previous Stage E, 20 mg of palladium on carbon at 10% by weight and with 2 ml of acetic acid.

7-(acetylamino)-1,2,3,5-tetrahydro-2-hydroxy-8-[(2-methoxyethoxy)methoxy]-3-oxo-1,4-methano-4H-2,4-benzodiazepine-5-carboxamide is obtained, of molecular formula $C_{17}H_{22}N_4O_7$ (M=394 g).

Stage H

The process is carried out as in Stage B of Example 11 with 65 mg of the product obtained in the previous Stage G, 1.5 ml of pyridine, 80 mg of the pyridine-$SO_3$ complex.

61 mg of the sodium salt of 7-(acëtylamino)-1,2,3,5-tëtrahydro-8[(2-mëthoxyëthoxy)mëthoxy]-3-oxo-2-(sulphooxy)-1,4-mëthano-4H-2,4-benzodiazëpine-5 carboxamide, of molecular formula $C_{17}H_{21}N_4O_{10}S.Na$ (M=473 g, M=496 g) is obtained in the form of pale yellow crystals.

The corresponding yield is 75.

Stage I

The process is carried out as indicated in Example 42 with 60 mg of the product obtained in the previous Stage H, and with 0.4 ml of anisole, 1 ml of trifluoroacetic acid and 1 ml of dichloromethane.

40 mg of the sodium salt of trans-7-(acetylamino)-1,2,3,5-tetrahydro-8-hydroxy-3-oxo-2-(sulphooxy)-1,4-methano-4H-2,4-benzodiazepine-5-carboxamide, of molecular formula $C_{13}H_{13}N_4O_8S.Na$ is obtained (M=409 g).

The corresponding yield is 81%.

NMR Spectrum of the Proton

In DMSO-$d_6$ at 300 MHz, chemical shifts and multiplicity: 3.35 (m) and 3.85 (d): N—C$\underline{H}_2$—CH; 4.50 (d): N—CH$_2$—C$\underline{H}$; 4.67 (s): C$\underline{H}$—C═O—NH$_2$; 7.36 (se) and 7.89 (se): CH═CO═N$\underline{H}_2$; 2.07 (se): C$\underline{H}_3$C═ON; 6.65 (s) and 7.63 (s) for the aromatic H's; 9.26 (s) and 9.94 (s): N$\underline{H}$—C═O and φ—OH. MS (negative electrospray) m/z M$^-$=385 g; 2 M$^-$+Na (−)=793 g.

Example 44

Sodium salt of 1,1-dimethylethyl 4,5,6,8-tetrahydro-6-oxo-5-(sulphooxy)-1H-4,7-methanoimidazo[4,5-e][1,3]diazepine-1-caraboxylate Stage A 20 g of ethyl 1H-imidazole-4,5-dicarboxylate, 26 g of $K_2CO_3$, 42.4 g of NaI are solubilized in 100 ml of DMF then 27.6 ml of 2-chloroethyl phenyl sulphide is added dropwise. The solution is then heated to 60° C. and left to react overnight.

Extraction is carried out with an ethyl acetate/heptane mixture 2:1 and phosphate. Then the organic phase is washed and dried over magnesium sulphate. After filtration, the solvent is evaporated off under reduced pressure and the reaction medium is purified on silica eluting with a heptane/ethyl acetate mixture 1:1. After evaporation of the solvent, 29.84 g of diethyl 1-[2-(phenylthio)ethyl]-1H-imidazole-4,5-dicarboxylate, of molecular formula $C_{17}H_{20}N_2O_4S$ is obtained (M=348.42 g).

The corresponding yield is 91%.

Stage B

The process is carried out as indicated in Stage C of Example 34 with 33.84 g (0.0971 mole) of the product obtained in the previous Stage A, 102 ml of soda and 280 ml of ethanol. 23 g of a mixture of the 4-ethyl 1-[2-(phenylthio)ethyl]-1H-imidazole-4,5-dicarboxylate and 5-ethyl 1-[2-(phenylthio)ethyl]-1H-imidazole-4,5-dicarboxylate compounds, of molecular formula $C_{15}H_{16}N_2O_4S$ is obtained (M=320.37 g).

The yield is 93%.

Stage C

The process is carried out as indicated in Stage A of Example 33 with 10.1 g (0.031 mole) of the compound obtained in the previous Stage B with 0.902 g of N-methyl morpholine, 4.52 g of isobutyl chloroformate, 3.5 g of sodium borohydride, 60 ml of methanol and 170 ml of THF.

10.5 g of ethyl 5-(hydroxymethyl)-1-[2-(phenylthio)ethyl]-1H-imidazole-4-carboxylate, of molecular formula $C_{15}H_{20}N_2O_3S$ is obtained (M=308.40 g).

The yield is quantitative.

Stage D

The process is carried out as indicated in Stage C of Example 22 with 18.1 g of the product obtained in the previous Stage C, 21.7 ml of $SOCl_2$ and 300 ml of chloroform.

23.5 g of ethyl 5-(chloromethyl)-1-[2-(phenylthio)ethyl]-1H-imidazole-4-carboxylate, of formula $C_{15}H_{19}ClN_2O_2S$ (M=326.85 g) is obtained in the form of white crystals.

The yield is quantitative.

Stage E

The process is carried out as indicated in Stage C of Example 33 with 23 g (63.66 mmoles) of the compound obtained in the previous Stage C, with 35.4 g of $K_2CO_3$, 17.4 ml of tert-butyl glycinate with 250 ml of acetonitrile.

29 g of ethyl 5-[[[2-(1,1-dimethylethoxy)-2-oxoethyl]amino]methyl]-1-[2-(phenylthio)ethyl]-1H-imidazole-4-carboxylate, of molecular formula $C_{21}H_{31}N_3O_4S$ (M=421.56 g) is obtained in the form of an oil.

The yield is quantitative.

Stage F

The process is carried out as indicated in Stage E of Example 22, with 29 g of the compound obtained in the previous Stage E, 16.5 g of $(BOC)_2O$ and 300 ml of THF.

20.8 g of ethyl 5-[[[(1,1-dimethylethoxy)carbonyl][2-(1,1-dimethylethoxy)-2-oxoethyl]amino]methyl]-1-[2-(phenylthio)ethyl]-1H-imidazole-4-carboxylate, of molecular formula $C_{26}H_{39}N_3O_{10}S$ (M=521.68 g) is obtained in the form of an oil.

Stage G

The process is carried out as indicated in Stage G of Example 22, with 20.2 g of the product obtained in the previous Stage F, two equivalents of potassium tert-butylate and 400 ml of THF.

13.9 g of bis(1,1-dimethylethyl)3,4,6,7-tetrahydro-7-oxo-3-[2-(phenylthio)ethyl]-5H-imidazo[4,5-c]pyridine-5,6-dicarboxylate, of molecular formula $C_{24}H_{31}N_3O_5S$ (M=473.60 g) is obtained in the form of white crystals.

The corresponding yield is 76%.

Stage H

The process is carried out as indicated in Stage H of Example 22, with 13.9 g (0.029 mole) of the compound obtained in the previous Stage G and with 140 ml of trifluoroacetic acid, 7.58 g of $(BOC)_2O$, 12.4 ml of triethylamine and 300 ml of toluene and 130 ml of tetrahydrofuran.

10.5 g of 1,1-dimethylethyl 3,4,6,7-tetrahydro-7-oxo-3-[2-(phenylthio)ethyl]-5H-imidazo[4,5-c]pyridine-5,6-carboxylate, of molecular formula $C_{19}H_{23}N_3O_3S$ (M=373.48 g) is obtained in the form of beige crystals.

The corresponding yield is 96%.

Stage I

The process is carried out as indicated in Stage A of Example 6 with 10.4 g (0.0278 mole) of the product obtained in the previous Stage H and with 30 ml of pyridine and 4.88 g of 2-O-benzylhydroxylamine hydrochloride.

11.1 g of 1,1-dimethylethyl 3,4,6,7-tetrahydro-7-[(phenylmethoxy)imino]-3-[2-(phenylthio)ethyl]-5H-imidazo[4,5-c]pyridine-5-carboxylate, of molecular formula $C_{26}H_{30}N_4O_3S$ (M=478.62 g) is obtained in the form of white crystals.

The corresponding yield is 84%.

Stage J

The process is carried out as indicated in Stage J of Example 22 with 11 g of the product obtained in the previous Stage I, 2.1 g of sodium cyanoborohydride, 30 ml of acetic acid.

9.5 g of 1,1-dimethylethyl 3,4,6,7-tetrahydro-7-[(phenylmethoxy)amino]-3-[2-(phenylthio)ethyl]-5H-imidazo[4,5-c]pyridine-5-carboxylate of molecular formula $C_{26}H_{32}N_4O_3S$ (M 480.63 g) is obtained in the form of an oil.

The yield is 82%.

Stage K 9.5 g of the product obtained in the previous Stage J is dissolved in 20 ml of ethyl acetate at 0° C. then 46 ml of a 4.3 M solution of hydrochloric acid in ethyl acetate is added. Agitation is carried out for 45 minutes at 20° C. followed by cooling down to 0° C. The precipitate obtained is filtered rapidly then washed with ether and dried under vacuum under $P_2O_5$.

8.33 g of 4,5,6,7-tetrahydro-7-[(phenylmethoxy)amino]-3-[2-(phenylthio)ethyl]-3H-imidazo[4,5-c]pyridine hydrochloride, of molecular formula $C_{21}H_{24}N_4OS$ (M=417.02 g) is obtained in the form of white crystals.

The yield is quantitative.

Stage L 8.1 g (0.018 mole) of the product obtained in the previous Stage K is dissolved in 1.7 liters of acetonitrile then 9 ml of triethylamine is added at 0° C. Then 1.75 ml of diphosphogene is added dropwise. Then agitation is carried out for two hours at ambient temperature. Then, two equivalents of triethylamine are added and the solution is agitated for 45 minutes. Then the solvent is evaporated off under reduced pressure, the residue is solubilized in dichloromethane containing 6% methanol. Then the organic phase is washed with a solution of $NaH_2PO_4$ 1M. The organic phase is dried over $MgSO_4$ and the solvent is evaporated off under reduced pressure.

A residue is obtained which is purified on silica eluting with a mixture of toluene/isopropyl alcohol at 20%. Then, the solvents are evaporated off under reduced pressure and the gum is crystallized from an ethyl acetate/ether mixture.

1.5 g of 1,4,5,8-tetrahydro-5-(phenylmethoxy)-1-[2-(phenylthio)ethyl]-6H-4,7-methanoimidazo[4,5-e][1.3]diazepin-6-one, of molecular formula $C_{22}H_{22}N_4O_2S$ (M=406.51 g) is obtained in the form of crystals.

The yield is 20%.

Stage M 1.5 g of the product obtained in Stage L is dissolved in dichloromethane. Then 1.85 g of methachloroperbenzoic acid is added at ambient temperature and the solution is agitated for 3 hours. After adding 50 ml of dichloromethane to the solution, the latter is washed with an aqueous solution of sodium bisulphite, then $NaHCO_3$. The organic phase is dried over magnesium sulphate and the solvent is evaporated under reduced pressure. The crude product is purified on silica eluting with a mixture of dichloromethane at 3% in methanol.

1.33 g of 1,4,5,8-tetrahydro-5-(phenylmethoxy)-1-[2-(phenylsulphonyl)ethyl]-6H-4,7-methanoimidazo[4,5-e][1,3]diazepin-6-one, of molecular formula $C_{22}H_{22}N_4O_4S$ (M=438.51 g) is obtained in the form of a white crystalline foam.

The corresponding yield is 84%.

Stage N 1.1 g of the product obtained in the previous Stage M is dissolved in 15 ml of anhydrous DMF. Then 0.11 g of sodium hydride is added under argon and at −10° C. After 45 minutes, 0.4 ml of acetic acid and 50 ml of toluene are added. The solvents are eliminated under reduced pressure, the residue obtained is purified on silica eluting with a mixture of toluene/isopropyl alcohol at 30%.

0.41 g of 1,4,5,8-tetrahydro-5-(phenylmethoxy)-6H-4,7-methanoimidazo[4,5-e][1,3]diazepin-6-one, of molecular formula $C_{14}H_{14}N_4O_2$ is obtained (M=270.29 g).

The corresponding yield is 61%.

Stage O 0.385 g of the product obtained in the previous Stage N is dissolved in 10 ml of THF then 0.31 g of $(BOC)_2O$ is added.

0.2 ml of triethylamine is then added followed by agitation for 2 hours 30 minutes. The solvents are evaporated off under reduced pressure and the residue is purified on silica with a mixture of methylene chloride/acetone at 5%.

0.44 g of 1,1-dimethylethyl 4,5,6,8-tetrahydro-6-oxo-5-(phenylmethoxy)-1H-4,7-methanoimidazo[4,5-e][1,3]diazepine-1-carboxylate, of molecular formula $C_{19}H_{22}N_4O_4$ (M=370.41 g) is obtained in the form of an oil.

The yield is quantitative.

Stage P

The process is carried out as indicated in Stage A of Example 11, with 0.44 g of the product obtained in the previous Stage O, 12 ml of ethanol, 60 mg of palladium on carbon at 10% by weight.

0.3 g of 1,1-dimethylethyl 4,5,6,8-tetrahydro-5-hydroxy-6-oxo-1H-4,7-methanoimidazo[4,5-e][1.3]diazepine-1-carboxylate, of molecular formula $C_{12}H_{16}N_4O_4$ (M=280.29 g) is obtained in the form of white crystals.

The corresponding yield is 91%.

Stage Q

The process is carried out as indicated in Stage B of Example 11 with 0.3 g of the product obtained in the previous Stage P, 3 ml of pyridine and 3 equivalents of the $SO_3$-pyridine complex.

0.196 g of the sodium salt of 1,1-dimethylethyl 4,5,6,8-tetrahydro-6-oxo-5-(sulphooxy)-1H-4,7-methanoimidazo[4,5-e][1,3]diazepine-1-carboxylate, of molecular formula $C_{12}H_{15}N_4O_7S.Na$ (M=382.33 g) is obtained in the form of yellow crystals.

The corresponding yield is 50%.

NMR Spectrum of the Proton

In DMS-$d_6$ at 300 MHz, chemical shifts and multiplicity: 1.56 (s): BOC; 3.22 (d) and 3.24 (d) and 3.52 (dd) and 3.53 (dd): N—CH$_2$—CH; 4.62 (d) and 4.71 (d): N—CH$_2$—CH; 4.11 and 4.24, 4.28, 4.31: N—CH$_2$—C=; 7.66 (s) and 8.08 (s): N=CH—N. MS (negative electrospray) m/z: (2M+Na)$^-$=741; (2M+H)$^-$=719; (M)$^-$=359

Example 45

Sodium salt of 1,4,5,8-tetrahydro-5-(sulphooxy)-6H-4,7-methanoimidazo[4,5-e][1.3]diazepin-6-one 0.155 g of the product obtained in Example 44 is dissolved in 2 ml of trifluoroacetic acid. Agitation is carried out for 5 minutes then the solvent is evaporated off under reduced pressure entraining with 2×10 ml of toluene. After drying, the residue is crystallized from acetone.

120 mg of the sodium salt and the trifluoroacetate of 1,4,5,8-tetrahydro-5-(sulphooxy)-6H-4,7-methanoimidazo[4,5-e][1.3]diazepine-6-one, of molecular formula $C_7H_7N_4O_5S.Na$ (M=282.21 g) is obtained in the form of beige crystals.

The yield is quantitative.

MS (negative electrospray) m/z: (2M+Na)$^-$=5.41; (2M+H)$^-$=519; (M)$^-$=259.

Example 46

Sodium salt of trans ethyl 1,2,3,5-tetrahydro-3-oxo-9-propoxy-2-(sulphooxy)-1,4-methano-4H-2,4-benzodiazepine-5-carboxylate Stage A 50 g of 3-methoxy-benzaldehyde is dissolved in 245 ml of acetic acid. At 0° C., 22 ml of bromine is added dropwise, followed by agitation at ambient temperature for 4 hours, then leaving overnight at ambient temperature. 300 ml of water is added to the solution and the expected product crystallizes. After filtration and washing with water and drying, 68 g of 2-bromo-5-methoxy-benzaldehyde, of molecular formula $C_8H_7Br.O_2$ is obtained (M=114 g).

The corresponding yield is 87%.

Stage B 30 g of the product obtained in the previous step B is dissolved in 200 ml of dichloromethane. 0.4 g of $ZnI_2$ then dropwise 20.86 ml of TMSCN are added at 0°. After agitating for 1 hour 30 minutes, the mixture is poured into a saturated aqueous solution of sodium bicarbonate. After decanting, the organic phase is dried over magnesium sulphate and the solvent is evaporated off under reduced pressure. The crude product is solubilized in 9 ml of ethanol and 6 ml of concentrated hydrochloric acid. After heating under reflux for 1 hour, the reaction medium is poured into a saturated solution of $NaHCO_3$, followed by extracting with ethyl acetate.

After evaporation of the solvent under reduced pressure, 41 g of ethyl 2-bromo-α-hydroxy-5-methoxy-benzeneacetate, of molecular formula $C_{11}H_{13}Br.O_4$ is obtained (M=288 g).

The corresponding yield is 63%.

Stage C

The process is carried out as indicated in Stage B of Example 23 with 23.5 g of the product obtained in the previous Stage C, 100 ml of pyridine, 6.31 ml of mesyl chloride.

32 g of expected compound of molecular formula $C_{17}H_{24}N.BrO_5$ (M=401 g) is obtained in the form of an oil.

The process is carried out as indicated in Stage C of Example 23 with 30 g of the product obtained in the previous Stage C, 130 ml of DMF, 16 g of tert-butyl glycinate and 9.66 ml of lutidine.

15.3 g of ethyl 2-bromo-α-[[2-(1,1-dimethylethoxy)-2-oxoethyl]amino]-5-methoxy-benzeneacetate, of molecular formula $C_{17}H_{24}BrNO_5$ (M=402.29 g) is obtained in the form of an oil.

The corresponding yield is 47%.

Stage E

The process is carried out as indicated in Stage D of Example 23 with 6 g of the product obtained in the previous Stage D, 60 ml of dichloromethane, 1.2 equivalent of triethylamine, 1.3 equivalent of trifluoroacetic anhydride.

6.05 g of ethyl 2-bromo-α-[[2-(1,1-dimethylethoxy)-2-oxoethyl](trifluoroacetyl)amino]-5-methoxy-benzeneacetate, of molecular formula $C_{19}H_{23}BrF_3NO_6$ is obtained (M=498.30 g).

The corresponding yield is 81%.

Stage F

The process is carried out as indicated in Stage E of Example 23 with 6.05 g of the product obtained in the previous Stage E, 30 ml of dichloromethane, 30 ml of trifluoroacetic acid.

5.2 g of ethyl 2-bromo-α-[[(carboxymethyl)(trifluoroacetyl)amino]-5-methoxy-benzeneacetate, of molecular formula $C_{15}H_{15}BrF_3NO_6$ (M=442.19 g) is obtained in the form of white crystals.

The corresponding yield is 97%.

Stage G

Step 1—Preparation of the Acid Chloride 61 g of the product obtained in Stage F is solubilized in 120 ml of $SOCl_2$. The reaction medium is heated at 80° C. for 2 hours followed by evaporating to dryness.

Step 2

The acid chloride is solubilized in 300 ml of $CH_3NO_2$. Then 76 g of aluminium chloride is added by fractions and agitation is carried out overnight at ambient temperature.

Then the reaction medium is poured into a heptane/ethyl acetate mixture and the organic phase is washed with $NaH_2PO_4$ 1M. After drying the organic phase over $MgSO_4$ and evaporation of the solvent under reduced pressure, the residue obtained is purified by chromatography on silica eluting with a heptane/ethyl acetate mixture 4:1. A residue is obtained which crystallizes from a pentane/ether mixture.

31 g of ethyl 8-bromo-1,2,3,4-tetrahydro-5-hydroxy-4-oxo-2-(trifluoroacetyl)-1-isoquinolinecarboxylate, of molecular formula $C_{14}H_{11}BrF_3NO_5$ is obtained (M=409.15 g).

The corresponding yield is 55%.

Stage H 30 g of the product obtained in the previous Stage G is dissolved in 250 ml of ethanol. Then 3 g of palladium on carbon at 10% by weight and 21.1 ml of triethylamine are added. The medium is placed under hydrogen pressure. After 1 hour 30 minutes, the catalyst is filtered then the filtrate is poured into a heptane/ethyl acetate mixture, the organic phase is washed with a 1M aqueous solution of $NaH_2PO_4$, then dried over magnesium sulphate and the solvent is evaporated off under reduced pressure. The crude product obtained is purified on silica eluting with a heptane/ethyl acetate mixture 4/1.

22.2 g of ethyl 1,2,3,4-tetrahydro-5-hydroxy-4-[(phenylmethoxy)imino]-2-(trifluoroacetyl)-1-isoquinolinecarboxylate of molecular formula $C_{14}H_{12}F_2NO_5$ is obtained (M=331.25 g).

The corresponding yield is 92%.

Stage I

The process is carried out as indicated in Stage A of Example 6 with 2 g of the product obtained in the previous Stage H, 1.05 g of O-benzylhydroxylamine hydrochloride. Agitation is carried out for 1 hour 30 minutes at ambient temperature then the solution is poured into an ethyl acetate/heptane mixture 2/1. The organic phase is washed with water then with a 1M aqueous solution of $NaH_2PO_4$. After drying over magnesium sulphate and evaporation of the solvent under reduced pressure, 2.95 g of a crude compound is obtained which crystallizes from an ether/pentane mixture.

2.85 g of ethyl 1,2,3,4-tetrahydro-5-(2-propenyloxy)-4-[(phenylmethoxy)imino]-2-(trifluoroacetyl)-1-isoquinolinecarboxylate, of molecular formula $C_{21}H_{19}F_3N_2O_5$ (M=436.39 g) is obtained in the form of beige crystals.

The corresponding yield is 94%.

Stage J 2.45 g (5.61 mmoles) of the product obtained in the previous Stage I is solubilized in 30 ml of acetone then 9.16 g of $K_2CO_3$ and 3.5 equivalents of allyl bromide are added. The reaction medium is heated overnight under reflux then the solution is poured into water and the organic phase is extracted with an ethyl acetate/heptane mixture. The organic phase is washed with a 1M aqueous solution of $NaH_2PO_4$ then, after drying over magnesium sulphate and evaporation of the solvent under reduced pressure, a crude product is obtained which is purified by chromatography on silica eluting with a heptane/ethyl acetate mixture 4/1.

2.35 g of ethyl 1,2,3,4-tetrahydro-4-[(phenylmethoxy)imino]-5-(2-propenyloxy)-2-(trifluoroacetyl)-1-isoquinolinecarboxylate, of molecular formula $C_{24}H_{23}F_3N_2O_5$ is obtained (M=476.47 g) is obtained in the form of a yellow oil.

The corresponding yield is 88%.

Stage K 25.2 g of the product obtained in the previous Stage J is solubilized in 300 ml of ethanol. Gaseous $NH_3$ is bubbled through the solution at 0° C. for 5 minutes. Then, agitation is carried out at ambient temperature for 3 hours. The solution is then poured into ethyl acetate and the organic phase washed with an aqueous solution of $NaH_2PO_4$ then dried over magnesium sulphate. The solvent is evaporated off under reduced pressure entraining with toluene.

21.2 g of ethyl 1,2,3,4-tetrahydro-4-[(phenylmethoxy)imino]-5-(2-propenyloxy)-1-isoquinolinecarboxylate, of molecular formula $C_{22}H_{24}N_2O_4$ (M=300.45 g) is obtained in the form of a yellow oil.

The yield obtained is quantitative.

Stage L

The process is carried out as indicated in Stage J of Example 23 with 22.5 g of the product obtained in the previous Stage K, and 1.1 equivalent of $(Boc)_2O$ and 300 ml of THF.

19.3 g of 2-(1,1-dimethylethyl) and 1-ethyl 3,4-dihydro-4-[(phenylmethoxy)imino]-5-(2-propenyloxy)-1.2 (1H)-isoquinolinedicarboxylate, of molecular formula $C_{27}H_{32}N_2O_6$ (M=480.57 g) is obtained in the form of white crystals.

The yield is 67%.

Stage M

The process is carried out as indicated in Stage B of Example 6 with 19.3 g of the product obtained in the previous Stage L, 250 ml of methanol, 40.5 g of sodium cyanoborohydride, 59 ml of boron trifluoride etherate.

21 g of 2-(1,1-dimethylethyl) and 1-ethyl 3,4-dihydro-4-[(phenylmethoxy)amino]-5-(2-propenyloxy)-1.2(1H)-isoquinolinedicarboxylate, of molecular formula $C_{27}H_{34}N_2O_6$ is obtained (M=482.58 g).

The corresponding yield is 79%.

Stage N

The process is carried out as indicated in Stage C of Example 6 with 15.3 g of the product obtained in the previous Stage M, 83 ml of a solution of hydrochloric acid at 140 g/l solubilized in 10 ml of ethyl acetate, 35 ml of 2N soda and 130 ml of methylene chloride.

12.1 g of ethyl 1,2,3,4-tetrahydro-4-[(phenylmethoxy)amino]-5-(2-propenyloxy)-1-isoquinolinecarboxylate, of molecular formula $C_{22}H_{26}N_2O_4$ (M=382.46 g) is obtained in the form of a colourless oil.

Stage O

The process is carried out as indicated in Stage N of Example 3 with 12.1 g of the product obtained in the previous Stage N, 3 l of acetonitrile, 1.92 ml of diphosgene and 9 ml of triethylamine.

7 g of ethyl 1,2,3,4-tetrahydro-3-oxo-2-(phenylmethoxy)-9-(2-propenyloxy)-1,4-methano-4H-2,4-benzodiazepine-5-carboxylate, of molecular formula $C_{23}H_{24}N_2O_5$ (M=408.48 g) is obtained NMR Spectrum of the Proton In $CDCl_3$ at 300 MHz, chemical shifts and multiplicity: 3.10 (d) and 3.60 (dd): N—$\underline{CH_2}$—CH-φ; 4.80 (d): N—$CH_2$—$\underline{CH}$ φ; 4.26 and 4.41: N—$\underline{CH_2}$—φ; 4.56 (m): O—$\underline{CH_2}$—CH=$CH_2$; 6.05 (m): O—$CH_2$—$\underline{CH}$=$CH_2$; 5.31 (qd) and 5.41 (qd): O—$CH_2$—CH=$\underline{CH_2}$; 4.92 and 4.96: O—$\underline{CH_2}$ φ; 6.61 (d) and 6.71 (d) and 7.19 (t) for the three aromatic hydrogens; 7.35 (m) and 7.44 (m) for the hydrogens of the phenyl group. IR ($CHCl_3$): 1755, 1645, 1600, 1583, 1497 $cm^{-1}$.

Example 47

Trans methyl 1,2,3,5-tetrahydro-3-oxo-9-(phenylmethoxy)-2-(sulphooxy)-1,4-methano-4H-2,4-benzodiazepine-5-carboxylate Stage A The process is carried out as indicated in Stage A of Example 6 with 21.9 g of the product obtained in Example 46, 7.25 g of O-allylhydroxylamine hydrochloride, and 200 ml of pyridine.

25.5 g of ethyl 1,2,3,4-tetrahydro-5-hydroxy-4-[(2-propenyloxy)imino]-2-(trifluoroacetyl)-1-isoquinolinecarboxylate, of molecular formula $C_{17}H_{17}F_3N_2O_5$ is obtained (M=386.33 g).

The yield obtained is quantitative.

Stage B

The process is carried out as indicated in Stage J of Example 46 with 29.4 g of the product obtained in the previous Stage A, 126 g of $K_2CO_3$, 32 ml of benzyl bromide and 450 ml of acetone.

34.75 g of ethyl 1,2,3,4-tetrahydro-5-(phenylmethoxy)-4-[(2-propenyloxy)imino]-2-(trifluoroacetyl)-1-isoquinolinecarboxylate, of molecular formula $C_{24}H_{23}F_3N_2O_5$ (M=476 g) is obtained in the form of a yellow oil.

The corresponding yield is 85%.

Stage C

The process is carried out as indicated in Stage B of Example 6 with 2 g of the product obtained in the previous Stage B, 3.97 g of sodium cyanoborohydride, 6.17 ml of boron trifluoride etherate and 100 ml of methanol.

1.42 g of ethyl 1,2,3,4-tetrahydro-5-(phenylmethoxy)-4-[(2-propenyloxy)amino]-2-(trifluoroacetyl)-1-isoquinolinecarboxylate, of molecular formula $C_{24}H_{25}F_3N_2O_5$ (M=478.47 g) is obtained in the form of an oil.

The corresponding yield is 70%.

Stage D

In a flask maintained at 0° C. under an argon atmosphere, 1.4 g of the product obtained in the previous Stage C is introduced into 25 ml of ethanol. Then, twice 120 mg of sodium borohydride is added. After 20 minutes, the reaction is stopped by adding a heptane/ethyl acetate mixture (1/1) at 0° C. Then a saturated aqueous solution of $NaHCO_3$ is added. Agitation is carried out for 5 minutes followed by decanting and extracting again with a heptane/ethyl acetate mixture (1/1). The organic phase is then dried over magnesium sulphate and the solvent is evaporated off under reduced pressure.

1.18 g of ethyl 1,2,3,4-tetrahydro-5-(phenylmethoxy)-4-[(2-propenyloxy)amino]-1-isoquinolinecarboxylate, of molecular formula $C_{22}H_{26}N_2O_4$ (M=382.46 g) is obtained in the form of an oil.

The yield obtained is quantitative.

Stage E

The process is carried out as indicated in Stage C of Example 3, with 1.15 g of the product obtained in the previous Stage D, 18 ml of acetonitrile, 0.2 ml of diphosgene and 0.88 ml of triethylamine.

0.41 g of methyl 1,2,3,5-tetrahydro-3-oxo-9-(phenylmethoxy)-2-(2-propenyloxy)-1,4-methano-4H-2,4-benzodiazepine-5-carboxylate, of molecular formula $C_{23}H_{24}N_2O_5$ is obtained (M=408.46).

The corresponding yield is 33%.

Stage F 0.524 g of the product obtained in the previous Stage E is dissolved under an argon atmosphere in 50 ml of dichloromethane. Then 0.307 ml of acetic acid and 741 mg of $Pd(P\phi Ph_3)_4$ are added. After agitation for 10 minutes, the solvent is evaporated off under reduced pressure and the crude product obtained is purified on silica eluting with a methylene chloride/acetone mixture (9/1).

0.4 g of ethyl 1,2,3,5-tetrahydro-2-hydroxy-3-oxo-9-(phenylmethoxy)-1,4-methano-4H-2,4-benzodiazepine-5-carboxylate, of molecular formula $C_{20}H_{20}N_2O_5$ is obtained (M=368.39 g).

The corresponding yield is 83%.

Stage G 0.090 g of the product obtained in the previous Stage F is dissolved in 4 ml of pyridine in the presence of molecular sieve. Then 3 equivalents of pyridine-$SO_3$ complex is added under argon and agitation is carried out for two hours at ambient temperature. Then the pyridine is evaporated and the crude product obtained is purified on silica eluting with an acetone/ethyl acetate/water mixture (5/4/0.5).

32 mg of trans methyl 1,2,3,5-tetrahydro-3-oxo-9-(phenylmethoxy)-2-(sulphooxy)-1,4-methano-4H-2,4-benzodiazepine-5-carboxylate, of molecular formula $C_{20}H_{20}N_2O_8S$ is obtained (M=448.48 g).

NMR of the Proton

In $CDCl_3$ at 300 MHz, chemical shifts and multiplicity: 1.20 (t): C$\underline{H_3}$—$CH_2$—O—C=O; 4.17 (q): $CH_3$—C$\underline{H_2}$—O—C=O; 3.34 (bd) and 3.71 (bt): N—C$\underline{H_2}$—CH; 5.30 (bs): N—$CH_2$—C$\underline{H}$; 4.99 and 5.13: φ—C$\underline{H_2}$—O; 5.09 (bs): C$\underline{H}$—$CO_2$-Et; 6.88 (d), 6.75 (d), 7.07 (t): for the aromatic 3H's; 7.16 (t), 7.29 (d), 7.45 (d): for the aromatic 5H's. MS (negative electrospray) m/z: (M−H)⁻=447. Infrared ($CHCl_3$): 1745, 1646, 1601, 1582, 1496 cm⁻¹.

Example 48

Trans ethyl-1,2,3,5-tetrahydro-9-hydroxy-3-oxo-2-(sulphooxy)-1,4-methano-4H-2,4-benzodiazepine-5-carboxylate 0.1 g of the product obtained in Example 47 is dissolved in 4 ml of THF. Then 25 mg of 10% palladium on carbon is added and the solution is placed under a hydrogen atmosphere.

Agitation is carried out for 5 hours at ambient temperature then the catalyst is filtered, the solvent is evaporated off and the residue is recrystallized from ether.

77 mg of trans methyl 1,2,3,5-tetrahydro-9-hydroxy-3-oxo-2-(sulphooxy)-1,4-methano-4H-2,4-benzodiazepine-5-carboxylate, of molecular formula $C_{14}H_{16}N_2O_5$ (M=292.09 g) is obtained in the form of grey crystals.

The yield is quantitative.

NMR of the Proton

In DMSO-$d_6$ at 300 MHz, chemical shifts and multiplicity: 1.25 (t): C$\underline{H_3}$—$CH_2$—O—C=O; 4.20 (q): $CH_3$—C$\underline{H_2}$—O—C=O; 3.52 (m): N—C$\underline{H_2}$—CH; 5.10 (d): N—$CH_2$—C$\underline{H}$; 4.88 (s): C$\underline{H}$—$CO_2$-Et; 6.71 (d), 6.74 (d) and 7.13 (t) for the aromatic 3H's; 9.56 (bs) mobile H. MS (negative electrospray) m/z: M⁻⁻=357.

Example 49

Sodium salt of trans ethyl 1,2,3,5-tetrahydro-3-oxo-9-propoxy-2-(sulphooxy)-1,4-methano-4H-2,4-benzodiazepine-5-carboxylate Stage A The process is carried out as indicated in Stage A of Example 11 with 150 mg (0.367 mmole) of the product obtained in Example 46, 6 ml of THF, 30 mg of palladium on carbon at 10% by weight.

120 mg of crude product ethyl 1,2,3,5-tetrahydro-2-hydroxy-3-oxo-9-propoxy-1,4-methano-4H-2,4-benzodiazepine-6-carboxylate, of molecular formula $C_{16}H_{20}N_2O_5$ is obtained (M=320.35 g).

Stage B

The process is carried out as indicated in Stage B of Example 11 with 117.6 mg of the product obtained in the previous Stage A with 2 ml of pyridine and 175.2 mg of pyridine-$SO_3$ complex.

143 mg of the sodium salt of trans ethyl 1,2,3,5-tetrahydro-3-oxo-9-propoxy-2-(sulphooxy)-1,4-methano-4H-2,4-benzodiazepine-5-carboxylate, of molecular formula $C_{16}H_{19}N_2NaO_8S$ is obtained (M=422.39 g).

The corresponding yield is 93%.

NMR Spectrum of the Proton

In $CDCl_3$ at 300 MHz, chemical shifts, multiplicity: 0.98 (t): $\underline{CH_3}$=CH=$CH_2$—O; 1.78 (m) $CH_3$=$\underline{CH_2}$=$CH_2$—O; 3.89 (m) $CH_3$=$\underline{CH_2}$—$CH_2$—O; 1.26 (r): $\underline{CH_3}$—$CH_2$; 4.22 (q): $CH_3$—$\underline{CH_2}$; 3.25 (bs) and 3.71 (bs): N—$\underline{CH_2}$; 5.13 (singlet), 5.19 (singlet): the CH's of the rings; 6.72 (d) and 6.86 (d) and 7.08 (r): the 3H's of the aromatic ring. MS (SIMS) m/z: $(M^+Na)^+$=445. IR $CHCl_3$: 1746, 1639, 1602, 1584 $cm^{-1}$.

Example 50

Sodium salt of methyl 5-fluoro-1,2,3,5-tetrahydro-3-oxo-2-(sulphooxy)-1,4-methano-4H-2,4-benzodiazepine-5-carboxylate Stage A1g of the compound prepared in Stage L of Example 3 is dissolved in 15 ml of anhydrous THF. 6.9 ml of a 0.5 M solution of potassium bis-trimethyl silylamide is added at a temperature of −78° C. Then, after contact for 10 minutes, 1.09 g of N-fluorobenzenesulphonamide is added in one go.

After agitation for 30 minutes, the reaction medium is poured into a heptane/ethyl acetate mixture 1/2 and the organic phase is washed with a 1M aqueous solution of $NaH_2PO_4$. After drying over magnesium sulphate and evaporation of the solvent under reduced pressure, 1.3 g of crude product is obtained which is purified on silica eluting with dichloromethane.

After recrystallization from ether, 0.1 g of the sodium salt of methyl 5-fluoro-1,2,3,5-tetrahydro-3-oxo-2-(2-propenyloxy)-1,4-methano-4H-2,4-benzodiazepine-5-carboxylate, of molecular formula $C_{15}H_{15}F.N_2O_4$ is obtained (M=306.30 g).

The corresponding yield is 62%.

Stage B

The process is carried out as indicated in Stage C of Example 7 with 0.4 g of the product obtained in the previous Stage A, 148 μl of acetic acid, 756 mg of Pd[$PPh_3$]$_4$, 8 ml of pyridine and 832 mg of $SO_3$-pyridine complex.

0.21 g of the sodium salt of methyl 5-fluoro-1,2,3,5-tetrahydro-3-oxo-2-(sulphooxy)-1,4-methano-4H-2,4-benzodiazepine-5-carboxylate, of molecular formula $C_{12}H_{10}FN_2O_7S.Na$ is obtained (M=368.28 g).

The corresponding yield is 23%.

NMR Spectrum of the Proton

In DMSO-$d_6$ at 300 MHz, chemical shifts and multiplicity: 3.65 (bs): N—$\underline{CH_2}$—CH; 4.78 (bs): N—$\underline{CH_2}$—CH; 3.72 (s): $\underline{CH_3}$—O—C=O—; from 7.21 to 7.68 (m, aromatic 4H). IR (Nujol): 1761, 1632 $cm^{-1}$. MS (negative electrospray) m/z: $M^-$=345.

Example 51

Sodium salt of methyl 1,2,3,5-tetrahydro-5-(methylthio)-3-oxo-2-(sulphooxy)-1,4-methano-4H-2,4-benzodiazepine-5-carboxylate Stage A 1 g of the product prepared in Stage L of Example 3 is dissolved in 15 ml of THF. Then, 6.9 ml of potassium bis-trimethyl silylamide is added dropwise and agitation is carried out for 10 minutes at −78° C. 437 mg of $CH_3SO_2SCH_3$ is added in one go. The solution is agitated for 30 minutes then poured into a heptane/ethyl acetate mixture, 1/2. The medium is washed with a 1N solution of $NaH_2PO_4$, then the organic phase is dried over $MgSO_4$ and the solvent is evaporated off under reduced pressure. The crude product obtained is purified by passing through a silica column eluting with a dichloromethane/acetone mixture 99/1. Then after recrystallization from ether, 0.65 g of methyl 1,2,3,5-tetrahydro-5-(methylthio)-3-oxo-2-(2-propenyloxy)-1,4-methano-4H-2,4-benzodiazepine-5-carboxylate, of molecular formula $C_{16}H_{18}N_2O_4S$ is obtained (M=334.40 g).

The corresponding yield obtained is 56%.

Stage B

The process is carried out as indicated in Stage C of Example 7 with 0.443 g of the product obtained in the previous Stage A, 10 ml of dichloromethane, 0.151 mg of acetic acid, 0.765 mg of Pd ($PPh_3$)$_4$ and 10 ml of pyridine and 0.845 g of $SO_3$-pyridine complex.

0.250 g of the sodium salt of methyl 1,2,3,5-tetrahydro-5-(methylthio)-3-oxo-2(sulphooxy)-1,4-methano-4H-2,4-benzodiazepine-5-carboxylate, of molecular formula $C_{13}H_{13}N_2O_7S_2.Na$ is obtained (M=396.38 g).

MS (negative electrospray) m/z: $M^-$=373.

NMR of the Proton

In DMSO-$d_6$ at 300 MHz, chemical shifts and multiplicity: 2.31 (s) $\underline{CH_3}$—S; 3.56 (dd) and 4.10 (d): N—$\underline{CH_2}$—CH; 4.70 (d) N—$CH_2$—$\underline{CH}$; 3.73 (s) $\underline{CH_3}$—O—C=O; 7.15 (bd) and 7.31 (m) and 7.39 (bt): aromatic 4H. IR (Nujol): 1760, 1736, 1635, 1576 $cm^{-1}$.

Example 52

Triethylammonium salt of trans methyl 4.5,6,8-tetrahydro-8-methyl-6-oxo-5-(sulphooxy)-4,7-methano-7H-thieno[2,3-e][1.3]diazepine-8-carboxylate Stage A The process is carried out as indicated in Stage A of Example 6 starting from 4.5 g of the product prepared in Stage F of Example 24, 19 ml of pyridine and 22.87 g of φPh$CH_2$O$NH_2$, HCl.

6.89 g 6-(1,1-dimethylethyl) and 7-methyl 4,7-dihydro-4-[(phenylmethoxy)imino]-thieno[2,3-c]pyridine-6.7 (5H)- dicarboxylate, of molecular formula $C_{21}H_{24}N_2O_5S$ is obtained (M=416.50 g).

The corresponding yield is 88%.

Stage B

In a flask under an inert atmosphere, 6.89 g of the product obtained in the previous Stage A is introduced into 70 ml of DMF. The reaction medium is cooled down to −5° C. and 1.03 ml of $CH_3I$, then 785 mg of NaH at 50% in oil are added.

Then, agitation is carried out for 1 hour at 20° C. and a heptane/ethyl acetate mixture 1/2 is added to the reaction medium. The organic phase is washed several times with water and with a 1N solution of $NaH_2PO_4$. The organic phase is dried over magnesium sulphate, filtered and the solvent evaporated off under reduced pressure. The crude product is purified by chromatography on silica eluting with a heptane/ethyl acetate mixture, 4/1.

6.14 g of 6-(1,1-dimethylethyl) and 7-methyl 4,7-dihydro-7-methyl-4-[(phenylmethoxy)imino]-thieno[2,3-c]pyridine-6,7(5H)-dicarboxylate, of molecular formula $C_{22}H_{26}N_2O_5S$ is obtained (M=430.53 g).

The corresponding yield is 56%.

Stage C

The process is carried out as indicated in Stage B of Example 6 with 6.14 g of the product obtained in the previous Stage B, 14.4 g of sodium cyanoborohydride, 22 ml of boron trifluoride etherate and 60 ml of methanol.

4.72 g of a cis and trans 6-(1,1-dimethylethyl) and 7-methyl 4,7-dihydro-7-methyl-4-[(phenylmethoxy)amino]-thieno[2,3-c]pyridine-6,7(5H)-dicarboxylate mixture, of molecular formula $C_{22}H_{28}N_2O_5S$ is obtained (M=432.54 g).

Stage D

The process is carried out as indicated in Stage C of Example 6 with 4.62 g of the product obtained in the previous Stage C, 10 ml of ethyl acetate, and 25 ml of a 4.3N solution of hydrochloric acid in ethyl acetate.

4.29 g of a cis and trans hydrochloride mixture is obtained in the form of white crystals.

The hydrochloride is released in a manner analogous to Stage C of Example 6 then the 2 cis and trans isomers are separated by chromatography on silica eluting with a heptane/acetonitrile mixture: 1/2.

0.7 g de trans methyl 4,5,6,7-tetrahydro-7-methyl-4-[(phenylmethoxy)amino]-thieno[2,3-c]pyridine-7-carboxylate, and 2.36 g de cis methyl 4,5,6,7-tetrahydro-7-methyl-4-[(phenylmethoxy)amino]-thieno[2,3-c]pyridine-7-carboxylate of molecular formula $C_{17}H_{20}N_2O_3S$ is obtained (M=332.42 g).

The overall yield is 87%.

Stage E

The process is carried out as indicated in Stage D of Example 6 with 0.7 g of the product obtained in the previous Stage D, 175 ml of acetonitrile, 0.607 ml of triethylamine and 0.126 ml of diphosgene.

0.52 g of trans methyl 4.5,6,8-tetrahydro-8-methyl-6-oxo-5-(phenylmethoxy)-4,7-methano-7H-thieno[2,3-e][1.3]diazepine-8-carboxylate, of molecular formula $C_8H_{18}N_2O_4S$ is obtained (M=358.42 g).

The corresponding yield is 67%.

Stage F

The process is carried out as indicated in Stage A of Example 11 with 0.1 g of the product obtained in the previous Stage E, 0.1 g of palladium on carbon at 30% by weight, and 2 ml of methanol and 1 ml of THF.

81 mg of trans methyl 4,5,6,8-tetrahydro-5-hydroxy-8-methyl-6-oxo-4,7-methano-7H-thieno[2,3-e][1,3]diazepine-8-carboxylate, of molecular formula $C_{11}H_{12}N_2O_4S$ is obtained (M=268.29 g).

The product is used as it is in the following step.

Stage G

The process is carried out as indicated in Stage B of Example 11 with the crude product obtained in the previous Stage F, 0.133 g of pyridine-$SO_3$ complex and 1 ml of pyridine.

After purification of the product on silica, 0.015 g of the triethylammonium salt of trans methyl 4,5,6,8-tetrahydro-8-methyl-6-oxo-5-(sulphooxy)-4,7-methano-7H-thieno[2,3-e][1,3]diazepine-8-carboxylate, of molecular formula $C_{11}H_{11}N_2O_7S_2C_6H_{16}N$ (M=347.35 g, 102.21 g) is obtained in the form of white crystals.

The yield obtained is 15%.

MS (negative electrospray) m/z: M−=347.

Example 53

Triethylammonium salt of cis methyl 4,5,6,8-tetrahydro-8-methyl-6-oxo-5-(sulphooxy)-4,7-methano-7H-thieno[2,3-e][1,3]diazepine-8-carboxylate Stage A 2.35 g of cis methyl 4,5,6,7-tetrahydro-7-methyl-4-[(phenylmethoxy)amino]-thieno[2,3-c]pyridine-7-carboxylate prepared in Stage D of Example 52 is introduced and the process is carried out as in Stage D of Example 46 with 600 ml of acetonitrile, 3.0 ml of TEA and 0.42 ml of diphosgene.

Cis methyl 4,5,6,8-tetrahydro-8-methyl-6-oxo-5-(phenylmethoxy)-4,7-methano-7H-thieno[2,3-e][1,3]diazepine-8-carboxylate, of molecular formula $C_{18}H_{18}N_2O_4S$ is obtained (M=358.42).

Stage B

The process is carried out as indicated in Stage F of Example 52 with 1.1 g of the product obtained in the previous Stage A, 2 ml of methanol and 100 mg of palladium on carbon at 10% by weight.

75 mg of cis methyl 4,5,6,8-tetrahydro-5-hydroxy-8-methyl-6-oxo-4,7-methano-7H-thieno[2,3-e][1,3]diazepine-8-carboxylate, of molecular formula $C_{11}H_{12}N_2O_4S$ is obtained (M=268.29 g).

The yield is quantitative.

Stage C

The process is carried out as in Stage G of Example 52 with 75 mg of the product obtained in the previous Stage B, 1 ml of pyridine and 0.33 g of $SO_3$-pyridine complex.

48 mg of the triethylammonium salt of cis methyl 4,5,6,8-tetrahydro-8-methyl-6-oxo-5-(sulphooxy)-4,7-methano-7H-thieno[2,3-e][1,3]diazepine-8-carboxylate of molecular formula $C_{11}H_{11}N_2O_7S_2$ (M=347.35 g) is obtained in the form of white crystals.

The corresponding yield obtained is 50%.

NMR of the Proton

In DMSO-$d_6$ at 300 MHz, chemical shifts and multiplicity: 1.75 (s) $\underline{CH_3}$—C; 3.21 (dd) and 3.50 (dd): N—$\underline{CH_2}$—CH—C≡; 4.73 (d): N—$CH_2$—$\underline{CH}$—C≡; 3.74 (s): $\underline{CH_3}$—O—C═O; 6.92 (d) and 7.53 (d): H thiophene. MS (negative electrospray) m/z: M−=347

Example 54

Sodium salt of trans-1,5-dihydro-5-[(phenylmethoxy)methyl]-2-(sulphooxy)-1,4-methano-4H-2,4-benzodiazepin-3(2H)-one Stage A 1.55 g of the product prepared in Stage A of Example 7 is solubilized in 20 ml of THF. 0.69 ml of N-methylmorpholine, then, 0.89 ml of isobutyl chloroformate are added dropwise at 0° C. The reaction mixture is then cooled down to −78° C. and 7 ml of methanol is added. Then, 0.45 g of $NaBH_4$ is added in one go. Agitation is carried out for 1 hour at −78° C. Once the reaction is completed, ethyl acetate and a saturated aqueous solution of $NaHCO_3$ are added. After extraction, drying and evaporation, 1.65 g of crude product is obtained which is purified by chromatography on silica eluting with a heptane/ethyl acetate mixture, 1/4.

0.95 g of 1,5-dihydro-5-(hydroxymethyl)-2-(2-propenyloxy)-1,4-methano-4H-2,4-benzodiazepin-3(2H)-one, of molecular formula $C_{14}H_{17}N_2O_2$ is obtained (M=245.30 g).

The corresponding yield obtained is 69%.

Stage B 0.4 g of the product obtained in the previous Stage A is solubilized in 10 ml of DMF, then 1.2 equivalent of benzyl bromide and 1 equivalent of sodium hydride are added at 20° C.

Agitation is carried out at −20° C. and after two hours, the solution is poured into a heptane/ethyl acetate mixture, 1/2.

After washing the organic phase with a 1M aqueous solution of sodium dihydrogen phosphate, then drying over $MgSO_4$ and filtration, the solvent is evaporated off under reduced pressure. 0.6 g of crude product is obtained which is purified by chromatography on silica eluting with a heptane/ethyl acetate mixture, 3/1.

0.42 g of 1,5-dihydro-5-[(phenylmethoxy)methyl]-2-(2-propenyloxy)-1,4-methano-4H-2,4-benzodiazepin-3(2H)-one, of molecular formula $C_{21}H_{22}N_2O_3$ (M=350.42 g) is obtained in the form of a colourless oil.

The yield obtained is 74%.

Stage C

The process is carried out as indicated in Stage C of Example 7 with 0.4 g of the compound obtained in the previous Stage B, 0.136 ml of acetic acid, 5 ml of dichloromethane, 0.69 g of $Pd(P\phi Ph_3)_4$, 0.57 g of pyridine-$SO_3$ complex and 5 ml of pyridine.

0.130 g of the sodium salt of trans-1,5-dihydro-5-[(phenylmethoxy)methyl]-2-(sulphooxy)-1,4-methano-4H-2,4-benzodiazepin-3(2H)-one, of molecular formula $C_{18}H_{17}N_2O_6S.Na$ (M=389.41 g, 22.99 g) is obtained in the form of beige crystals.

NMR of the Proton

In DMSO-$d_6$ at 300 MHz, chemical shifts and multiplicity: 3.40 (dd) and 3.60 (d): N—$\underline{CH_2}$—CH—N; 4.61 (d): N—$CH_2$—$\underline{CH}$—N; 3.87 (dd) and 3.96 (dd): O—$\underline{CH_2}$CH—N; 4.46 (dd): O—$CH_2$—$\underline{CH}$—N; 4.56:O$\underline{CH_2}$φPh and from 7.10 to 7.40 for the 4 aromatic hydrogens. MS (negative electrospray) m/z: M⁻=389. Infrared (Nujol): 1755, 1608, 1494 cm⁻¹.

Example 55

Sodium salt of trans-1,5-dihydro-5-(hydroxymethyl)-2-(sulphooxy)-1,4-methano-4H-2,4-benzodiazepin-3(2H)-one 0.110 g of the product obtained in Example 54 is solubilized in 2 ml of methanol then 0.020 g of palladium on carbon at 10% by weight is added. After reacting for 6 hours under a hydrogen atmosphere, 2 equivalents of acetic acid are then added followed by agitating at ambient temperature for 12 hours. After filtration of the reaction medium, the solvent is evaporated off under reduced pressure. The residue is then solubilized in 2 ml of methanol. A further 100 mg of 10% palladium on carbon is then added and hydrogen is reintroduced for 4 hours. After filtration of the catalyst and washing with methanol and with THF, the solution is evaporated to dryness, the residue is crystallized from ether and 25 mg of the sodium salt of trans-1,5-dihydro-5-(hydroxymethyl)-2-(sulphooxy)-1,4-methano-4H-2,4-benzodiazepin-3(2H)-one, of molecular formula $C_{13}H_{11}N_2O_6S.Na$ is isolated (M=299.28 g, 22.99 g).

The corresponding yield is 30%.

NMR Spectrum of the Proton

In DMSO-$d_6$ at 300 MHz, chemical shifts and multiplicity: 3.35 (dd) and 3.55 (d): =CN—$\underline{CH_2}$—CH—N; 4.25 (dd): =C—N—$CH_2$—$\underline{CH}$—N; 4.60 (d): C—N—$\underline{CH}$(C=)—$CH_2$OH; 3.82 (m): C—N—$\underline{CH}$(C=)—$\underline{CH_2}$OH; 5.04 (d): C—N—CH(C=)—$CH_2$O$\underline{H}$; 7.10 (bd) and 7.20 (m) and 7.3 (dt): the aromatic 4H's. MS (negative electrospray) m/z: M⁻=299.

Example 56

Sodium salt of trans-5-[[(aminocarbonyl)oxy]methyl]-1,5-dihydro-2-(sulphooxy)-1,4-methano-4H-2,4-benzodiazepin-3(2H)-one Stage A 0.4 g of the product prepared in Stage A of Example 54 in 8 ml of dichloromethane is introduced into a flask placed under argon in the presence of molecular sieve. Then the reaction medium is cooled down to 0° C. and 0.239 g of DMAP and 0.39 g of 4-nitrophenylchloroformate are added. Agitation is carried out for 45 minutes, then the solvent is evaporated off under reduced pressure and 4 ml of DMF is added. A viscous suspension is obtained through which gaseous ammonia is bubbled at 0° C. for 20 seconds. Then ethyl acetate and an aqueous solution of $NaHCO_3$ are added. The aqueous phase is extracted again with THF then the combined organic phases are washed several times with a saturated aqueous solution of $NaHCO_3$. After drying over magnesium sulphate, filtration and evaporation of the solvent under reduced pressure, 0.650 g of crude product is obtained which is purified on a silica column eluting with dichloromethane containing 10% of acetone.

0.365 g of 5-[[(aminocarbonyl)oxy]methyl]1,5-dihydro-2-(2-propenyloxy)-1,4-methano-4H-2,4-benzodiazepin-3(2H)-one, of molecular formula $C_{15}H_{17}N_3O_4$ (M=303.32 g) is obtained in the form of colourless foam.

The corresponding yield is 72%.

Stage B

The process is carried out as indicated in Stage C of Example 7 with 0.33 g of the product obtained in the previous Stage A, 0.13 ml of acetic acid, 0.63 g of $Pd(P\phi Ph_3)_4$, 0.517 g of pyridine-$SO_3$ complex and 4 ml of pyridine.

188 mg of the sodium salt of trans-5-[[(aminocarbonyl)oxy]methyl]-1,5-dihydro-2-(sulphooxy)-1,4-methano-4H-2,4-benzodiazepin-3(2H)-one, of molecular formula $C_{12}H_{12}N_3O_7S.Na$ (M=342.31 g, 22.99 g) is obtained in the form of white crystals.

NMR of the Proton

In DMSO-$d_6$ at 300 MHz, chemical shifts and multiplicity: 3.38 (dd) and 3.57 (d): =C—N—CH$_2$—CH—N; 4.62 (d): =C—N—CH$_2$—CH—N; 4.32 (dd) and 4.44 (dd): COO—CH$_2$—CH(—N)—C=; 4.35 (t): COO—CH$_2$—CH(—N)—C=; 7.13 (bd) and 7.24 (bt) and 7.27 (bd) and 7.35 (bt): for the aromatic 4H's; 6.52 (bs) and 6.80 (bs): NH$_2$ mobile absorptions. MS (negative electrospray) m/z: M-=342.

Example 57

Sodium salt of 1,1-dimethylethyl [[trans-4,5,6,8-tetrahydro-6-oxo-5-(sulphooxy)-4,7-methano-7H-thieno[2,3-e][1,3]diazepin-8-yl]methyl]-carbamate Stage A The process is carried out as indicated in Stage G of Example 3 with 50 g (160.58 mmoles) of the product prepared in Stage F of Example 24, 1500 ml of methanol, 225 ml of CH$_2$Cl$_2$, 1.6 g of 95% NaBH$_4$, 51.4 g of 6-(1,1-dimethylethyl) and 7-methyl 4,7-dihydro-4-hydroxy-thieno[2,3-c]pyridine-6.7(5H)-dicarboxylate, of molecular formula $C_{14}H_{15}NO_5S$ is obtained (M=313.38 g).

Stage B

The process is carried out as indicated in Stages H and I of Example 3 with 59.7 g of the product obtained in Stage A, 583 ml of CH$_2$Cl$_2$, 39.3 ml of triethylamine, 48.74 g (279.8 mmoles) of (CH$_3$SO$_2$)$_2$O, 68.9 g of benzyl-O—NH$_2$.

47.0 g of 6-(1,1-dimethylethyl) and 7-methyl 4,7-dihydro-4-[(phenylmethoxy)amino]-thieno[2,3-c]pyridine-6.7(5H)-dicarboxylate, of chemical formula $C_{21}H_{26}O_5N_2S_1$ is obtained (M=418.515 g).

The corresponding yield is 60.2%.

Stage C

The process is carried out as indicated in Stage J of Example 3, with 47 g of the product obtained in Stage B, 79 ml of ethyl acetate, 261 ml of a saturated solution of gaseous HCl in ethyl acetate.

44.12 g of the hydrochloride of methyl 4,5,6,7-tetrahydro-4-[phenylmethoxy)amino]-thieno[2,3-c]pyridine-7-carboxylate, of molecular formula $C_{16}H_{20}N_2O_3S_2Cl_2$ is obtained (M=391.318 g).

Stage D

The process is carried out as indicated in Stage K of Example 3 with 44.1 g of the product obtained in Stage C, 250 ml of water, 1000 ml of CH$_2$Cl$_2$, 35 ml of a concentrated solution of ammonium hydroxide.

34.6 g of methyl 4,5,6,7-tetrahydro-4-[(phenylmethoxy)amino]-thieno[2,3-c]pyridine-7-carboxylate, of molecular formula $C_{16}H_{18}N_2O_3S$ is obtained (M=318.4 g).

The corresponding yield is 96.7%.

Stage E

The process is carried out as indicated in Stage L of Example 3, with 34.1 g of the product obtained in Stage D, 8.8 l of CH$_3$CN, 30.8 ml of TEA, 6.5 ml of diphosgene.

37.2 g of trans methyl 4,5,6,8-tetrahydro-6-oxo-5-(phenylmethoxy)-4,7-methano-7H-thieno[2,3-e][1,3]diazepine-8-carboxylate, of molecular formula $C_{17}H_{16}N_2O_4S$ is obtained (M=344.39 g).

The corresponding yield is 80%.

Stage F

The process is carried out as indicated in Stage A of Example 7, with 3.35 g of the product obtained in Stage E, 10.7 ml of 1N NaOH, 20 ml of dioxane, 16 ml of H$_2$O. 2.25 g of trans methyl 4,5,6,8-tetrahydro-6-oxo-5-(phenylmethoxy)-4,7-methano-7H-thieno[2,3-e][1,3]diazepine-8-carboxylate, of molecular formula $C_{16}H_{14}N_2O_4S$ is obtained (M=330.36 g).

The yield is 71%.

Stage G

The process is carried out as indicated in Stage A of Example 54, with 1 g of the product obtained in Stage F, 1.1 equivalent of N-methylmorpholine, 1.05 equivalent of isobutyl chloroformate, 4 ml of methanol, 0.23 g of NaBH$_4$ and 15 ml of THF.

0.7365 g of 4,8-dihydro-8-(hydroxymethyl)-5-(phenylmethoxy)-4,7-methano-7H-thieno[2,3-e][1,3]diazepin-6(5H)-one of molecular formula $C_{16}H_{16}N_2O_3S$ is obtained (M 316.38 g).

The corresponding yield is 77%.

Stage H

The process is carried out as indicated in Stage B of Example 23, with 0.635 g (0.2 mmole) of the product obtained in Stage G, 10 ml of CH$_2$Cl$_2$, 0.324 ml of TEA, 0.171 ml of mesyl chloride (1.1 equivalent).

0.790 g of 4,8-dihydro-8-[[(methylsulphonyl)oxy]methyl]-5-(phenylmethoxy)-4,7-methano-7H-thieno[2,3-e][1,3]diazepin-6(5H)-one, of molecular formula $C_{17}H_{18}N_2O_5S_2$ is obtained (M=394.47 g).

The corresponding yield is quantitative.

Stage I 0.780 g of the product obtained in Stage H is dissolved in 8 ml of DMF, 0.320 g of NaN$_3$ (2.5 equivalents) is added and the reaction medium is heated to 60° C. After heating for 15 hours, another 2.5 equivalents of NaN$_3$ are added and heating is continued at 60° C. for a further 8 hours. The reaction medium is poured into CH$_2$Cl$_2$, washed with a solution of NaH$_2$PO$_4$ then with H$_2$O followed by drying over MgSO$_4$ then concentrating by evaporation of the solvent under vacuum.

0.61 g of (azidomethyl)-4,8-dihydro-5-(phenylmethoxy)-4,7-methano-7H-thieno[2,3-e][1,3]diazepin-6 (5H)-one, of molecular formula $C_{16}H_{15}N_5O_2S$ is obtained (M=341.39 g).

The corresponding yield is 82%.

Stage J 0.736 g of the product obtained in Stage I is dissolved in 10 ml of toluene, then 2.26 ml of a 1M solution of Me$_3$P in THF is added dropwise at 20° C. After 60 minutes, the reaction is terminated. The reaction medium is then cooled down to 0° C. and 0.256 g of BOC-ON (1.05 eq.) is added. After 1 hour at 20° C., the reaction mixture is poured into a heptane/ethyl acetate mixture (1/1) and washed with a 1 M solution of NaH$_2$PO$_4$ followed by drying over MgSO$_4$ and evaporating to dryness. The crude solid is purified on silica eluting with a heptane/ethyl acetate mixture (2/1).

0.66 g of 1,1-dimethylethyl [[4,5,6,8-tetrahydro-6-oxo-5-(phenylmethoxy)-4,7-methano-7H-thieno[2,3-e][1,3]diazepin-8-yl]methyl]-carbamate, of molecular formula $C_{11}H_{25}N_3N_4S$ is obtained (M=415.52 g).

Stage K

The process is carried out as indicated in Stage A of Example 11 with 0.09 g of the product obtained in the previous Stage J, 100 mg of 30% palladium on carbon and 2 ml of methanol.

79 mg of crude product 1,1-dimethylethyl [[4,5,6,8-tetrahydro-5-hydroxy-6-oxo-4,7-methano-7H-thieno[2,3-e][1,3]diazepin-8-yl]methyl]-carbamate of molecular formula $C_{14}H_{19}O_3N_4S$ (M=325.39 g) is obtained which is used as it is in the following step.

The yield is quantitative.

Stage L

The process is carried out as indicated in Stage B of Example 11 with 0.51 g of the product obtained in the previous Stage K, 5 ml of pyridine, 0.75 g of pyridine-$SO_3$ complex.

0.250 g of the sodium salt of 1,1-dimethylethyl [[trans-4,5,6,8-tetrahydro-6-oxo-5-(sulphooxy)-4,7-methano-7H-thieno[2,3-e][1,3]diazepin-8-yl]methyl]-carbamate is obtained in the form of beige crystals.

The corresponding yield is 54%.

NMR Spectrum of the Proton

In DMSO-$d_6$ at 300 MHz, chemical shifts and multiplicity: 3.32 (m): NH—$\underline{CH_2}$—CH; 4.47 (bt): NH—CH$_2$—$\underline{CH}$; 7.19 (bt): $\underline{NH}$—CH$_2$—CH; 3.31 (m): N—$\underline{CH_2}$—CH; 4.70 (bs): N—CH$_2$—$\underline{CH}$; 6.96 (d) and 7.43 (d): the hydrogens of the thiophene; 1.41 (s): OC($\underline{CH_3}$)$_3$. MS (negative electrospray) m/z: M⁻=404.

Example 58

Sodium salt and trifluoroacetate of trans-8-(aminomethyl)-4,8-dihydro-5-(sulphooxy)-4,7-methano-7H-thieno[2,3-e][1.3]diazepin-6(5H)-one The process is carried out as indicated according to Example 45 with the product obtained in Example 57, Stage L, in 0.5 ml of trifluoroacetic acid.

32 mg of the sodium salt and trifluoroacetate of trans-8-(aminomethyl)-4,8-dihydro-5-(sulphooxy)-4,7-methano-7H-thieno[2,3-e][1.3]diazepin-6(5H)-one is obtained in the form of beige crystals.

The yield is quantitative.

NMR Spectrum of the Proton

In DMSO-$d_6$ at 300 MHz, chemical shifts and multiplicity: 3.25 (dd) and 3.38 (m): NH$_2$—$\underline{CH_2}$—CH; 4.71 (ed): NH$_2$—CH$_2$—$\underline{CH}$; 3.39 (bd) and 3.51 (d): N—$\underline{CH_2}$—CH; 4.77 (d): N—CH$_2$—$\underline{CH}$; 7.01 (d) and 7.52 (d): the 2H's of the thiophene; 7.94 (bs): $\underline{NH_2}$. MS spectrum (negative electrospray) m/z: M⁻=304.

Example 59

Sodium salt of N-[[trans-4,5,6,8-tetrahydro-6-oxo-5-(sulphooxy)-4,7-methano-7H-thieno[2,3-e][1,3]diazepin-8-yl]methyl]-acetamide 100 mg of the product obtained in Example 58 is solubilized in 1 ml of pyridine then 1.5 equivalents of acetic anhydride and 5 mg of DMAP are added at 0° C. followed by agitating at ambient temperature. The solvents are then evaporated off under reduced pressure and the residue is solubilized in a methylene chloride/ethanol/triethylamine mixture, 70/30/05. The product is then exchanged by passing through Dowex 50WX8 resin in Na⁺ form, then the solution is lyophilized.

35 mg of the sodium salt of N-[[trans-4,5,6,8-tetrahydro-6-oxo-5-(sulphooxy)-4,7-methano-7H-thieno[2,3-e][1,3]diazepin-8-yl]methyl]-acetamide, of molecular formula $C_{11}H_{12}N_3O_6S_2$ is obtained (M=346.36 g).

NMR Spectrum of the Proton

In DMSO-$d_6$ at 300 MHz, chemical shifts and multiplicity: 3.38 (m) and 3.51 (m): NH—$\underline{CH_2}$—CH—N; 4.49 (dd): NH—CH$_2$—$\underline{CH}$—N; 8.10 (bt): $\underline{NH}$—CH$_2$—CH—N; 3.33 (m): N—$\underline{CH_2}$—CH; 4.73 (dd): N—CH$_2$—$\underline{CH}$; 6.96 (d) and 7.40 (d) for the H's of the thiophene; 1.89 (s): $\underline{CH_3}$—CO. MS (negative electrospray) m/z: M⁻=346.

Example 60

Sodium salt of trans-4.5,6,8-tetrahydro-N-methyl-6-oxo-5-(sulphooxy)-4,7-methano-7H-thieno[2,3-e][1.3]diazepine-8-carboxamide Stage A The process is carried out as indicated in Stage B of Example 10, with 0.15 g of the product prepared in Stage F of Example 57, 0.285 g of BOP, 0.091 g of HOBT, 60 mg of NH$_2$Me,HCl, 0.313 ml of DIEA.

0.115 g of 4,5,6,8-tetrahydro-N-methyl-6-oxo-5-(phenylmethoxy)-4,7-methano-7H-thieno[2,3-e][1.3]diazepine-8-carboxamide, of molecular formula $C_{17}H_{17}N_3O_3S$ is obtained (M=343.41 g).

The corresponding yield is 73%.

Stage B

The process is carried out as indicated in Stage A of Example 11 with 0.15 g of the product obtained in the previous Stage A, 20 mg of 30% palladium on carbon and 2 ml of ethanol and 1 ml of acetic acid.

90 mg of 4,5,6,8-tetrahydro-5-hydroxy-N-methyl-6-oxo-4,7-methano-7H-thieno[2,3-e][1,3]diazepine-8-carboxamide, of molecular formula $C_{10}H_{11}O_3S$ is obtained (M=253.28 g).

The corresponding yield is 90%.

Stage C

The process is carried out as indicated in Stage B of Example 11 with 90 mg of the product obtained in the previous Stage B, 170 mg of $SO_3$-pyridine complex and 2 ml of pyridine.

30 mg of the sodium salt of trans-4,5,6,8-tetrahydro-N-methyl-6-oxo-5-(sulphooxy)-4,7-methano-7H-thieno[2,3-e][1.3]diazepine-8-carboxamide, of molecular formula $C_{10}H_{10}N_3O_6S_2$.Na is obtained in the form of pale yellow crystals (M=332.34 g, 22.99 g).

The corresponding yield is 24%.

NMR of the Proton

In DMSO-$d_6$ at 300 MHz, chemical shifts and multiplicity: 2.67 (bd): $\underline{CH_3}$—NH—CO—CH; 8.35 (bq): CH$_3$—$\underline{NH}$—CO—CH; 4.94 (s): CH$_3$—NH—CO—$\underline{CH}$; 3.36 (d) and 3.48 (dd): N—$\underline{CH_2}$—CH; 4.73: N—CH$_2$—$\underline{CH}$; 6.94 (d) and 7.45 (bd) for the hydrogens of the thiophene. MS (negative electrospray) m/z: M⁻=332.

Example 61

Trans methyl 4,5,6,8-tetrahydro-6-oxo-5-(phenylmethoxy)-1H-4,7-methanopyrazolo[3,4-e][1,3]diazepine-8-carboxylate Stage A: Preparation of [2-(phenylthio)ethyl]hydrazine
Step 1

In a flask placed under a nitrogen atmosphere, 100 g of 2-bromoethylphenyl sulphide dissolved in 1 l. of ethanol is introduced and 184.2 g of hydrazine hydrate is added. The reaction medium is heated at 100° C. overnight. Then, once the reaction is complete, the solvent is distilled under reduced pressure at 80° C.-90° C. Then, 65 g of potassium carbonate and 1 l. of methylene chloride are added to the medium. Agitation is carried out for 15 minutes, then the organic phase is extracted with 2×500 ml of water, then the organic phase is dried over magnesium sulphate, filtered and evaporated under reduced pressure. The residue is then taken up in 750 ml of an ethanol/water mixture to which 12 ml of concentrated sulphuric acid is added dropwise. The product crystallizes and the precipitate is filtered then rinsed with an ethanol/water solution, 80/20, then with ether. The product is then dried under reduced pressure.

81.84 g of the hemisulphate salt of [2-(phenylthio)ethyl]-hydrazine, of molecular formula, $C_8H_{12}N_2S+1/2$ of $H_2SO_4$. is obtained (M=217.3 g).

The yield obtained is 81%.

Step 2

79.7 g of the [2-phenylthio)ethyl]-hydrazine obtained in the previous Step 1 is dissolved in 1.9 l of dichloromethane.

Then 400 ml of 1N soda is added, and the reaction medium is agitated vigorously. The organic phase is then extracted with dichloromethane, then the organic phase is dried over $MgSO_4$ followed by evaporating under reduced pressure.

The product of molecular formula $C_8H_{12}N_2S$ is obtained (M=168.26 g) is obtained with a quantitative yield.

The yield obtained is 89%.

Stage B

The process is carried out as indicated in Stage B of Example 5 with 79 g of the product prepared in Stage A of Example 5 and 54.5 g of [2-(phenylthio)ethyl]-hydrazine and 1 l. of methanol.

The compound 1,1-dimethylethyl 1,4,5,7-tetrahydro-4-oxo-1-[2-(phenylthio)ethyl]-6H-pyrazolo[3,4-c]pyridine-6-carboxylate, of molecular formula $C_{19}H_{23}N_3O_3S$ is obtained (M=373.48 g).

The corresponding yield obtained is 57.6%.

Stage C

The process is carried out as indicated in Stage A of Example 18 with 74.5 g of the product obtained in the previous Stage B, 7.58 g of sodium borohydride and 372 ml of methanol.

72.5 g of the compound 1,1-dimethylethyl 1,4,5,7-tetrahydro-4-hydroxy-1-[2-(phenylthio)ethyl]-6H-pyrazolo[3,4-c]pyridine-6-carboxylate, of molecular formula $C_{19}H_{25}N_3O_3S$ is obtained (M=375.49 g).

The corresponding yield is 97%.

Stage D 75 g of the product obtained in the previous Stage C is dissolved in 1 l. of dichloromethane at 0° C. 118 g of 70% methachloroperbenzoic acid is added, followed by agitating for 1 hour 30 minutes at ambient temperature. 1.5 l. of dichloromethane and 1.6 l. of 0.5N sodium thiosulphate are added to the reaction medium. After extraction of the organic phase, the reaction medium is washed again with 1 l. of sodium thiosulphate then with 1.5 l. of $NaHCO_3$ and finally with 1.5 l. of water. The aqueous phases are then re-extracted again with dichloromethane, then the different organic phases are combined, dried over magnesium sulphate, filtered, then the solvent is evaporated off under reduced pressure.

The crude product is recrystallized from isopropyl ether in order to produce 81 g of the compound 1,1-dimethylethyl 1,4,5,7-tetrahydro-4-hydroxy-1-[2-[1-propenylsulphonyl] ethyl]-6H-pyrazolo[3,4-c]pyridine-6-carboxylate of molecular formula $C_{19}H_{25}N_3O_5S$ is obtained (M=407.49 g).

The corresponding yield is 99%.

Stage E

In a flask placed under an inert atmosphere and at a temperature of –30° C., 57.2 g of the product obtained in the previous Stage D is dissolved in 572 ml of anhydrous THF.

Then, 337 ml of a 1M solution of potassium tert-butylate in THF is added. Agitation is carried out for 1 hour then 20 ml of acetic acid is added to the reaction medium. An aqueous solution of $NaHCO_3$ bicarbonate and NaCl is then added, then the organic phase is extracted several times with ethyl acetate. The organic phases are dried over magnesium sulphate, filtered and the solvent evaporated off under reduced pressure. 57.4 g of crude product is recovered which is then purified on a silica eluting with a dichloromethane/acetone mixture, 4/6.

After evaporation of the solvent 38.6 g of 1,1-dimethylethyl 1,4,5,7-tetrahydro-4-hydroxy-6H-pyrazolo[3,4-c]pyridine-6-carboxylate, of molecular formula $C_{11}H_{17}N_3O_3$ is obtained (M=239.28 g).

The corresponding yield is 84%.

Stage F

In a flask placed under a nitrogen atmosphere, 35 g of the product obtained in the previous Stage E is dissolved in 890 ml of dichloromethane. 49.77 g of $Ph_3CCl$ is added then the solution is cooled down to –30° C. with a dry ice/acetone mixture. 24.7 ml of triethylamine is then added, and the reaction medium is agitated while being left to return to ambient temperature for 4 hours 30 minutes. Then, after evaporation of the solvent under reduced pressure, the residue is poured into 1.6 l. of ethyl acetate and washed with 1.8 l. of water. The organic phase is then dried over magnesium sulphate, filtered, and the solvent evaporated off under reduced pressure. The residue is taken up in ethyl ether and the precipitate obtained is washed with pentane.

After drying, 62.5 g of 1,1-dimethylethyl 2,4,5,7-tetrahydro-4-hydroxy-2-(triphenylmethyl)-6H-pyrazolo[3,4-c]pyridine-6-carboxylate, of molecular formula $C_{30}H_{31}N_3O_3$ is obtained (M=481.60 g). 1

The yield is 87%.

Stage G

The process is carried out as indicated in Stage B of Example 18 with 22.1 g of the product obtained in Stage F and 81 ml of tert-butyllithium 1.7 mole/l. in pentane, 230 ml of THF and carbon dioxide. The reaction medium is hydrolyzed by the addition of 100 ml of water and 300 ml of AcOEt then acidified to pH=4 by the addition of formic acid. The aqueous phase is extracted several times with AcOEt, then the organic phase is dried over $MgSO_4$, filtered and the solvent is evaporated off under reduced pressure in order to produce 29.8 g of crude product. The latter is dissolved in 300 ml of ether, then extracted with 3×200 ml of a saturated solution of $NaHCO_3$. The aqueous phase is acidified to pH=4 by the addition of formic acid, then extracted with AcOEt. After drying over $MgSO_4$, filtering and evaporating the solvent under reduced pressure, 14.8 g of acid of molecular formula $C_{31}H_{31}N_3O_5$ is obtained (M=525.61 g).

The 15 g of compound obtained is then esterified in the presence of 3.7 g of $K_2CO_3$ and 4.9 ml of dimethyl sulphate.

Agitation is carried out for 1 hour at ambient temperature then 7.4 ml of triethylamine is added. After 40 minutes, 300 ml of ethyl acetate and 200 ml of water are added. After agitation and decanting, the aqueous phase is re-extracted with ethyl acetate. The organic phases are washed with a solution of water saturated in NaCl. The organic phases are then dried over magnesium sulphate and the solvent is evaporated off under reduced pressure.

11.23 g of 6-(1,1-dimethylethyl) and 7-methyl 2,4,5,7-tetrahydro-4-hydroxy-2-(triphenylmethyl)-6H-pyrazolo[3,4-c]pyridine-6,7-dicarboxylate, of molecular formula $C_{32}H_{33}N_3O_5$ is obtained (M=739.64 g).

The corresponding yield over both stages is 42%.

Stage H

In a flask under an argon atmosphere, 10 g of the product obtained in the previous Stage G is solubilized in 50 ml of dichloromethane. 2.8 g of triethylamine then 4.8 g of $(CH_3SO_2)_2O$ diluted in 1 ml of dichloromethane are added.

Agitation is carried out for 1 hour at −70° C. then 6.8 g of O-benzylhydroxylamine is added. Agitation is again carried out for 10 minutes at −78° C., for 1 hour 20 minutes at −50° C., and finally overnight at 0° C. The reaction medium is left at 20° C. for 1 hour, then dichloromethane is added and the organic phase is washed with a solution of tartaric acid then with an aqueous solution of NaCl. The organic phase is dried over $MgSO_4$, followed by filtering and the solvent is evaporated off under reduced pressure. 11.9 g of product is obtained which is purified on silica eluting with a petroleum ether/ethyl acetate mixture, 8/2.

8.9 g of 6-(1,1-dimethylethyl) and 7-methyl 2,4,5,7-tetrahydro-4-[(phenylmethoxy)amino]-2-(triphenylmethyl)-6H-pyrazolo[3,4-c]pyridine-6,7-dicarboxylate, of molecular formula $C_{39}H_{40}N_4O_5$ is obtained (M=644.78 g).

The corresponding yield is 75%.

Stage I

In a flask maintained at 0° C., 10 g of the product obtained in the previous Stage H is dissolved in 70 ml of ethyl acetate.

35 ml of a saturated solution of NCl in ethyl acetate is added then the reaction medium is agitated for 3 hours. After evaporation of the solvent, the reaction medium is taken up in water and the aqueous phase is washed with AcOEt. The aqueous phase is then adjusted to pH=10 with a 20% ammonium hydroxide solution then extraction is carried out three times with ethyl acetate. After drying over magnesium sulphate, filtration, and evaporation of the solvent under reduced pressure, 4.21 g of compound 4,5,6,7-tetrahydro-4-[(phenylmethoxy)amino]-2H-pyrazolo[3,4-c]pyridine-7-carboxylate, of molecular formula $C_{15}H_{18}N_4O_3$ is obtained (M=302.34 g).

The corresponding yield in the two Stages I and J is 89.7%.

Stage J

The process is carried out as indicated in Stage L of Example 3 with 9.24 g of the product obtained in the previous Stage I, 12.3 ml of triethylamine, 1.85 ml of diphosgene and 3 liters of acetonitrile.

9.6 g of methyl trans-4,5,6,8-tetrahydro-6-oxo-5-(phenylmethoxy)-1H-4,7-methanopyrazolo[3,4-e][1,3]diazepine-8-carboxylate, of molecular formula $C_{16}H_{16}N_4O_4$ is obtained (M=328.33 g).

The corresponding yield is 95.6%.

NMR of the Proton

DMSO-$d_6$ at 300 MHz at 60° C., chemical shifts and multiplicity: 3.37 (dd) and 3.42 (d): N—CH$_2$—CH; 4.54: N—CH$_2$—CH; 3.74 (s) CH$_3$—O—CO; 4.90 (bs): O—CH$_2$-Ph; 7.29 to 7.44 (m): aromatic 5H's; 5.02 (s): CH—COO; 7.69 (s): N=CH; 7.83 (bs) and 12.7 (b): mobile H.

Example 62

Triethylammonium salt of trans methyl 1-ethyl-4,5,6,8-tetrahydro-6-oxo-5-(sulphooxy)-1H-4,7-methanopyrazolo[3,4-e][1,3]diazepine-8-carboxylate Stage A In a flask maintained at 0° C. and under a nitrogen atmosphere, 0.1 g of the product obtained in Example 61 is introduced into 0.8 ml of DMF. 0.052 g of iodoethane and 0.015 g of NaH at 50% in oil are added, then agitation is carried out for 15 minutes at 0° C. and the reaction medium is allowed to return to ambient temperature. Agitation is carried out for 1 hour 30 minutes, then ethyl acetate is added and the organic phase is washed with an aqueous solution of NH$_4$Cl, then the aqueous phase is extracted with ethyl acetate. After drying the organic phase over magnesium sulphate and filtration, the solvent is evaporated off under reduced pressure. 102 mg of product is obtained which is purified on silica eluting with a heptane/ethyl acetate mixture 1/1 with 0.1% TEA.

22.4 mg of methyl 1-ethyl-4,5,6,8-tetrahydro-6-oxo-5-(phenylmethoxy)-1H-4,7-methanopyrazolo[3,4-e][1,3]diazepine-8-carboxylate and 29 mg of methyl 2-ethyl-4,5,6,8-tetrahydro-6-oxo-5-(phenylmethoxy)-4H-4,7-methanopyrazolo[3,4-e][1,3]diazepine-8-carboxylate, of molecular formula $C_{18}H_{20}N_4O_4$ is obtained (M=358.38 g).

Stage B

The process is carried out as in Stage A of Example 11 with 22 mg of methyl 1-ethyl-4,5,6,8-tetrahydro-6-oxo-5-(phenylmethoxy)-1H-4,7-methano pyrazolo[3,4-e][1,3]diazepine-8-carboxylate in 1 ml of methanol and with 13.2 mg of palladium on carbon at 10% by weight.

15.8 mg of methyl 1-ethyl-4,5,6,8-tetrahydro-5-hydroxy-6-oxo-1H-4,7-methanopyrazolo[3,4-e][1,3]diazepine-8-carboxylate, of molecular formula $C_{11}H_{14}N_4O_4$ is obtained (M=266.26 g).

The corresponding yield is 88%.

Stage C

In a flask placed under an inert atmosphere, 0.0158 g of the product obtained in the previous Stage B is introduced into 1 ml of pyridine, then 0.028 g of the pyridine-SO$_3$ complex is added. Agitation is carried out overnight at ambient temperature, followed by filtering, diluting the solution with methylene chloride mixture, washing with water, evaporating the solvent under reduced pressure and a crude product is obtained which is purified on silica eluting with a dichloromethane/ethanol mixture, 95/5 with 0.1% TEA.

11 mg of the triethylammonium salt of trans methyl 1-ethyl-4,5,6,8-tetrahydro-6-oxo-5-(sulphooxy)-1H-4,7-methanopyrazolo[3,4-e][1,3]diazepine-8-carboxylate, of molecular formula $C_{11}H_{13}N_4O_7S$ $C_6H_{16}N$ is obtained (M=447.51 g, 102.20 g).

The yield is 41.4%.

LC/MS: General Conditions: Kromasil C column (18 4.6×250 mm, 5μ oven at 30° C. Flow rate=1 ml/minute. $V_{inj}$=15 μl Detection: λ=200-400 mm MS/ESP mode±CV=50 V Eluent: A=H$_2$O (0.1% HCO$_2$H) B=CH$_3$CN Gradient:

| time | A % | B % |
| --- | --- | --- |
| 0.00 | 80.0 | 20.0 |
| 15.00 | 50.0 | 50.0 |

-continued

| time | A % | B % |
|---|---|---|
| 25.00 | 20.0 | 80.0 |
| 40.00 | 80.0 | 20.0 |
| 50.00 | 80.0 | 20.0 |

LC/ESP −: RT=5.62 minutes. m/z=[2M+Na]$^+$=713 [M]$^-$=345; {M−CH$_3$OH}$^-$=313.

Example 63

Triethylammonium salt of trans methyl 2-ethyl-4,5,6,8-tetrahydro-6-oxo-5-(sulphooxy)-4H-4,7-methanopyrazolo[3,4-e][1.3]diazepine-8-carboxylate Stage A The process is carried out as indicated in Stage A of Example 11 with 0.029 g of methyl 2-ethyl-4,5,6,8-tetrahydro-6-oxo-5-(phenylmethoxy)-4H-4,7-methano pyrazolo[3,4-e][1,3]diazepine-8-carboxylate, 0.5 ml of methanol and 0.0174 g of palladium on carbon.

20.1 mg of methyl 2-ethyl-4,5,6,8-tetrahydro-5-hydroxy-6-oxo-4H-4,7-methanopyrazolo[3,4-e][1.3]diazepine-8-carboxylate, of molecular formula C$_{11}$H$_{14}$N$_4$O$_4$ (M=266.26 g).

The corresponding yield is 85%.

Stage B

The process is carried out as indicated in Stage C of Example 62 with 0.02 g of the product obtained in the previous Stage A, 0.036 g of pyridine-SO$_3$ complex and 1 ml of pyridine.

21 mg of the triethylammonium salt of trans methyl 2-ethyl-4,5,6,8-tetrahydro-6-oxo-5-(sulphooxy)-4H-4,7-methanopyrazolo[3,4-e][1.3]diazepine-8-carboxylate, of molecular formula C$_{11}$H$_{13}$N$_4$O$_7$S+C$_6$H$_{16}$N is obtained (M=345.31 g+102.20 g).

The corresponding yield is 62%.

LC/ESP results: see general conditions Example 62 RT=5.01 minutes. m/z: M$^-$=345.

Example 64

Sodium salt of N-[4,6,7,8-tetrahydro-6-oxo-7-(sulphooxy)-5,8-methano-5H-thiazolo[4,5-e][1,3]diazepin-2-yl]-acetamide Stage A 2.69 g of the product prepared in Stage C of Example 20 in 50 ml of THF is introduced into a flask placed under a nitrogen atmosphere. Then, 1.22 g of DMAP is added and the solution is cooled down to 0° C. 0.94 ml of acetic anhydride is then added followed by agitating for 1 hour 30 minutes while allowing the reaction mixture to return to ambient temperature. Once the reaction is complete, ethyl acetate and ice are added to the solution. The organic phase is washed three times with water then dried over magnesium sulphate and the solvent is evaporated under reduced pressure. 2.95 g of crude product is isolated which is recrystallized from acetonitrile. After separating and drying under vacuum, 2.39 g of 1,1-dimethylethyl 2-(acetylamino)-6,7-dihydro-7-oxo-thiazolo[4,5-c]pyridine-5 (4H)-carboxylate, of molecular formula C$_{13}$H$_{17}$N$_3$O$_4$S is obtained (M=311.36 g).

The yield obtained is 77%.

Stage B

The process is carried out as indicated in Stage A of Example 18 with 2.39 g of the product obtained in the previous Stage A, 290 mg of NaBH$_4$, 15 ml of methanol and 15 ml of THF.

2.02 g of 1,1-dimethylethyl 2-(acetylamino)-6,7-dihydro-7-hydroxy-thiazolo[4,5-c]pyridine-5 (4H)-carboxylate, of molecular formula, C$_{13}$H$_{19}$N$_3$O$_4$S (M=313.38 g) is obtained in the form of colourless crystals.

The yield obtained is 84%.

Stage C

The process is carried out as indicated in Stage H of Example 61, with 900 mg of the product obtained in the previous Stage B, 750 mg of (CH$_3$SO$_2$)$_2$O, 15 ml of DMF, 600 µl of triethylamine and 1.06 g of O-benzylhydroxylamine.

617 mg of the pyridinium salt of 1,1-dimethylethyl 2-(acetylamino)-6,7-dihydro-7-[(phenylmethoxy)amino]-thiazolo[4,5-c]pyridine-5 (4H)-carboxylate, of molecular formula C$_{20}$H$_{26}$N$_4$O$_4$S is obtained (M=418.51 g).

The yield is 25. %.

Stage D 559 mg of the product obtained in the previous Stage C, in 15 ml of dichloromethane is introduced into a flask in the presence of 293 µl of anisole. Then the solution is cooled down to 0° C. and 14 ml of tricfluoroacetic acid is added rapidly. The solution is agitated for two hours while allowing the temperature to return to ambient temperature, then the solvent is evaporated off under reduced pressure. The reaction medium is diluted with ethyl acetate and is washed twice with water then the aqueous phases are extracted with ethyl acetate. The combined organic phases are dried over sodium sulphate then evaporated under reduced pressure. The crude product obtained is taken up with ethyl acetate and extracted twice with a 1M solution of hydrochloric acid. The aqueous phase is then washed with ethyl acetate then the aqueous phase is adjusted to pH 12 with a 2M soda solution. Extraction is carried out twice with ethyl acetate followed by washing with water. The organic phases are then combined in order to be dried over sodium sulphate and filtered, then the solvent is evaporated off under reduced pressure. 184 mg of N-[4,5,6,7-tetrahydro-7-[(phenylmethoxy)amino]thiazolo[4,5-c]pyridin-2-yl]-acetamide, of molecular formula C$_{15}$H$_{18}$N$_4$O$_2$S is obtained (M=318.40 g) is isolated.

The yield is 43%.

Stage E

The process is carried out as indicated in Stage L of Example 3 with 184 mg of the product obtained in the previous Stage D, 241 µl of triethylamine, 38 µl of diphosgene and 125 ml of acetonitrile.

70 mg of N-[4,6,7,8-tetrahydro-6-oxo-7-(phenylmethoxy)-5,8methano-5H-thiazolo[4,5-e][1,3]diazepin-2-yl]-acetamide, of molecular formula C$_{16}$H$_{16}$N$_4$O$_3$S is obtained (M=344.39 g).

The corresponding yield is 35%.

Stage F 43 mg of the compound obtained in the previous Stage E in 4.5 ml of methanol is introduced into a flask then 215 mg of 30% palladium on carbon is added in several goes. The medium is maintained under hydrogen for several hours. Once the reaction is complete, the catalyst is filtered and the solvent is evaporated off under reduced pressure. 20 mg of the expected product is obtained N-(4,6,7,8-tetrahydro-7-hydroxy-6-oxo-5,8-methano-5H-thiazolo[4,5-e][1.3]diazepin-2-yl)-acetamide, of molecular formula C$_9$H$_{10}$N$_4$O$_3$S is obtained (M=254.26 g).

103

Stage G

The crude product obtained in the previous Stage F is used which is dissolved in 0.4 ml of pyridine. Then 41 mg of the pyridine-$SO_3$ complex is added. Agitation is carried out overnight at ambient temperature, then the pyridine is evaporated under vacuum. The residue is taken up with ethyl acetate in the presence of a saturated aqueous solution of $NaH_2PO_4$. Extraction is carried out twice with ethyl acetate with an aqueous solution of $NaH_2PO_4$. Finally 25.7 mg of tetrabutylammonium dihydrogen sulphate is added to the aqueous phase followed by extracting with ethyl acetate. The organic phase is dried over $Na_2SO_4$ followed by filtering and drying under reduced pressure. 17 mg of crude product is isolated which is purified on silica eluting with a chloroform/acetonitrile mixture (4/6). After evaporation of the fractions, 8 mg of the tetrabutylammonium salt of N-[4,6,7,8-tetrahydro-6-oxo-7-(sulphooxy)-5,8-methano-5H-thiazolo[4,5-e][1,3]diazepin-2-yl]-acetamide is collected which is converted to the sodium salt of N-[4,6,7,8-tetrahydro-6-oxo-e7-(sulphooxy)-5,8-methano-5H-thiazolo[4,5-e][1,3]diazepin-2-yl]-acetamide, of molecular formula $C_9H_9NaO_6S_2 \cdot Na^+$ (M=333.23 g) by passing through Dowex 50WX8 resin in $Na^+$ form.

The yield obtained over the two Stages F and G is 6.7%.

MS (negative electrospray) m/z: $M^-$=333.

Example 65

Sodium salt of 7,8-dihydro-7-(sulphooxy)-5,8-methano-5H-thieno[2,3-e][1,3]diazepin-6 (4H)-one Stage A 3.9 g (22.89 mmoles) of methyl 3-formyl-2-thiophene carboxylate is dissolved in 39 ml of methanol. The reaction medium is cooled down in an ice-cold water bath and 305 mg (7.66 mmoles) of 95% $NaBH_4$ is added five times over five minutes. Agitation is carried out for one hour at 2° C. Then 39 ml of ethyl acetate and 39 ml of a 1M aqueous solution of $NaH_2PO_4$ are added. After decanting, the organic phase is extracted with 20 ml of ethyl acetate then washed with 20 ml of water half saturated with HCl.

After drying over magnesium sulphate, filtration and evaporation of the solvent under vacuum, 3.9 g of methyl 3-(hydroxymethyl)-2-thiophenecarboxylate, of molecular formula $C_7H_8O_3S$ is obtained (M=172.20 g).

The yield obtained is quantitative.

Stage B

The process is carried out as indicated in Stage C of Example 22 with 3.9 g (22.65 mmoles) of the product obtained in the previous Stage A, 39 ml of dichloromethane and 7.8 ml (107.56 mmoles) of $SOCl_2$.

3.85 g of methyl 3-(chloromethyl)-2-thiophenecarboxylate, of molecular formula $C_7H_7ClO_2S$ is obtained (M=190.65 g).

The yield is 89%.

Stage C

The process is carried out as indicated in Stage D of Example 22 with 3.84 g (20.4 mmoles) of the chlorinated product obtained in the previous Stage B, 41.5 ml of acetonitrile, 11.15 g of $K_2CO_3$ and 8.45 ml of tert-butyl glycinate.

3.76 g of methyl 3-[[[(1,1-dimethylethoxy)carbonyl]amino]methyl]-2-thiophenecarboxylate, of molecular for-

104 mula $C_{13}H_{19}NO_4S$ (M=285.36 g) is obtained after purification.

The corresponding yield is 65%.

Stage D

The process is carried out as indicated in Stage E of Example 22 with 3.73 g (13.07 mmoles) of the product obtained in the previous Stage C, 37 ml of THF and 3.17 g (14.38 mmoles) of 99% $(BOC)_2O$-

5.35 g of methyl 3-[[[(1,1-dimethylethoxy)carbonyl][2-(1,1-dimethylethoxy)-2-oxoethyl]amino]methyl]-2-thiophenecarboxylate, of molecular formula $C_{18}H_{27}NO_6S$ is obtained (M=385.48 g).

The yield obtained is quantitative.

Stage E

The process is carried out as indicated in Stage F of Example 22, with 5.3 g (12.95 mmoles) of the product obtained in the previous Stage D, 21 ml of anhydrous THF, 2.97 g (25.9 mmoles) of 98% potassium tert-butylate.

3.74 g of bis(1,1-dimethylethyl)6,7-dihydro-7-oxo-thieno[3,2-c]pyridine-5,6 (6H)-dicarboxylate, of molecular formula $C_7H_{20}NO_5S$ (M=353.44 g) is obtained in the form of yellow crystals.

The corresponding yield is 82%.

Stage F

The process is carried out as indicated in Stage H of Example 22, with 3.65 g (10.33 mmoles) of the product obtained in the previous Stage E, 29 ml of trifluoroacetic acid.

2.76 g of the trifluoroacetic salt of 4,5,6,7-tetrahydro-7-oxo-thieno[3,2-c]pyridinium, of molecular formula $C_7H_7NO_5S, CF_3CO_2H$ (M=267.23 g) is obtained in the form of yellow crystals.

The corresponding yield is 82.6%.

2.24 g (8.38 mmoles) of the product obtained previously is suspended in 22.5 ml of THF. Then 1.4 ml (10 mmoles) of triethylamine is added at ambient temperature. After dissolution of the components, 2.03 g (9.22 mmoles) of di-tert-butyl carbonate is introduced. Agitation is carried out for one hour at ambient temperature, then 30 ml of a two thirds saturated aqueous solution of NaCl is introduced, extraction is carried out with 15 ml of ethyl acetate, the organic phase is washed with 15 ml of a 0.1M aqueous solution of $NaH_2PO_4$ and with 10 ml of a salt water solution. After drying over magnesium sulphate, filtration and evaporation of the solvents under reduced pressure, 2.3 g of 1,1-dimethylethyl 6,7-dihydro-7-oxo-thieno[3,2-c]pyridine-5 (4H)-carboxylate, of molecular formula $C_{12}H_{15}N_3S$ (M=253.32 g) is obtained.

The corresponding yield is 92%.

Stage G

The process is carried out as indicated in Stage I of Example 22 with 253 mg of the product obtained in the previous Stage F, 181 mg of O-alkylhydroxylamine hydrochloride, 243 µl of pyridine and 5 ml of ethanol.

328 mg of 1,1-dimethyl 6,7-dihydro-7-[(2-propenyloxy)imino]-thieno[3,2-c]pyridine-5(4H)-carboxylate, of molecular formula $C_{15}H_{20}N_2O_3S$ is obtained (M=308.40 g).

The yield is quantitative.

Stage H

The process is carried out as indicated in Stage B of Example 6, with 1 g (3.24 mmoles) of the product obtained in Stage G, 32 ml of methanol, 3.26 g (51.84 mmoles) of sodium cyanoborohydride and 4.93 ml (38.88 mmoles) of boron trifluoride etherate.

664 mg of 1,1-dimethylethyl 6,7-dihydro-7-[(2-propenyloxy)amino]-thieno[3,2-c]pyridine-5 (4H)-carboxylate, of molecular formula $C_{15}H_{22}N_2O_3S$ (M=310.4182 g) is obtained in the form of a yellow oil.

The corresponding yield is 66%.

Stage I

The process is carried out as indicated in Stage D of Example 64 with 588 mg of the product obtained in the previous Stage H, 20 ml of methylene chloride, 0.38 ml of anisole and 19 ml of trifluoroacetic acid.

326 mg of 4,5,6,7-tetrahydro-7-[(2-propenyloxy)amino]-thieno[3,2-c]pyridine, of molecular formula $C_{10}H_{14}N_2OS$ (M=210.29 g) is obtained in the form of a colourless oil.

The corresponding yield is 82%.

Stage J

The process is carried out as indicated in Stage L of Example 3 using 307 mg of the product obtained in the previous Stage I, 609 l of TEA, 97 µl of diphosgene and 150 ml of acetonitrile.

128 mg of 7,8-dihydro-7-(2-propenyloxy)-5,8-methano-5H-thieno[3,2-e][1,3]diazepin-6(4H)-one, of molecular formula $C_{11}H_{12}N_2O_2S$ is obtained (M=236.29 g) is obtained in the form of an oil.

The corresponding yield is 37%.

Stage K

The process is carried out as indicated in Example C of Example 7 with 128 mg of the product obtained in the previous Stage J, 2 ml of dichloromethane, 93 µl of acetic acid, 313 mg of $Pd(PPh_3)_4$, 295 mg of pyridine-$SO_3$ complex and 2 ml of pyridine.

58 mg of the sodium salt of 7,8-dihydro-7-(sulphooxy)-5,8-methano-5H-thieno[2,3-e][1,3]diazepin-6 (4H)-one, of molecular formula $C_8H_7N_2NaO_5S_2$ is obtained (M=298.27 g).

The yield is 36%.

NMR of the Proton

In DMSO-$d_6$ at 300 MHz, chemical shifts and multiplicity: 3.30 (d), 3.60 (dd): N—CH$_2$—CH; 4.78 (d): N—CH$_2$—CH; 4.19 and 4.28: N—CH$_2$—C=; 6.88 (d), 7.45 (d), the H's of the thiophene. MS (negative electrospray): m/z: [2M+Na]$^-$=573, [2M+H]$^-$=551, [M]$^-$=275.

Example 66

Sodium salt of 4,8-dihydro-5-(sulphooxy)-4,7-methano-7H-isoxazole[4,5-e][1,3]diazepin-6 (5H)-one Stage A 12 mg (44.7 mmoles) of 1,1-dimethylethyl 4-[(dimethylamino)methylene]-3,5-dioxo-1-piperidinecarboxylate with 7.82 mg (112 mmoles) of hydroxylamine hydrochloride is introduced into 144 ml of methanol in a flask, the reaction medium is then agitated for 16 hours at 20° C. and then the solvent is evaporated off under reduced pressure. The mixture is poured into 10 ml of water followed by extracting with ethyl acetate (3×10 ml). The phases organic obtained are collected, dried over Na$_2$SO$_4$, filtered then the solvent is evaporated off under reduced pressure. 3.93 g of 1,1-dimethylethyl 4,7-dihydro-4-(hydroxyimino)-isoxazolo[5,4-c]pyridine-6(5H)-carboxylate, of molecular formula $C_{11}H_{15}N_3O_4$ is obtained (M=253.26 g).

The yield is 35%.

Stage B

In a flask placed under a nitrogen atmosphere, 3.5 g (14 mmoles) of the compound obtained in Stage A is placed in 60 ml of DMF. After dissolution, the solution is cooled down to 0° C. then 2.26 ml of allyl bromide and 1.01 g of NaH at 50% in oil are added, agitation is carried out for 1 hour at 20° C. then the reaction is stopped by pouring the suspension into an ice-water mixture. Ethyl acetate is added and the reaction medium is left to decant followed by extracting 3 times with ethyl acetate, collecting the ethyl acetate phases and washing twice with demineralized water. The organic phases are combined and dried over MgSO$_4$, followed by filtering, rinsing then evaporating under reduced pressure. 6.57 g of yellow oil is obtained which is purified by chromatography on silica eluting with a hexane/ethyl acetate mixture (6/4).

3.43 g of 1,1-dimethylethyl 4,7-dihydro-4-(hydroxyimino)-isoxazolo[5,4-c]pyridine-6 (5H)-carboxylate, of molecular formula $C_{14}H_{19}N_3O_4$ is obtained (M=293.33 g).

The corresponding yield is 77.3%.

Stage C 2.71 g (9.24 mmoles) of the compound obtained in Stage B and 38 ml of methanol are placed in a three-necked flask. The mixture is cooled down to −5° C.-10° C., then 9.14 g (0.138 mmole) of NaBH$_3$CN is added. 14.05 cm$^3$ (0.111 mole) of boron trifluoride etherate is then added dropwise. Agitation is carried out for 5 minutes at −5° C., then at 20° C. for 1 hour, then the reaction medium is poured into a saturated NaHCO$_3$/ethyl acetate mixture, and agitated for 10 minutes.

After decanting, extraction is carried out with 4×150 cm$^3$ of ethyl acetate, the phases organic are washed with 1×150 cm$^3$ of a 2N NaOH solution, then with 2×150 cm$^3$ of water (to a neutral pH). The organic phase is dried over MgSO$_4$, followed by rinsing with ethyl acetate then the solvent is evaporated off under reduced pressure in order to obtain 4.2136 g of a light yellow oil which is purified by chromatography on silica using a hexane/ethyl acetate mixture (7/3) as eluent.

1.11 g of 1,1-dimethylethyl 4,7-dihydro-4-[(2-propenyloxy)amino]-isoxazolo[5,4-c]pyridine-6(5H)-carboxylate, of molecular formula $C_{14}H_{21}N_3O_4$ is obtained (M=295.34 g).

The corresponding yield is 41%.

Stage D 1.24 g of the compound obtained in Stage C (4.21 mmoles) and 8.7 cm$^3$ of ethyl acetate are placed in a 50 cm$^3$ three-necked flask equipped with a magnetic stirrer and a temperature detector. The solution is cooled down to 0° C. then 8.7 cm$^3$ of a saturated solution of gaseous HCl in ethyl acetate is added dropwise. Agitation is maintained for 5 minutes at 0° C. then the temperature of the solution is taken to 20° C. After agitating for two hours at 20° C., the solvent is evaporated off under reduced pressure in order to obtain a white powder to which an ethyl acetate/water mixture is added and a 20% solution of ammonium hydroxide is added. After dissolution and agitation for 10 minutes, decanting is carried out, followed by extracting again with 3× ethyl acetate. The organic phase is dried over MgSO$_4$, filtered and rinsed with ethyl acetate. Finally, the solvent is evaporated off under reduced pressure in order to obtain 0.740 g of 4,5,6,7-tetrahydro-4-[(2-propenyloxy)amino]-isoxazolo[5,4-c]pyridine, of molecular formula $C_9H_{13}N_3O_2$ is obtained (M=195.22 g).

The corresponding yield is 90%.

Stage E 0.661 g (3.38 mmoles) of the compound obtained in Stage D and 227 ml of CH$_3$CN as well as 1.24 ml (8.8 mmoles) of TEA are placed in a three-necked flask placed under a nitrogen atmosphere. 0.209 ml (1.72 mmoles) of diphosgene is added to the reaction medium at −5° C./−10° C. in one go. Agitation is then carried out for 5 minutes at this temperature, then the reaction medium is maintained at 20° C. The reaction medium is then poured into 150 ml of ethyl acetate followed by washing with 100 ml of demineralized water. Two further washes with demineralized water are carried out. After decanting, the aqueous phases are extracted with 1×100 ml of ethyl acetate followed by decanting. The organic phases are combined then dried over $MgSO_4$, rinsed with ethyl acetate then the solvent is evaporated off under reduced pressure in order to obtain 0.894 g of white crystals which are purified by chromatography on silica using a $CH_2Cl_2$/acetone eluent (97/3).

0.5573 g of 4,8-dihydro-5-(2-propenyloxy)-4,7-methano-7H-isoxazolo[4,5-e][1,3]diazepin-6(5H)-one, of molecular formula $C_{10}H_{11}N_3O_3$ (221.22 g).

The corresponding yield is 74.8%.

Stage F

The process is carried out as indicated in Stage C of Example 7 with 250 mg of the product obtained in Stage E, 4 ml of $CH_2Cl_2$, 0.038 ml of ethanol, 0.653 g of $Pd(PPh_3)_4$ as well as 4.8 ml of pyridine, and 566.5 mg of $SO_3$-pyridine complex in order to obtain 0.133 g of the sodium salt of 4,8-dihydro-5-(sulphooxy)-4,7-methano-7H-isoxazolo[4,5-e][1,3]diazepin-6(5H)-one, of molecular formula $C_7H_6N_3Na.O_6S$ (283.20 g).

The corresponding yield is 41%.

NMR Spectrum of the Proton.

In $D_2O$, at 300 MHz, chemical shifts and multiplicity: 3.40 (d) and 3.88 (d, d): N—$CH_2$—O—$CH$; 5.15 (d): N—$CH_2$—$CH$; 4.60 and 4.66: N—$CH_2$—C=; 8.77 (s): HC=. MS (negative electrospray) m/z: [M]$^-$=260

Example 67

Sodium salt of 5,9-dihydro-6-(sulphooxy)-5,8-methano-8H-pyrido[2,3-e][1,3]-diazepin-7(6H)-one]

Stage A 8 ml (51.6 mmoles) of ethyl 2-methylnicotinate is dissolved in 93 ml of carbon tetrachloride. Then 2.9 ml of acetic acid, 17.73 g of N-bromosuccinimide and 0.185 g of AIBN are added. The mixture is placed under a 500 W lamp for 4 ours. Then the red solution and the gum obtained are poured into an ice-cold solution of sodium bicarbonate. The aqueous phase is extracted with dichloromethane, dried and the solvent is evaporated off under reduced pressure. 14.74 g of red oil is obtained containing the expected brominated derivative. Then the oil obtained is dissolved in 90 ml of anhydrous THF in the presence of 6 ml of triethylamine and 15 g (72 mmoles) of tert-butyl N-benzyl-glycinate. Agitation is carried out for 24 hours at ambient temperature, followed by diluting with water then extracting with ethyl acetate. The organic phase is dried over magnesium sulphate then the solvent is evaporated off under reduced pressure. 25 g of product is obtained in the form of a resin which is purified by chromatography on silica eluting with a cyclohexane/ethyl acetate mixture (80/20). After evaporation of the solvent, 14.18 g of ethyl 2-[[[2-(1,1-dimethylethoxy)-2-oxoethyl](phenylmethyl)amino]methyl]-3-pyridinecarboxylate, of molecular formula $C_{21}H_{26}N_2O_4$ (M=370.45 g) is obtained in the form of an orange-coloured oil.

The yield obtained is 71.6%.

Stage B 0.740 g of the product obtained in the previous Stage A is dissolved in 8 ml of THF and the reaction medium is placed under an inert atmosphere. Then this solution is cooled down to −70° C. and a solution containing 0.448 g of potassium tert-butylate in 4 ml of THF is introduced over 15 minutes. Agitation is carried out for two hours at −78° C. then the solution is poured into a saturated aqueous solution of monosodium phosphate. Extraction is carried out with ethyl acetate. The organic phase is dried over magnesium sulphate then the solvents are evaporated off under reduced pressure. 0.664 g of 1,1-dimethylethyl 7,8-dihydro-5-hydroxy-7-(phenylmethyl)-1,7-naphthyridine-6-carboxylate, of molecular formula $C_{20}H_{22}N_2O_3$ M−338.41 g) is obtained in the form of a yellow oil.

The yield obtained is 98%.

Stage C 4.26 g of the product obtained as described in the previous Stage D is dissolved in 6 ml of dichloromethane then the solution is cooled down to 0° C. 20 ml of trifluoroacetic acid is added slowly. Agitation is carried out for 30 minutes at 0° C. and for 1 hour at 20° C. and the solvent is evaporated off under reduced pressure. The residue obtained is dissolved in 20 ml of methanol then sodium borohydride is introduced slowly into this solution until saturation and agitation is maintained overnight at 0° C. The solution is then diluted with an aqueous solution of monosodium phosphate, extraction is carried out with dichloromethane. 2.74 g of crude product is obtained which is purified by chromatography on silica eluting with a dichloromethane/methanol mixture (95/5). 1.99 g of product 7,8-dihydro-7-(phenylmethyl)-1,7-naphthyridin-5-(6H)-ol, of molecular formula $C_{15}H_{16}N_2O$ is obtained (M=240.31 g).

The corresponding yield is 65.8%.

Stage D

A mixture containing 0.980 g of the product obtained in the previous stage, 30 ml of ethanol, 8.16 ml of 2N hydrochloric acid and 0.445 g of 10% palladium on carbon is placed under a hydrogen atmosphere for 4 hours. Then after 4 hours, the catalyst is filtered, followed by washing with ethanol and a 0.1N solution of HCl and the solvents are evaporated off under reduced pressure. Hydrogenolysis is carried out again under the same conditions as previously.

The crude product obtained 5,6,7,8-tetrahydro-1,7-naphthyridin-5-ol is used without purification in the following step.

Stage E

The crude product obtained in the previous Stage D is dissolved in 3 ml of THF, 1.8 ml of triethylamine and 1.520 g of di-tert-butyl carbonate is added. Agitation is carried out for 72 hours at 0° C. The reaction mixture is then concentrated under reduced pressure and the residue is purified by chromatography on silica eluting with a dichloromethane/methanol mixture (95/5). After evaporation of the solvents, 0.771 g of 1,1-dimethylethyl 5,8-dihydro-5-hydroxy-1,7-naphthyridine-7(6H)-carboxylate, of molecular formula $C_{13}H_{18}N_2O_3$ (M=250.30 g) is obtained in the form of a brown oil.

The corresponding yield is 75%.

Stage F

A solution containing 0.5 g of the product obtained in the previous Stage E, 10 ml of dichloromethane, 2 ml of acetonitrile and 3 ml of triethylamine is cooled down to −70° C. under an inert atmosphere. 0.52 g of mesyl anhydride is then introduced in one go. Agitation is carried out for 30 minutes at −70° C. then 1 ml of O-allyl hydroxylamine is introduced. The reaction medium is left to return to ambient temperature and agitation is continued overnight. DMAP is added and the solution is taken to 30° C. for 5 hours after eliminating the solvent under reduced pressure. The reaction medium is then diluted with dichloromethane, washed with a dilute HCl solution then washed with water. Once the organic phase is dried over magnesium sulphate and the solvents are evaporated off under reduced pressure, 0.6 g of crude product is obtained which is purified by chromatography on silica eluting with a cyclohexane/ethyl acetate mixture (5/5). 0.35 g of 1,1-dimethylethyl 5,8-dihydro-5-[(2-propenyloxy)amino]-1,7-naphthhyridine-7(6H)-carboxylate, of molecular formula $C_{16}H_{23}N_3O$ is obtained (M=305.38 g).

The corresponding yield is 57%.

Stage G 0.330 g of the product obtained in the previous Stage F is dissolved in 4 ml of ethyl acetate. 7 ml of a saturated solution of gaseous HCl in ethyl acetate is added. The white suspension is agitated for two hours. Then, the suspension is adjusted to an alkaline pH using ammonium hydroxide. The reaction medium is diluted with water followed by extraction with ethyl acetate and the organic phase is evaporated under reduced pressure and 0.176 g of crude product is obtained which is purified by chromatography on silica eluting with a DCM/methanol mixture (95/5). 0.156 g of the sodium salt of 5,9-dihydro-6-(sulphooxy)-5,8-methano-8H-pyrido[2,3-e][1,3]diazepin-7-(6H)-one.

The corresponding yield obtained is 70%.

Stage H

A solution containing 0.114 g (0.55 mmole) of the product obtained in the previous Stage G, 5 ml of acetonitrile is cooled down to 0° C. under an inert atmosphere. 0.034 ml of diphosgene is added slowly followed by agitating for 30 minutes at 0° C. 0.16 ml of triethylamine is then introduced dropwise followed by agitating overnight. The reaction medium is diluted with water followed by extracting with dichloromethane. The organic phase is dried followed by evaporating under reduced pressure. 0.189 g is obtained in the form of an oil which is taken up in 1 ml of pyridine and a catalytic quantity of DMAP. This solution is taken to 30° C. for 30 minutes, then the pyridine is evaporated under reduced pressure and the residue is diluted with water followed by extracting with dichloromethane. After drying and evaporation of the solvent, 0.1 g of resin is obtained which is purified by chromatography on silica eluting with a dichloromethane/methanol mixture (95/5). 0.085 g of 5,9-dihydro-6-(2-propenyloxy)-5,8-methano-8H-pyrido[2,3-e][1,3]diazepin-7(6H)-one, of molecular formula $C_{12}H_{13}N_3O_2$ is recovered (M=231.26 g).

The corresponding yield is 66%.

Stage I

The process is carried out as indicated in Stage M of Example 3 with 0.039 g of the product obtained in the previous Stage H, 0.6 ml of dichloromethane, 0.1 g of palladium tetrakistriphenylphosphine, 0.081 g of the $SO_3$-pyridine complex and 0.6 ml of pyridine. 0.030 g of the sodium salt of 5,9-dihydro-6-(sulphooxy)-5,8-methano-8H-pyrido[2,3-e][1,3]diazepin-7(6H)-one, of molecular formula $C_9H_8N_3NaO_5S$ is obtained (M=293.24 g).

The corresponding yield is 48%.

NMR Spectrum of the Proton

In DMSO-$d_6$ at 300 MHz, chemical shifts and multiplicity: 3.57 (d) and 3.76 (dd): N—$CH_2$—CH; 4.94 (d): N—$CH_2$—CH; 4.31 and 4.58: N—$CH_2$—C=; 7.44 (dd) and 7.72 (dd) and 8.67 (dd) for the aromatic 3H's.

Example 68

Sodium salt of trans methyl 2,5,6,8-tetrahydro-2-methyl-6-oxo-5-sulphooxy)-4H-4,7-methanopyrazolo[3,4-e][1,3]diazepine-8-carboxylate Stage A The process is carried out as indicated in Stage A of Example 62 with 600 mg (1.83 mmole) of the product obtained in Example 61, 80 mg of NaH at 50% in oil, 174 µl of dimethyl sulphate in order to obtain 72 mg of methyl 2,5,6,8-tetrahydro-2-methyl-6-oxo-5-(phenylmethoxy)-4H-4,7-methanopyrazole[3,4-e][1,3]diazepine-8-carboxylate, of molecular formula $C_{17}H_{18}N_4O_4$ (M=342.36 g).

The corresponding yield is 11.5%.

Stage B

The process is carried out as indicated in Stage A of Example 11 with 52 mg (0.155 mmole) of the product obtained in Stage A, 1 ml of a $CH_3OH/THF$ mixture 2/1, 10 mg of 30% Pd/C, in order to obtain 37 mg of methyl 2,5,6,8-tetrahydro-5-hydroxy-2-methyl-6-oxo-4H-4,7-methanopyrazolo[3,4-e][1,3]diazepine-8-carboxylate, of molecular formula $C_{10}H_{12}N_4O_4$ (M=252.23 g).

The corresponding yield is 96.6%.

Stage C 37 mg (0.146 mmole) of the compound obtained in Stage B is introduced into 0.75 ml of pyridine, then 70 mg of pyridine-$SO_3$ complex is added. Agitation is carried out overnight at 20° C. 0.15 ml of demineralized water is added, followed by agitating for 10 minutes and evaporating the solvent under reduced pressure. The crude product is purified on a layer of $XAD_4$ resin eluting with $H_2O$ with 5% acetone, the acetone of the fractions containing the product is evaporated off and lyophilization is carried out. The pyridinium salt solution is exchanged on Dowex 50W×8 resin in $Na^+$ form. After lyophilization of the sulphate and sodium salt fractions, 18 mg of the sodium salt of methyl 2,5,6,8-tetrahydro-2-methyl-6-oxo-5-(sulphooxy)-4H-4,7-methanopyrazolo[3,4-e][1,3]diazepine-8-carboxylate, of molecular formula $C_{10}H_{11}N_4O_7S.Na$ is recovered (M=354.27 g).

The corresponding yield is 34.8%.

NMR Spectrum of the Proton in Solvent $D_2O$ at MHz, chemical shifts and multiplicity: 3.54 (d) and 3.79 (dd): N—$CH_2$—CH; 4.97 (d): N—$CH_2$—CH; 3.88 (s): N—$CH_3$; 3.89 (s): O—$CH_3$; 5.43 (s): N—$CH$—CO; 7.73 (s): N—$CH$=C. MS (negative electrospray) m/z: $[M]^-$=331

Example 69

Triethylammonium salt of trans methyl 2-ethyl-4,5,6,8-tetrahydro-6-oxo-5-(sulphooxy)-4,7-methano-7H-thieno[2,3-e][1,3]diazepine-8-carboxylate Stage A In a 60 ml flask equipped with a magnetic stirrer, 5.09 g (14.7 mmoles) of methyl 4,5,6,8-tetrahydro-6-oxo-5-(phenylmethoxy)-4,7-methano-7H-thieno[2,3-e][1,3]diazepine-8-carboxylate prepared in Stage E of Example 57 is dissolved under argon in 100 ml of $CCl_4$, the reaction medium is cooled down with an ice bath, then 1.87 g (7.4 mmoles) of iodine, 3.81 g of $PhI(OCOCF_3)_2$ are added. The reaction medium is allowed to return to 20° C. After agitating for 2 to 3 hours at 20° C., the solution is poured into a 0.5N aqueous solution of sodium thiosulphate, extraction is carried out with ethyl acetate followed by washing again with a 0.5N aqueous solution of sodium thiosulphate, washing with a saturated aqueous solution of sodium chloride, then with a phosphate buffer solution, pH=7.0, and finally with a saturated aqueous solution of sodium chloride. After drying over $MgSO_4$ and evaporating the solvents under reduced pressure, the crude reaction product is obtained which is purified by chromatography on silica eluting with a $CH_2Cl_2$/ethyl acetate mixture (95/5), TEA=0.1%.

4.88 g of methyl 4,5,6,8-tetrahydro-2-iodo-6-oxo-5-(phenylmethoxy)-4,7-methano-7H-thieno[2,3-e][1,3]diazepine-8-carboxylate, of molecular formula $C_{17}H_{15}N_2IO_4S$ is obtained (M=470.289 g).

The yield is 70%.

Stage B 300 mg (0.6379 mmole) of the product obtained in Stage A, 12 ml of DMF previously degassed using argon are dissolved in a flask placed under an argon atmosphere, then 372 μl (1.2758 mmoles) of vinyl-tributylstanane is added, followed by 36.7 mg (0.0637 mmole) of bis-1,2-diphenylphosphino ethane palladium chloride. After agitating the solution for 17 hours, the solvent is eliminated by evaporation, the reaction medium is diluted with 60 ml of ethyl acetate, 60 ml of an aqueous solution of KF is added and vigorous agitation is carried out for 30 minutes. The reaction medium is filtered and the aqueous phase is re-extracted with ethyl acetate, and finally the organic extracts are washed with a saturated aqueous solution of sodium chloride. After drying over $MgSO_4$, evaporating to dryness under vacuum and purification by chromatography on silica, eluting initially with a $CH_2Cl_2$ mixture with 0.1% TEA and then with a $CH_2Cl_2$/ethyl acetate mixture (95/5), 0.1% TEA, 208.7 mg of methyl 2-ethenyl-4,5,6,8-tetrahydro-6-oxo-5-(phenylmethoxy)-4,7-methano-7H-thieno[2,3-e][1,3]diazepine-8-carboxylate, of molecular formula $C_{19}H_{18}N_2O_4S$ is obtained (M=370.43 g).

Stage C

In a 30 ml flask, 51.1 mg (0.138 mmole) of the product obtained in Stage B is dissolved in 5 ml of methanol, then 51 mg of 30% palladium on active carbon is added, the reaction medium is placed under a hydrogen atmosphere for 20 hours. After dilution of the reaction suspension by adding 5 ml of $CH_2Cl_2$, agitation is carried out for 10 minutes, followed by filtering. Extraction is carried out with a $CH_2Cl_2$/methanol mixture (1/1) followed by evaporating to dryness under vacuum. 37.1 mg of methyl 2-ethyl-4,5,6,8-tetrahydro-5-hydroxy-6-oxo-4,7-methano-7H-thieno[2,3-e][1.3]diazepine-8-carboxylate, of molecular formula $C_{12}H_{14}N_2O_4S$ is obtained (M=282.321 g).

The corresponding yield is 95.2%.

Stage D

Step 1

The process is carried out as indicated in Stage C of Example 62 with 37.1 mg (0.1314 mmole) of the product obtained in Stage C, 0.85 ml of pyridine and 62.7 mg (0.3942 mmole) of $SO_3$-pyridine complex.

7.3 mg of the triethylammonium salt of 8-methyl 2-ethyl-4,5,6,8-tetrahydro-6-oxo-5-(sulphooxy)-4,7-methano-7H-thieno[2,3-e][1,3]diazepine-8-carboxylate, of molecular formula $C_{18}H_{29}O_7N_3S_2$ is obtained (M=463.57 g).

MS (negative electrospray): $[M]^-=361$

Example 70

Triethylammonium salt of trans methyl 4,5,6,8-tetrahydro-2-methyl-6-oxo-5-(sulphooxy)-4,7-methano-7H-thieno[2,3-e][1,3]diazepine-8-carboxylate Stage A In a flask placed under an argon atmosphere, 330 mg (0.7 mmole) of the product obtained in Step A of Example 69 is dissolved in 12 ml of DMF previously degassed with argon, then 97.2 μl of tetramethyltin (17 mmoles) is added, then 9.5 mg of bis-(triphenylphospheno)palladium chloride (0.07 mmole) is added. The mixture is taken to 75° C., for 6 hours, followed by evaporating the solvent under reduced pressure, diluting the dry extract with 10 ml of ethyl acetate, adding 10 ml of a saturated aqueous solution of KF and agitating vigorously for 30 minutes. After filtering, the aqueous phase is re-extracted with ethyl acetate, the organic extracts are washed with a saturated aqueous solution of sodium chloride, followed by drying over $MgSO_4$ and evaporating under vacuum. After chromatography on a silica column eluting with a $CH_2Cl_2$/ethyl acetate mixture (95/5), TEA=0.1%, 40.8 mg of methyl 4,5,6,8-tetradhydro-2-methyl-6-oxo-5-(phenylmethoxy)-4,7-methano-7H-thieno[2,3-e][1,3]diazepine-8-carboxylate, of molecular formula $C_{18}H_{18}N_2O_4S$ is obtained (M=358.419 g).

The corresponding yield is 16.2%.

Stage B

The process is carried out as indicated in Stage A of Example 11 with 52.2 mg (0.1456 mmole), 5 ml of methanol, 52.2 mg of the product obtained in Step A.

34.2 mg of methyl 4,5,6,8-tetrahydro-5-hydroxy-2-methyl-6-oxo-4,7-methano-7H-thieno[2,3-e][1,3]diazepine-8-carboxylate, of molecular formula $C_{11}H_{12}N_2O_4S$ is obtained (M=268.294 g).

The corresponding yield is 87.5%.

Stage C

The process is carried out as indicated in Stage B of Example 62 with 34.2 mg of product of Stage B, 0.8 ml of pyridine kept on a sieve, 60.9 mg of $SO_3$-pyridine complex (0.3824 mmole). After purification on silica, eluting with a $CH_2Cl_2$/methanol mixture (80/20), TEA=0.5%, 8.5 mg of the triethylammonium salt of trans methyl 4,5,6,8-tetrahydro-2-methyl-6-oxo-5-(sulphooxy)-4,7-methano-7H-thieno[2,3-e][1,3]diazepine-8-carboxylate, of molecular formula $C_{17}H_{27}O_7N_3S_2$ is obtained (449.55 g).

The corresponding yield is 14.5%.

MS (negative electrospray) m/z: $[M]^-=347$

Example 71

Trans-4,5,6,8-tetrahydro-6-oxo-5-[(phenylsulphonyl)oxy]-4,7-methano-7H-thieno[2,3-e][1,3]diazepine-8-carboxamide Stage A The process is carried out as indicated in stage A of Example 11 with 40 mg (0.12 mmole) of 4,5,6,8-tetrahydro-6-oxo-5-(phenylmethoxy)-4,7-methano-7H-thieno[2,3-e][1,3]diazepine-8-carboxamide obtained according to Stage A of Example 60, replacing NH$_2$Me,HCl with NH$_4$Cl, 2.1 ml of ethanol, 40 mg of 30% palladium on active carbon.

30 mg of the product mentioned above is obtained

The corresponding yield is 46%.

Stage B

The product obtained in stage A is dissolved in 1 ml of pyridine with 15 μl of PhSO$_2$Cl is agitated at 20° C. for 1 hour, then diluted with CH$_2$Cl$_2$ and washed with a 10% aqueous solution of tartaric acid. Then after evaporation of the solvent under reduced pressure, purification is carried out by chromatography on silica eluting with 20% CH$_2$Cl$_2$/ethyl acetate.

20.9 mg of trans-4,5,6,8-tetrahydro-6-oxo-5-[(phenylsulphonyl)oxy]-4,7-methano-7H-thieno[2,3-e][1,3]diazepine-8-carboxamide, of molecular formula C$_{15}$H$_{13}$N$_3$O$_5$S$_2$ is obtained (M=371.42 g).

The corresponding yield is 46%.

NMR Spectrum of the Proton

In DMSO, at 300 MHz, chemical shifts and multiplicity: 3.4 (dd) and 3.53 (d): N—C$\underline{H}_2$—CH; 4.45 (d): CH$_2$—C$\underline{H}$; 5.04 (s): N—C$\underline{H}$—CO—; 7.61 (bs) and 7.84 (bs): CO—N$\underline{H}_2$; 7.01 (d) and 7.53 (d): the 2 hydrogens of the thiophene; 7.74 (bd), 7.88 (bt) and 8.03 (bd) for the 5 aromatic hydrogens. MS (positive electrospray) m/z: [2M+H$^-$]$^+$=759, [M+H]+=380.

Example 72

Sodium salt of N-[5,6,7,9-tetrahydro-7-oxo-6-(sulphooxy)-5,8-methano-8H-pyrimido[4,5-e][1,3]diazepin-2-yl]-acetamide Stage A A reaction mixture comprising 5 g (18.6 mmoles) of the compound prepared in Stage A of Example 5 is heated under reflux for 1 hour 30 minutes in the presence of 4.9 g of acetyl guanidine and 150 ml of toluene, followed by concentrating under reduced pressure and the residue obtained is purified by chromatography on silica eluting with a dichloromethane/methanol mixture (95/5). In this way 11% of expected product and 63% of deacetylated product are obtained. 3.07 g of the intermediate deacetylated product is taken up in 2 ml of acetic anhydride, immersed in an oil bath at 1300 or 140° C. for 20 minutes then cooled down and concentrated under reduced pressure. The residue is taken up with a solution of sodium bicarbonate followed by extracting with dichloromethane and drying over Na$_2$SO$_4$. The solvent is evaporated off under reduced pressure then purification is carried out by chromatography. In this way at total of 3.49 g of 1,1-dimethylethyl 2-(acetylamino)-5,8-dihydro-5-oxo-pyrido[3,4-d]pyrimidine-7 (6H)-carboxylate, of molecular formula C$_{14}$H$_{18}$N$_4$O$_4$ is obtained (M=306.32 g).

The overall yield is 61%.

Stage B

A solution containing 0.65 g of the product obtained in the previous Stage A in 15 ml of ethanol is cooled down to 0° C. under an inert atmosphere. 0.088 g of sodium borohydride is introduced slowly followed by agitating for 30 minutes at 0° C. The solution is poured into a saturated ice-cold solution of monosodium phosphate followed by extracting with dichloromethane. After drying and evaporation of the solvents under reduced pressure, 0.546 g of 1,1-dimethylethyl(2-acetylamino)-5,8-dihydro-5-hydroxypyrido[3,4-d]pyridine-7(6H)-carboxylate, of molecular formula C$_{14}$H$_{20}$N$_4$O$_4$ is obtained (M=308, 34 g).

The corresponding yield is 84%.

Stage C

A solution containing 1.54 g of the alcohol obtained in the previous Stage B, 15 ml of dichloromethane and 0.86 ml of triethylamine is cooled down to −20° C. under an inert atmosphere. Then 0.42 ml of mesyl chloride is introduced slowly. The reaction medium is left to return to 0° C. then 15 ml of O-allyl-hydroxylamine is added. The mixture is also agitated for 4 days at 0° C. The solvents are evaporated off under reduced pressure, then the residue is purified by chromatography on silica eluting with a dichloromethane/methanol mixture (95/5).

0.870 g of 1,1-dimethylethyl 2-(acetylamino)-5±8-dihydro-5-[(2-propenyloxy)-amino]-pyrido[3,4-d]pyrimidine-7 (6H)-carboxylate, of molecular formula C$_{17}$H$_{25}$N$_5$O$_4$ is obtained (M=363.42 g).

The corresponding yield is 50%.

Stage D 1.368 g (3.76 mmoles) of the compound obtained in the previous Stage C is dissolved in 5 ml of ethyl acetate. 10 ml of ethyl acetate saturated with gaseous HCl is introduced over 5 minutes into the previous solution. Agitation is carried out for 30 minutes then the is reaction medium is concentrated to a small volume before adding 5 ml of water, 2 ml of ammonia then the solution is saturated with NaCl and extraction is carried out with dichloromethane.

0.991 g of residue is obtained which is purified by chromatography on silica eluting with a dichloromethane/methanol/ammonia mixture (90/10/1).

0.313 g of N-[5,6,7,8-tetrahydro-5-[(2-propenyloxy)amino]pyrido[3,4-d]pyrimidin-2-yl]-acetamide, of molecular formula C$_{12}$H$_{17}$N$_5$O$_2$ is obtained (M=263.30 g).

The corresponding yield obtained is 32%.

Stage E 0.413 g (1.58 mmole) of the compound obtained in the previous Stage D is dissolved in 14 ml of acetonitrile. The reaction medium is cooled down to 0° C. and placed under an inert atmosphere before adding 0.07 ml of diphosgene. It is then left to return to ambient temperature and 0.33 ml of triethylamine is introduced. Agitation is then carried out for 4 hours, followed by eluting with ethyl acetate and washing with water. After drying the organic phase and evaporation under reduced pressure of the solvent, the residue is purified by chromatography on silica eluting with a dichloromethane/methanol mixture (90/10).

0.127 g of N-[5,6,7,9-tetrahydro-7-oxo-6-(2-propenyloxy)-5,8-methano-8H-pyrimido[4,5-e][1,3]diazepin-2-yl]-acetamide, of molecular formula C$_{13}$H$_{15}$N$_5$O$_3$ is obtained (M=289.30 g).

The corresponding yield is 28%.

Stage F 0.12 g of the product obtained in the previous Stage E, 1.4 ml of dichloromethane, 0.05 ml of acetic acid, 0.240 g of tetrakis-(triphenylphosphine)-palladium are placed under an inert atmosphere. After reacting for 30 minutes, 1 ml of pyridine and 0.196 g of SO$_3$-pyridine complex is introduced. Agitation is maintained for 20 hours followed by hydrolysis with ice, then the solvent is evaporated off under reduced pressure.

630 mg of crude product is obtained which is purified by chromatography on silica eluting with a dichloromethane/acetone/triethylamine mixture (60/40/1). 68 mg of the expected product is recovered with a yield of 26%. This product is then converted to the sodium salt by passing through Dowex 50Wx8 resin in Na+ form. 28 mg of the sodium salt of N-[5,6,7,9-tetrahydro-7-oxo-6-(sulphooxy)-5,8-methano-8H-pyrimido[4,5-e][1,3]diazepin-2-yl]-acetamide, of molecular formula $C_{10}H_{10}N_5O_6S.Na$ is obtained (M=328.29 g, 22.99 g).

The corresponding yield is 76%.

NMR of the Proton

In DMSO-$d_6$ at 300 MHz, chemical shifts and multiplicity: 2.16 (bs): $\underline{CH_3}$—CO—NH; 3.40 (d) and 3.60 (dd): N—$\underline{CH_2}$—CH; 4.04 and 4.40: N—$\underline{CH_2}$=C; 4.79 (d): N—$CH_2$—$\underline{CH}$; 8.34 (s): N—$\underline{CH_2}$=C; 10.63: $CH_3$—CO—$\underline{NH}$. MS (negative electrospray) m/z: M–=328.

Example 73

Triethylammonium salt of trans-2-bromo-4,5,6,8-tetrahydro-6-oxo-5-(sulphooxy)-4,7-methano-7H-thieno[2,3-e][1,3]diazepine-8-carboxamide In a 5 ml flask under magnetic stirring, 21.4 mg (6.27 $10^{-2}$ mmoles) of the product obtained in Stage C of Example 25 is mixed with 1 ml of $H_2O$, 6 mg of $NaHCO_3$ is added, followed by 1 equivalent of $Br_2$ in solution in 0.1 ml of $CH_2Cl_2$. After 2 hours, the solvent is evaporated off under reduced pressure followed by lyophilizing. The sodium salt is extracted twice with 12 ml of acetone followed by evaporation under reduced pressure. The residue is dissolved in 1 ml $H_2O$ and purified on a preparative plate eluting with $CH_2Cl_2$/acetone with 0.1% TEA. 16 mg of the triethylammonium salt of trans-2-bromo-4,5,6,8-tetrahydro-6-oxo-5-(sulphooxy)-4,7-methano-7H-thieno[2,3-e][1,3]diazepine-8-carboxamide, of molecular formula $C_9H_7BrN_3O_6S_2.Na$ is obtained (M=420.20 g).

The corresponding yield is 50%.

NMR Spectrum of the Proton

In $D_2O$, at 300 MHz, chemical shifts and multiplicity: 1.29 (t): $\underline{CH_3}$—$CH_2$; 3.21 (q): $CH_3$—$\underline{CH_2}$; 3.48 (d) and 3.79 (dd): N—$\underline{CH_2}$—CH; 5.29 (s): $\underline{CH}$—CO—$NH_2$; 7.20 (s): $\underline{HC}$=CBr. MS (positive electrospray) m/z: [M]$^+$=102 MS (negative electrospray) m/z: [M]$^-$=396.

Example 74

Triethylammonium salt of trans methyl 2,5,6,8-tetrahydro-6-oxo-5-(sulphooxy)-4H-4,7-methanopyrazolo[3,4-e][1,3]diazepine-8-carboxylate Stage A In a flask placed under an argon atmosphere at 0° C., 0.157 g (0.478 mmole) of the compound prepared in Example 61, 0.8 ml of $CH_2Cl_2$, 0.101 g (0.717 mmole) of $C_6H_5COCl$, and 0.073 g (0.717 mmole) of TEA are mixed together. The temperature is allowed to return to 20° C., then after 1 hour, the reaction mixture is evaporated to dryness under reduced pressure. The residue is taken up in ethyl acetate, washed with $H_2O$ then the organic phase is dried over $MgSO_4$, filtered and the solvent is evaporated off under reduced pressure. After purification by chromatography on silica, eluting with a $CH_2Cl_2$/acetone mixture (98/2) with 0.1% TEA, TEA=0.1%), 58.4 mg of methyl 2-benzoyl-2,5,6,8-tetrahydro-6-oxo-5-(phenylmethoxy)-4H-4,7-metha-nopyrazolo[3,4-e][1,3]diazepine-8-carboxylate, of molecular formula $C_{23}H_{20}N_4O_5$ is obtained (M=433.4 g).

The corresponding yield is 60%.

Stage B

The process is carried out as indicated in Stage A of Example 11 with 55 mg (0.127 mmole) of the product obtained in Stage A, 17 mg of 30% palladium on active carbon, and 2 ml of THF.

42 mg of methyl 2-benzoyl-2,5,6,8-tetrahydro-5-hydroxy-6-oxo-4H-4,7-methanopyrazolo[3,4-e][1,3]diazepine-8-carboxylate, of chemical formula $C_{16}H_{14}NaO_5$ is obtained (M=342.31 g).

The corresponding yield is 97%.

Stage C

The process is carried out as indicated in Stage B of Example 62 with 42 mg (0.123 mmole) of the product obtained in Stage B, 59 mg (0.368 mmole) of pyridine/$SO_3$ complex and 2 ml of pyridine. After purification by chromatography on a silica column, eluting with a $CH_2Cl_2$/methanol mixture (85/15), with 0.1% TEA, 16.6 mg of the triethylammonium salt of methyl trans-2,5,6,8-tetrahydro-6-oxo-5-(sulphooxy)-4H-4,7-methanopyrazolo[3,4-e][1,3]diazepine-8-carboxylate, of chemical formula $C_{16}H_{13}N_4O_3S.C_6H_{16}N$. is obtained (M=421.37, 102.20)

The corresponding yield is 31%.

LC/MS: see general conditions of Example 62

Results: RT=3.71 min.: m/z [2M+Na]$^-$=657, [M]$^-$=317

Example 75

Sodium salt of 1,4,5,8-tetrahydro-5-(sulphooxy)-6H-4,7-methanopyrazolo[3,4-e][1,3]diazepin-6-one Stage A 6 g (19.3 mmoles) of the product obtained in Stage H of Example 17 are solubilized in 180 ml of THF, 180 ml of tert-butanol and 60 ml of water. 3.92 g (29 mmoles) of N-methylmorpholine N-oxide then 2.98 mg (0.579 mmole) of osmium tetraoxide are introduced. Agitation is carried out at ambient temperature for 54 hours. After evaporation of the THF, the medium is taken up in a 1M aqueous solution of $NaH_2PO_4$. Extraction is carried out with a mixture of ethyl acetate/heptane at 20% then with dichloromethane/methylene chloride and THF. After drying of the organic phase over $MgSO_4$ then evaporation of the solvents under reduced pressure, 6.16 g of 1-(2,3-dihydroxypropyl)-1,4,5,8-tetrahydro-5-(phenylmethoxy)-6H-4,7-methanopyrazolo[3,4-e][1,3]diazepin-6-one, of molecular formula $C_{17}H_{20}N_4O_4$ is obtained (M=344.37 g).

The corresponding yield obtained is 93%.

Stage B 6.13 g (17.8 mmoles) of the product obtained in the previous Stage A is dissolved in 140 ml of THF. Then 45 ml of methanol is added followed by 45 ml of water. The solution obtained is cooled down to 0° C. Then 6.08 g of sodium metaperiodate is added. Agitation is carried out for 2 hours while allowing the temperature to rise to 20° C. After 2 hours 1052 g of sodium metaperiodate is added and agitation is carried out for a further 40 minutes. Once the reaction is complete, 260 ml of a 1M aqueous solution of $NaH_2PO_4$ is added, then the solution is saturated with solid NaCl followed by extraction with THF and with a mixture ethyl acetate/heptane at 30%. The organic phase is washed with a saturated aqueous solution of $NaH_2PO4$ then dried over $MgSO_4$. After evaporation of the solvent under reduced pressure 9.98 g of 4,5,6,8-tetrahydro-6-oxo-5-(phenylmethoxy)-1H-4,7-methanopyrazolo[3,4-e][1,3]diazepine-1-acetaldehyde, of molecular formula $C_{16}H_{16}N_4O_4$ is obtained (M=342.39 g).

The yield obtained is quantitative.

Stage C 5.6 g of the product obtained in the previous Stage A is dissolved in 100 ml of ethanol then 2.71 g of $NaBH_4$ is added by portions at 0° C. Agitation is carried out for 2 hours at 0° C. then the ethanol is evaporated off, ice then methylene chloride are added and little by little a 1M aqueous solution of $NaH_2PO_4$ is added. The gas evolution is significant. Then the aqueous phase is extracted with methylene chloride and the organic phase is washed with a thiosulphate solution in order to eliminate the $NaIO_4$ residues. After drying the organic phase over $MgSO_4$, the solvents are evaporated off under reduced pressure.

A solid residue is obtained which is crystallized from a mixture of ethyl ether and isopropanol. After filtration, 3.45 g of 1,4,5,8-tetrahydro-1-(2-hydroxyethyl)-5-(phenylmethoxy)-6H-4,7-methano-pyrazolo[3,4-e][1,3]diazepin-6-one, of molecular formula $C_{16}H_{18}N_4O_3$ is obtained (M=314.35 g).

The corresponding yield is 62%.

Stage D 1.35 g (4.29 mmoles) of the product obtained in the previous Stage C is dissolved in 50 ml of THF. Then 0.69 ml of pyridine is added at ambient temperature, followed by 1.46 g of triphenylphosphine. 1.42 g of iodine is added in portions then after 2 hours, 200 mg of iodine, 220 mg of triphenylphosphine and 0.13 ml of pyridine are added. A solution of $NaH_2PO_4$ is poured into the reaction medium then extraction is carried out using an ethyl acetate/heptane mixture and the organic phase is washed with a saturated aqueous solution of NaCl. After evaporation of the solvents of the organic phase under reduced pressure, 1.6 g of crude product is obtained which is purified by chromatography on silica eluting with a 10% dichloromethane/acetonitrile mixture. 1.60 g of the product 1,4,5,8-tetrahydro-1-(2-iodoethyl)-5-(phenylmethoxy)-6H-4,7-methanopyrazolo[3,4-e][1,3]diazepin-6-one, of molecular formula $C_{17}H_{17}IN_4O_2$ is obtained (M=424.24 g).

The yield obtained is 80%.

Stage E 1.6 g (3.77 mmoles) of the product obtained in the previous Stage D is dissolved in 16 ml of anhydrous DMF. 260 mg of potassium cyanide is added and agitation is carried out at ambient temperature for 20 hours. The reaction medium is washed with water then extraction is carried out with a mixture of ethyl acetate/heptane at 20%. The organic phase is dried over magnesium sulphate then after evaporation of the solvents under reduced pressure, a crude residue is obtained which is purified by chromatography on silica eluting first with dichloromethane then a mixture of dichloromethane/methanol at 10%. After evaporation of the fractions containing the expected product, 1.20 g of 4,5,6,8-tetrahydro-6-oxo-5-(phenylmethoxy)-1H-4,7-methanopyrazolo[3,4-e][1,3]diazepine-1-propanenitrile, of molecular formula $C_{17}H_{17}N_5O_2$ is obtained (M=323.36 g).

The corresponding yield is 98%.

Stage F 500 mg (1.546 mmole) of the product obtained in the previous Stage E is dissolved in 5 ml of DMF. The solution is cooled down to 0° C. then 68 mg of sodium hydride is added. Agitation is carried out for 3 hours at 0° C. Then the reaction medium is poured into an aqueous solution of $NaH_2PO_4$ and extraction is carried out with an ethyl acetate/heptane mixture. The organic phase is dried over magnesium sulphate then the solvents are evaporated off under reduced pressure. 448 mg of crude product obtained is purified on silica eluting with a mixture of methylene chloride/methanol at 10%. 177 mg of 1,4,5,8-tetrahydro-5-(phenylmethoxy)-6H-4,7-methanopyrazolo[3,4-e][1,3]diazepin-6-one, of molecular formula $C_{14}H_{14}N_4O_2$ is obtained (M=270.29 g).

The corresponding yield is 42%.

Stage G 163 mg of the product obtained in the previous Stage F is dissolved in 8 ml of ethanol in the presence of a drop of acetic acid. 400 mg of palladium on carbon at 10% by weight is then introduced then the medium is maintained under a hydrogen atmosphere for 20 minutes. Once the reaction is complete, the catalyst is eliminated by filtration then the THF is evaporated under reduced pressure in the presence of toluene in order to entrain the remaining acetic acid in an azeotropic manner. 92.8 mg of 1,4,5,8-tetrahydro-5-hydroxy-6H-4,7-methanopyrazolo[3,4-e][1,3]diazepin-6-one, of molecular formula $C_7H_8N_4O_2$ is obtained in the form of a white powder (M=180.17 g).

The corresponding yield is 85%.

Stage H 92 mg of the product obtained in the previous Stage G is dissolved in 2 ml of pyridine. Then 325 mg of the pyridine-$SO_3$ complex is added. After one night at 20° C., the pyridine is evaporated entraining with toluene. The product is then taken up in water then passed through Dowex 50Wx8 resin in $Na^+$ form. After evaporation of the fractions containing the expected product, the residue is taken up in methanol then after filtration and evaporation of the solvent under reduced pressure, a residue is obtained which once concretized in ether produces 140 mg of the sodium salt of 1,4,5,8-tetrahydro-5-(sulphooxy)-6H-4,7-methanopyrazolo[3,4-e][1,3]diazepin-6-one, of molecular formula $C_7H_7N_4O_5S.Na$ (M=282.21 g).

The corresponding yield is 97.3%.

NMR Spectrum of the Proton

In DMSO-$d_6$, chemical shifts and multiplicity: 3.14 (d) and 3.50 (dd): N—CH$_2$—CH; 4.71 (d): N—CH$_2$—CH; 4.22 (m): N—CH$_2$C=; 7.68 (bs): N=CH; 12.64 (bs) mobile H MS (negative electrospray) m/z: [2M–+Na]⁻=541; [2M–+H]⁻=519; [M–+MeOH]⁻=291; [M]⁻=59.

Pharmacological Study of the Products of the Invention

Activity In Vitro, Method of Dilutions in Liquid Medium

A series of tubes is prepared in which the same quantity of sterile nutritive medium is distributed. Increasing quantities of the product to be studied are distributed into each tube, then each tube is sown with a bacterial strain.

After incubation for twenty-four hours in a heating chamber at 37° C., the growth inhibition is evaluated by transillumination, which allows the minimal inhibitory concentrations (M.I.C.) to be determined, expressed in µg/ml.

Therefore tests with the following products of the invention were carried out:

the sodium salt of trans-3-oxo-4-(sulphooxy)-2,3,4,5-tetrahydro-2,5-methano-1H-2,4-benzodiazepine-1-carboxamide;

the sodium salt of 3-methyl-5-(sulphooxy)-5,6,7,8-tetrahydro-4,7-methano-4H-[1,2,3]-triazolo[4,5-e][1,3]diazepine-6(3H)-one;

the sodium salt of trans-1-methyl-6-oxo-5-(sulphooxy)-4,5,6,8-tetrahydro-4,7-methano-1H-pyrazolo[3,4-e][1,3]diazepine-8(7H)-carboxamide;

the sodium salt of trans-N-methyl-3-oxo-4-(sulphooxy)-2,3,4,5-tetrahydro-2,5-methano-1H-2,4-benzodiazepine-1-carboxamide;

the sodium salt of 5-(sulphooxy)-5,6,7,8-tetrahydro-4,7-methano-4H-furo[2,3-e][1,3]diazepine-6-one;

the pyridinium salt of 1-propyl-5-(sulphooxy)-4,5,7,8-tetrahydro-4,7-methano-imidazo[4,5-e][1,3]diazepine-6(1H)-one;

the sodium salt of methyl trans-6-oxo-5-(sulphooxy)-5,6,7,8-tetrahydro-4,7-methano-4H-furo[2,3-e][1,3]diazepine-8-carboxylate;

the sodium salt of 1-methyl-5-(sulphooxy)-5,6,7,8-tetrahydro-4,7-methano-4H-pyrazolo[3,4-e][1,3]diazepine-6(1H)-one;

the sodium salt of trans-3-oxo-N-(4-pyridinylmethyl)-4-(sulphooxy)-2,3,4,5-tetrahydro-2,5-methano-1H-2,4-benzodiazepine-1-carboxamide;

the sodium salt of trans-6-oxo-5-(sulphooxy)-5,6,7,8-tetrahydro-4,7-methano-4H-thieno[2,3-e][1,3]diazepine-8-carboxamide;

the sodium salt of trans-6-oxo-5-(sulphooxy)-5,6,7,8-tetrahydro-4,7-methano-4H-furo[2,3-e][1,3]diazepine-8-carboxamide.

These compounds have the activities set out in the following table:

| Gram-positive MIC μg/ml at 24 hours | |
|---|---|
| S. aureus SG511 | 1.25-40 |
| S. aureus Exp54146 | 1.25-40 |
| S. pyogenes A561 | <0.08-20 |
| Gram-negative MIC μg/ml at 24 hours | |
| E. coli UC1894 | <0.15-10 |
| E. coli 250HT7 | <0.15-20 |
| E. cloacae 1321E | <0.15-40 |

The compounds according to the invention therefore show an anti-bacterial activity.

Example 76

In this example, a pharmaceutical composition was prepared for injection.

This pharmaceutical composition contained:

| the compound of Example 9 | 500 mg |
|---|---|
| a sterile aqueous excipient | s.q.f. 10 ml. |

The invention claimed is:

1. A compound selected from the group consisting of a compound the formula:

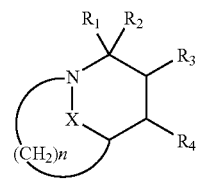

(I)

wherein:
a) either $R_1$ is selected from the group consisting of hydrogen, —COOH, —CN, —COOR, —$(CH_2)_{n'}R_5$, —$CONR_6R_7$ and

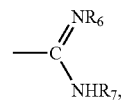

R is selected from the group consisting of alkyl of 1 to 6 carbon atoms, optionally substituted by pyridyl, a —$CH_2$-alkenyl of 3 to 9 carbon atoms, (poly)alkoxyalkyl of 1 to 4 oxygen atoms and 3 to 10 carbon atoms, aryl of 6 to 10 carbon atoms, aralkyl of 7 to 11 carbon atoms, the ring of the aryl or aralkyl optionally substituted by at least one member of the group consisting of —OH, —$NH_2$, —$NO_2$, alkyl of 1 to 6 carbon atoms, alkoxy of 1 to 6 carbon atoms and at least one halogen, $R_5$ is selected from the group consisting of —COOH, —CN, —OH, —$NH_2$, —CO—$NR_6R_7$, —COOR, —OR, —OCOH, —OCOR, —OCOOR, —OCONHR, —$OCONH_2$, —$OSO_2R$, —NHR, —NHCOR, —NH-COH, —$NHSO_2R$, —NH—COOR, —NH—CO—NHR, —NH—CO—$NH_2$ and $N_3$, R being defined as above, $R_6$ and $R_7$ are individually selected from the group consisting of hydrogen, alkyl of 1 to 6 carbon atoms, aryl 6 to 10 carbon atoms and aralkyl of 7 to 11 carbon atoms and alkyl of 1 to 6 carbon atoms substituted by pyridyl, n' is 1 or 2, $R_3$ and $R_4$ together form a phenyl or a heterocycle of aromatic character with 5 or 6 vertices containing 1 to 4 heteroatoms chosen from nitrogen, oxygen and sulfur, and optionally substituted by at least one R', R' being selected from the group consisting of hydrogen, and the alkyl of 1 to 6 carbon atoms, optionally substituted by at least one member of the group consisting of hydroxy, oxo, halogen, cyano, nitro, alkenyl of 2 to 6 carbon atoms, halogen, amino, —OH, protected —OH, —OR, —NHCOH, —NHCOR, —NH-COOR, —COOH, —COOR, —$C(C_6H_5)_3$ and —$CH_2$—$CH_2$—$S(O)_m$-R, R being as defined previously and m being 0, 1 or 2, or b) $R_4$ is hydrogen or —$(CH_2)_{n'1}R_5$, n'1 being 0, 1 or 2 and $R_5$ being as defined above, and $R_1$ and $R_3$ together form a phenyl or an optionally substituted heterocycle, as defined above, in both case a) and b)

$R_2$ is selected from the group consisting of hydrogen, halogen, R, —$S(O)_mR$, —OR, —NHCOR, —NHCOOR and —$NHSO_2R$, m and R being as defined previously, X is —C(O)—B— linked to the nitrogen atom by the carbon atom, B is —$NR_8$ linked with the carbonyl by the nitrogen and $R_8$ is selected from the group consisting of hydrogen, —OH, —R, —OR, —Y —OY, —$Y_1$, —$OY_1$, —$Y_2$, —$OY_2$, —$Y_3$, —O—$CH_2$—$CH_2$—S(O)m-R, —SiRaRbRc and —OSiRaRbRc, Ra, Rb and Rc are individually alkyl of 1 to 6 carbon atoms or aryl 6 to 10 carbon atoms and R and m are as defined previously, Y is selected from the group consisting of —COR, —COOR, —$CONH_2$, —CONHR, —CONHOH, —$CONHSO_2R$, —$CH_2COOH$, —$CH_2COOR$, —$CH_2CONHOH$, —$CH_2CONHCN$, —$CH_2$tetrazole, protected —$CH_2$tetrazole, —$CH_2SO_3H$, —$CH_2SO_2R$, —$CH_2PO(OR)_2$, —$CH_2PO(OR)(OH)$, —$CH_2PO(R)(OH)$ and —$CH_2PO(OH)_2$, $Y_1$ is selected from the group consisting of —$SO_2R$, —$SO_2NHCOH$, —$SO_2NHCOR$, —$SO_2NHCOOR$, —$SO_2NHCONHR$, —$SO_2NHCONH_2$ and —$SO_3H$, $Y_2$ is selected fro the group consisting of —$PO(OH)_2$, —$PO(OR)_2$, —PO(OH)(OR) and —PO(OH)(R), $Y_3$ is selected from the group consisting of: tetrazole, tetrazole substituted by R, squarate, —NH or —NR tetrazole, —NH or —NR tetrazole, substituted by R, —$NHSO_2R$ and —$NRSO_2R$, R being defined as above, n is 1 or 2 and its pharmaceutically acceptable salts with a base or acid.

2. A compound of claim 1 wherein $R_2$ is hydrogen.

3. A compound of claim 1 wherein $R_3$ and $R_4$ together form a phenyl or heterocycle, optionally substituted, as defined in claim 1.

4. A compound of claim 1 wherein $R_3$ and $R_4$ together form phenyl or heterocycle selected from the group consisting of thienyl, furyl, pyrazolyl and triazolyl, optionally substituted.

5. A compound of claim 1 wherein $R_1$ is selected from the group consisting of hydrogen, —$COOCH_3$, —$COOC_2H_5$, —$CONH_2$, —$CONHCH_3$, —$CONHCH_3$, —$CONHCH_2$-phenyl and —$CONHCH_2$-pyridyl.

6. A compound of claim 1 wherein $R_8$ is —$Y_1$ or —$OY_1$ which $Y_1$ is selected from the group consisting of —$SO_2R$, —$SO_2NHCOR$, —$SO_2NHCOOR$, —$SO_2NHCONHR$ and —$SO_3H$ and R is as defined in claim 1.

7. A compound of claim 1 wherein $R_8$ is selected from the group consisting of hydrogen, hydroxyl, —CO-phenyl, —O-allyl, —$OCH_2COOH$ and —O-benzyl.

8. A compound selected from the group consisting of:

the sodium salt of trans-3-oxo-4-(sulphooxy)-2,3,4,5-tetrahydro-2,5-methano-1H-2,4-benzodiazepine-1-carboxamide;

the sodium salt of 3-methyl-5-(sulphooxy)-5,6,7,8-tetrahydro-4,7-methano-4H-[1,2,3]-triazolo[4,5-e][1,3]diazepine-6 (3H)-one;

the sodium salt of trans-1-methyl-6-oxo-5-(sulphooxy)-4,5,6,8-tetrahydro-4,7-methano-1H-pyrazolo[3,4-e][1,3]diazepine-8(7H)-carboxamide;

the sodium salt of trans-N-methyl-3-oxo-4-(sulphooxy)-2,3,4,5-tetrahydro-2,5-methano-1H-2,4-benzodiazepine-1-carboxamide;

the sodium salt of 5-(sulphooxy)-5,6,7,8-tetrahydro-4,7-methano-4H-furo[2,3-e][1,3]diazepine-6-one;

the pyridinium salt of 1-propyl-5-(sulphooxy)-4,5,7,8-tetrahydro-4,7-methano-imidazo[4,5-e][1,3]diazepine-6(1H)-one;

the sodium salt of trans methyl 6-oxo-5-(sulphooxy)-5,6,7,8-tetrahydro-4,7-methano-4H-furo[2,3-e][1,3]diazepine-8-carboxylate;

the sodium salt of 1-methyl-5-(sulphooxy)-5,6,7,8-tetrahydro-4,7-methano-4H-pyrazolo[3,4-e][1,3]diazepine-6(1H)-one;

the sodium salt of trans-3-oxo-N-(4-pyridinylmethyl)-4-(sulphooxy)-2,3,4,5-tetrahydro-2,5-methano-1H-2,4-benzodiazepine-1-carboxamide;

the sodium salt of trans-6-oxo-5-(sulphooxy)-5,6,7,8-tetrahydro-4,7-methano-4H-thieno[2,3-e][1,3]diazepine-8-carboxamide;

the sodium salt of trans-6-oxo-5-(sulphooxy)-5,6,7,8-tetrahydro-4,7-methano-4H-furo[2,3-e][1,3]diazepine-8-carboxamide;

the sodium salt of trans-1,2,3,5-tetrahydro-8-hydroxy-3-oxo-2-(sulphooxy)-1,4-methano-4H-2,4-benzodiazepine-5-carboxamide;

the sodium salt of trans-7-(acetylamino)-1,2,3,5-tetrahydro-8-hydroxy-3-oxo-2-(sulphooxy)-1,4-methano-4H-2,4-benzodiazepine-5-carboxamide;

the sodium salt of trans-1,5-dihydro-5-(hydroxymethyl)-2-(sulphooxy)-1,4-methano-4H-2,4-benzodiazepin-3 (2H)-one;

the sodium salt of trans-4,5,6,8-tetrahydro-N-methyl-6-oxo-5-(sulphooxy)-4,7-methano-7H-thieno[2,3-e][1,3]diazepine-8-carboxamide;

the sodium salt of 7,8-dihydro-7-(sulphooxy)-5,8-methano-5H-thieno[2,3-e][1,3]diazepin-6(4H)-one and the triethylammonium salt of trans-2-bromo-4,5,6,8-tetrahydro-6-oxo-5-(sulphooxy)-4,7-methano-7H-thieno[2,3-e][1,3]diazepine-8-carboxamide.

9. An antibacterial composition comprising an antibacterial amount of a compound of claim 1 and a pharmaceutical carrier.

10. A method of combating bacterial infections in warm-blooded animals comprising administering to warm-blooded animals in need thereof an antibacterially effective amount of a compound of claim 1.

* * * * *